US008273950B2

(12) United States Patent
Lepelley et al.

(10) Patent No.: US 8,273,950 B2
(45) Date of Patent: Sep. 25, 2012

(54) POLYNUCLEOTIDES ENCODING PHENYLPROPANOID AND FLAVONOID BIOSYNTHETIC PATHWAY ENZYMES IN COFFEE

(75) Inventors: Maud Lepelley, Tours (FR); Gerald Cheminade, Nantes (FR); James Gérard McCarthy, Noizay (FR); Vincent Petiard, Tours (FR); Chenwei Lin, Menlo Park, CA (US); Steven D. Tanksley, Dryden, NY (US)

(73) Assignees: Nestec S. A., Vevey (CH); Cornell University, Ithaca, NY (US)

( * ) Notice: Subject to any disclaimer, the term of this patent is extended or adjusted under 35 U.S.C. 154(b) by 656 days.

(21) Appl. No.: 12/083,431

(22) PCT Filed: Oct. 13, 2006

(86) PCT No.: PCT/US2006/040686
§ 371 (c)(1),
(2), (4) Date: Sep. 4, 2009

(87) PCT Pub. No.: WO2007/044992
PCT Pub. Date: Apr. 19, 2007

(65) Prior Publication Data
US 2010/0037357 A1 Feb. 11, 2010

Related U.S. Application Data

(60) Provisional application No. 60/726,298, filed on Oct. 13, 2005.

(51) Int. Cl.
*C12N 15/29* (2006.01)
*C12N 15/63* (2006.01)
*C12N 15/82* (2006.01)
*C12N 9/88* (2006.01)
*C12N 5/10* (2006.01)
*A01H 5/00* (2006.01)

(52) U.S. Cl. ............... 800/285; 536/23.6; 435/320.1; 435/252.3; 435/419; 435/468; 435/232; 800/295; 800/317

(58) Field of Classification Search ........................ None
See application file for complete search history.

(56) References Cited

U.S. PATENT DOCUMENTS 6,441,273 B1 8/2002 Aldwinckle et al.
2002/0173633 A1* 11/2002 Saltveit et al. ............... 536/23.1

OTHER PUBLICATIONS

Database EMBL *Coffee canephora* phenylalanine ammonia-lyase 2. Oct. 4, 2002, Campa et al, XP002442603 retrieved from EBI. Database accession No. AF460204.*
Marraccini et al, Molecular cloning of the complete 11S seed storage protein gene of *Coffee arabica* and promoter analysis in transgenic tobacco plants. 1999 Plant Physiol. Biochem. 37:273-282.*
Lesschaeve et al, Polyphenols: factors influencing their sensory properties and their effects on food and beverage preferences. 2005 Am. J. Clin. Nutr. 81(suppl):330S-5S.*
Ohl et al, Functional Properties of a Phenylalanin Ammonia-Lyase Promoter from *Ardibopsis*, 1990, Plant Cell 2:837-848.*
Bazzano, L. A. et al., "Fruit and Vegetable Intake and Risk of Cardiovascular Disease in US Adults: The First National Health and Nutrition Examination Survey Epidemiologic Follow-Up Study," *Am. J. of Clin. Nutr.*, vol. 76, pp. 93-99, 2002.
Bomati, E. et al., "Structural Elucidation of Chalcone Reductase and Implications for Deoxychalcone Biosynthesis." *J. Biol. Chem.*, vol. 280:30496-30503, 2005.
Bovy, A. et al. "High-Flavonol Tomatoes Resulting From the Heterologous Expression of the Maize Transcription Factor Genes LC and C1," *Plant Cell*, vol. 14, pp. 2509-2526, 2002.
Christensen, A. B. et al., "A Flavonoid 7-O-Methyltransferase Is Expressed in Barley Leaves in Response to Pathogen Attack," *Plant Mol. Biol.*, vol. 36:219-227, 1998.
Clifford M. N. "Diet-Derived Phenols in Plasma and tissues and Their Implications for health," *Planta Medica*, vol. 70, pp. 1103-1114, 2004.
Cos, P. et al., "Proanthocyandins in Health Care: Current and New Trends," *Curr. Med. Chem.*, vol. 11, pp. 1345-1359, 2003.
Daglia, M. et al. "In Vitro and Ex Vivo Antihydroxyl Radical Activity of Green and Roasted Coffee," *J. of Agric. Food Chem.* 52: 1700-1704, 2004.
Dixon, R. and Paiva, N. "Stress-induced Phenylpropanoid metabolism," *Plant Cell*, vol. 7, 1085-1097, 1995.
Dixon, R. and Steele, C. "Flavonoids and Isoflavonoids—A Gold Mine for Metabolic Engineering," *Trends Plant Sci.*, vol. 4: 394-400, 1999.
Dixon, R. A. "Engineering of Plant Natural Product Pathways," *Curr. Op. Plant Biol.*, vol. 8: 329-336, 2005.
Dixon, R. et. al. "Proanthocyanidins—A Final Frontier in Flavonoid Research?" *New Phytol.*, vol. 165:9-28, 2005.
Duarte, J. et al., "Protective Effects of the Flavonoid Quercetin in Chronic Nitric Oxide Deficient Rats," *J. Hypertension*, vol. 20:1843-1854, 2002.
Duthie, G. and Crozier, A. Plant-Derived Phenolic Antioxidants, *Curr. Op. Lipidol.*, vol. 11: 43-47, 2002.
Frankel, E. N. et al. "Inhibition of Oxidation of Human Low-Density Lipoprotein by Phenolic Substances in Red Wine," *Lancet*, vol. 341:454-457. 1993.
Frydman, A. et al. "Citrus Fruit Bitter Flavors: Isolation and Functional Characterization of the Gene Cm1,2rhat Encoding A 1,2 Rhamnosyltransferase, A Key Enzyme in the Biosynthesis of the Bitter Flavonoids of Citrus," *Plant J.*, vol. 40:88-100, 2004.

(Continued)

*Primary Examiner* — David T Fox
*Assistant Examiner* — Steven Bernacki
(74) *Attorney, Agent, or Firm* — Potter Anderson & Corroon LLP

(57) ABSTRACT

Polynucleotides encoding polypeptides that comprise the biosynthetic pathway for phenylpropanoids and flavonoids in the coffee plant are disclosed. Also disclosed are methods for using these polynucleotides and polypeptides for the manipulation of flavor, aroma, and other features of coffee beans, as well as the manipulation resistance to pathogen, herbivore, and insect attack in the coffee plant.

18 Claims, 41 Drawing Sheets

OTHER PUBLICATIONS

Garcia-Saura, M. F. et al. "Effects of Chronic Quercetin Treatment in Experimental Renovascular Hypertension," *Mol. Cell. Biochem.*, vol. 270: 147-155, 2005.

Go, M. et al. Chalcones: An Update on Cytotoxic and Chemoprotective Properties. *Curr. Med. Chem.*, vol. 12: 483-499, 2005.

Grassi, D. et al. "Short-Term Administration of Dark Chocolate Is Followed by a Significant Increase in Insulin Sensitivity and a Decrease in Blood Pressure in Healthy Persons," *Am. J. of Clin. Nutr.*, vol. 81: 611-614, 2005.

Gupta, S. et al. "Inhibition of Prostate Carcinogenesis in TRAMP Mice by Oral Infusion of Green Tea Polyphenols," *Proc. Natl. Acad. Sci. USA.*, vol. 98:10350-10355, 2001.

Hamberger, B. and Hahlbrock, K. "The 4-Coumarate : Coa Ligase Gene Family in *Arabidopsis thaliana* Comprises One Rare, Sinapate-Activating and Three Commonly Occurring Isoenzymes," *Proc. Natl. Acad. of Sci. U.S.A.* , vol. 101: 2209-2214, 2004.

Hertog, M. G. et al. "Dietary Antioxidant Flavonoids and Risk of Coronary Heart Disease: The Zutphen Elderly Study," *Lancet*, vol. 342:1007-1011, 1993.

Hertog, M. G. et al. Dietary Antioxidant Flavonoids and Cancer Risk in the Zutphen Elderly Study. *Nutr. Cancer*, vol. 22:175-184, 1994.

Hu. W. et al. "Compartmentalized Expression of Two Structurally and Functionally Distinct 4-Coumarate:Coa Ligase Genes in Aspen (*Populus tremuloides*),". *Proc. Natl. Acad. Sci. U.S.A.* vol. 95: 5407-5412, 1998.

Huang, M. T. et al. "Inhibitory Effects of Curcumin on in Vitro Lipoxygenase and Cyclooxygenase Activities in Mouse Epidermis," *Cancer Res.*, vol. 51:813-819, 1991.

Ishimi, Y. et al. "Selective Effects of Genistein, A Soybean Isoflavone, on B-Lymphopoiesis and Bone Loss Caused by Estrogen Deficiency," *Endocrinol.*, vol. 140: 1893-1900, 1999.

Jang, M. et al. "Cancer Chemopreventative Activity of Resveratrol, A Natural Product Derived From Grapes," *Science*, vol. 275: 218-220, 1997.

Johnson, E. T. et al. "Alteration of a Single Amino Acid Changes the Substrate Specificity of Dihydroflavonol 4-Reductase," *Plant J.*, vol. 25: 325-333, 2001.

Joung, J. Y. et al. "An Overexpression of Chalcone Reductase of *Pueraria montana* Var. *lobata* Alters Biosynthesis of Anthocyanin and 5'-Deoxyflavonoids in Transgenic Tobacco," *Biochem. Biophys. Res. Commun.*, vol. 303:326-331, 2003.

Kaltenbach, M. et al. "Flavonoid Hydroxylase From *Catharanthus roseus*: Cdna, Heterologous Expression, Enzyme Properties and Cell-Type Specific Expression in Plants," *Plant J.*, vol. 19:183-193, 1999.

Kobayashi, H. et al. "Flavonoids Induce Temporal Shifts in Gene-Expression of Nod-Box Controlled Loci in *Rhizobium* Sp. NGR234," *Mol. Microbiol.*, vol. 51: 335-347, 2004.

Kotkar, H. M. et al. "Antimicrobial and Pesticidal Activity of Partially Purified Flavonoids of *Annona squamosa*," *Pest Manag. Sci.*, vol. 58:33-37, 2002.

Lahtinen, M. et al. "Defensive Effect of Surface Flavonoid Aglycones of *Betula poubescens* Leaves Against First Instar *Epirrita autumnata* Larvae," *J. Chem. Ecol.*, vol. 30:2257-2268, 2004.

Lamartiniere, C. et al. "Genistein Chemoprevention: Timing and Mechanisms of Action in Murine Mammary and Prostate," *J. Nutr.*, vol. 132: 552S-558S, 2002.

Lattanzio, V. et al. "Role of Endogenous Flavonoids in Resistance Mechanism of Vigna to Aphids," *J. Agric. Food Chem.*, vol. 48:5316-20, 2000.

Lee, D. and Douglas, C. J. "Two Divergent Members of a Tobacco 4-Coumarate:Coenzyme A Ligase (4CL) Gene Family. Cdna Structure, Gene Inheritance and Expression, and Properties of Recombinant Proteins," *Plant Physiol.*, vol. 112:193-205, 1996.

Lesschaeve, I. and Noble, A. "Polyphenols: Factors Influencing Their Sensory Properties and Their Effects on Food and Beverage Preferences," *Am. J. Clin. Nutr.*, vol. 81(1 Suppl):300S-335S, 2005.

Lindermayr, C. "Divergent Members of a Soybean (*Glycine Max* L.) 4-Coumarate : Coenzyme A Ligase Gene Family—Primary Structures, Catalytic Properties, and Differential Expression," *Eur. J. Biochem.*, vol. 269: 1304-1315, 2002.

Marraccini, P. et al. "Molecular Cloning of the Complete 11S Seed Storage Protein Gene of *Coffea arabica* and Promoter Analysis in the Transgenic Tobacco Plants," *Plant Physiol. Biochem.*, vol. 37:273-282, 1999.

Marraccini, P. et al. "Rubisco Small Subunit of *Coffea arabica*: Cdna Sequence, Gene Cloning and Promoter Analysis in Transgenic Tobacco Plants," *Plant Physiol. Biochem.*, vol. 41:17-25, 2003.

Monagas, M. et al. "Updated Knowledge About the Presence of Phenolic Compounds in Wine," *Crit. Rev. Food Sci. Nutr.*, vol. 45:85-118, 2005.

Onyilagha, J. C. et al. "Effect of Flavonoids on Feeding Preference and Development of the Crucifer Pest *Mamestra configurata* Walker," *J. Chem. Ecol.*, vol. 30:109-124, 2004.

Peters, D. J. and Constabel, C. P. "Molecular Analysis of Herbivore-Induced Condensed Tannin Synthesis: Cloning and Expression of Dihydroflavonol Reductase From Trembling Aspen (*Populus tremuloides*)," *Plant J.*, vol. 32: 701-712, 2002.

Raes, J. et al. "Genome-Wide Characterization of the Lignification Toolbox in *Arabidopsis*," *Plant Physiol.*, vol. 133: 1051-1071, 2003.

Ralston, L. et al. "Subramanian S, Matsuno M, Yu O (2005) Partial Reconstruction of Flavonoid and Isoflavonoid Biosynthesis in Yeast Using Soybean Type I and Type II Chalcone Isomerases," *Plant Physiol.*, vol. 137: 1375-1388, 2005.

Ramirez-Coronel, M. et al. "Characterization and Estimation of Proanthocyanidins and Other Phenolics in Coffee Pulp (*Coffea arabica*) by Thiolysis-High Performance Liquid Chromatography," *J. Agric. Food Chem.*, vol. 52: 1344-1349, 2004.

Rice-Evans, C. "Flavonoid Antioxidants," *Curr. Med. Chem.*, vol. 8:797-807, 2001.

Rogers, J. et al. "Changes to the Content of Sugars, Sugar Alcohols, Myo-Inositol, Carboxylic Acids and Inorganic Anions in Developing Grains From Different Varieties of Robusta (*Coffea canephora*) and arabica (*C. arabica*) Coffees," *Plant Science*, vol. 149: 115-123, 1999.

Rohde, A, et al. "Molecular Phenotyping of the Pal1 and Pal2 Mutants of *Arabidopsis thaliana* Reveals Far-Reaching Consequences on and Carbohydrate Metabolism," *Plant Cell* vol. 16: 2749-2771, 2004.

Saito, K. et al, "Direct Evidence for Anthocyanidin Synthase as a 2-Oxoglutarate-Dependent Oxygenase: Molecular Cloning and Functional Expression of Cdna From a Red Forma of *Perilla frutescens*," *Plant J.*, vol. 17:181-189, 1999.

Schneider, K. et al. "The Substrate Specificity-Determining Amino Acid Code of 4-Coumarate : CoA Ligase," *Proc. Natl. Acad. Sci. U.S.A.*, vol. 100: 8601-8606, 2003.

Setchell, K. and Cassidy, A. "Dietary Isoflavones: Biological Effects and Relevance to Human Health," *J. Nutr.*, vol. 129: 758S-767S, 1999.

Shimada, N. et al. "A Cluster of Genes Encodes the Two Types of Chalcone Isomerase Involved in the Biosynthesis of General Flavonoids and Legume-Specific 5-Deoxy(Iso)Flavonoids in *Lotus japonicus*," *Plant Physiol.*, vol. 131: 941-951, 2003.

Sivakumaran, S. et al. "Variation in antimicrobial action of proanthocyanidins from *D. rectum* against rumen bacteria," *Phytochem.*, vol. 65: 2485-2497, 2004.

Sugihara, N. et al. "Anti- and Pro-Oxidative Effects of Flavonoids on Metal-Induced Lipid Hydroperoxide-Dependent Lipid Peroxidation in Cultured Hepatocytes Loaded With Alpha-Linoleic Acid. *Free Rad.,"Biol. Med.*, vol. 27: 1313-1323, 1999.

Tanaka, Y. et al. "Molecular and Biochemical Characterization of Three Anthocyanin Synthetic Enzymes From *Gentiana triflora*," *Plant Cell Physiol.*, vol. 37:711-716, 1996.

Tanner, G. J. et al. "Proanthocyanidin Biosynthesis in Plants. Purification of Legume Leucoanthocyanidin Reductase and Molecular Cloning of Its Cdna," *J. Biol. Chem.*, vol. 278: 31647-31656, 2003.

Wellmann, F. et al. "Significance of C-Terminal Sequence Elements for *Petunia* Flavanone 3 Beta-Hydroxylase Activity," *Febs Letters*, vol. 561: 149-154, 2004.

Winkel-Shirley, B. "Biosynthesis of Flavonoids and Effects of Stress," *Curr. Op. Plant Biol.* vol. 5: 218-223, 2002.

Wood, J. G, et al. "Sirtuin Activators Delay Aging by Mimicking Calorie Restriction in Yeast and Metazoans," *J. Nutr.*, vol. 134: 3518S-3519S, 2004.

Xie, D. Y. et al., "Molecular and Biochemical Analysis of Two Cdna Clones Encoding Dihydroflavonol-4-Reductase From *Medicago truncatula*," *Plant Physiol.*, vol. 134: 979-994, 2004.

Xie, D. Y. et al. "Role of Anthocyanidin Reductase, Encoded by BANYULS in Plant Flavonoid Biosynthesis," *Science*, vol. 299: 396-399, 2003.

Yamagishi, M. et al. "Effects of *cacao* Liquor Proanthocyanidins on Phip-Induced Mutagenesis in Vitro, and in Vivo Mammary and Pancreatic Tumorigenesis in Female Spraguedawley Rats," *Cancer Lett.*, vol. 185:123-130, 2002.

Yamane, T. et al. "Inhibitory Effects and Toxicity of Green Tea Polyphenols for Gastrointestinal Carcinogenesis," *Cancer*, vol. 77(8 Suppl):1662-1667, 1996.

Yan, L. J. et al. "*Ginko biloba* Extract (Egb 761) Protects Human Low Density Lipoproteins Against Oxidative Modification Mediated by Copper," *Biochem. Biophys. Res. Comm.*, vol. 212:360-366, 1995.

Yang, C. S. et al., "Tea and Tea Polyphenols Inhibit Cell Hyperproliferation, Lung Tumorigenesis, and Tumor Progression," *Exp. Lung Res.*, vol. 2:629-639, 1998.

Yen, W. J. et al. "Antioxidant Properties of Roasted Coffee Residues," *J. Agric. Food Chem.*, vol. 53: 2658-2663, 2005.

Yilmaz, Y. and Toledo, R. T. "Health Aspects of Functional Grape Seed Constituents," *Trends Food Sci. Technol.*, vol. 15: 422-433, 2004.

Yoshimoto, T. et al. "Flavonoids: Potent Inhibitors of Arachidonate 5-Lipoxygenase," *Biochem Biophys. Res. Comm.*, vol. 116:612-618, 1983.

Yu, O. et al. "Production of the Isoflavones Genistein and Diadzein in Non-Legume Dicot and Monocot Tissues," *Plant Physiology*, vol. 124: 781-794, 2000.

Database UniProt Phenylalanine ammonia-lyase 1 (EC 4.3.1.5) Mar. 1, 2003 XP002442590 retrieved from EBI. Database accession No. Q8H6WO.

Database EMBL *Coffea canephora* phenylalanine ammonia lyase 1. Oct. 4, 2002. Campa et al. XP00244602 retrieved from EBI. Database accession No. AF460203.

Database EMBL *Coffea canophera* phenylalanine ammonia lyase 2. Oct. 4, 2002, Campa et al., XP002442603 retrieved from EBI. Database accession No. AF460204.

Campa., C. et al., "Genetic mapping of caffeoyl-coenzyme A 3-0-methyltransferase Chlorogenic acid content." Theoretical and Applied Genetis, Springer, Berlin, DE. vol. N, (2003) vol. 107 No. 4, pp. 751-756.

Database UniProt Phenylalanine ammonia lyase *Catharanthus roseus* Oct. 1, 2000, Kiyota et al.: XP002442592 retrieved from EBI. Database accession No. Q9MAX1, abstract.

Database EMBL *Catharanthus roseus* phenylalanine ammonia lyase May 12, 2000, Kiyota et al., XP002442593 retrieved from EBI. Database accession No. AB042520, abstract.

Database UniProt Phenylalanine ammonia lyase Ipomea nil Jun. 1, 2001 m Bajazawa et al, XP002442594 retrieved from EBI. Database accession No. Q9AXI5, abstract.

Database EMBL Ipomea nif phenylalanine ammonia lyase Jan. 17, 2001, Nakazawa et al.: XP002442595 retrieved from EBI. Datebase accession No. AF325496, abstract.

Database UniProt Phenylalanine ammonia lyase—Tobacco May 1, 1992, XP002442596 retrieved from EBI. Database accession No. P25872, abstract.

Database EMBL *Nicotiana tabacum* phenylalanine ammonia lyase Sep. 21, 1993, Nagai et al.; XP002442597, Database accession No. D17467.

Ky, C.-L et al.: "Caffeine, trigonelline, Chlorogenic acids and sucrose diversity in wild *Coffea arabica* L., and *C. canephora* P. accesions," Food Chemistry, vol. 75, No. 2, No, (2001), pp. 223-230.

* cited by examiner

```
pcccp19k7    T T G G A A T G G T G C T C C G C T A C C G T T G T G T T A A A T G C C A C T C C A C G G   392
ccd25c13     T T G G A A T G G T G C T C C G C T A C C G T T G T G T T A A A T G C C A C T C C A C G G   801
Race1_CcPAL2                                                                                             406
GW1_CcPAL2                                                                                               2118 pcccp19k7    C A C G T T G A G C A G A T T T T T A G C T G T T G T A C T C G G T G A A G G C C G A C A G   437
ccd25c13     C A C G T T G A G C A G A T T T T T A G C T G T T G T A C T C G G T G A A G G C               840
Race1_CcPAL2                                                                                             406
GW1_CcPAL2                                                                                               2118 pcccp19k7    A A G A G C A G G C T T C C T T G A G G A A T A T T T T G T T T T A C T G T A G T A G C A   482
ccd25c13                                                                                                 840
Race1_CcPAL2                                                                                             406
GW1_CcPAL2                                                                                               2118 pcccp19k7    A A C T G T T T T T T C T C T A C T T T T T T T T T T T T T T T T T T T G G T G T T G T   527
ccd25c13                                                                                                 840
Race1_CcPAL2                                                                                             406
GW1_CcPAL2                                                                                               2118 pcccp19k7    T G T T G T C A A T T A T C A C G A T C T A C T C C T A C T T C C A T C T A T T A T T T T   572
ccd25c13                                                                                                 840
Race1_CcPAL2                                                                                             406
GW1_CcPAL2                                                                                               2118 pcccp19k7    T C T C T A T C T T T T T T G T C T C T C G T G A T T T A T G T A C A G A T A A A T T A T T   617
ccd25c13                                                                                                 840
Race1_CcPAL2                                                                                             406
GW1_CcPAL2                                                                                               2118 pcccp19k7    G T A A T T T G T T G G G A T T T C T C A A A T T T T G T G A G G A T T T G A A T G A A A   662
ccd25c13                                                                                                 840
Race1_CcPAL2                                                                                             406
GW1_CcPAL2                                                                                               2118 pcccp19k7    A A A A A A A A A A A                                                                         673
ccd25c13                                                                                                 840
Race1_CcPAL2                                                                                             406
GW1_CcPAL2                                                                                               2118
```

```
Cc4CL1       P G I S D A A V V S M K D E A A G E V P V A F V V R A S G S K I S E D E I K Q F I S N Q V  370
Cc4CL2 (pGC3) S D I S D A A V V P M K D D A A G E V P V A F V V K S K D S N I T E D E I K E Y I K K Q V  503
Ca4CL2 (pGC1) S D I S D A A V V P M K D D A A G E V P V A F V V K S K D S N I T E D E I K E Y I K K Q V  502
At4CL1       P Q I T D V A V V A M K E E A A G E V P V A F V V K S K D S E L S E D D V K Q F V S K Q V  525
At4CL2       P E I N D V A V V A M K E E D A G E V P V A F V V R S K D S N I S E D E I K Q F V S K Q V  516
At4CL3       H S I A D A A V V P Q N D E V A G E V P V A F V V R S N G N D I T E E D V K E Y V A K Q V  526
At4CL4       P S I D D A A V V A M K D E V A D E V P V A F V A R S Q G S Q L T E D D V K S Y V N K Q V  450
Nt4CL1       P N I S D A A V V P M K D E Q A G E V P V A F V V R S N G S A I T E D E V K D F I S K Q V  508
Nt4CL2       P N I S D A A V V P M K D E Q A G E V P V A F V V R S N G S T I T E D E V K D F I S K Q V  502

Cc4CL1       I F Y K R I H R V F P M Q K I P K A P S G K I L R K D L R A K L A A E V A C N                405
Cc4CL2 (pGC3) I F Y K R I N R V F F V D A I P K S P S G K I L R K D L R A R L A A G V P K                547
Ca4CL2 (pGC1) I F Y K R I N R V F F V D A I P K S P S G K I L R K D L R A R L A A G V P K                547
At4CL1       V F Y K R I N K V F F T E S I P K A P S G K I L R K D L R A K L A N G L                   561
At4CL2       V F Y K R I N K V F F T D S I P K A P S G K I L R K D L R A R L A N G L M N               555
At4CL3       V F Y K R L H K V P F V A S I P K S P S G K I L H K D L K A K L C                        561
At4CL4       V H Y K R I K M V F F I E V I P K A V S G K I L R K D L R A K L E T M C S K              485
Nt4CL1       I F Y K R V K R V F F V E T V P K S P S G K I L R K D L R A R L A A G V P N              547
Nt4CL2       I F Y K R I K R V F F V D A I P K S P S G K I L R K D L R A K L A A G L P N              542
```

| | | |
|---|---|---|
| CcCHI | M S L S L S V G E V H V D G H V F P P A A K K P P G S D Q N F F L G G A G A R G L E I E G | 45 |
| PhCHI | M S P S V S V T E M H V E N Y V F A P T V N P A G S S N T L F L A G A G H R G L E I Q G | 44 |
| LjCHI-2 | M A L P - S V T A L Q V E N V A F P P T L I K P P A S A N T L F L G G A G E R G L H I Q D | 44 |
| GmCHI-2 | M A F P - S V T S V T V E N V T F P P T - V K P P C S P N T F F L A G A G V R G L Q I H H | 43 |
| CcCHI | K F I K F T A I G V Y M E E T A I P S L A V K W K G K T A E E L T E S V E F F R D L V T G | 90 |
| PhCHI | K F V K F T A I G V Y L E E S A I P F L A E K W K G K T P E E L T D S V E F F R D V V T G | 89 |
| LjCHI-2 | K F V K F T A I G I Y L Q D T A V P S L A V K W K G K P V D E L T E S V Q F F R D I V T G | 89 |
| GmCHI-2 | A F V K F T A L C I Y L Q Y D A L S F L S V K W K T K S T H Q L T E S D Q F F S D I V T G | 88 |
| CcCHI | P F E K F I R V T M I L P L T G R Q Y S E K V A E N C S A Y W K A V G I Y T D A E G K A I | 135 |
| PhCHI | P F E K F T R V T M I L P L T G K Q Y S E K V A E N C V A H W K G I G T Y T D D E G R A I | 134 |
| LjCHI-2 | P F E K F M Q V T M I L P L T G Q Q Y S E K V S E N C V A I W K H L G I Y T D E E G K A I | 134 |
| GmCHI-2 | P F E K F M Q V T M I K P L T G Q Q Y S E K V A E N C V A L W R S L G I Y T D S E A E A I | 133 |
| CcCHI | E M F L D I F Q N E S F P P G A S I L F T Q S P L G S L T I S F S K D S S I P E V S N A V | 180 |
| PhCHI | E K F L D V F R S E T F P P G A S I M F T Q S P L G S L T I S F A K D D S L T G T A N A V | 179 |
| LjCHI-2 | D K F V S V F K D Q T F P P G S S I L F T V L P K G S L A I S F S K D G S I P E V E S A V | 179 |
| GmCHI-2 | D K F L S V F K D L T F P P G S S I L F T V S P N G S L T I S E S G D E T I P E V T S A V | 178 |
| CcCHI | V E N K L I S E A V L E S I G K N G V S P D T K K S L A I R L S E L L K V F D N N N N N | 225 |
| PhCHI | I E N K Q L S E A V L E S L I G K H G V S P A A K C S V A E R V A E L L K - - - - - - - - | 216 |
| LjCHI-2 | I D N K L L S E A V L E S M I G A H G V S P A A K Q S L A S R L S E L F K - - - - - - - - | 216 |
| GmCHI-2 | I E N K L L S E A V L E S M I G K N C V S P A A K Q S L A S R S S H L F K - - - - - - - - | 215 |
| CcCHI | V T A D N K K L E A D G A I A A E A P G E K Q V N G V Q V P V Q V P | 259 |
| PhCHI | - - - - - K S Y A E E A S V F G K P E T E K S T I - - - - P V I G V | 241 |
| LjCHI-2 | - - - - - H H A E V | 221 |
| GmCHI-2 | - - - - - E P G V C D P Q S H K | 226 |

Fig. 12a

```
CcCHI-like  M G T - E V V K V D E I P F P L Q V T P - S T T K P L S L L G H G I T D I E I H F L Q I K  43
GmCHI-4A    M A T - E E V L V D E I T Y P T K I T - - - T T K P L S L L G H G I T D M E I H F I H V K  41
GmCHI-1A    M A T I S A V Q V E F L E F P A V V T S P A S G K T Y F L G G A G E R G L T I E G K F I K  45

CcCHI-like  F T A I G V Y M D S E I V T Y L Q - Q W K G K K C T D L A E D D D F F E A L I S A P V D K  87
GmCHI-4A    F Y S I G V Y L E P E V V G H L D - Q F K G K S A K E L E D N E E F F N A L L S A P V E K  85
GmCHI-1A    F T G I G V Y L E D K A V P S L A A K W K G K T S E E L V H T L H F Y R D I I S G P F E K  90

CcCHI-like  F L R I V V I K E I K G S Q Y G V Q L E S A V R D R L A A D D R Y X D E E A A L E E L I  137
GmCHI-4A    F I R L V V I K E I K G A Q Y G V Q I E T A V R D R L A A E D K Y E E E E E A L E K V I  130
GmCHI-1A    L I R G S K I L P L A G A E Y S K K V M E N C V A H M K S V G T Y G D A E A A I E K F A  135

CcCHI-like  E F F Q P K Y F K K D S I L T Y Y F P A G S S A S A E I A F T T E G K E E S K I K V E N A  177
GmCHI-4A    E F F Q S K Y F K K L S V I T Y H F P A N - S A T A E I V V S L E G K E D S K Y V I E N A  174
GmCHI-1A    E A F K N V N F A P G A S V F Y R Q S P D G I L G L S F S E D A T I P E K E A A V I E N K  180

CcCHI-like  N V V E T I K K W Y L G G T R G V S Q T T I S S L A N T L A A E L S K E                    213
GmCHI-4A    N V V E A I K K W Y L G G S S A V S S T I Q S L A S T F S Q E L S K                       208
GmCHI-1A    A V S A A V L E T M I G - E H A V S P D L K R S L A S R L P A V L S I H G I I V          215
```

```
CcF3'5'H   A Q E E M D R V T G R N R R I V D X L E S D I P K L R Y L Q A I C K E A F W K H L S A P L   45
CrF3'5'H   A Q E E M D Q V I G R N R R - - - L M E S D I P K L P Y L Q A I C K E T F R K H P S T P L   42
GlF3'5'H   A Q D E M D R V I G R D R R - - - L L E S D I P N L P Y L Q A I C K E T F R K H P S T P L   42

CcF3'5'H   N L P R - I A S Q A C E V N G Y C I P K N T G L S V N I W A I G R D P D V W - E N P L D F   88
CrF3'5'H   N L P R - I A Q K D C Q V N G Y Y I P K G T R L S V N I W A I G R D P N V W - E N P L E F   85
GlF3'5'H   N L P R N C I R G H V D V N G Y Y I P K G T R L N V N I W A I G R D P S V W G D N P N E F   87

CcF3'5'H   H P D R F L S G K H A K L D P P P P V N D F E L F H S I W G L E E N L C W S Q K V G S A S   133
CrF3'5'H   N P D R F L S G K M A K I E P R G - - N D F E L I P - - F G A G R R I C A G T R M G I V L   120
GlF3'5'H   D P E R P L Y G R N A K I D P R G - - N H F E L L P - - F G A G R R I C A G T R M G I L L   121

CcF3'5'H   V E Y V L G T L V H S F D W K L P - A E V I E L N M E E S F G L A - - - - V P L K A K V S   177
CrF3'5'H   V E Y I L G T L V H S F D W K L P F D D I N E L N M D E S F G L A L Q K A V P L V A M V S   177
GlF3'5'H   V E Y I L G T L V H S F D W K L G F S E - D E L N M D E T F G L A L Q K A V P L A A M V I   172

CcF3'5'H   P R L A L N S Y S A                                                                         185
CrF3'5'H   P R L P I N A Y S P                                                                         185
GlF3'5'H   P R L P L H V L Y A P                                                                       182
```

Fig. 13b

```
CcDFR    MEGDIATSAAAKGTVCVTGAAGFIGSWLVMRLLERGYVVRATVRD  45
MtDFR1   M.G.....S..MAETVCVTGASGFIGSWLVMRLMERGYMVRATVRD  38
MtDFR2   M.G.....S..VSETVCVTGASGFIGSWLVMRLMERGYTVRATVRD  38

CcDFR    PGNMKKVKHLLDLPKASTHLTLWKADMTEEGSFDEATQGCEGVFH  90
MtDFR1   PENLKKVSHLLELPGAKGKLSLWKADLGEEGSFDEAIKGCTGVFH  83
MtDFR2   PDNMKKVKHLLELPGANSKLSLWKADLGEEGSFDEAIKGCTGVFH  83

CcDFR    VATPMDFDSKDPENEIIKPTINGALNIIRSCVKAKTVKRLVYTSS  135
MtDFR1   VATPMDFESKDPENEMIKPTIKGVLDIMKACLKAKTVRRFIFTSS  128
MtDFR2   VATPMDFESKDPEKEVINPTINGLLDIMKACKKAKTVRRLVFTSS  128

CcDFR    AGTVNVQEHQQPVYDETNWSDLDFIYSTKMTGWMYFVSKLLAEKE  180
MtDFR1   AGILNVTEDQKPLWDESCWSDVEFCRRVKMTGWMYFVSKTLAEQE  173
MtDFR2   AGILDVTEQQNSVIDETCWSDVEFCRRVKMTGWMYEVSKTLAEQE  173

CcDFR    AWEVSKQSNIDEISLIPTLVVGPFIMPTFPPSLITALSLITGNEA  225
MtDFR1   AWKFAKEHNMDFITIIPPLVVGPFLIPTMPPSLITALSPITGNEA  218
MtDFR2   AWKFSKEHNIDFVSIIPPLVVGPFIMPSMPPSLITALSLITGYEA  218

CcDFR    HYSIIRQGQFVHVDDLCEAHIFLYEDPTAEGRYICSSHDATIHDL  270
MtDFR1   HYSILKQGQFVHLDDLCEAHIFLFEHMEVEGRYLCSACEANIHDI  263
MtDFR2   HYSIIKQGQYIHLDDLCLAHIFLFENPKAHGRYICCSHEATIHEV  263

CcDFR    AKLIAEKWPEYSIPELKGVDKDIPVVSFSSKKLVGKGFQYKYTL   314
MtDFR1   AKLINTKYPEYNIPTKFNNIPDELELVRFSSKKIKDLGFEFKYSL  308
MtDFR2   AKLINKKYPEFNVPTKEKDIPDDLEIIKESSKKILTDLGFIFKYSL 308

CcDFR    EDMFRAAIDTCREKGLLPYSTQTHENGKEKEPLPVANKDQASGQV  359
MtDFR1   EDMYTEAIDTCIEKGLLPKFVKS----TNK                334
MtDFR2   EDMFTGAIETCREKGLLPKVTETPVNDTMKK               339

CcDFR    NAPLPDSAEK  369
MtDFR1              334
MtDFR2              339
```

```
CcANR   - - - M A A Q A I E L K K A C V I G G S G F L A S F L V K L L L Q K G Y A V N T T V R D P  42
MtANR   M A S I K Q I E I E K K K A C V I G G T G F V A S L L I K Q L L E K G Y A V N T T V R D L  45
AtANR   - M D Q T L T H T G S K K A C V L G G T G N L A S I L I K H L L Q S G Y K V N T T V R D P  44
CsLAR   - - - M E A Q P T A P K A A C V V G G T G F V A A T L I K L L L E K G Y A V N T T V R D P  42

CcANR   G N Q K K I T H L L A L Q S L G D L K V F K A D L T D E A S F D A P V A G C D L V F H V A  87
MtANR   D S A N K T S H L I A L Q S L G E L N L F K A E L T I E E D F D A P I S G C E L V F Q L A  90
AtANR   E N E K K I A H L R Q L Q E L G D L K I F K A D L T D E D S F E S S F S G C E Y I F H V A  89
CsLAR   G N Q K K T S H L L A L K G S G N L K I F R A D L T D E Q S E D T P V A G C D L V F H V A  87

CcANR   A P V N F A S E D P E N D M I K P A I Q G V V N V L K A C V K A G S V K R V I F T S S A A  132
MtANR   T P V N F A S Q D P E N D M I K P A I K G V L N V L K A C V R A K E V K R V I L T S S A A  135
AtANR   T P I N F K S E D P E K D M I K P A I Q G V I N V L K S C L K S K S V K R V I Y T S S A A  134
CsLAR   T P V N F A S E D P E N D M L K P A L Q G V V N V L K A C A K A G T V K R V I L T S S A A  132

CcANR   A V T I N E I K G T G L L M D E G N W T D V E F L S S A K P P T W G Y P V S K T L A E K E  177
MtANR   A V T I N E L E G T G H V M D E T N W S D V E F L N T A K P P T W G Y P V S K V L A E K A  180
AtANR   A V S I N N L S G T G L V M N E E N W T D I D F L T E E K P F N W G Y P I S K V L A E K K  179
CsLAR   A V S I N K L N G T G L V M D E S H W T D T E F L N S A K P P T W G Y P L S K T L A E K A  177

CcANR   A W K F A E E K K I D L I T V I P S L L A G P P L T P D V P S S V N L A M S L I T G N E F  222
MtANR   A W K F A E E N N I D L I T V I P T L L I G P S L T Q D I P S S V A M G M S L L T G N D F  225
AtANR   A W E F A E E N K I N L V T V I P A L A G N S L L S D P S S L S L S M S F I T G K E M      224
CsLAR   A W K F A E E N N I N L I T V I P T L M A G P S L T A D V R S I G L A M S L I T G N E F  222

CcANR   L I N G L K G M Q M L A G S I S I T H V E D V C E A H I F L A E K K S A S G R Y I C C A A  267
MtANR   L I N A L K G M Q F L S G S I S I T H V E D I C R A H I F V A E K E S T S G R Y I C C A H  270
AtANR   H V T G L K E M Q K L S G S I S F V H V D D L A R A H L F L A E K E I T A S G R Y I C C A Y  269
CsLAR   L I N G L K G M Q M L G G S I S L S H V E D V C R A H V F V A E K E A S G R Y I C C A V  267

CcANR   N T S V P D L A N F L S K R Y P D Y K I P T E F E G F P S K A K L I I S S E K L I K E G F  312
MtANR   N T S V P E L A K F L S K R Y P Q Y K V P T E F D D F P S K A K L I S S G K L I K E G F  315
AtANR   H T S V P E I A D F L I Q R Y P K Y N V L S E F E G L S I P K L T L S S Q K L I N E G F  314
CsLAR   S T S V P E L A K E L N K R Y P E Y N V P T D F G D F P S K A K L I L S S E K L T K E G F  312

CcANR   N F K H G I E D I Y Q D A L A Y F K A K G L L Q H                                          337
MtANR   S F K H S I A E T F D Q T V E Y L K T Q G I K                                              338
AtANR   R F E Y G I N E M Y D Q M I E Y F E S K G L I K A K E S                                    342
CsLAR   S F K Y G I E E I Y Q S V E Y F K A K G I L K N                                            337
```

Fig. 15c

POLYNUCLEOTIDES ENCODING PHENYLPROPANOID AND FLAVONOID BIOSYNTHETIC PATHWAY ENZYMES IN COFFEE

This is a U.S. National Phase of International Application No. PCT/US2006/040686, filed Oct. 13, 2006, which claims benefit of U.S. Provisional Application No. 60/726,298, filed Oct. 13, 2005, the entire contents of each of which are incorporated by reference herein.

FIELD OF THE INVENTION

The present invention relates to the field of agricultural biotechnology. In particular, the invention features polynucleotides from coffee plants that encode enzymes responsible for flavonoid synthesis, as well as methods for using these polynucleotides and polypeptides for gene regulation and manipulation of flavor, aroma and other features of coffee beans.

BACKGROUND OF THE INVENTION

Various publications, including patents, published applications and scholarly articles, are cited throughout the specification. Each of these publications is incorporated by reference herein, in its entirety. Citations not fully set forth within the specification may be found at the end of the specification.

Coffee aroma and flavor are key components in consumer preference for coffee varieties and brands. The characteristic aroma and flavor of coffee stems from a complex series of chemical reactions involving flavor precursors (Maillard reactions) that occur during the roasting of the bean. Flavor precursors include chemical compounds and biomolecules present in the green coffee bean. To date, over 800 chemicals and biomolecules have been identified as contributing to coffee flavor and aroma. (Flament, I., 2002 "Coffee Flavor Chemistry" J. Wiley U.K.). Because coffee consumers are becoming increasingly sophisticated, it is desirable to produce coffee with improved aroma and flavor in order to meet consumer preferences. Both aroma and flavor may be artificially imparted into coffee products through chemical means. See, for example, U.S. Pat. No. 4,072,761 (aroma) and U.S. Pat. No. 3,962,321 (flavor). However, to date, there is little information concerning the influence of natural coffee grain components such as polysaccharides, proteins, pigments, and lipids, on coffee aroma and flavor. One approach is to select varieties from the existing germplasm that have superior flavor characteristics. A disadvantage to this approach is that, frequently, the highest quality varieties also possess significant negative agronomics traits, such as poor yield and low resistance to diseases and environmental stresses. It is also possible to select new varieties from breeding trials in which varieties with different industrial and agronomic traits are crossed and their progeny are screened for both high quality and good agronomic performance. However, this latter approach is very time consuming, with one crossing experiment and selection over three growing seasons taking a minimum of 7-8 years. Thus, an alternative approach to enhancing coffee quality would be to use techniques of molecular biology to enhance those elements responsible for the flavor and aroma that are naturally found in the coffee bean, or to add aroma and flavor-enhancing elements that do not naturally occur in coffee beans. Genetic engineering is particularly suited to achieve these ends. For example, coffee proteins from different coffee species may be swapped. In the alternative, the expression of genes encoding naturally occurring coffee proteins that positively contribute to coffee flavor may be enhanced. Conversely, the expression of genes encoding naturally occurring coffee proteins that negatively contribute to coffee flavor may be suppressed.

Coffees from different varieties and origins exhibit significant flavor and aroma quality variations when the green grain samples are roasted and processed in the same manner. The quality differences are a manifestation of chemical and physical variations within the grain samples that result mainly from differences in growing and processing conditions, and also from differences in the genetic background of both the maternal plant and the grain. At the level of chemical composition, at least part of the flavor quality can be associated with variations in the levels of small metabolites, such as sugars, acids, phenolics, and caffeine found associated with grain from different varieties. It is accepted that there are other less well characterized flavor and flavor-precursor molecules. In addition, it is likely that structural variations within the grain also contribute to differences in coffee quality. One approach to finding new components in the coffee grain linked to coffee quality is to study the genes and proteins differentially expressed during the maturation of grain samples in different varieties that possess different quality characteristics. Similarly, genes and proteins that participate in the biosynthesis of flavor and flavor-precursor molecules may be studied.

The flavonoids form a large group of ubiquitous plant secondary metabolites, with over 4000 molecules of this class identified to date (Bovy et al. (2002) and Yilmaz et al. (2004)). Flavonoids are derived from the condensation of p-coumaroyl-CoA, which is synthesized from phenylalanine via the early phenylpropanoid pathway, and three molecules of malonyl-CoA, which is generated by the TCA cycle. (Dixon et al. (1999); Winkel-Shirley (2002); and Dixon (2005)). The various flavonoid metabolites contribute in different ways to the normal functioning and survival of the plant. For example, the red, blue and purple anthocyanin pigments found in flowers participate in plant reproduction by their involvement in attracting insects for pollination. (Winkel-Shirley (2002)). Other flavonoids, the brown proanthocyanidin pigments (also termed condensed tannins), are believed to have antimicrobial properties and thus have been proposed to contribute to microbial resistance. (Sivakumaran et al. (2004); and Cos et al. (2005)). Yet another group of flavonoids, the isoflavones which are synthesised primarily in leguminous plants, are involved in plant-microbe interactions. (Dixon (2005)). For example, isoflavones are continuously excreted from the roots of legumes and molecules such as daidzein have been shown to induce nodulation related genes in the nodulating *Rhizobium* bacteria (Kobayashi et al. (2004)).

In recent years, an increasing number of studies have focused on the relationship between plant-derived foods containing flavonoids and human health. Both academic and applied interest in this area is stimulated by the fact that some widely consumed plant foods are relatively rich in flavonoid/phenolic compounds and by the fact that people who consume higher quantities of these foods appear to have lower risks for certain significant heath problems, such as cardiovascular disease and cancer. (Bazzano et al. (2002); Clifford (2004); Cos et al. (2005); and Go et al. (2005)). The importance of flavonoids to human and animal health is supported by detailed experimental data, which indicate that flavonoids can have specific functional interactions within mammalian cells. For example, the antioxidant properties of flavonols, such as kaempferol and quercetin, have been broadly shown to give some protection against oxidative stress. (Sugihara et al. (1999); and Duthie et al. (2000)). Daily oral administration of the flavonoid quercetin has been shown to exhibit both antihypertensive and antioxidative effects in hypertensive rats. (Garcia-Saura et al. (2005)).

The flavonoids present in dark chocolate are currently being intensively studied, and a recent study showed that consumption of dark chocolate rich in flavonoids may lower blood pressure, presumably through the ability of one or more of the flavonoids to increase nitric oxide bioavailability. (Grassi et al. (2005)). Resvertrol is another flavonoid related molecule that is currently of interest. This phytoalexin is found in grapes and other foods, and has been found to be active as a cancer chemoprevention agent, (Jang et al. (1997)), and to have the potential to delay aging via its ability to activate Sir-2 like proteins (Sirtuins). (Wood et al. (2004)). Higher dietary intake of other flavonoids, like the isoflavonoids found in soy, has also been associated with reduced levels of cancer, (Setchell et al. (1999)), and dietary intake of the isoflavone genistein has been shown to reduce the susceptibility of rats to mammary cancer, (Lamartiniere et al. (2002), and helps prevent bone loss caused by estrogen deficiency in female mice. (Ishimi et al. (1999)).

The early steps of the plant phenylpropanoid pathway leading to the key flavonoid precursors p-coumaryl-CoA have been described in several plants (FIG. 1A; Dixon et al. (1995); and Winkel-Shirley (2002). The first step in the phenylpropanoid pathway is the deamination of phenylalanine to cinnamic acid by L-phenylalanine ammonia lyase (PAL). Four different PAL genes have been characterized in *Arabidopsis* and these appear to fall into two different groups. (Raes et al. (2003)). As expected for a major branch-point between the plant primary and secondary metabolic pathways, the expression and activities of the different PAL isoforms are under complex regulatory control. (Dixon et al. (1995); and Rohde et al. (2004)). The next enzyme in the pathway is the protein trans cinnamate-4-hydroxylase (C4H; CYP73A5). Only one gene has been found for this P450-dependent mono-oxygenase in *arabidopsis*, while in some other plants, two or more C4H genes can been found that fall into two distinct classes. (Raes et al. (2003)). The next step, the production of p-coumaryl-CoA, is carried out by 4-coumarate:CoA ligase (4CL). In the *arabidopsis* genome, there are at least four 4CL genes and nine 4CL-like genes. (Raes et al. (2003)). In addition to forming p-coumaryl CoA, the 4CL proteins characterized from *arabidopsis*, as well as the characterized 4CL proteins from soybean we found to be capable of forming CoA esters with caffeic acid and ferulic acid at different efficiencies, and the At4CL4 protein of *arabidopsis* and the Gm4CL1 protein of soybean were also found to be capable of forming CoA esters with 5-hydroxyferulic acid and sinapic acid. (Hu et al. (1998); Lindermayr et al. (2002); Schneider et al. (2003); and Hamberger et al. (2004)).

A number of recent reviews on the core flavonoid synthesis pathway have been published (Winkel-Shirley (2002) and Dixon (2005), and the current understanding of this pathway is outlined schematically in FIG. 1B. (Winkel-Shirley (2002), and Xie et al. (2004)). The first step of this pathway, which is catalyzed by chalcone synthase (CHS), is the condensation of p-coumaryl CoA with three molecules of malonyl CoA to form tetrahydroxychalcone (naringenin chalcone). In some plants, particularly the leguminous plants, the enzyme chalcone reductase (CHR) can also be present (FIG. 1B). This enzyme is thought to act on an intermediate of the CHS multistep reaction, and the CHS/CHR coupled reaction is proposed to yield chalcone (4,2',4',6'-tetrahydroxychalcone) and deoxychalcone (4,2',4'-trihydroxychalcone). (Bomati et al. (2005)). These CHS/CHR products are then precursors for a group of phytoalexins that are often produced in response to herbivore and pathogen attacks, and for the synthesis of CHR derived products that are involved in symbiotic root nodulation by nitrogen fixing *Rhizobium* bacteria. (Dixon et al. (1999)).

In the core flavonoid pathway, the product of CHS (naringenin chalcone) is transformed into (2S)-5,7,4'-trihydroxyflavanone (naringenin) by chalcone isomerase (CHI). Two types of CHI have been found, with type I being ubiquitous in the plant kingdom, while the type II CHI, which has a broader substrate range, appears to be most frequently found in leguminous plants. (Ralston et al. (2005)). The next reaction in the pathway is the addition of a hydroxyl group at the C3 position of the C ring to form 2,3-dihydrokaempferol (DHK) and is catalyzed by F3betaH, a 2-oxoglutarate dependent dioxygenase. (Dixon et al. (1999); Wellman et al. (2004); and Dixon (2005)). As indicated in FIG. 1B, DHK can be further hydroxylated at the 3' and 5' positions of the B ring by the P450 dependent enzymes F3'H and F3'5'H forming 2,3-dihydroquercetin (DHQ) and 2,3dihydromyricetin (DHM) respectively. Dihydroflavonol-4-reductase (DFR) catalyses the next reaction, the addition of a hydroxyl group at the 4 position of ring C of DHK, DHQ, and DHM (synthesized by the F3H family of enzymes) to yield leucopelargonidin, leucocyanidin or leucodelephinidin respectively. However, some plant DFR proteins do not accept the monohydroxylated DHK and thus these plants may not be able to make the associated downstream products. (Johnson et al. (2001)). Only one DFR gene has been found in plants such as *Arabidopsis* and tomato, and interestingly, in plants with several DFR genes, it appears that only one of these genes produces an active protein. (Xie et al. (2004)). The products of DFR are key precursors for the synthesis of the anthocyanins and condensed tannins and it has been noted that herbivore attack induces DFR expression in plants. Furthermore, this induction is associated with an increase in the synthesis of condensed tannins, a group of molecules that have been implicated in protecting plants from herbivores. (Peters et al. (2002)). Immediately downstream of DFR, the enzyme anthocyanidin synthase (ANS; leucoanthocyanidin dioxygenase) is capable of forming anthocyanidins from the different DFR products (i.e., from the leucoanthocyanins), and these ANS products can be subsequently glycosylated to form the anthocyanins. In addition, leucoanthocyanidin reductase (LAR) can also convert the leucoanthocyanidins to form 2,3-trans-flavan-3-ols (catechins). The related 2,3-cis-flavan-3-ols (epicatechins) are formed via the action of ANS and anthocyanidin reductase (ANR) which uses NADPH to reduce anthocyanidins. (Xiet et al. (2003)). Finally, there is little currently known about the last step(s) involved in the formation of condensed tannins from trans- and cis-flavan-3-ol monomers.

It is well known that flavonoids, and related glycosylated derivatives, make significant flavor contributions to beverages produced from plant ingredients. For example, grapefruit citrus are known to have a bitter flavor, which is in part due to the presence of a flavanone (flavanone-7-neohesperidosides), while oranges, in contrast, are generally less bitter, having only tasteless flavanone-7-rutinosides. (Frydman A et al. (2004). Likewise, it is well known that the flavonoids and related molecules in grapes contribute significantly to the astringency and bitterness characteristics of different wines (Monagas M et al. (2005)). Finally, fruit juices and other beverages such as tea contain anthocyanidins at levels that contribute significantly to the flavor and astringency of these beverages. (Dixon R et al. (2005b); and, Lesschaeve I et al. (2005)). The anthocyanidins are monomers, oligomers and polymers of molecules produced by the flavonoid pathway.

Considering the observations above, it can thus be expected that by altering the levels, and/or the molecular profiles of the precursors, or by altering the polymerization levels and profiles of the final products in the starting plant material, it could be possible to alter the flavor and astringency profiles of beverages made from these raw materials.

There is currently little information published on the presence of flavonoids in the green or roasted coffee grain and whether these molecules or derivatives thereof contribute to the flavor of coffee. However, there is one recent report that suggests that flavonoids are present in roasted coffee. (Yen et al. (2005)). It is noted, however, that the method used by these investigators to determine flavonoid content is a generalized total flavonoid method and thus could provide an artificially inflated measurement of this broad class of molecules in roasted coffee. Accordingly, more detailed work is required to examine the flavonoids present in both the coffee grain and in the roasted product. One study has recently been carried out that begins to address the flavonoids present in the fruit part of the coffee cherry (pericarp). It has been found that ripe coffee *arabica* cherry fruit contains three major classes of flavonoids: the flavan-3-ols (monomers and procyanidins), flavonols, and anthocyanidins. (Ramirez-Coronel et al. (2004)). Given the known roles these compounds play in other plants, it can be presumed that the coffee flavonoids are also involved in protecting the fruit tissues from UV and oxidation related stresses, and in protecting the cherries from microbial and insect attack. Because of the health benefits of flavonoids in the human diet, and because these molecules also have agronomic benefits (herbivore/pathogen and stress resistance), it is of interest to examine the flavonoid pathway in coffee.

From the foregoing discussion, it will be appreciated that modulating flavonoid content in coffee grain by genetically modulating the production of the proteins responsible for early phenylpropanoid and flavonoid biosynthesis would be of great utility to enhance the aroma and flavor of coffee beverages and coffee products produced from such genetically engineered coffee beans. Enhanced flavonoid content and/or altered flavonoid profile in the coffee bean may also positively contribute to the overall health and wellness of consumers of coffee beverages and products produced from such coffee beans. In addition, modulating flavonoid content in the coffee plant has implications for protecting the coffee fruit from ultraviolet, oxidative, microbial, or insect stress or damage. Accordingly, a need exists to identify, isolate and utilize genes and enzymes from coffee that are involved in the biosynthesis of early phenylpropanoids and flavonoids.

SUMMARY OF THE INVENTION

The invention described herein features genes encoding enzymes in the pathways that lead to flavonoid biosynthesis in coffee plants, their encoded polypeptides, and methods for using these polynucleotides and polypeptides for gene regulation and manipulation of flavor, aroma and other features of coffee beans.

One aspect of the invention features a nucleic acid molecule isolated from coffee (*Coffea* spp.), having a coding sequence that encodes a flavonoid pathway enzyme. In one embodiment, the enzyme is a phenylalanine ammonia lyase that is at least 85.2% identical to SEQ ID NO:20. In another embodiment, the enzyme is a phenylalanine ammonia lyase that is at least 83.9% identical to SEQ ID NO:21. In another embodiment, the enzyme is a phenylalanine ammonia lyase that is at least 82.6% identical to SEQ ID NO:22. In another embodiment, the enzyme is a trans cinnamate-4-hydroxylase that is at least 89.9% identical to SEQ ID NO:23. In another embodiment, the enzyme is a 4-coumarate:CoA ligase that is at least 81.1% identical to SEQ ID NO:24. In another embodiment, the enzyme is a 4-coumarate:CoA ligase that is at least 81.9% identical to SEQ ID NO:25. In another embodiment, the enzyme is a 4-coumarate:CoA ligase that is at least 81% identical to SEQ ID NO:26. In another embodiment, the enzyme is a chalcone synthase that is at least 90.5% identical to SEQ ID NO:27. In another embodiment, the enzyme is a chalcone reductase that is at least 60.7% identical to SEQ ID NO:28. In another embodiment, the enzyme is a chalcone reductase that is at least 61.6% identical to SEQ ID NO:29. In another embodiment, the enzyme is a chalcone reductase that is at least 61.3% identical to SEQ ID NO:30. In another embodiment, the enzyme is a chalcone isomerase that is at least 63.4% identical to SEQ ID NO:31. In another embodiment, the enzyme is a chalcone isomerase that is at least 64.3% identical to SEQ ID NO:32. In another embodiment, the enzyme is a flavanone 3-hydroxylase that is at least 82.4% identical to SEQ ID NO:33. In another embodiment, the enzyme is a flavonoid 3',5'-hydroxylase that is at least 67.8% identical to SEQ ID NO:34. In another embodiment, the enzyme is a dihydroflavonol-4-reductase that is at least 67.6% identical to SEQ ID NO:35. In another embodiment, the enzyme is a leucoanthocyanidin dioxygenase that is at least 73.1% identical to SEQ ID NO:36. In another embodiment, the enzyme is a leucoanthocyanidin reductase that is at least 59.9% identical to SEQ ID NO:37. In another embodiment, the enzyme is an anthocyanidin reductase that is at least 77.4% identical to SEQ ID NO:38.

In certain embodiments, the nucleic acid molecule is a gene having an open reading frame that comprises the coding sequence. Alternatively, it may comprise an mRNA molecule produced by transcription of that gene, or a cDNA molecule produced by reverse transcription of the mRNA molecule. The invention also features an oligonucleotide between 8 and 100 bases in length, which is complementary to a segment of the aforementioned nucleic acid molecule.

Another aspect of the invention features a vector comprising the above-described flavonoid pathway enzyme-encoding nucleic acid molecules. In certain embodiments, the vector is an expression vector selected from the group of vectors consisting of plasmid, phagemid, cosmid, baculovirus, bacmid, bacterial, yeast and viral vectors. In certain embodiments, the vector contains the coding sequence of the nucleic acid molecule operably linked to a constitutive promoter. In other embodiments, the coding sequence is operably linked to an inducible promoter. In other embodiments, the coding sequence of the nucleic acid molecule is operably linked to a tissue specific promoter, such as a seed specific promoter, preferably a coffee seed specific promoter.

According to another aspect of the invention, a host cell transformed with the aforementioned vector is provided. The host cell may be a plant, bacterial, fungal, insect or mammalian cell. In certain embodiments, the host cell is a plant cell selected from any one of coffee, tobacco, *Arabidopsis*, maize, wheat, rice, soybean barley, rye, oats, sorghum, alfalfa, clover, canola, safflower, sunflower, peanut, cacao, tomato tomatillo, potato, pepper, eggplant, sugar beet, carrot, cucumber, lettuce, pea, aster, begonia, chrysanthemum, delphinium, zinnia, and turfgrasses. The invention also features a fertile transgenic plant produced by regenerating the transformed plant cell. In a specific embodiment, the fertile transgenic plant is a *Coffea* species.

Another aspect of the invention features a method to modulate flavor or aroma of coffee beans. The method comprises modulating production of one or more flavonoid pathway enzymes within coffee seeds. In some embodiments, the method comprises increasing production of the one or more flavonoid pathway enzymes, e.g., by increasing expression of one or more endogenous flavonoid pathway enzyme-encoding genes within the coffee seeds, or by introducing a flavonoid pathway enzyme-encoding transgene into the plant. In other embodiments, the method comprises decreasing production of the one or more flavonoid pathway enzymes, e.g., by introducing a nucleic acid molecule into the coffee that inhibits the expression of one or more of the flavonoid pathway enzyme-encoding genes.

Other features and advantages of the invention will be understood by reference to the drawings, detailed description and examples that follow.

BRIEF DESCRIPTION OF THE DRAWINGS

FIG. 5. Protein sequence alignment of new PAL sequences with PAL sequences in the public database. A) Alignment of the protein sequences CaPAL1 (pML8), CcPAL2 (in-silico assembly, partial) and CaPAL3 (pML14) (SEQ ID NOs.: 20, 21) with other *Coffea* PAL sequences. The alignment was performed using ClustalW method in the MegAlign software. Amino acids marked in grey are generally conserved in the majority of the sequences at this position. GenBank Accession Numbers are given in parentheses. CcPAL1 AAN32866 (*Coffea canephora*, AAN32866, full protein) (SEQ ID NO: 48), CcPAL2 AAN32867 CcPAL2 (*Coffea canephora*, AAN32867, full protein) (SEQ ID NO: 49). B) Protein sequence alignment of CaPAL1 (pML8) (SEQ ID NO: 20), CcPAL2 (in-silico assembly, partial) (SEQ ID NO: 22) and CaPAL3 (pML14) (SEQ ID NO: 21) with other PAL protein sequences. The alignment was done with CLUSTAL-W. Amino acids marked in grey are generally conserved in the majority of the sequences at this position. GenBank Accession Numbers are given in parentheses. ZmPAL1 (*Zea mays*, AAL40137) (SEQ ID NO: 50), AtPAL1 (*Arabidopsis thaliana*, AAP59438, Cochrane et al., 2004) (SEQ ID NO: 51), AtPAL2 (*Arabidopsis thaliana*, AAP59439, Cochrane et al., 2004) (SEQ ID NO: 52), AtPAL4 (*Arabidopsis thaliana*, AAP59440, Cochrane et al., 2004) (SEQ ID NO: 53), PcPAL1 (*Petroselinum crispum*, Parsley, CAA68938) (SEQ ID NO: 54), PcPAL2 (*Petroselinum crispum*, Parsley, CAA57056) (SEQ ID NO: 55) and PcPAL3 (*Petroselinum crispum*, Parsley, CAA57057) (SEQ ID NO: 56).

FIG. 6. Protein sequence alignment of CcC4H with plant C4H protein sequences. The alignment of protein sequence (SEQ ID NO: 23) encoded by CcC4H (SEQ ID NO: 4) with other C4H proteins available in the NCBI database was done using CLUSTAL W. Amino acids marked in grey are generally conserved in the majority of the sequences at this position. GenBank Accession Numbers are given in parentheses. AtC4H (*Arabidopsis thaliana*, BAA24355) (SEQ ID NO: 57), MsC4H (*Medicago sativa*, P37114) (SEQ ID NO: 158), PbC4H (*Populus balsamifera*, AAG50231) (SEQ ID NO: 58).

Figure 1A:
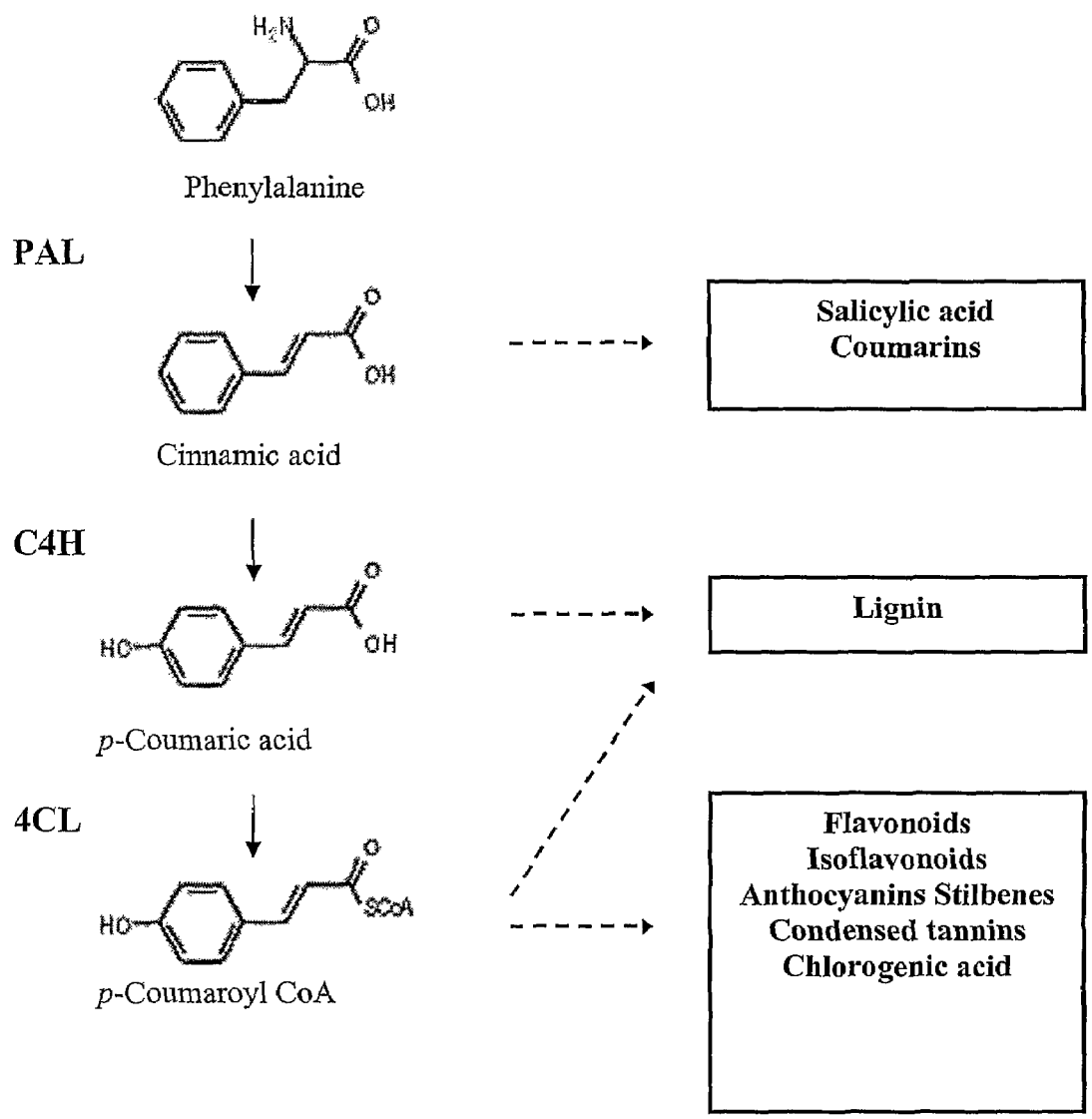
FIG. 1. Schematic overview of early phenylpropanoid and the flavonoid pathways. A) General phenylpropanoid metabolism. The early part of this pathway is dependent on the activity of the three enzymes noted. PAL, phenylalanine lyase; C4H, cinnamate-4-hydroxylase; and 4CL, 4-coumarate:coenzyme A ligase. B) Plant flavonoid pathway (modified from Xie et al. (2004) CHS, chalcone synthase; CHI, chalcone isomerase; F3H, flavanone 3-hydroxylase; F3'H, flavonoid 3'-hydroxylase; F3',5'H, flavonoid 3',5'-hydroxylase; DFR, dihydroflavonol-4-reductase; ANS, anthocyanidin synthase (also known as LDOX for leucoanthocyanidin dioxygenase); GT, anthocyanidin glucosyl transferase; LAR, leucoanthocyanidin reductase. ANR, anthocyanidin reductase (also called BAN, i.e., BANYULS protein); CHR, chalcone reductase (CHS/CHR are believed to work together to generate 4,2',4'-trihydroxychalcone, also called deoxychalcone, Bomati et al., 2005). Tetrahydroxychalcone (4,2', 4',6'-tetrahydroxychalcone) and trihydroxychalcone (4,2',4'-trihydroxychalcone) are also known as chalcone and deoxychalcone, respectively. A to C on the naringenin structure indicate the standard nomenclature assigned to the three flavonoid rings. After 3-O-glycosylation of anthocyanidins to form anthocyanins by GT, anthocyanins may be further modified by additional glycosylation, methylation, and acylation.
Figure 1B:
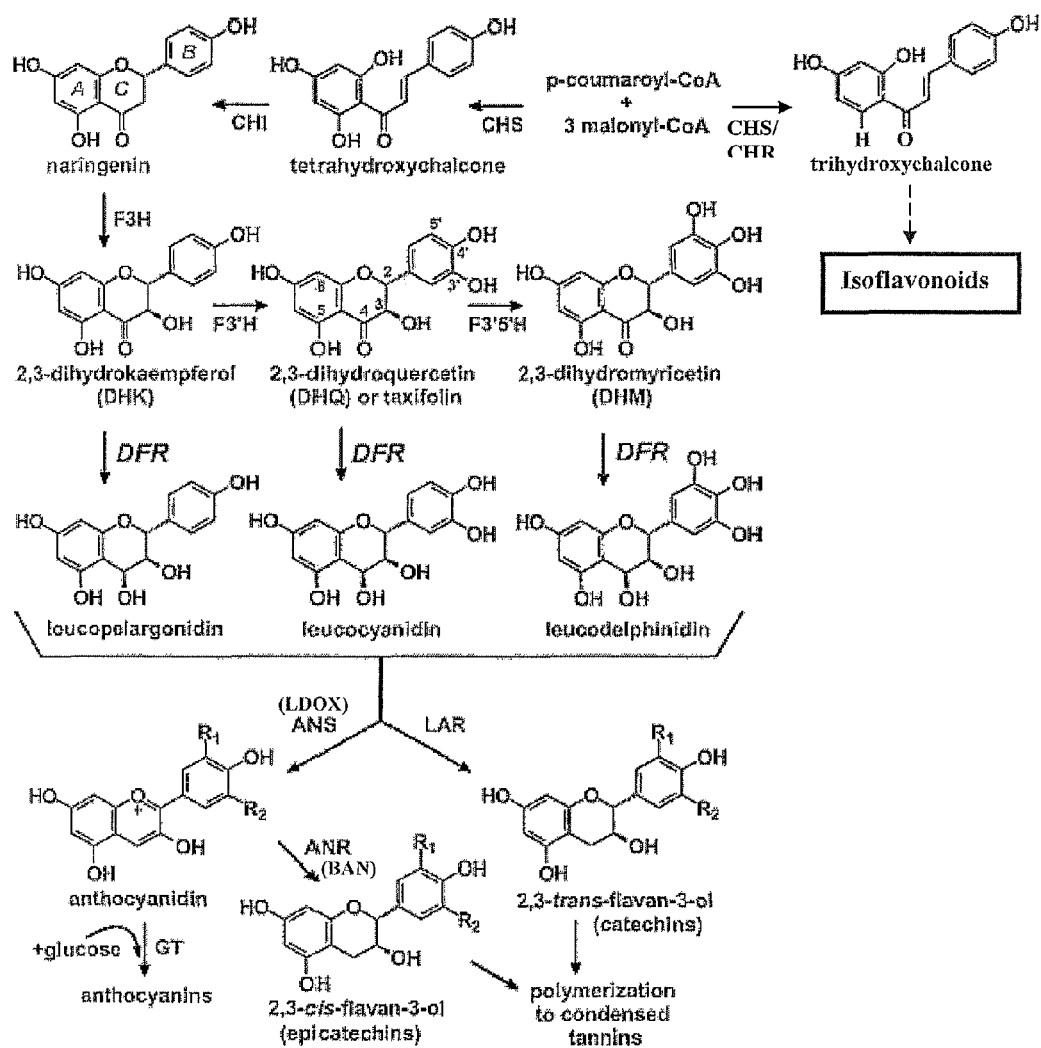

5, 7). The full protein-coding region is shown as a hatched bar, the 3' untranslated region is shown as a thin black line, and the grey bar represents genomic sequences 5' to the ORFs of Cc4CL2 and Ca4CL2 (upstream of the translation start codon, ATG. The border between the promoter and 5'UTR are not yet defined. B) The cDNA sequence of pccc124i21 and the genomic sequences GW1_Ca4CL2 (SEQ ID NO: 61) and GW1_Cc4CL2 (SEQ ID NO: 62) were aligned with the inserts of pGC1 (Ca4CL2) (SEQ ID NO: 5) and pGC3 (Cc4CL2) (SEQ ID NO: 7). The alignment was done using the CLUSTAL-W program and manually optimized.

Figure 9:
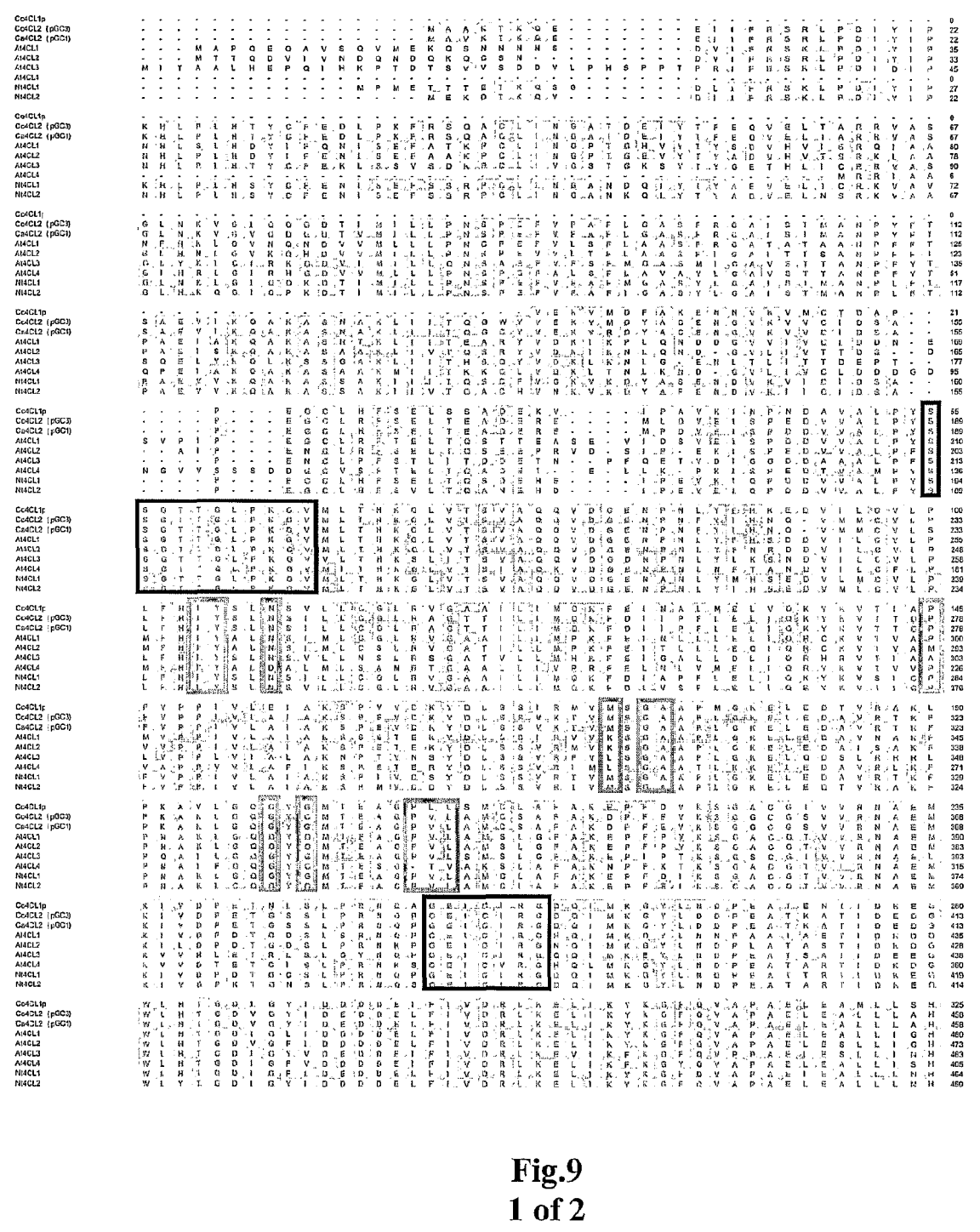

FIG. 9. Protein sequence alignment of the coffee Cc4CL1 (partial), Cc4CL2 (pGC3) and Ca4CL2 (pGC1) protein sequences with other plant 4CL sequences. Alignment of the coffee 4CL protein sequences (Cc4CL1, Cc4CL2 (in pGC3), and Ca4CL2 (in pGC1) (SEQ ID NOs: 25, 26, 24) with other 4CL proteins available in the NCBI database was done using the CLUSTAL-W program. Amino acids marked in grey are generally conserved in the majority of the sequences at this position. GenBank Accession Numbers are given in parentheses: At4CL1 (*Arabidopsis thaliana*, Q42524) (SEQ ID NO: 63), At4CL2 (*Arabidopsis thaliana*, NP_188761.1) (SEQ ID NO: 64), At4CL3 (*Arabidopsis thaliana*, Q9S777) (SEQ ID NO: 65), At4CL4 (*Arabidopsis thaliana*, AAM19949) (SEQ ID NO: 66), Nt4CL1 (*Nicotiana tabacum*, O24145) (SEQ ID NO: 67), Nt4CL2 (*Nicotiana tabacum*, T03789) (SEQ ID NO: 68). Boxed regions have been proposed and presented in an alignment by Schneider et al., (2003): Blue boxes indicate two conserved peptide motifs. Green boxes indicate the 12 amino acids residues that are proposed to function as the 4CL substrate specificity.

Figure 10:
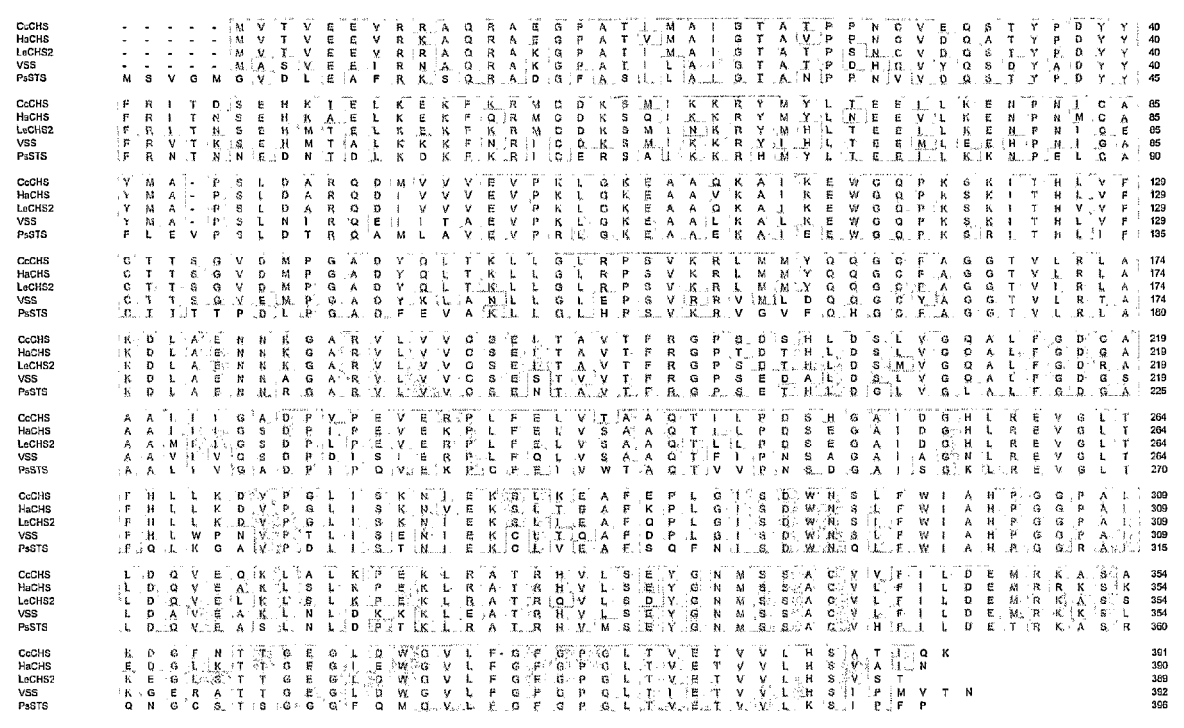

FIG. 10. Protein sequence alignment of CcCHS with plant chalcone synthase (CHS) and stilbene synthase protein sequences. Alignment of the protein (SEQ ID NO: 27) encoded by the CcCHS (SEQ ID NO: 8) with other CHS proteins available in the NCBI database was done using the CLUSTAL W program. Amino acids marked in grey are generally conserved in the majority of the sequences at this position. GenBank Accession Numbers are given in parentheses. Chalcone synthases (CHS) sequences: HaCHS (*Hypericum androsaemum*, AAG30295) (SEQ ID NO: 69) and LeCHS (*Lycopersicon esculentum*, CAA38981) (SEQ ID NO: 70). Stilbene Synthases (SS or STS): VSS (*Vitis*, AAB19887) (SEQ ID NO: 71) and PsSTS (*Pinus strobus*, CAA87013) (SEQ ID NO: 72).

Figure 11:
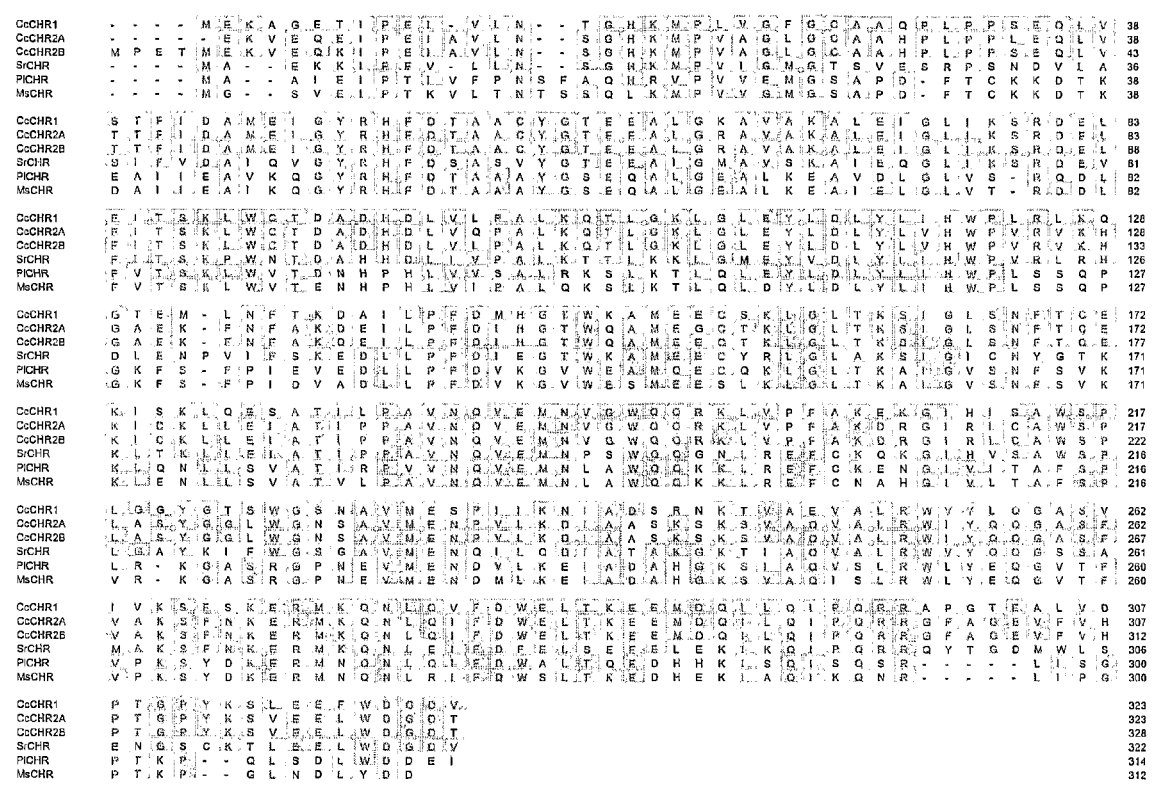

FIG. 11. Protein sequence alignment of CcCHR1, CcCHR2A and CcCHR2B with other plant CHR protein sequences. Manually optimized alignment of putative proteins (SEQ ID NOs: 28, 29, 30) encoded by CcCHR1, CcCHR2A and CcCHR2B (SEQ ID NOs: 9, 10, 11) with other CHR proteins available in the NCBI database was done in the MegAlign software. Amino acids marked in grey are generally conserved in the majority of the sequences at this position. GenBank Accession Numbers are given in parentheses. SrCHR (*Sesbania rostrata*, CAA11226) (SEQ ID NO: 73), PlCHR (*Pueraria Montana* var. *lobata*, AAM12529) (SEQ ID NO: 74) and MsCHR (*Medicago sativa*, AAB41555) (SEQ ID NO: 75).

FIG. 12. Protein sequence alignment of CcCHI with plant CHI protein sequences. A) Manually optimized alignment of putative protein (SEQ ID NO: 31) encoded by CcCHI (SEQ ID NO: 12) with other CHI proteins available in the NCBI database was done using CLUSTAL W program. Amino acids marked in grey are generally conserved in the majority of the sequences at this position. GenBank Accession Numbers are given in parentheses. PhCHI (*Petunia×hybrida*, PIR ID ISPJA1) (SEQ ID NO: 76), LjCHI-2 (*Lotus corniculatus* var. *japonicus*, BAC53984 Type I CHI) (SEQ ID NO: 77) and GmCHI-2 (*Glycine max*, AAT94360, Type I CHI) (SEQ ID NO: 78). B) Alignment of putative protein (SEQ ID NO: 32) encoded by CcCHI-like (SEQ ID NO: 13) with other CHI proteins available in the NCBI database was done using the CLUSTAL W program in the MegAlign software. Amino acids marked in grey are generally conserved in the majority of the sequences at this position. GenBank Accession Numbers are given in parentheses GmCHI-4A (*Glycine max*, AAT94362) (SEQ ID NO: 79) and GmCHI-1A (*Glycine max*, AAT94358, Type II CHI) (SEQ ID NO: 80).

Figure 13A:
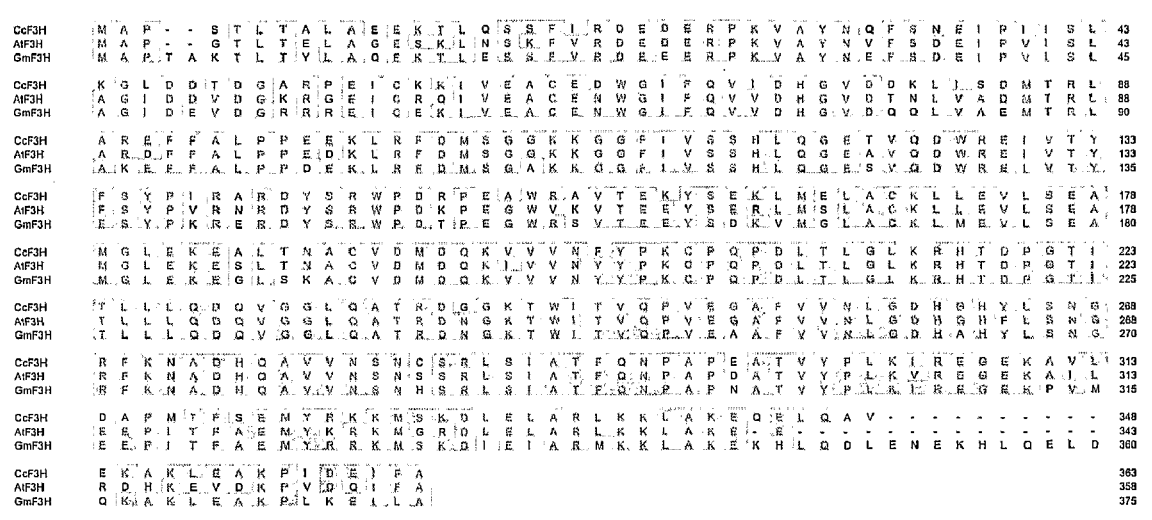

FIG. 13. Protein sequence alignment of CcF3H with plant F3H protein sequences. A) Alignment of the protein (SEQ ID NO: 33) encoded by CcF3H (SEQ ID NO: 14) with other F3H proteins available in the NCBI database was done using the CLUSTALW program. Amino acids marked in grey are generally conserved in the majority of the sequences at this position. GenBank Accession Numbers are given in parentheses. AtF3H (*Arabidopsis thaliana*, AAC68584) (SEQ ID NO: 81), GmF3H (*Glycine max*, AAT94365) (SEQ ID NO: 82). B) Alignment of partial putative protein (SEQ ID NO: 34) encoded by the CcF3'5'H (SEQ ID NO: 15) with biochemically-characterized F3'5'H proteins available in the NCBI database over the same region was done using the CLUSTAL W program. Amino acids marked in grey are generally conserved in the majority of the sequences at this position. GenBank Accession Numbers are given in parentheses. CrF3'5'H (*Catharanthus roseus*, CAA09850) (SEQ ID NO: 83) and GtF3'5'H (*Gentiana triflora*, Q96581) (SEQ ID NO: 84).

FIG. 14. Protein sequence alignment of CcDFR with plant DFR protein sequences. Manually optimized alignment of putative protein (SEQ ID NO: 35) encoded by the CcDFR (SEQ ID NO: 16) with biochemically-characterized DFR proteins from *Medicago truncatula* MtDRF1 (GenBank Accession Number AAR27014) (SEQ ID NO: 85) and MtDFR2 (GenBank Accession Number AAR27015) (SEQ ID NO: 86) available in the NCBI database was done using the MegAlign software (Lasergene package, DNASTAR). Amino acids marked in grey are generally conserved in the majority of the sequences at this position.

FIG. 15. Protein sequence alignments. A) Alignment of the protein (SEQ ID NO: 36) encoded by the CcLDOX (SEQ ID NO: 17) with other LDOX (ANS) proteins available in the NCBI database was done using the CLUSTAL W program. Amino acids marked in grey are generally conserved in the majority of the sequences at this position. GenBank Accession Numbers are given in parentheses. AtLDOX (*Arabidopsis thaliana*, CAD91994) (SEQ ID NO: 87), PfANS (*Perilla frutescens*, O04274) (SEQ ID NO: 88), FiANS (*Forsythia×intermedia*, CAA73094) (SEQ ID NO: 89), InANS (*Ipoinoea nil*, BAB71810) (SEQ ID NO: 90). B) Alignment of the protein (SEQ ID NO: 37) encoded by the CcLAR (SEQ ID NO: 18) with other LAR proteins available in the NCBI database was done using the CLUSTAL W program. Amino acids marked in grey are generally conserved in the majority of the sequences at this position. GenBank Accession Numbers are given in parentheses. VvLAR (*Vitis vinifera*, CAI26309) (SEQ ID NO: 91), LuLAR (*Lotus uliginosus*, AAU45392) (SEQ ID NO: 92), DuLAR (*Desmodium uncinatum*, Q84V83) (SEQ ID NO: 93). C) Protein sequence alignment of CcANR (SEQ ID NO: 38) with plant anthocyanidin and leucoanthocyanidin reductase protein sequences. Alignment of putative protein (SEQ ID NO: 38) encoded by the CcANR (SEQ ID NO: 19) with other anthocyanidin and leucoanthocyanidin reductase proteins available in the NCBI database was done using the CLUSTAL W program. Amino acids marked in grey are generally conserved in the majority of the sequences at this position. GenBank Accession Numbers are given in parentheses. MtANR (*Medicago truncatula*, AAN77735) (SEQ ID NO: 94), AtANR (*Arabidopsis thaliana*, AAF23859 Xie et al. (2003)) (SEQ ID NO: 95) and CsLAR (*Camellia sinensis*, AAT68773) (SEQ ID NO: 96). Despite the fact that CsLAR is currently annotated as an LAR protein, the alignment of this apparently uncharacterized protein strongly suggests it has an ANR-like activity and is not an LAR protein.

Figure 16:
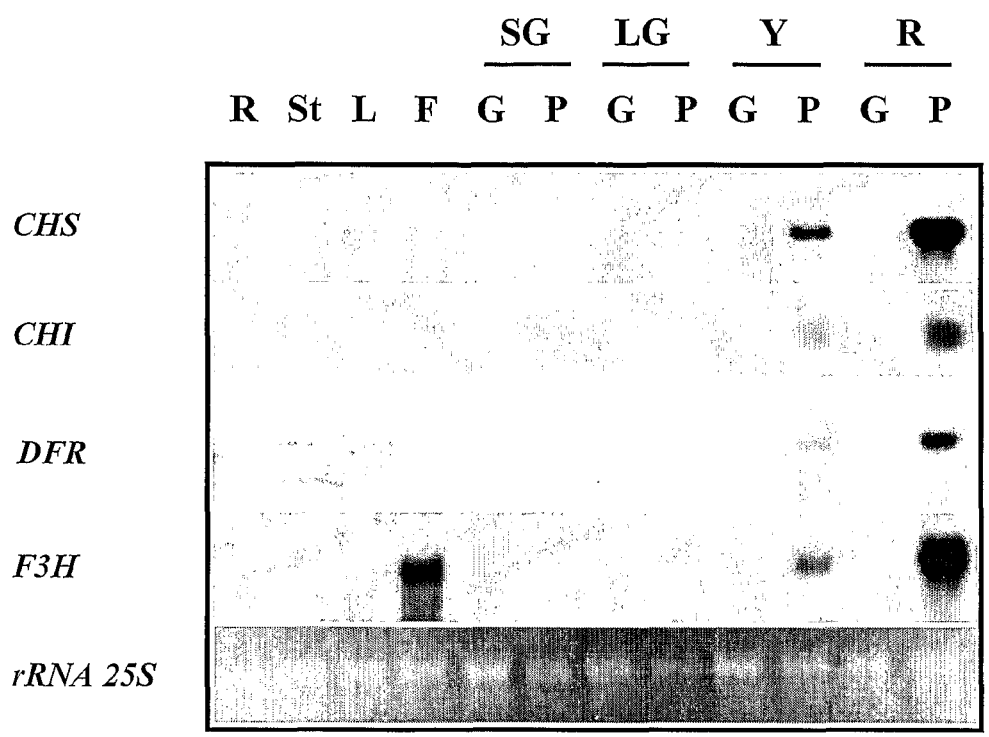

FIG. 16. RNA blot analysis of CHS, CHI, DFR and F3H expression in whole plant and during coffee bean maturation in *Coffea Arabica* T2308. About 5 μg of RNA from roots (R), stem (St), leaves (L), flowers (F) and from coffee beans harvested at four different maturation stages Small-Green (SG), Large-Green (LG), Yellow (Y) and Red (R) were separated on denaturing agarose gel. For each maturation stage, coffee cherries have been separated into pericarp (P) and grain (G). Membranes have been probed with either CcCHS (cccp8j10 clone) (SEQ ID NO: 8 or 97) or CcCHI (cccp22k18 clone) (SEQ ID NO: 12) or CcDFR (cccp5115 clone) (SEQ ID NO: 16) or CcF3H (cccp5120 clone) (SEQ ID NO: 14) probes as indicated on the left. A photo of one of the gels showing the ethidium bromide staining of the rRNA25S demonstrates that equivalent amounts of RNA were loaded in each lane. Similar results were obtained for all the blots (data not shown).

Figure 17:
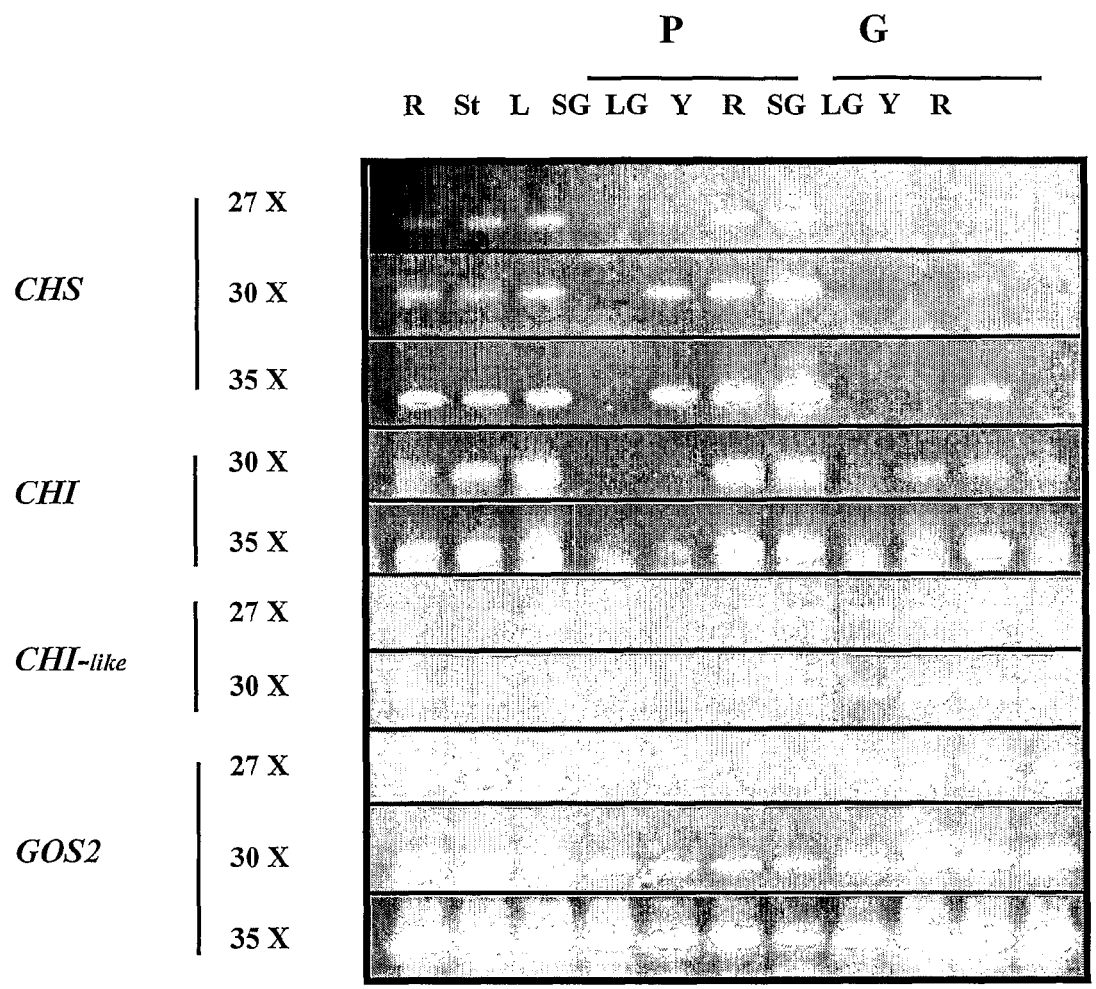

FIG. 17. Comparison of transcript accumulation of CHS, CHI and CHI-like genes involved in flavonoid metabolism in roots, stems, and leaves and during coffee bean maturation in *Coffea arabica* T2308 by RT-PCR. cDNA were prepared from 1 μg of total RNA isolated roots (R), stem (St), leaves (L), seed (S) and pericarp (P) at four maturation stages: Small Green (SG), Large Green (LG), Yellow (Y) and Red (R). RT-PCR analysis was performed using gene-specific primers for CcCHS, CcCHI, CcCHI-like, and GOS2.

Figure 18:
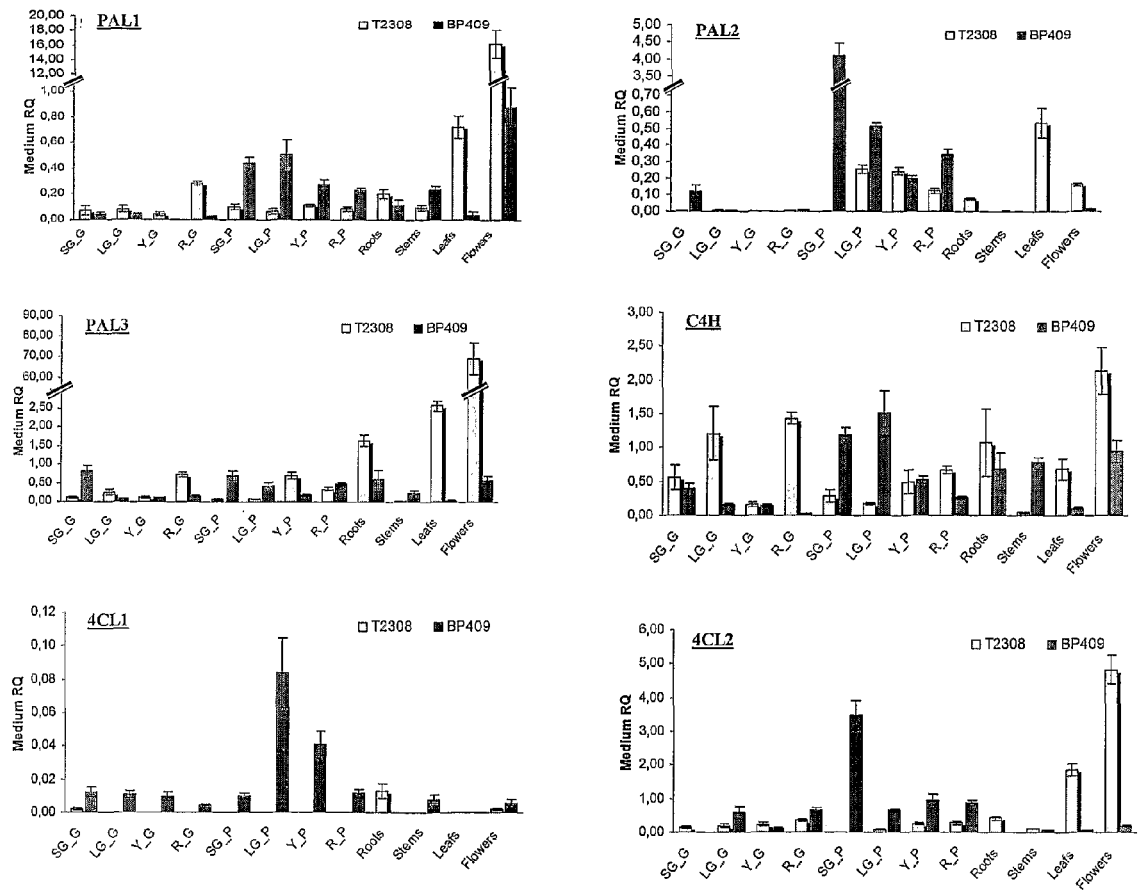

FIG. 18. Tissue-specific expression profile of PAL1, PAL2, PAL3, C4H, 4CL1, and 4CL2 (SEQ ID NOs: 1-7) in *C. canephora* (robusta, BP409) and *C. arabica* (arabica, T2308) using quantitative RT-PCR. Total RNA was isolated from root, stem, flower, leaf and from the grain (G) and pericarp (P) of the cherries harvested at four different maturation stages: Small-Green (SG), Large-Green (LG), Yellow (Y) and Red (R). The RQ value for each tissue sample was determined by normalizing the transcript level of this sample versus the rpl39 transcript level in that tissue. Data shown represent mean values obtained from three amplification reactions and the error bars indicate standard deviation.

Figure 19:
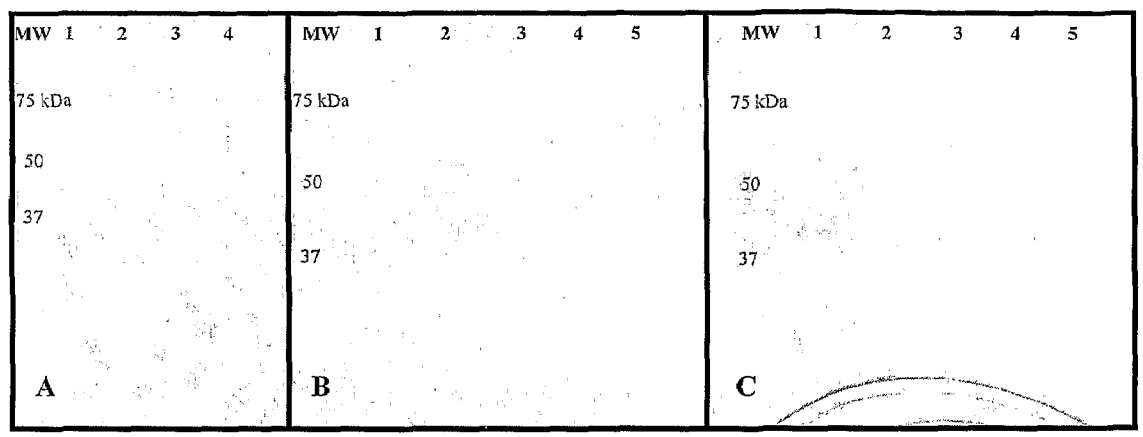

FIG. 19. Analysis of Ca4CL2 (pGC5) (SEQ ID NO: 24) and Cc4CL2 (pGC8) (SEQ ID NO: 26) expression (A) and purification (B and C) performed on SDS-PAGE 12% stained with coomassie blue. A-Lanes: 1. Crude extract of non-inducted B121 recombinant cells with pGC5, 2. Crude extract of inducted B121 recombinant cells with pGC5, 3. Crude extract of non-inducted B121 recombinant cells with pGC8, 4. Crude extract of inducted B121 recombinant cells with pGC8. B-Lanes: 1. first wash of column purification, 2-5. fractions of successive elutions for Ca4CL2. C-Lanes: 1. first wash of column purification, 2-5. fractions of successive elutions for Cc4CL2. MW: Molecular weight marker (Unstained Precision Broad Range (Biorad #161-0362)).

DETAILED DESCRIPTION OF ILLUSTRATIVE EMBODIMENTS

Definitions

Various terms relating to the biological molecules and other aspects of the present invention are used throughout the specification and claims.

The term "phenylpropanoid and flavonoid biosynthetic pathways" refers to polypeptides that participate in phenylpropanoid and flavonoid biosynthesis in plants, and more specifically, in coffee plants. This term encompasses the specific mechanism of action of each respective protein in the pathway, and includes the enzymatic generation of flavonoid precursors in the early steps of the phenylpropanoid pathway. The polypeptides include without limitation, phenylalanine ammonia lyase ("PAL"), cinnamate 4-hydroxylase ("C4H"), 4-coumarate:CoA ligase ("4CL"), chalcone synthase ("CHS"), chalcone isomerase ("CHI"), chalcone reductase ("CHR"), flavone 3-hydroxylase ("F3H"), dihydroflavonol 4-reductase ("DFR"), anthocyanidin reductase ("ANR"), and anthocyanidin synthase, also referred to as leucoanthocyanidin dioxygenase ("ANS"), as exemplified herein.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide," also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al, Protein Synthesis: Posttranslational Modifications and Aging, Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g., chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, such as an amino acid or polypeptide, when the sequence is expressed. The coding sequence may comprise untranslated sequences (e.g., introns or 5' or 3' untranslated regions) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene." Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

Description:

In one of its aspects the present invention features nucleic acid molecules from coffee that encode a variety of proteins involved in the phenylpropanoid and flavonoid biosynthetic pathways. Representative examples of nucleic acid molecules encoding proteins that comprise the phenylpropanoid and flavonoid biosynthetic pathways were identified from databases of over 47,000 expressed sequence tags (ESTs) from several *Coffea canephora* (robusta) cDNA libraries made with RNA isolated from young leaves and from the grain and pericarp tissues of cherries harvested at different stages of development. Overlapping ESTs were identified and "clustered" into unigenes (contigs) comprising either complete or partial coding sequences. The unigene sequences were annotated by performing a BLAST search of each individual sequence against the NCBI (National Center for Biotechnology Information) non-redundant protein database.

BLAST searches of the coffee EST databases using biochemically characterized protein sequences from public databases revealed gene sequences representing several important enzymes of the phenylpropanoid and flavonoid biosynthetic pathways in the coffee plant. The full open reading frame for some of these sequences were obtained, and a partial open reading frame was obtained for several other sequences. In some cases, the partial coding sequence data were used as the starting point for experiments to isolate the full coding sequence by either 5' RACE or the genome walking technique. The cDNAs obtained and their encoded proteins are referred to herein as follows:

ingly, when the term polypeptides or proteins that "comprise the phenylpropanoid and flavonoid biosynthetic pathways" is used herein, it is intended to encompass all *Coffea* proteins that have the general physical, biochemical, and functional features described herein, as well as the polynucleotides that encode them.

Considered in terms of their sequences, the polynucleotides of the invention that encode proteins that comprise the phenylpropanoid and flavonoid biosynthetic pathways include allelic variants and natural mutants of SEQ ID NOs: 1-19, which are likely to be found in different varieties of *C. arabica* and *C. canephora*, and homologs of SEQ ID NOs: 1-19 likely to be found in different coffee species. Because such variants and homologs are expected to possess certain differences in nucleotide and amino acid sequence, this invention provides isolated polynucleotides encoding proteins that comprise the phenylpropanoid and flavonoid biosynthetic pathways that have at least about 60%, preferably at least about 61%, 62%, 63%, 64%, 65%, 66%, 67%, 68%, 69% or 70%, more preferably at least about 71%, 72%, 73%, 74%, 75%, 76%, 77%. 78%, 79%, or 80%, even more preferably 81%, 82%, 83%, 84%, 85%, 86%, 87%, 88%, 89%, and even more preferably 90%, 91%, 92%, 93%, 94%, 95%, and most preferably 96%, 97%, 98% and 99% or more identity with any one of SEQ ID NOs:20-38, and comprise a nucleotide sequence having equivalent ranges of identity to any one of SEQ ID NOs:1-19. Because of the natural sequence variation likely to exist among proteins that comprise the phenylpropanoid and flavonoid biosynthetic pathways, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded

| Enzyme | cDNA | (SEQ ID NO:) | encoded protein | (SEQ ID NO:) |
|---|---|---|---|---|
| Phenylalanine Ammonia Lyase | CaPAL1 | 1 | CaPAL1 | 20 |
|  | CaPAL3 | 2 | CaPAL3 | 21 |
|  | CcPAL2 | 3 | CcPAL2 | 22 |
| Trans Cinnamate-4-Hydroxylase | CcC4H | 4 | CcC4H | 23 |
| 4-Coumarate: CoA Ligase | Ca4CL2 | 5 | Ca4CL2 | 24 |
|  | Cc4CL1 | 6 | Cc4CL1 | 25 |
|  | Cc4CL2 | 7 | Cc4CL2 | 26 |
| Chalcone Synthase | CcCHS | 8 | CcCHS | 27 |
| Chalcone Reductase | CcCHR1 | 9 | CcCHR1 | 28 |
|  | CcCHR2A | 10 | CcCHR2A | 29 |
|  | CcCHR2B | 11 | CcCHR2B | 30 |
| Chalcone Isomerase | CcCHI | 12 | CcCHI | 31 |
|  | CcCHI-like | 13 | CcCHI-like | 32 |
| Flavanone 3-Hydroxylase | CcF3H | 14 | CcF3H | 33 |
| Flavonoid 3',5'-Hydroxylase | CcF3'5'H | 15 | CcF3'5'H | 34 |
| Dihydroflavonol-4-Reductase | CcDFR | 16 | CcDFR | 35 |
| Leucoanthocyanidin Dioxygenase | CcLDOX | 17 | CcLDOX | 36 |
| Leucoanthocyanidin Reductase | CcLAR | 18 | CcLAR | 37 |
| Anthocyanidin Reductase | CcANR | 19 | CcANR | 38 |

Although polynucleotides encoding proteins that catalyze key steps of the phenylpropanoid and flavonoid biosynthetic pathways from *Coffea arabica* and *Coffea canephora* are described and exemplified herein, this invention is intended to encompass nucleic acids and encoded proteins from other *Coffea* species that are sufficiently similar to be used interchangeably with the *C. arabica* and *C. canephora* polynucleotides and proteins for the purposes described below. Accordprotein. Accordingly, such variants and homologs are considered substantially the same as one another and are included within the scope of the present invention.

The gene regulatory sequences associated with genes encoding proteins that comprise the phenylpropanoid and flavonoid biosynthetic pathways are of practical utility and are considered within the scope of the present invention. Promoters and other gene regulatory sequences of genes encoding proteins that comprise the phenylpropanoid and flavonoid biosynthetic pathways from any coffee species may be obtained by the methods described below, and may be utilized in accordance with the present invention. Promoters and regulatory elements governing tissue specificity and temporal specificity of the expression of genes encoding proteins that comprise the phenylpropanoid and flavonoid biosynthetic pathways may be used to advantage, alter or modify the expression of proteins that comprise the phenylpropanoid and flavonoid biosynthetic pathways toward the goal of enhancing the flavor and aroma of coffee products produced from coffee beans comprising such modifications, among other utilities.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOs:1-19, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology with part or all of the coding and/or regulatory regions genes encoding proteins that comprise the phenylpropanoid and flavonoid biosynthetic pathways may be identified by using hybridization and washing conditions of appropriate stringency. It will be appreciated by those skilled in the art that the aforementioned strategy, when applied to genomic sequences, will, in addition to enabling isolation of coding sequences for genes encoding proteins that comprise the phenylpropanoid and flavonoid biosynthetic pathways, also enable isolation of promoters and other gene regulatory sequences associated with genes encoding proteins that comprise the phenylpropanoid and flavonoid biosynthetic pathways, even though the regulatory sequences themselves may not share sufficient homology to enable suitable hybridization.

As a typical illustration, hybridizations may be performed according to the method of Sambrook et al, using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm = 81.5° C. + 16.6 \text{ Log } [Na+] + 0.41(\% G+C) - 0.63$$
$$(\% \text{ formamide}) - 600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4-TOPO (Invitrogen, Carlsbad, Calif.) or pET28a+ (Novagen, Madison, Wis.), all of which can be propagated in a suitable E. coli host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting genes encoding proteins that comprise the phenylpropanoid and flavonoid biosynthetic pathways or mRNA in test samples of plant tissue, e.g., by PCR amplification, or for the positive or negative regulation of expression genes encoding proteins that comprise the phenylpropanoid and flavonoid biosynthetic pathways at or before translation of the mRNA into proteins. Methods in which oligonucleotides or polynucleotides may be utilized as probes for such assays include, but are not limited to: (1) in situ hybridization; (2) Southern hybridization (3) Northern hybridization; and (4) assorted amplification reactions such as polymerase chain reactions (PCR) (including RT-PCR) and ligase chain reaction (LCR).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of polypeptides that comprise the phenylpropanoid and flavonoid biosynthetic pathways may be produced by expression in a suitable prokaryotic or eukaryotic system. For example, part or all of a DNA molecule, such as the cDNAs having SEQ ID NOs: 1-19, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The polypeptides that comprise the phenylpropanoid and flavonoid biosynthetic pathways produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The polypeptides that comprise the phenylpropanoid and flavonoid biosynthetic pathways of the invention, prepared by the aforementioned methods, may be analyzed according to standard procedures.

Polypeptides that comprise the phenylpropanoid and flavonoid biosynthetic pathways purified from coffee, or produced recombinantly, may be used to generate polyclonal or monoclonal antibodies, antibody fragments or derivatives as defined herein, according to known methods. Antibodies that recognize and bind fragments of the polypeptides that comprise the phenylpropanoid and flavonoid biosynthetic pathways of the invention are also contemplated, provided that the antibodies are specific for polypeptides that comprise the phenylpropanoid and flavonoid biosynthetic pathways. For example, if analyses of the proteins or Southern and cloning analyses (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

Flavonoids play a role in many aspects of human health and wellness. Flavonoids have been demonstrated to be powerful antioxidants (Rice-Evans, C 1991), have been shown to inhibit oxidation of LDL in vitro (DeWhalley, C V et al. 1990; Frankel, E N et al. 1993; and Yan, L J et al. 1995), are anti-hypertensive (Duarte, J et al. 2002), and may be anti-inflammatory (Yoshoimoto et al. 1983; and Huang, M T et al. 1991). In addition, evidence indicates that dietary flavonoids reduce the risk of coronary heart disease mortality (Hertog, M G et al. 1993), and may be protective against certain cancers. (Yang, C S et al. 1998; Yamane, T et al. 1996; Gupta, S et al. 2001; Yamagishi, M et al. 2002; and Hertog, M G et al. 1994). This list of health benefits attributable to flavonoids is meant to be illustrative and not exhaustive, and it is presumed that there are many other beneficial health effects attributable to flavonoids presently unknown. Accordingly, the coffee polypeptides that comprise the biosynthetic pathways of phenylpropanoids and flavonoids described and exemplified herein are expected to find utility in a variety of food, health, and wellness applications. For example, the coffee polypeptides that comprise the biosynthetic pathways of phenylpropanoids and flavonoids, or their respective flavonoid products, may be utilized as dietary supplements. In addition, the antioxidant properties of flavonoids may prove advantageous in both food and cosmetic products.

One or more of the aforementioned applications for the polypeptides that comprise the phenylpropanoid and flavonoid biosynthetic pathways may be pursued by exploiting the availability of the polynucleotides encoding polypeptides that comprise the phenylpropanoid and flavonoid biosynthetic pathway described herein to generate significant quantities of pure protein using recombinant organisms (e.g., in the yeast *Picia pastoris* or in food compatible Lactobacilli, or in plant cells), and then testing the proteins in new or established assays for antioxidant potential, antihypertensive potential, immunoproliferative potential, chemoprotective or chemotherapeutic potential, and the like. Similar testing may be carried out using the flavonoids produced by these proteins according to suitable means established or developed in the art. If specific purified proteins, or flavonoid products produced by such proteins are found to be particularly useful, natural versions of those proteins and their flavonoid products also may be isolated from coffee grains or other plant parts, or from tissues and organs of other plants enriched in those phenylpropanoid and flavonoid biosynthetic pathways enzymes.

Vectors, Cells, Tissues and Plants:

Also featured in accordance with the present invention are vectors and kits for producing transgenic host cells that contain a polynucleotide encoding polypeptides that comprise the phenylpropanoid and flavonoid biosynthetic pathways, or an oligonucleotide, or homolog, analog or variant thereof in a sense or antisense orientation, or a reporter gene and other constructs under control of cell or tissue-specific promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a gene encoding a polypeptide that comprises the phenylpropanoid and flavonoid biosynthetic pathways, or nucleic acid sequences that inhibit the production or function of a plant's endogenous polypeptides that comprise the phenylpropanoid and flavonoid biosynthetic pathways. This is accomplished by transforming plant cells with a transgene that comprises part of all of a coding sequence for a polypeptide that comprises the phenylpropanoid and flavonoid biosynthetic pathways, or mutant, antisense or variant thereof, including RNA, controlled by either native or recombinant regulatory sequences, as described below. Transgenic plants from coffee species are preferred, including, without limitation, *C. abeokutae, C. arabica, C. arnoldiana, C. aruwemiensis, C. bengalensis, C. canephora, C. congensis C. dewevrei, C. excelsa, C. eugenioides*, and *C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae.* Transgenic plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' regulatory sequences (e.g., promoters and translational regulatory sequences) and 3' regulatory sequences (e.g., terminators). In a preferred embodiment, a coding sequence encoding a polypeptide that comprises the phenylpropanoid and flavonoid biosynthetic pathways under control of its natural 5' and 3' regulatory elements is utilized. In other embodiments, coding and regulatory sequences are swapped (e.g., CcDFR coding sequence operably linked to the CcF3H promoter) to alter the protein content of the seed of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35 S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants with coding sequences to express polypeptides that comprise the phenylpropanoid and flavonoid biosynthetic pathways under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound-induced gene promoters (e.g., hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name only a few.

Tissue-specific and development-specific promoters are also contemplated for use in the present invention. Non-limiting examples of seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta.-phaseolin, napin, beta.-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and *C. canephora* 11S seed storage protein (Marraccini et al., 1999, Plant Physiol. Biochem. 37: 273-282). See also WO 00/12733, where seed-preferred promoters from end1 and end2 genes are disclosed. Other *Coffea* seed specific promoters may also be utilized, including but not limited to the oleosin gene promoter described in commonly-owned, co-pending PCT Application No. US2006/026121, the dehydrin gene promoter described in commonly-owned, co-pending PCT Application No. US2006/026234, and the 9-cis-epoxycarotenoid dioxygenase gene promoter described in commonly-owned, co-pending PCT Application No. US2006/34402. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreducatase (GOX), *Bromoxynil nitrilase* (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby the protein products can be expressed in coffee plants in order that the proteins may play a role in protecting the coffee plant from pathogens, and from herbivore or insect attack, and in the enhancement of flavor and/or aroma of the coffee beverage or coffee products ultimately produced from the bean of the coffee plant expressing the protein. Similarly, the polypeptides of the invention can be used in any one of a number of methods whereby the phenylpropanoids, flavonoids, and other such phytochemical products synthesized from the polypeptides may play a role in protecting the plant from pathogens, and from herbivore or insect attack, and in the enhancement of flavor and/or aroma of the coffee beverage or coffee products ultimately produced from the bean of the coffee plant containing the phenylpropanoids and flavonoids.

With respect to protection of the plant from attack by pathogens, herbivores, and insects, increasing evidence indicates that at least some flavonoids and some flavonoid secondary metabolites are produced at increased levels in certain plants as part of the defense response, or play a role in passive resistance to attack. (Lahtinen, M et al. (2004); Onyilagha, J C et al. (2004); Kotkar, H M et al. (2002); Lattanzio, V et al. (2000), and Christensen, A B et al. (1998)). Accordingly, the ability to manipulate production of polypeptides that comprise the biosynthetic pathway for phenylpropanoids and flavonoids in a plant, or even to use the polynucleotides and proteins of the invention to monitor such gene expression, will enable study and manipulation of the response of the coffee plant to pathogen, herbivore, or insect attack. This knowledge will enable the generation of modified coffee plants that are better equipped against disease or devastation by herbivores or insects.

With respect to flavor and aroma of roasted coffee grain, it is expected that the polypeptides that comprise the phenylpropanoid and flavonoid biosynthetic pathways exert some influence on the generation of coffee flavors via the Maillard reaction that occurs during roasting, by means of the content of the proteins themselves, or the products such as phenylpropanoids or flavonoids they produce. Proteins, and particularly protein degradation products (peptides and amino acids), represent an important group of flavor precursors (Spanier et al, 2004). Therefore, relatively abundant proteins such as those that comprise the phenylpropanoid and flavonoid biosynthetic pathways can be expected to make some contribution to the flavor generating reactions that occur during coffee roasting. Such a contribution may stem from the concentration of the proteins themselves in the coffee bean, or the concentration of the phenylpropanoids or flavonoids ultimately produced from the proteins. The ability to monitor (e.g., through marker-assisted breeding) or manipulate protein expression profiles for polypeptides that comprise the phenylpropanoid or flavonoid biosynthetic pathway is provided by the polynucleotides of the present invention, in accordance with the methods described herein.

Thus, one aspect of the present invention features methods to alter the profile of polypeptides that comprise the phenylpropanoid or flavonoid biosynthetic pathway in a plant, preferably coffee, comprising increasing or decreasing an amount or activity of one or more polypeptides that comprise the phenylpropanoid or flavonoid biosynthetic pathway in the plant. For instance, in one embodiment of the invention, a gene encoding a polypeptide that comprises the phenylpropanoid or flavonoid biosynthetic pathway under control of its own expression-controlling sequences is used to transform a plant for the purpose of increasing production of that polypeptide in the plant. Alternatively, a coding region for a polypeptide that comprises the phenylpropanoid or flavonoid biosynthetic pathway is operably linked to heterologous expression controlling regions, such as constitutive or inducible promoters.

Loss-of-function (null) mutant plants may be created or selected from populations of plant mutants currently available. It will also be appreciated by those of skill in the art that mutant plant populations may also be screened for mutants that over-express or under-express a particular polypeptide that comprises the phenylpropanoid or flavonoid biosynthetic pathway, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al, 2004, *Plant Physiol.* 135 (2): 630-636; Gilchrist & Haugln, 2005, *Curr. Opin. Plant Biol.* 8 (2): 211-215). The methods to make mutant populations are well known in the art.

The nucleic acids of the invention can be used to identify mutant polypeptides that comprise the phenylpropanoid and flavonoid biosynthetic pathways in various plant species. In species such as maize or *Arabidopsis*, where transposon insertion lines are available, oligonucleotide primers can be designed to screen lines for insertions in the genes encoding polypeptides that comprise the phenylpropanoid and flavonoid biosynthetic pathways. Through breeding, a plant line may then be developed that is heterozygous or homozygous for the interrupted gene.

A plant also may be engineered to display a phenotype similar to that seen in null mutants created by mutagenic techniques. A transgenic null mutant can be created by expressing a mutant form of a selected polypeptide that comprises the phenylpropanoid and flavonoid biosynthetic pathways to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al., 1997, *Genetics* 145: 163-171; Kolch et al, 1991, *Nature* 349: 426-428).

Another kind of transgenic null mutant can be created by inhibiting the translation of mRNA encoding the polypeptides that comprise the phenylpropanoid and flavonoid biosynthetic pathways by "post-transcriptional gene silencing." The gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the coding sequence antisense strand is expressed by a transgene. In another embodiment, hybridizing sense and antisense strands of part or all of the coding sequence for polypeptides that comprise the phenylpropanoid and flavonoid biosynthetic pathways are transgenically expressed.

In another embodiment, phenylpropanoid and flavonoid genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, *Differentiation* 72: 65-73; Baulcombe, 2004, Nature 431: 356-363; Herr, 2004, *Biochem. Soc. Trans.* 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by any common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al, 1998, *Plant J.* 16 (6): 651-659). Plant cells are transformed with a copy of the endogenous gene targeted for repression. In many cases, this results in the complete repression of the native gene as well as the transgene. In one embodiment, a gene encoding a polypeptide that comprises the phenylpropanoid and flavonoid biosynthetic pathways from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or transgenic plants that exhibit one or more of the aforementioned desirable phenotypes can be used for plant breeding, or directly in agricultural or horticultural applications. They will also be of utility as research tools for the further elucidation of the participation of polypeptides that comprise the phenylpropanoid and flavonoid biosynthetic pathways in flavor, aroma and other features of coffee seeds associated with pigments and photosynthesis. Plants containing one transgene or a specified mutation may also be crossed with plants containing a complementary transgene or genotype in order to produce plants with enhanced or combined phenotypes.

The present invention also features compositions and methods for producing, in a seed-preferred or seed-specific manner, any selected heterologous gene product in a plant. A coding sequence of interest is placed under control of a seed-specific coffee promoter and other appropriate regulatory sequences, to produce a seed-specific chimeric gene. The chimeric gene is introduced into a plant cell by any of the transformation methods described herein or known in the art. These chimeric genes and methods may be used to produce a variety of gene products of interest in the plant, including but not limited to: (1) detectable gene products such as GFP or GUS, as enumerated above; (2) gene products conferring an agronomic or horticultural benefit, such as those whose enzyme activities result in production of micronutrients (e.g., pro-vitamin A, also known as beta-carotene) or antioxidants (e.g., ascorbic acid, omega fatty acids, lycopene, isoprenes, terpenes); or (3) gene products for controlling pathogens or pests, such as described by Mourgues et al, (1998), TibTech 16: 203-210 or others known to be protective to plant seeds or detrimental to pathogens.

The following examples are provided to illustrate the invention in greater detail. The examples are intended illustrate, not to limit, the invention.

EXAMPLE 1

Materials and Methods for Subsequent Examples

Plant material. Freshly harvested roots, young leaves, stems, flowers and fruit at different stages of development were harvested from *Coffea arabica* L. cv. Caturra T-2308 and young leaf tissues were harvested from *Coffea canephora* var. BP409 grown under greenhouse conditions at Tours (25° C., 70 RH). All other tissues from *Coffea canephora* BP-409 were grown in the field in East Java, Indonesia. The development stages are defined as follows: small green fruit (SG), large green fruit (LG), yellow fruit (Y) and red fruit (R). Fresh tissues were frozen immediately in liquid nitrogen, then stored at −80° C. until used for RNA extraction.

RNA Preparation. Total RNA was extracted from the various tissues of *Coffea arabica* (T2308) and *Coffea canephora* (BP409) as described previously (Rogers et al. 1999). In the case of the coffee cherries from the Small Green (SG), Large Green (LG), Yellow (Y), and Red (R) stages, these were first separated into pericarp and grain tissues and then the RNA was extracted as described above.

cDNA Preparation. Four different methods of cDNA preparation were carried out:

Method 1: 1 µg of total RNA and 50 ng oligo $dT_{(18)}$ (Sigma) was dissolved in DEPC-treated water (12 µl final volume). This mixture was subsequently incubated at 70° C. for 10 min and then rapidly cooled down on ice. Next, 4 µl of 5× first strand buffer (Invitrogen, Carlsbad, Calif.), 2 µl of DTT 0.1M (Invitrogen) and 1 µl of dNTP mix (10 mM each, Invitrogen), were added. The reaction mixes were incubated at 42° C. for 2 min before adding 1 µl of SuperScript III Rnase H-Reverse transcriptase (200 U/µl, Invitrogen). After addition of the enzyme, the reactions were incubated at 25° C. for 10 min., then at 42° C. for 50 min, followed by enzyme inactivation by heating at 70° C. for 10 min. The cDNA samples generated were then diluted ten-fold in sterilized water and stored at −20° C. This cDNA was then used at different dilutions as noted in the various experiments outlined below.

Method 2: 1 µg total RNA sample (Table 1), plus 870 ng oligo dT (Proligo) was made up to a final volume of 13 µl with DEPC-treated water. This mixture was incubated at 65° C. for 5 min to denature the nucleic acids, and the samples were then put on ice. Next, 4 µl of 5× buffer Transcriptor RT Reaction Buffer (Roche), 10 U of Ribonuclease Inhibitor (Sigma), 1 mM final of each dNTP (Roche) and 10 U of Transcriptor Reverse Transcriptase (20 U/µL, Roche) were added. The 20 µL final reaction mixes were mixed by vortexing and briefly centrifuged. The reactions were then incubated at 55° C. for 50 min. 1 U of RNase H (Invitrogen) was then added to the reaction mixes, followed by an incubation at 37° C. for 30 min. The samples were then stored at −20° C.

Method 3 for cDNA preparation was identical to Method 2, except different primers were used and 30 pmoles of Gene-Specific Primer (see Table 1 and Table 3) were substituted for the 870 ng oligo dT for the priming step. The samples were then stored at −20° C.).

Method 4 for cDNA preparation closely followed the manufacturer's protocol for First Strand cDNA Synthesis method in 5' RACE system for Rapid Amplification of cDNA Ends kit (Invitrogen). In brief, 1 µg total RNA sample (Table 1), plus 10 pmoles Gene-Specific Primer (Tables 1 and 3) was diluted to a final volume of 15.5 µl with DEPC-treated water. This mixture was incubated at 70° C. for 10 min to denature the nucleic acids, and the samples were then put on ice for 1 min and centrifuged. Next, 2.5 µl of 10×PCR buffer (Invitrogen), 2.5 µl of $MgCl_2$, 25 mM (Invitrogen), 2.5 µl of DTT 0.1M (Invitrogen) and 1 µl of dNTP mix (10 mM each, Invitrogen), were added to a final volume of 24 µl with DEPC-treated water. These reaction mixes were incubated at 42° C. for 1 min before adding 1 µl of SuperScript II Rnase H-Reverse Transcriptase (200 U/µl, Invitrogen). After addition of enzyme, the reactions were incubated at 42° C. for 50 min, followed by enzyme inactivation by heating at 70° C. for 15 min. The tubes were then briefly centrifuged and 1 µL of RNase mix was then added to the reaction and incubated for 30 min at 37° C. The samples were then stored at −20° C.

TABLE 1 cDNA Production for the Different 5' RACE Experiments.

| Experiment | RNA origin variety + stage | cDNA synthesis method used | Primers Used for First Strand cDNA Synthesis |
| --- | --- | --- | --- |
| CcPAL1-5' RACE | BP409, Flowers | Method 3 | PAL1-RT1 |
| CcPAL2-5' RACE | BP409, Pericarp (mixed stages) | Method 2 | oligo dT |
| CcPAL3-5' RACE | BP409, Pericarp (mixed stages) | Method 4 | PAL3-RT1 |
| Cc4CL1-5' RACE | BP409, Pericarp (mixed stages) | Method 3 | 4CL1-RT1 |

The sources of the RNA used, the cDNA synthesis method employed, and the primers used for first strand cDNA synthesis are given for each 5' RACE Experiment. The DNA sequences of the primers are given in Table 3. In order to have a full representation of the pericarp RNA made at different stages, approximately equivalent amounts of pericarp tissue from stages small green, large green, yellow and red of total RNA were mixed after being prepared as described in the methods indicated in the table (see methods). BP409, *Coffea canephora* (robusta).

5' RACE Reactions (Rapid Amplification of cDNA Ends). 5' RACE reactions were carried out closely following the manufacturer's protocol described in the kit for the 5' RACE system for Rapid Amplification of cDNA Ends (Invitrogen). The cDNA preparations used in this experiment were first purified to remove any unincorporated nucleotides (as they would interfere in the dC tailing reaction) using S.N.A.P. columns (Invitrogen) according to the instructions given by the manufacturer. Once purified, the cDNA were recovered in 50 µL of sterilized water and stored at −20° C. before being used for 5'RACE PCR. The specific cDNA used for each reaction are noted in Table 1. The 5' RACE experiments all began with a TdT tailing of each specific S.N.A.P. purified cDNA. The poly dC tailing reaction proceeded as follows: 25 µl reactions were set up with 5 µl of the purified cDNA, 11.5 µl DEPC treated water, 5 ul 5×TdT tailing buffer (Invitrogen), and 2.5 µl 2 mM dCTP. The reactions were then incubated at 94° C. for 3 minutes, and chilled on ice. 1 µl of TdT was then added and the reaction was incubated for 10 minutes at 37° C. The reactions were terminated by heating 10 minutes at 65° C. and again placed on ice.

The first round 5' RACE PCR1 reactions were performed in a final 50 µl volume, as follows: 5 µL of each tailed cDNA, 5 µl of 10×Taq Polymerase Buffer (Stratagene buffer), 400 nM of the gene-specific-primer 1 (Tables 2 and 4) and of the Abridged Anchor Primer (AAP) (Table 4), 1 µl of dNTP mix (10 mM each, Invitrogen) and 2.5 U of Taq DNA polymerase (Stratagene). The first round PCR cycling conditions were: denaturing at 94° C. for 2 min, then 94° C. for 1 min, annealing at the temperatures specified in Table 2 for 1 min 30 seconds, and extension at 72° C. for 3 min, for 45 or 55 cycles (Table 2). An additional final extension step was carried out at 72° C. for 7 min. The PCR products were then analyzed by agarose gel electrophoresis and ethidium bromide staining.

The second round of PCR reactions were performed in a final volume of 50 µl volume, as follows: 5 µL of 1% diluted PCR1 (First Round) product; 5 µl of 10×Taq Polymerase Buffer (Stratagene buffer), 200 nM of gene-specific-primer 2 (Tables 2 and 4) and of the Abridged Universal Amplification Primer (AUAP), (Table 4), 1 µl of dNTP mix (10 mM each, Invitrogen) and 2.5 U of Taq DNA polymerase (Stratagene). The reaction protocol was: denaturing at 94° C. for 2 min, then 94° C. for 1 min, annealing at the temperature specified in Table 2 for 1 min 30, and extension at 72° C. for 3 min for 45, 50, or 55 cycles (Table 2). An additional final extension step was carried out at 72° C. for 7 min. PCR products were then analyzed by agarose gel electrophoresis and ethidium bromide staining.

TABLE 2

Primers and PCR Conditions Used for the Different 5' RACE Experiments.

| Experiment | Gene Specific Primers (SEQ ID No.:) | Annealing Temperature | Number of cycles |
|---|---|---|---|
| CcPAL1-5' RACE | | | |
| First round RACE PCR | PAL1-GSP1 (103) | 50° C. | 45 |
| CcPAL2-5' RACE | | | |
| First round RACE PCR | PAL2-GSP1 (104) | 55° C. | 45 |
| Second round RACE PCR | PAL2-GSP2 (105) | 53° C. | 50 |
| CcPAL3-5' RACE | | | |
| First round RACE PCR | PAL3-GSP1 (106) | 55° C. | 55 |
| Second round RACE PCR | PAL3-GSP2 (107) | 55° C. | 55 |
| Cc4CL1-5' RACE | | | |
| First round RACE PCR | 4CL1-GSP1 (108) | 55° C. | 45 |
| Second round RACE PCR | 4CL1-GSP2 (109) | 53° C. | 50 |

The primers, annealing temperatures, and the number of cycles are given for the various 5' RACE PCR reactions. The DNA sequences of the primers are given in Table 4.

TABLE 3

List of Gene Specific Primers used for First Strand cDNA Synthesis experiments.

| Primers | Sequences | SEQ ID NO: |
|---|---|---|
| PAL1-RT1 | 5' GACGTAAGAGCTTCCATCC 3' | 98 |
| PAL3-RT1 | 5' GGCCTTCAAGTTCTCCTC 3' | 99 |
| 4CL1-RT1 | 5' CATACTTATCCACCACAGG 3' | 100 |

TABLE 4

List of primers used for 5'Race PCR experiment

| Primers | Sequences | SEQ ID NO: |
|---|---|---|
| AAP | 5' GGCCACGCGTCGACTAGTACGGGII GGGIIGGGIIG 3' | 101 |
| AUAP | 5' GGCCACGCGTCGACTAGTAC 3' | 102 |
| PAL1-GSP1 | 5' CTCGGGTTTGCCATTCATC 3' | 103 |
| PAL2-GSP1 | 5' CCTCCAAATGCCTCAGATC 3' | 104 |
| PAL2-GSP2 | 5' CCTGATTGTGTTGCTCGGC 3' | 105 |
| PAL3-GSP1 | 5' TTCAATATGTCCACAGCTTCTG 3' | 106 |
| PAL3-GSP2 | 5' TGACGTCTTGGTTGTGTTGCTC 3' | 107 |
| 4CL1-GSP1 | 5' GCAATTGTCACCTTATATTTTTGCAC 3' | 108 |
| 4CL1-GSP2 | 5' CCACAAAGCAACACAGAATTCAG 3' | 109 |

DNA Sequencing. Plasmid DNA was purified using Qiagen kits according to the instructions given by the manufacturer. Plasmid DNA and PCR products were sequenced by GATC Biotech AG (Konstanz, Germany) using the dideoxy termination method (Sanger et al., 1977). In some cases, the unique PCR fragments produced from the 5' RACE and genome walking experiments were directly sequenced, without purification or cloning, using the same primers as in the PCR amplification reactions. Computer analysis was performed using Laser Gene software package (DNASTAR). Homologies with sequences in the public GenBank database were verified using different BLAST programs (Altschul et al. 1990).

Northern Blotting. Total RNA was extracted from the various tissues of *Coffea arabica* (T2308) as described (Rogers et al. 1999). In the case of the coffee cherries from the Small Green (SG), Large Green (LG), Yellow (Y), and Red (R) stages, these were first separated into pericarp and grain tissues and then the RNA was extracted from each.

A total of 5 µg of RNA was run on a 1.2% (w/v) denaturing RNA gel containing formaldehyde. The total RNA samples from each plant tissue were heated at 65° C. for 15 min in presence of 7 µL "RNA Sample Loading Buffer" (without ethidium bromide, Sigma), and then put immediately on ice for 2 minutes before being loaded onto the 1.2% RNA gel. The gels were run at 60 Volts for 5 hours. The gel was then soaked twice in 10×SSC for 20 min. The RNA in the gel was transferred overnight by capillary transfer to a "Positive TM Membrane" (Qbiogene) in 10×SSC, and the RNA was fixed by heating the blot for 30 min at 80° C. Probes were generated using "Rediprime™ II random prime labelling system" kit (Amersham) in the presence of ($P^{32}$) dCTP. Hybridization was carried out at 65° C. for 24 h in hybridization solution (5×SSC, 40 μg/ml Denatured Salmon Sperm DNA, 5% [w/v] SDS, and 5× Denhardt's solution). Then, the membrane was washed twice at 65° C. using 2×SSC, 0.1% SDS [w/v] and 1×SSC, 0.1% SDS [w/v] for 30 minutes each wash.

The probes used were hybridized with the appropriate $^{32}$P-dCTP labeled PCR fragment obtained after PCR amplification with T7 (5'TAATACGACTCACTATAGG3') (SEQ ID NO: 110) and T3 (5'ATTAACCCTCACTAAAGGGA3') (SEQ ID NO: 111) primers and the corresponding clone.

Semi-quantitative RT-PCR. RNA was extracted from the various tissues of *Coffea arabica* and *Coffea canephora*, and cDNA was prepared according to Method 1, described above. The cDNA samples generated were then diluted ten-fold and 1 μl samples of the diluted material were used for semi-quantitative RT-PCR under the following reaction conditions (final volume 50 μl): 1×PCR reaction buffer (Stratagene), 2% DMSO (v/v), gene specific primers at 600 nM each (Table 5), 2.5 units of Taq DNA polymerase (Stratagene). The cycling protocol was as follows: 94° C. for 2 min; then 94° C. for 1 min, 60° C. for 1 min 30 seconds and 72° C. for 1 min and 27, 30 or 35 cycles (number of cycles noted in FIG. 17). An additional final step of elongation was carried out for 7 minutes at 72° C. 15 μl of the PCR products were analyzed by agarose gel electrophoresis and ethidium bromide staining. The oligonucleotides (CcCHS, CcCHI, CcCHI-like, or GOS2 specific primers) used for the RT-PCR reactions and length of PCR products obtained are listed in Table 5.

TABLE 5

Sequences of the CcCHS, CcCHI, CcCHI-like and GOS2 gene-specific primers used to perform the PCR reactions steps for RT-PCR.

| Gene | Primers | Sequences | SEQ ID NO: | Length of PCR product |
|---|---|---|---|---|
| GOS2 | Gos26 | 5' TACCCGACCCGAACCCCAATT 3' | 112 | 485 bp |
| | Gos27 | 5' ACACCAGATGAATGCACACTG 3' | 113 | |
| CcCHS | cccp8j10-FWD | 5' GATCCCGTTCCCGAAGTTGAGAGG 3' | 114 | 503 bp |
| | cccp8j10-REV | 5' CATGATTACTTTTGAATCGTGGCGC 3' | 115 | |
| CcCHI | cccp22k18-FWD | 5' CCCACCTGGAGCCTCTATTCTGTT 3' | 116 | 272 bp |
| | cccp22k18-REV | 5' CCCCGTCGGCCTCAAGTTTC 3' | 117 | |
| CcCHI-like | cccp12o15-FWD | 5' GCTATAATTTCTGCCCCCGTGGAC 3' | 118 | 497 bp |
| | cccp12o15-REV | 5' GAAGACCATGAATCCCAACACCAG 3' | 119 | |

TABLE 6

List of primers and TaqMan probes for the quantitative RT-PCR experiments.

| Primers and Probes | Sequences | SEQ ID NO: |
|---|---|---|
| rpl39-F1 | 5' GAACAGGCCCATCCCTTATTG 3' | 120 |
| rpl39-R1 | 5' CGGCGCTTGGCATTGTA 3' | 121 |
| rpl39-MGB1 | 5' ATGCGCACTGACAACA 3' | 122 |
| CcPAL1-F1 | 5' GTCAACACCTCCATCTTCCAAAA 3' | 123 |
| CcPAL1-R1 | 5' TGGTAGGACAGCCTTCAGTTCA 3' | 124 |
| CcPAL1-MGB1 | 5' ATTGCTGCATTTGAAG 3' | 125 |
| CcPAL2-F2 | 5' GCTCCGCTACCCTTGTGTTAA 3' | 126 |
| CcPAL2-R2 | 5' CACCGAGTACAACAGCTAAAATCTG 3' | 127 |
| CcPAL2-MGB2 | 5' TCCACGGCACGTTGA 3' | 128 |
| CcPAL3-F1 | 5' GTTTGCCCTCTTTTTGGAATGTT 3' | 129 |
| CcPAL3-R1 | 5' TATGGGACGAAAATACAAGGATCTTAA 3' | 130 |
| CcPAL3-MGB1 | 5' TCCAAGTTGTCACTAGCT 3' | 131 |
| CcC4H-F1 | 5' TTTTGGAAGAGGAGTCTAAGGTTGA 3' | 132 |

Real time RT-PCR (QRT-PCR) experiments. The cDNA used for these experiments was prepared according to Method 1, described above. TaqMan-PCR was performed as recommended by the manufacturer (Applied Biosystems, Perkin-Elmer). All reactions contained 1× TaqMan buffer (Perkin-Elmer) and 5 mM MgCl$_2$, 200 μM each of dATP, dCTP, dGTP and dUTP, and 0.625 units of AmpliTaq Gold polymerase. PCR was carried out using 800 nM of each gene specific primers, forward and reverse, and 200 nM TaqMan probe. Primers and probes were designed using PRIMER EXPRESS software (Applied Biosystems) (Table 6). Reaction mixtures were incubated for 2 min at 50° C. and 10 min at 95° C., followed by 40 amplification cycles of 15 sec at 95° C./1 min at 60° C.

TABLE 6-continued

List of primers and TaqMan probes for the quantitative RT-PCR experiments.

| Primers and Probes | Sequences | SEQ ID NO: |
|---|---|---|
| CcC4H-R1 | 5' GCTTCTCCTACCAACACCGAAT 3' | 133 |
| CcC4H-MGB1 | 5' TGGCAACGACTTCCGGTA 3' | 134 |
| Cc4CL1-F1 | 5' GCTAAGCTTGCAGCTGAAGTTG 3' | 135 |
| CcC4CL1-R1 | 5' TCTCTCCTTTTCTCCCAAAACG 3' | 136 |

TABLE 6-continued

List of primers and TaqMan probes
for the quantitative RT-PCR experiments.

| Primers and Probes | Sequences | SEQ ID NO: |
|---|---|---|
| Cc4CL1-MGB1 | 5' AGTCTCTACAACAACGCT 3' | 137 |
| Cc4CL2-F2 | 5' GCTGCTGTTGTCCCAATGAA 3' | 138 |
| Cc4CL2-R2 | 5' CGGTGATGTTGGAATCTTTTGA 3' | 139 |
| Cc4CL2-MGB2 | 5' CAGGCGAAGTTCCA 3' | 140 |

Samples were quantified in the GeneAmp 7500 Sequence Detection System (Applied Biosystems). Quantification of transcript levels was carried out using the method of relative quantification, using the constitutively expressed ribosomal protein rpl39 as the reference. In order to use the method of relative quantification, it was necessary to show that the amplification efficiency for the gene sequences was roughly equivalent to the amplification efficiency of the reference sequence (rpl39 cDNA sequence) using the specifically defined primer and probe sets. To determine this relative equivalence, plasmid DNA containing the appropriate cDNA sequences were diluted 1/1000, 1/10,000, 1/100,000, and 1/1,000,000, and using the Q-PCR conditions described above, the slope of the curve Ct=f(Log quantity of DNA) was calculated for each plasmid/primer/TaqMan probe set. Plasmid/primer/TaqMan probe sets giving curves with slopes close to 3.32, which represents an efficiency of 100%, are considered acceptable. The plasmid/primer/TaqMan probe sets used (Table 6) all gave acceptable values for Ct=f(Log quantity of DNA).

Isolation of the 5' Coding Sequences of CcPAL2, Ca4CL2 and Cc4CL2 Using Primer-Assisted Genome Walking. Total genomic DNA was extracted from fresh leaves of *C. arabica* T2308 and *C. canephora* BP409 harvested from the greenhouse in Tours using the method of Crouzillat et al., (1996). Primer-assisted walking was performed using the Universal GenomeWalker kit (BD Biosciences) according to the manufacturer's protocol. The eight GenomeWalker libraries used here were constructed from the *C. arabica* T2308 and the *C. canephora* BP409 genomic DNA that had been digested with the restriction enzymes DraI, EcoRV, PvuI, StuI, and then blunt-end ligated to the GenomeWalker Adaptor of the Universal GenomeWalker kit. The genomic DNA digestions and the GenomeWalker Adaptor ligation reactions were carried out in accordance with the kit user manual.

The eight libraries were then employed as templates in PCR reactions using the PAL2-GSP gene-specific primers, PAL2-GW-GSP1 and PAL2-GW-GSP2 (SEQ ID NOs: 143, 144)) or those for 4CL2-GSP (4CL2-GW-GSP1 and 4CL2-GW-GSP2 (SEQ ID NOs.: 145, 146)) (Table 7). The PCR reaction mixtures contained 1 µL of GenomeWalker library template, 5 µl 10×PCR buffer (LA buffer II Mg++ plus), 200 µM of each dNTP, 400 nM of each primer (API and either PAL2-GW-GSP1 or 4CL2-GW-GSP1) and 0.5 U of DNA polymerase Takara LA Taq (Cambrex Bio Science) in a final volume of 50 µl. The following conditions were used for the first round of PCR: after denaturing at 94° C. for 2 min, the first seven cycles were performed at 94° C. for 25 seconds and annealing/elongation at 72° C. for 3 min. A further 31 cycles were carried out at 94° C. for 25 seconds and annealing and elongation at 67° C. for 3 min. An additional final step of elongation was done at 67° C. for 7 min. The second PCR reaction was set up exactly as described above for the first round, except the DNA substrate was 1 µl of the first amplification reaction which had been diluted 1/50. The PCR cycling conditions were as follows: 5 cycles of denaturing at 94° C. for 25 seconds and annealing/elongation at 72° C. for 3 min. A further 25 cycles were carried out at 94° C. for 25 seconds, followed by 3 minutes at an annealing/elongation temperature of 67° C. An additional final step of elongation was carried out at 67° C. for 7 min. The resulting PCR fragments were analyzed by agarose gel electrophoresis.

Three PCR products were obtained and cloned in pCR4-TOPO vector. One PCR product was obtained with the *C. canephora* BP409/DraI digested library (the sequence obtained was called GW1_CcPAL2 (SEQ ID NO: 44), which was cloned into pCR4-TOPO to generate the plasmid pML18. A second PCR product was obtained with the *C. canephora* BP409/EcoRV digested library (the sequence obtained was called GW1_Cc4CL2), which was cloned into pCR4-TOPO to generate the plasmid pML21. A third PCR product was obtained with the *C. arabica* T2308/StuI digested library (the sequence obtained was called GW1_Ca4CL2), which was cloned into pCR4-TOPO to generate the plasmid pML22.

TABLE 7

List of primers used for
GenomeWalker experiments.

| Primers | Sequences | SEQ ID NO: |
|---|---|---|
| AP1 | 5' GTAATACGACTCACTATAGGGC 3' | 141 |
| AP2 | 5' ACTATAGGGCACGCGTGGT 3' | 142 |
| PAL2-GW-GSP1 | 5' TTCCCTCCATGCAAGGCTTTGTTTCTCG 3' | 143 |
| PAL2-GW-GSP2 | 5' GGTCCTAGCCACTGTGGTGAAGTACGAA 3' | 144 |
| 4CL2-GW-GSP1 | 5' GCCCACATAGCAAAATTGAGTTCAGCGAAT 3' | 145 |
| 4CL2-GW-GSP2 | 5' GGAACAGAGGCAAAACGCACATCATCACTT 3' | 146 |

Isolation of cDNA Containing the Complete ORF's for *Coffea arabica* CaPAL1 and CaPAL3 Using Gene-Specific Primers. The existing *canephora* cDNA sequence (pcccwc22w18n3) (SEQ ID NO: 39) found in the database, and the new 5' *canephora* sequence obtained from 5' RACE (Race1_CcPAL1) (SEQ ID NO: 40) were used to design 2 specific primers in the 5' and 3' UTR sequences to amplify the complete ORF sequence of CaPAL1 (pML8) (SEQ ID NO: 1). To amplify the complete ORF sequence of CaPAL3 (pML14) (SEQ ID NO: 2), the cDNA sequence found in the database (pcccp1611) (SEQ ID NO: 45), and the 5' region of the published sequence from *Coffea canephora* PAL1 (GenBank Accession Number: AF460203) (SEQ ID NO: 47), which has high similarity to the pcccp1611 and Race1_CcPAL3 sequences (SEQ ID NOs: 45, 46), served to design 2 specific primers in the 5' and 3' UTR sequences of this gene. The cDNA used to isolate the complete ORF sequences are noted in Table 8, and the sequences of the specific primers for each PCR reaction are given in Table 9.

The PCR reactions were performed in 50 µl reactions as follows: 5 µL of cDNA from *Coffea arabica* T2308 (Table 8), 5 ul 10×PCR buffer (La PCR Buffer II Mg$^{++}$ plus), 600 nM of the each gene specific primer, 200 µM of each dNTP, and 0.5 U of DNA polymerase Takara LA Taq (Cambrex Bio Science). After denaturing at 94° C. for 2 min, amplification was carried out according to the following protocol: 40 cycles of denaturing at 94° C. for 1 minute, 1 min at the specified annealing temperature (Table 8), and 2 min of extension at 72° C. An additional final step of extension was carried out at 72° C. for 7 mm. The PCR products were analyzed by agarose gel electrophoresis and ethidium bromide staining. Fragments of the expected size were then cloned in pCR4-TOPO using TOPO TA Cloning Kit for Sequencing (Invitrogen) according to the instructions given by the manufacturer. The cloned inserts were then sequenced.

TABLE 8

Isolation of cDNA sequences encoding the full length protein sequences for *Coffea arabica* PAL1 (CaPAL1), PAL3 (CaPAL3), 4CL2 (Ca4CL2) and *Coffea canephora* 4CL2 (Cc4CL2).

| Gene | cDNA (Source of RNA) | Gene Specific Primers | Annealing Temperature | SEQ ID NOs: |
|---|---|---|---|---|
| CaPAL1 | T2308*, G-Y | PAL1-FullUp1/PAL1-FullLow1 | 47° C. | 147/148 |
| CaPAL3 | T2308*, G-Y | PAL3-FullUp1/PAL3-FullLow1 | 52° C. | 149/150 |
| Ca4CL2 | T2308*, P-Y | 4CL2-FullUp1/4CL2-FullLow1 | 55° C. | 151/152 |
| Cc4CL2 | BP409*, P-Y | 4CL2-FullUp1/4CL2-FullLow1 | 56° C. | 151/152 |

The specific cDNA, primers, and PCR annealing temperatures used to amplify the complete ORF sequences are presented. G-Y, grain at the yellow developmental stage; P-Y, pericarp at the yellow developmental stage. These cDNA were synthesized using Method 1.

TABLE 9

Sequences of the primers used for the amplification of cDNA sequences encoding the full length protein sequences of CaPAL1, CaPAL3, Ca4CL2 and Cc4CL2.

| Primers | Sequences | SEQ ID NO: |
|---|---|---|
| PAL1-FullUp1 | 5' CACCACTGCTACTGCTTCA 3' | 147 |
| PAL1-FullLow1 | 5' ACATTGAAGGATTTGATAA 3' | 148 |
| PAL3-FullUp1 | 5' ATGGAGTGCGCTAATGGAAATG 3' | 149 |
| PAL3-FullLow1 | 5' TTCAACATTTATGGCAACGAAC 3' | 150 |
| 4CL2-FullUp1 | 5' TAGCTCGTAGTAACCCTTCAACA 3' | 151 |
| 4CL2-FullLow1 | 5' TCGACAATCACACACCATAATCG 3' | 152 |

Isolation of cDNA Containing the Complete ORF of 4CL2 from *Coffea canephora* and *Coffea arabica* Using Gene-Specific Primers. The existing 4CL cDNA sequences found in the database, and the new 5' sequences obtained from primer assisted genome walking experiments were used to design 2 gene-specific primers in the 5' and 3' UTR sequences of the coffee 4CL2 gene (Tables 8 and 9) to amplify the complete ORF sequence from *Coffea arabica* and *Coffea canephora* (Table 8). The amplified products were Ca4CL2 (pGC1) (*arabica*) (SEQ ID NO: 5) and Cc4CL2 (pGC3) (*canephora*) (SEQ ID NO: 6). The cDNA used to isolate the complete ORF's are noted in Table 8, and the sequences of the specific primers for each PCR reaction are given in Table 9.

The PCR reactions were performed using the Takara LA Taq DNA polymerase (Cambrex Bio Science). The PCR reactions were performed in 50 µl reactions as follows: 3 µL of cDNA (Table 8), 5 µl 10×PCR buffer (La PCR Buffer II Mg$^{++}$ plus), 300 nM of the each gene specific primer, 200 µM of each dNTP, and 0.5 U of DNA polymerase Takara LA Taq (Cambrex Bio Science). After denaturing at 94° C. for 2 min, the amplification reaction was carried out as follows: 25 cycles of 1 min at 94° C., 1 min at annealing temperature (noted in Table 8) and extension for 2 min 30 seconds at 72° C. An additional final step of extension was carried out at 72° C. for 7 min.

The PCR products were analyzed by agarose gel electrophoresis and ethidium bromide staining. Fragments of the expected size were then cloned in pCR4-TOPO using TOPO TA Cloning Kit for Sequencing (Invitrogen) according to the instructions given by the manufacturer. The cloned inserts were then sequenced.

EXAMPLE 2

Isolation and Characterization of *Coffea* cDNA Clones Encoding Phenylalanine Ammonia Lyases (PAL)

To find cDNA encoding coffee phenylalanine ammonia lyases, the protein sequences of biochemically characterized PAL proteins *Petroselinum crispum* PAL1 (GenBank Accession Number CAA68938, Appert et al., 1994) (SEQ ID NO: 54) and of *Zea Mays* PAL1 (GenBank Accession Number AAL40137, Rösler et al., 1997) (SEQ ID NO: 50) were used as the query sequences for a BLAST search against the Nestlé/Cornell unigene set 5 using the tblastn algorithm. The first search with the *P. crispum* PAL1 protein sequence uncovered 3 unigenes exhibiting relatively high levels of homology: #121018 (e value=0), #120370 (e value=e-123) and #119778 (e value=e-116). The second search with PAL1 from *Zea Mays* uncovered the same 3 unigenes #121018 (e value=0), #120370 (e value=9e-85) and #119778 (e value=e-81).

*Coffea arabica* CaPAL1 (Full ORF). The first unigene found with high similarity to plant PAL proteins was unigene #121018. The longest cDNA of this unigene (pcccwc22w18n3) (SEQ ID NO: 39) was isolated from the 22 weeks whole cherries library and sequenced. The insert of pcccwc22w18n3 (SEQ ID NO: 39) was found to be 1637 bp long, and to encode a partial protein sequence of 470 amino acids. Because the full length *P. crispum* protein was 716 amino acids long, it was assumed that the coffee PAL encoded by pcccwc22w18n3 (SEQ ID NO: 39) was missing over 246 amino acids at the N terminal. To find the missing 5' coding region of this gene, specific primers were designed from the 5' end of the sequence in pcccwc22w18n3 (SEQ ID NO: 39) for use in the well-established technique of 5' RACE PCR.

Figure 2A:
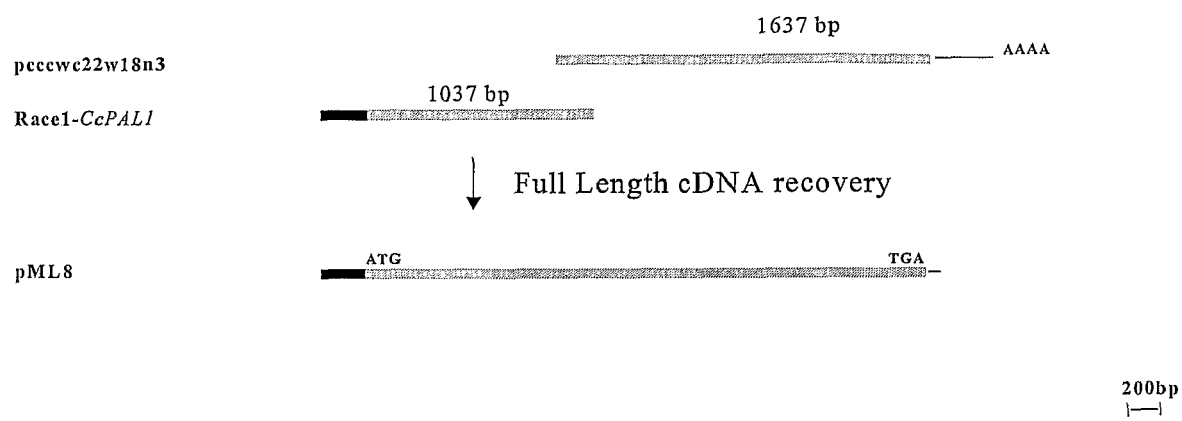
FIG. 2. Characterization of the complete ORF for CaPAL1 from *Coffea arabica*. A) The full protein-coding region is shown as a hatched bar and the 5' untranslated region and 3' untranslated region are shown as a thick black and a thin black bars, respectively. The translation start codon (ATG) and stop (TGA) codons are indicated. B) The insert sequence (SEQ ID NO: 1) of pML8 was aligned with the cDNA sequences pcccwc22w18n3 (SEQ ID NO: 39) and Race1_CcPAL1 (SEQ ID NO: 40). The alignment was done using the CLUSTAL W program (Lasergene package, DNASTAR) and manually optimized. Nucleic acids marked in grey match the pML8 (CaPAL1) insert sequence (SEQ ID NO: 1).
Figure 2B:
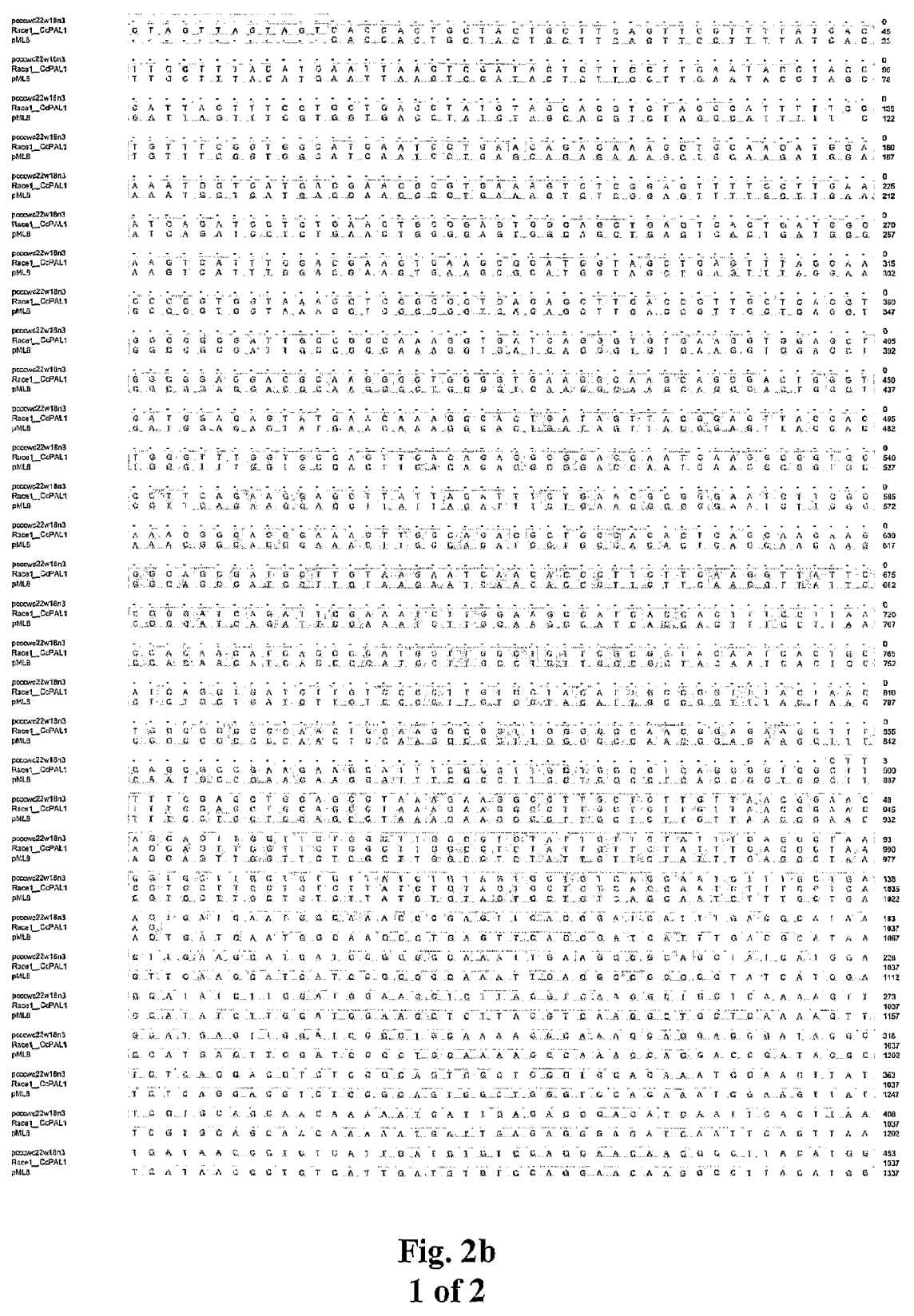
Figure 2B:
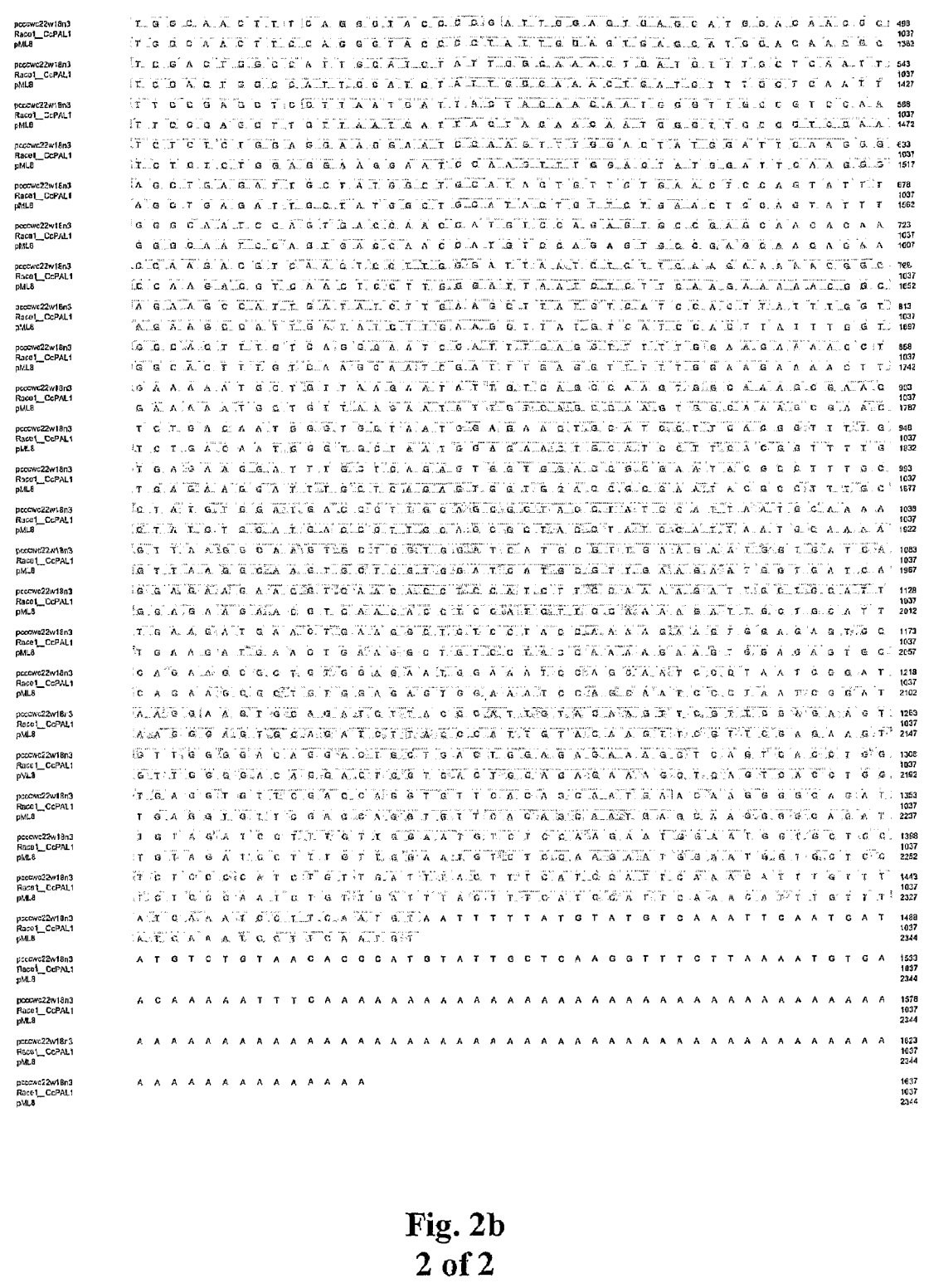

A unique fragment of approximately 1050 bp was obtained using cDNA prepared from *C. canephora* (BP-409) flower RNA and Method 3 described in Example 1, above. The primers and the RACE PCR1 conditions are noted in Tables 1-4 and in Example 1. The PCR fragment obtained was sequenced directly (without purification) using the specific PCR amplification primer PAL1-GSP1 and an additional primer (5' GTGCCTTTGTTCATACTCTCCATC 3') (SEQ ID NO: 153). The resulting sequence (Race1_CcPAL1) (SEQ ID NO: 40) was 1037 bp long and, as expected, overlapped the 5' end of the sequence in pcccwc22w18n3 (SEQ ID NO: 39) (FIG. 2, 140 bp of overlapping sequence).

This *C. canephora* sequence (Race1_CcPAL1) (SEQ ID NO: 40) and the insert of pcccwc22w18n3 (SEQ ID NO: 39), allowed the design of two new primers capable of specifically amplifying the complete ORF sequence of the coffee CaPAL1. The amplification of the complete ORF was carried out using cDNA made by Method 1 from RNA of *C. arabica* (T2308) grain (yellow stage: see Table 8 and Table 9) and following PCR conditions noted in Example 1 and in Table 8. This experiment generated the plasmid pML8 (FIGS. 2A and 2B), which contained the cDNA sequence (SEQ ID NO: 1) for CaPAL1 (SEQ ID NO: 20). Sequence analysis of the pML8 insert (SEQ ID NO: 1) indicated that this cDNA was 2344 bp long, with a complete ORF of 2136 bp that encoded a polypeptide (SEQ ID NO: 20) of 711 amino acids having an estimated molecular weight of 77.10 kDa.

Figure 5A:
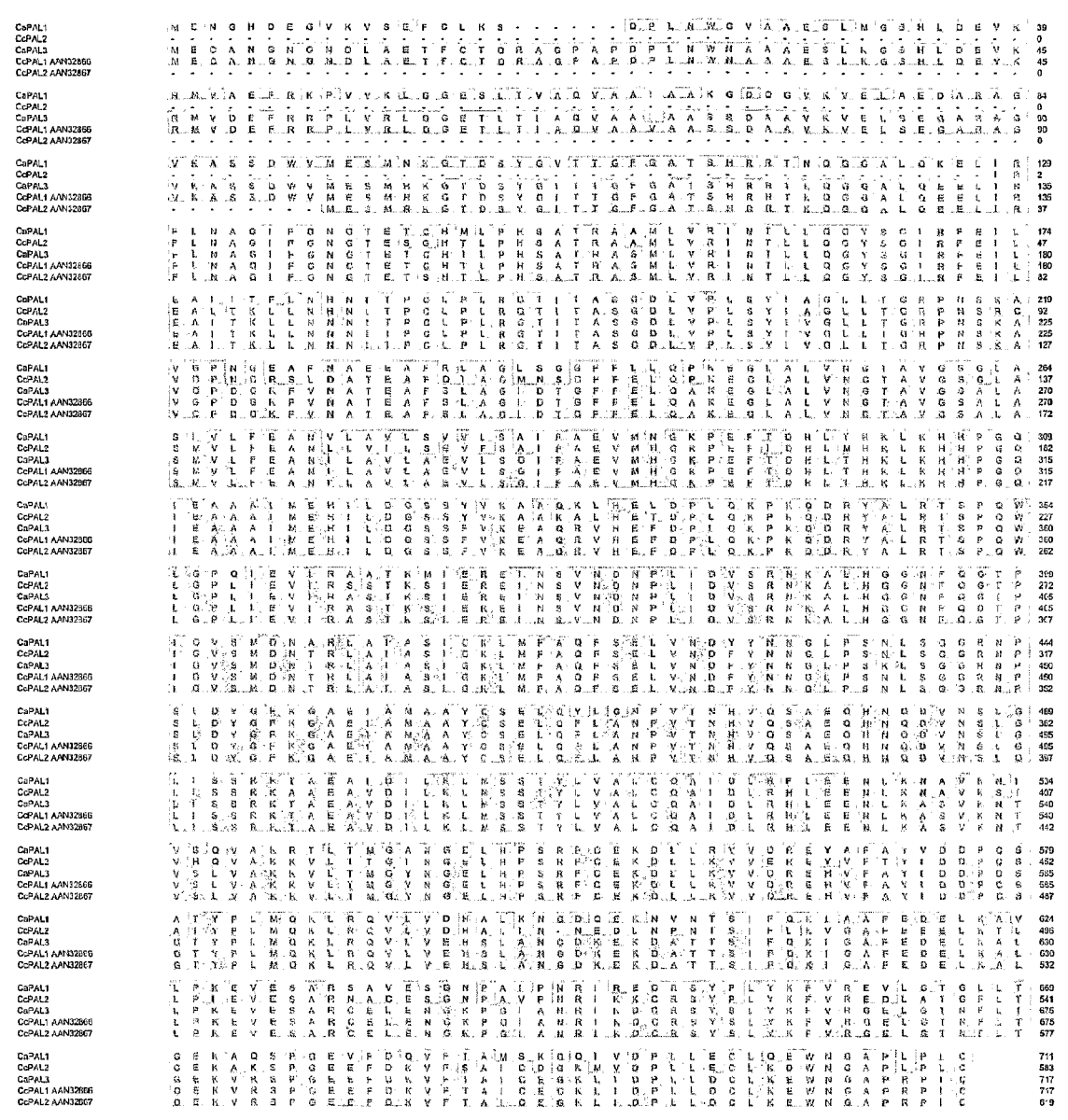

An alignment of the complete ORF encoded by pML8 (CaPAL1) (SEQ ID NO: 1) and two complete *Coffea canephora* PAL protein sequences available in public databanks, CcPAL1 (GenBank Accession Number AAN32866) (SEQ ID NO: 48) and CcPAL2 (GenBank Accession Number AAN32867) (SEQ ID NO: 49) is presented in FIG. 5A. These data demonstrate that CaPAL1 (SEQ ID NO: 20) has 83.1% and 74.3% identity at the amino acid level with the full length *Coffea canephora* CcPAL1 and CcPAL2 sequences (SEQ ID NOs: 48, 49), demonstrating that CaPAL1 is a new unique coffee PAL sequence. In addition, two partial PAL sequences from *Coffea arabica* were present in the NCBI database (GenBank Accession Numbers AAF27654 and AAF27655).

Figure 5B:
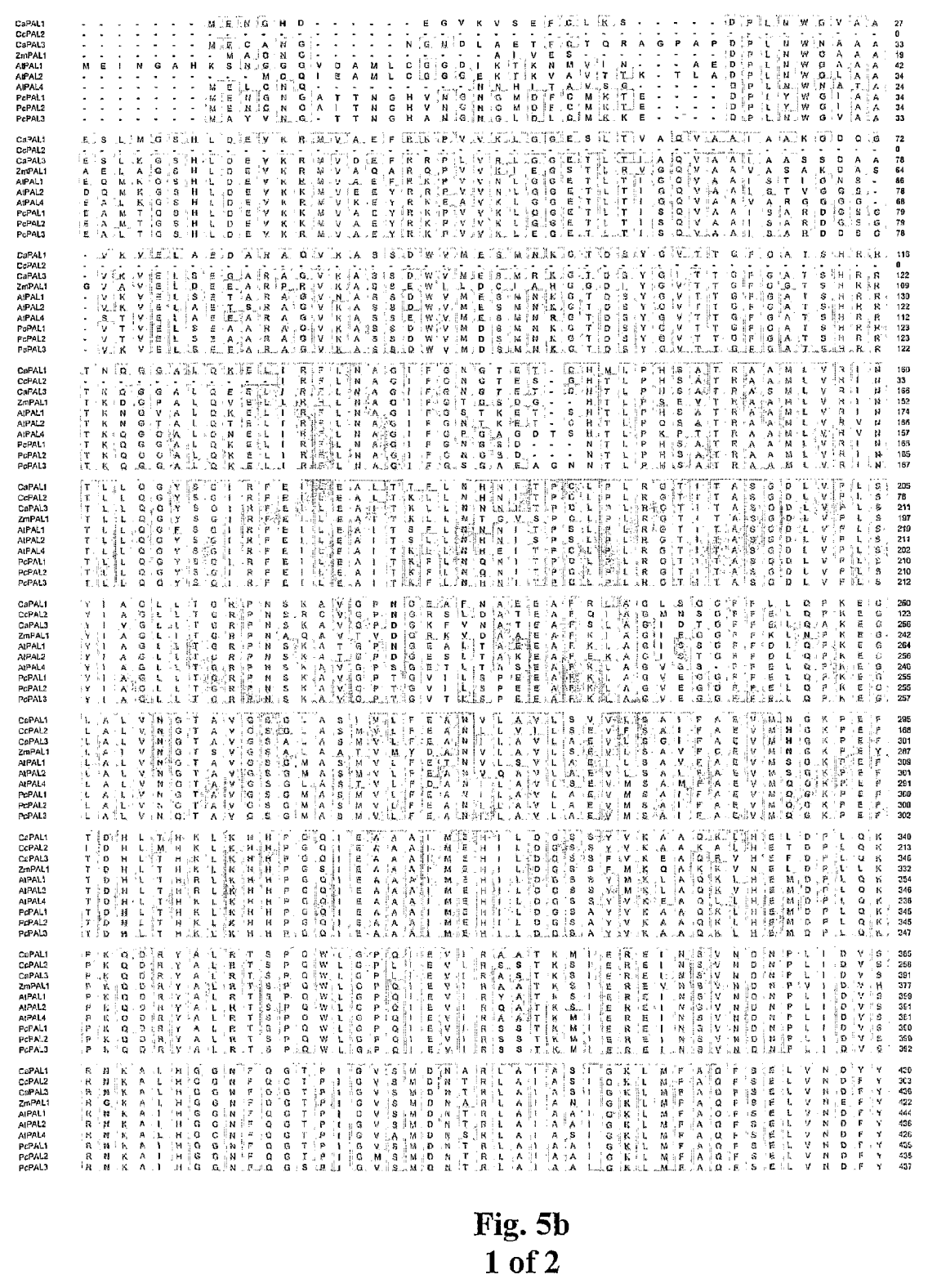
Figure 5B:
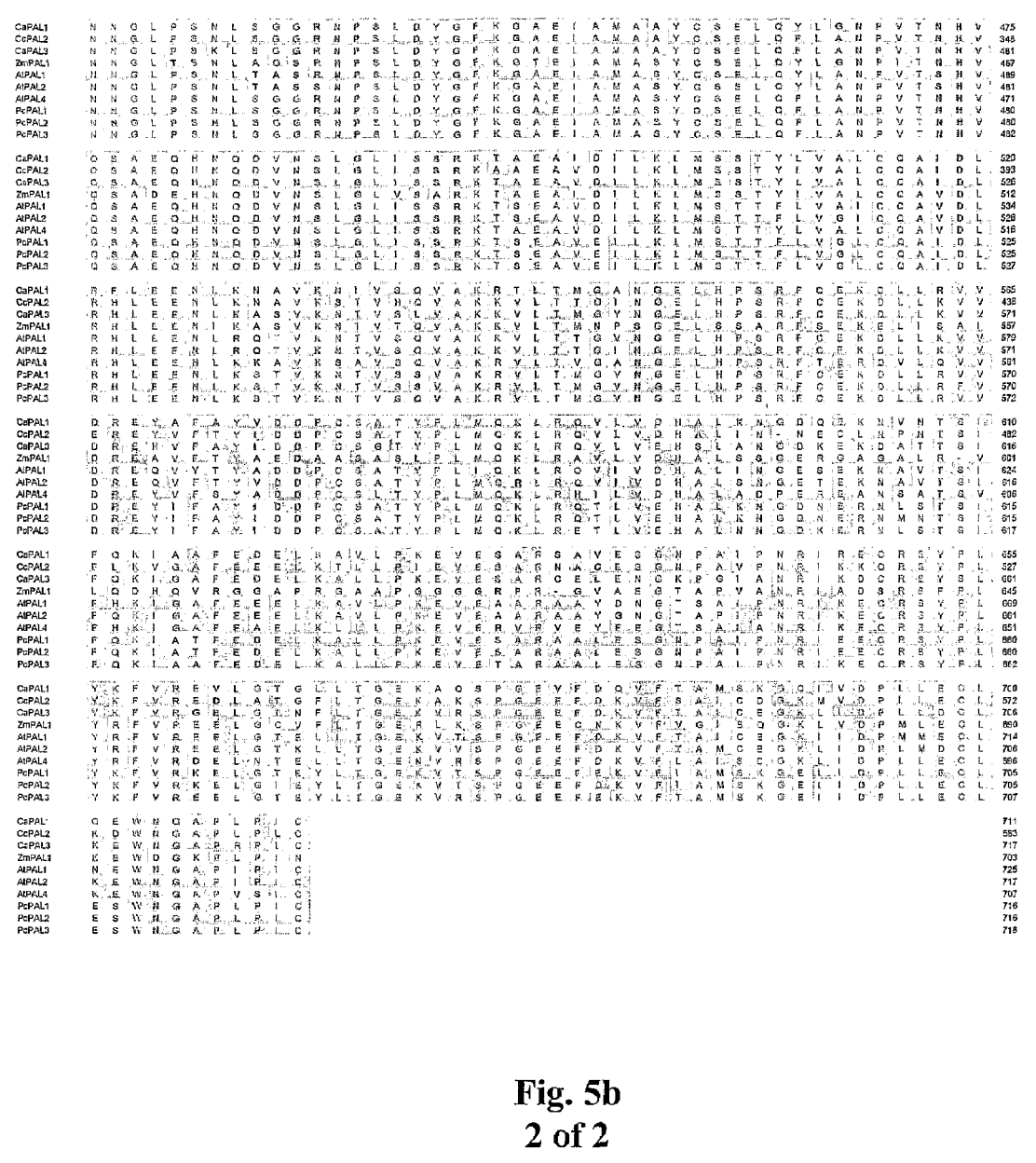

An alignment of CaPAL1 (pML8) (SEQ ID NO: 1) with biochemically-characterized PAL proteins (FIG. 5B) shows that the newly isolated CaPAL1 coffee sequence exhibits 67.9%, 81.6%, 80.3%, 80%, 85%, 84.8% and 85.2% identity with *Zea Mays* PAL1 (SEQ ID NO: 50), *Arabidopsis thaliana* PAL1, PAL2, PAL4 (SEQ ID NOs: 51, 52, 53) and the *P. crispum* PAL1, PAL2 and PAL3 sequences (SEQ ID NOs: 54, 55, 56), respectively. These data confirm the annotation of the newly discovered ORF of pML8 as a coffee PAL protein (FIG. 5B). This alignment also shows that at protein level, the CaPAL1 sequence (SEQ ID NO: 20) presented here shares 69.8% and 83.1% identity with the isolated partial CaPAL2 (described below) and the complete CaPAL3 contained in pML14 (SEQ ID NO: 2) (described below).

*Coffea canephora* CcPAL2 (partial ORF). The second coffee unigene sequence found with high similarity to the plant PAL proteins was unigene #119778. It was not possible to recover the longest cDNA of this unigene (pccc125c13) from the libraries, so the original database EST sequence for this EST was used. The next longest EST clone pcccp19k7 was isolated and sequenced. The 840 bp EST for pccc125c13 (SEQ ID NO: 42) and the 673 bp cDNA contained in pcccp19k7 (SEQ ID NO: 41) were aligned using the Seqman software (DNASTAR). The resulting contiguous sequence showed that the two sequences were identical over the 431 bp overlapping region, thereby confirming they both belong to the same cDNA (FIG. 3).

The length of the unique sequence resulting from the contig of these two sequence was found to be 1082 bp long, and to encode a partial ORF sequence of 261 amino acids. Because the full length *P. crispum* PAL1 protein was 716 amino acids long, this coffee cDNA was assumed to be missing over 454 amino acids at the N terminal. To isolate the 5' end of this coffee PAL, specific primers were first designed for a 5' RACE PCR reaction. Using cDNA prepared from *C. canephora* (BP-409) pericarp RNA (all stages mixed, Table 1) according to the cDNA synthesis Method 2 described in Example 1, above, the primers PAL2-GSP1 and PAL2-GSP2 (SEQ ID NOs: 104, 105) (Tables 1-4), and the RACE PCR conditions described in Example 1 and in Table 2, a unique fragment of approximately 400 bp was obtained. The PCR fragment was sequenced without purification using the specific primer PAL2-GSP2 (SEQ ID NO: 105) that was employed for the amplification of this fragment. The resulting sequence (Race1_CcPAL2) (SEQ ID NO: 43) was 406 bp long and, as expected, overlapped the 5' end of the sequence cccl25c13 (SEQ ID NO: 42) (FIG. 3B, 63 bp of overlapping sequence).

Because the newly isolated *C. canephora* 5' end sequence (Race1_CcPAL2) (SEQ ID NO: 43) was still missing the 5' end, a genome walker experiment was performed on eight libraries to try to recover the 5' sequence. These experiments used the primers PAL2-GW-GSP1 and PAL2-GW-GSP2 (SEQ ID NOs: 143, 144) (Table 7) designed from the 5' end of the *C. canephora* Race1_CcPAL2 sequence (SEQ ID NO: 43) and were carried out following Primer-Assisted Genome Waking PCR conditions described in Example 1. A unique PCR fragment of approximately 2100 bases pair (estimation of length in gel) was obtained with the *C. canephora* BP409/DraI digested library, cloned in the pCR4-TOPO vector and sequenced using the T3 and T7 universal primers and two gene specific internal primers. This resulting plasmid was called pML18, and the insert sequence (GW1_CcPAL2) (SEQ ID NO: 44) was found to be 2118 bp long and to overlap the sequence Race1_CcPAL2 (SEQ ID NO: 43) by 67 bp (FIG. 3A).

Figure 3A:
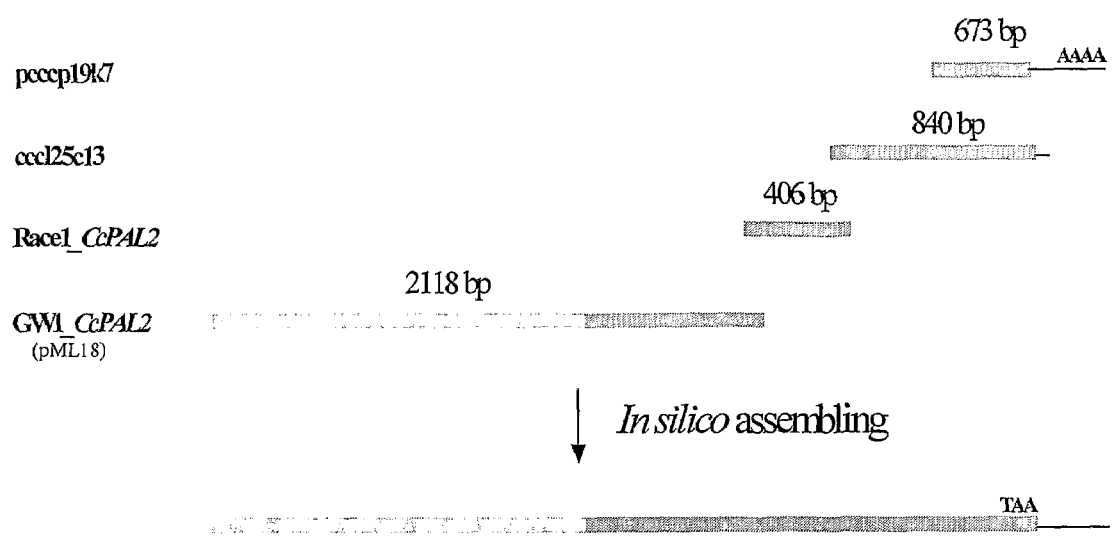
FIG. 3. Characterization of the partial ORF for CcPAL2 from *Coffea canephora*. A) In-silico generation of the consensus sequence for *C. canephora* CcPAL2 (SEQ ID NO: 3). The partial protein-coding region is shown as a hatched bar, the 3' untranslated region is shown as a thin black line, and the grey bar represents a genomic sequence believed to be an intron. B) The insert sequence of pcccp19k7 (SEQ ID NO: 41) and the partial insert sequence for the clone cccl25c13 (SEQ ID NO: 42) were aligned with the cDNA sequence Race1_CcPAL2 (SEQ ID NO: 43) and the genomic sequence GW1_CcPAL2 (SEQ ID NO: 44) to generate the in-silico partial sequence for CcPAL2 (SEQ ID NO: 3). The alignment was done using the CLUSTAL W program and manually optimized.
Figure 3B:
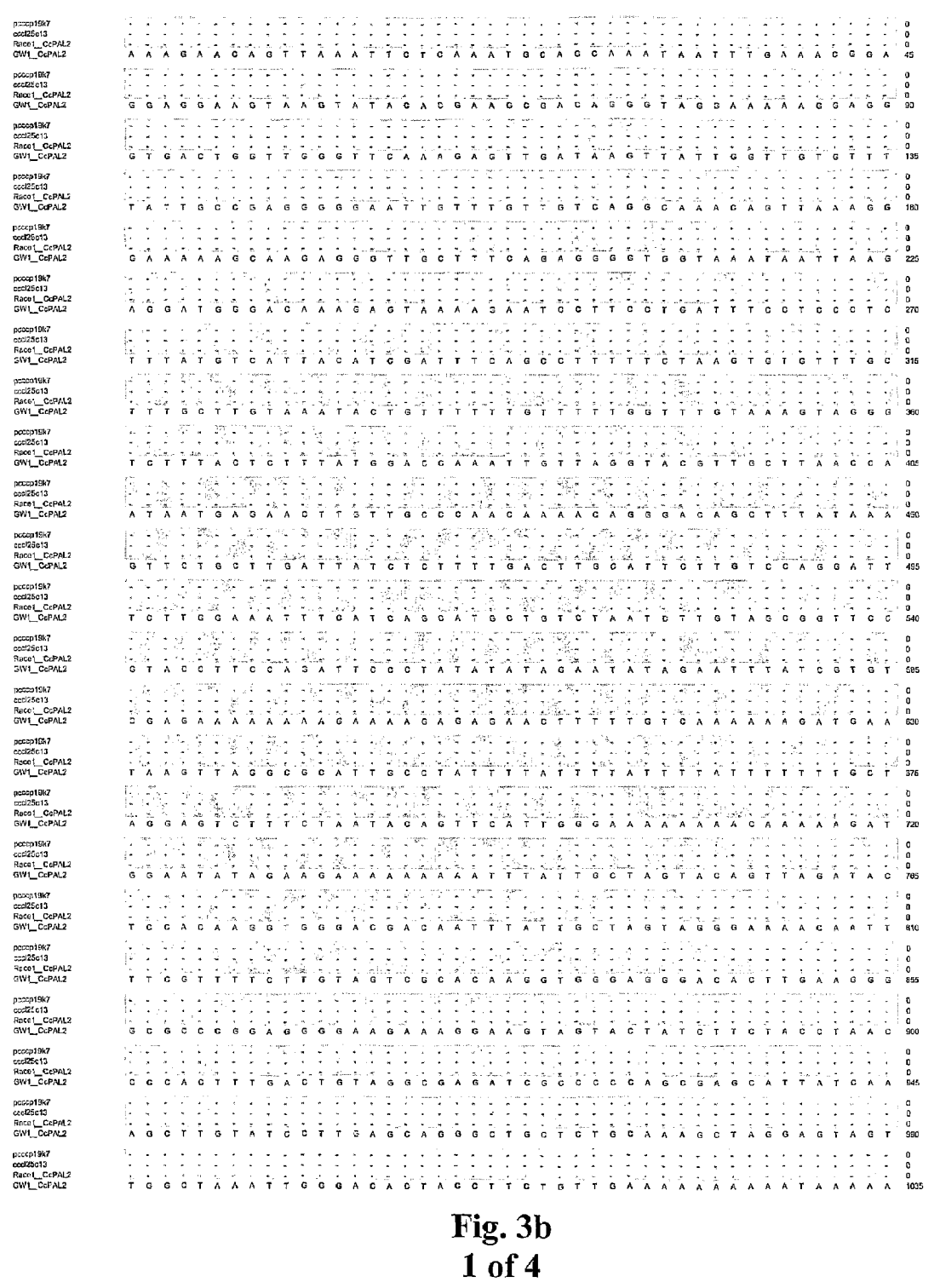
Figure 3B:
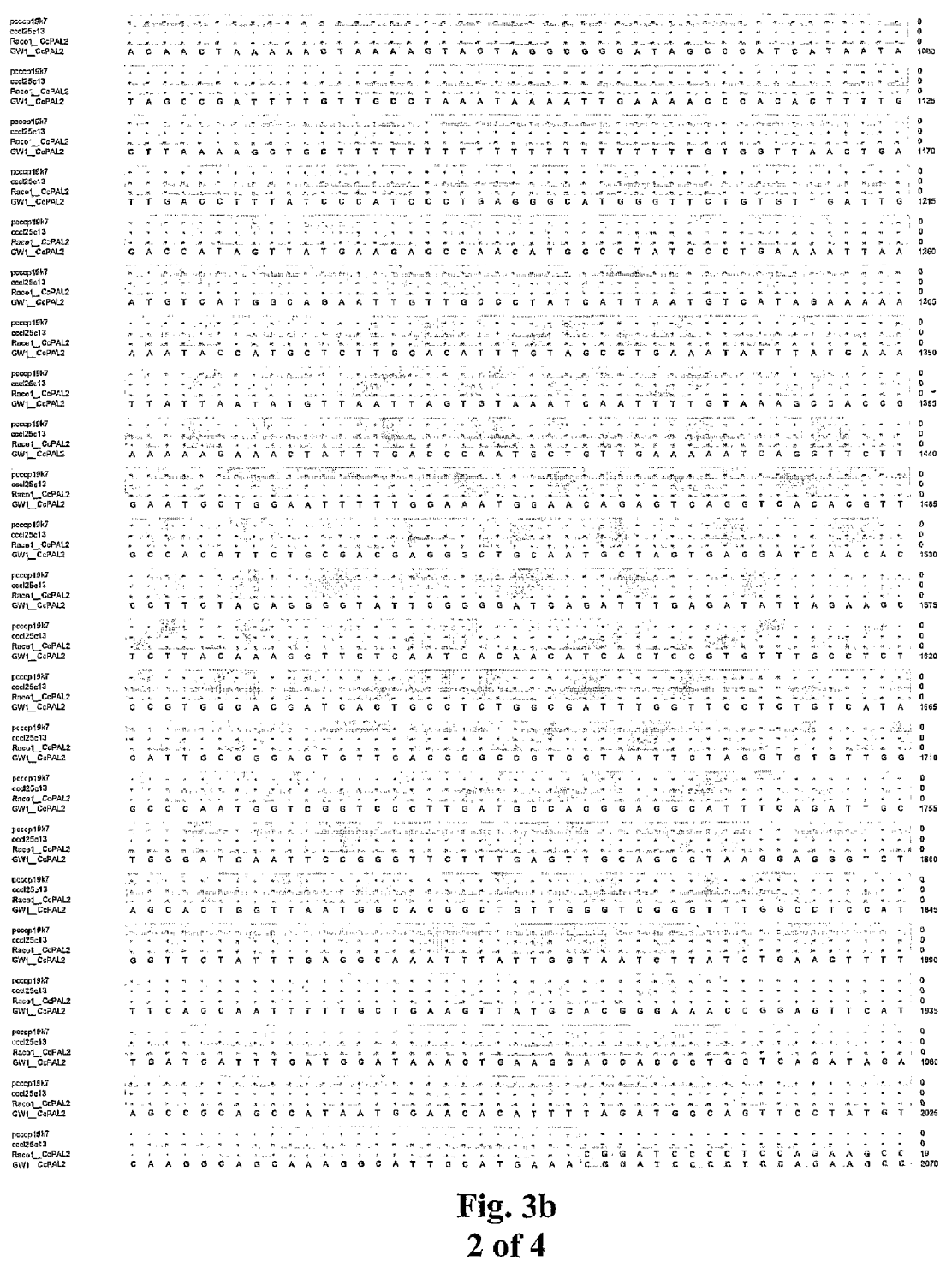
Figure 3B:
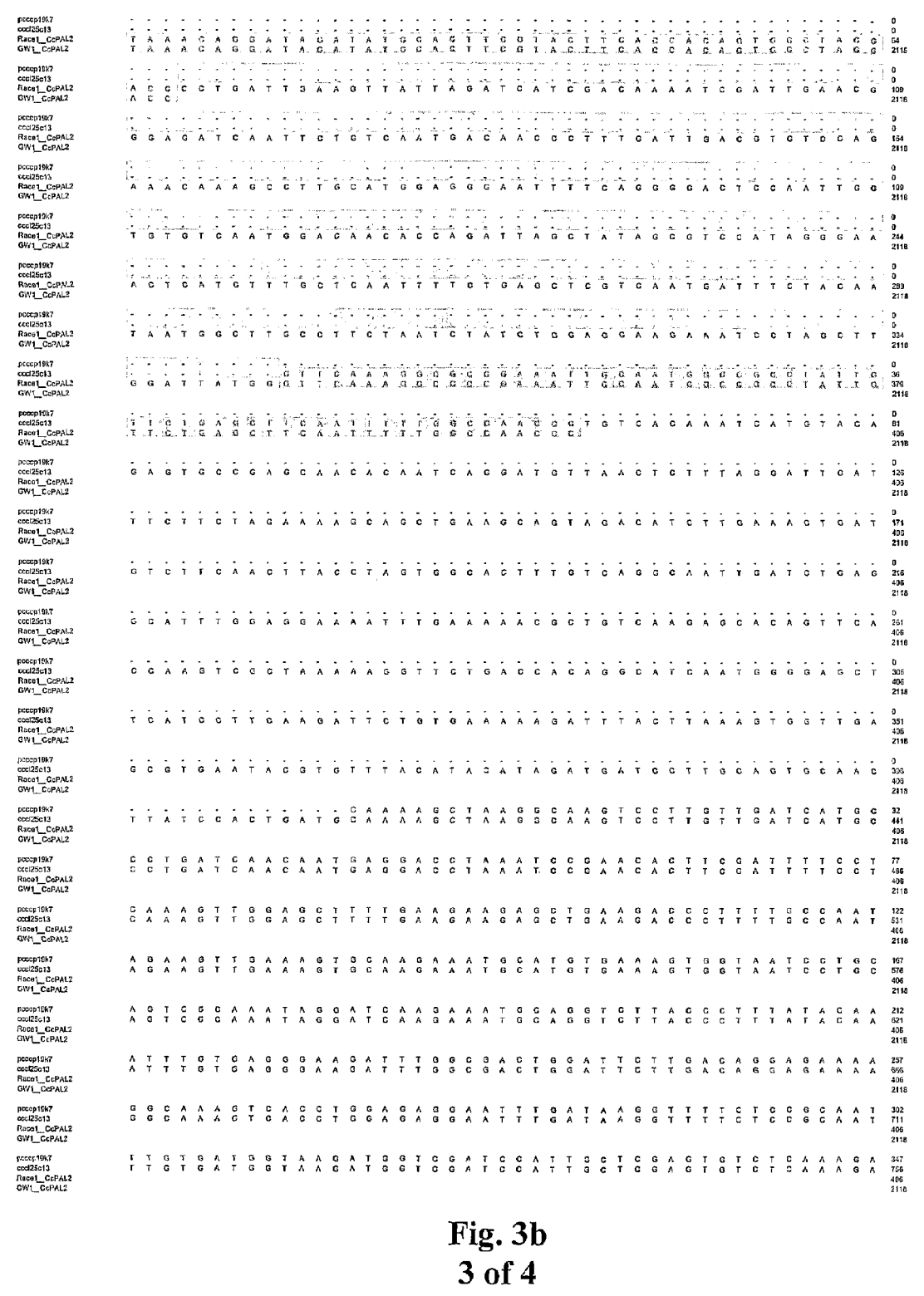

The various *canephora* PAL2 sequences noted in FIG. 3A were aligned using Seqman software (DNASTAR). The alignment showed that there was 100% identity in the overlapping regions (FIG. 3B), meaning that these sequences are from the same gene. The gene associated with the full 3476 bp contig generated was named CcPAL2 (SEQ ID NO: 3). The longest ORF in the CcPAL2 contiguous sequence was found to be 1752 bp (position 1430 to 3181) because the first 1429 first bp of the genomic sequence GW1_CcPAL2 (SEQ ID NO: 44) were associated with a large intron. The partial ORF of the CcPAL2 contig sequence encoded a partial protein of 583 aa. Based on the alignment of this 583 amino acid ORF with the full length *P. crispum* PAL1 protein (SEQ ID NO: 54) (716 aa) using Clustal-W (FIG. 5B), it is assumed that the coffee cDNA for CcPAL2 (SEQ ID NO: 3) is a partial, and its ORF is missing over 134 amino acids at the N-terminal end. Additional 5'RACE or an additional primer assisted genome walk procedures are expected to isolate the missing 5' coding sequence of the CcPAL2 (SEQ ID NO: 3) gene.

The alignment of the partial CcPAL2 protein sequence (SEQ ID NO: 22) with the two *Coffea canephora* PAL sequences available in the NCBI databank and with the two other coffee PAL sequences described here, shows that CcPAL2 (SEQ ID NO: 22) is a unique coffee PAL (FIG. 5A). The identity scores from this alignment show that the partial CcPAL2 protein sequence (SEQ ID NO: 22) has 85.2% and 85.2% identity with the publicly available full length *Coffea canephora* PAL1 (GenBank Accession Number AAN32866) (SEQ ID NO: 48) and PAL2 (GenBank Accession Number AAN32867) (SEQ ID NO: 49) sequences, and 69.8% with the CaPAL1 (SEQ ID NO: 20) and 85.1% with the CaPAL3 (SEQ ID NO: 21) described herein.

Another alignment (not shown) revealed that the CcPAL2 protein sequence (SEQ ID NO: 22) also shares 84.5% and 83.8% identity with the two partial PAL publicly available from *Coffea arabica* (GenBank Accession Numbers AAF27654 and AAF27655, respectively) over the region in common for all three sequences. These data confirm that the newly discovered partial ORF of CcPAL2 represents a new coffee PAL protein sequence.

Another alignment between the partial CcPAL2 protein sequence, several biochemically characterized PAL proteins, and the two other coffee PAL sequences presented here is shown in FIG. 5B. The newly discovered partial CcPAL2 sequence exhibits 69.6%, 81.6%, 81.5%, 82%, 83.5%, 83.4% and 83.9% identity with *Zea Mays* PAL1 (SEQ ID NO: 50), *Arabidopsis thaliana* PAL1, PAL2, PAL4 (SEQ ID NOs: 51, 52, 53) and the *P. crispum* PAL1, PAL2 and PAL3 (SEQ ID NOs: 54, 55, 56) sequences, respectively. The alignment data strongly supports the argument that the partial ORF of CcPAL2 represents a coffee PAL protein sequence. It also clearly shows that CcPAL2 (SEQ ID NO: 22) is a different gene product from the new CaPAL1 (SEQ ID NO: 20) and CaPAL3 (SEQ ID NO: 21) presented here, exhibiting 69.8% and 85.1% identity with these sequences.

*Coffea arabica* CaPAL3 (Full ORF). The third coffee unigene sequence found with high similarity to the plant PAL proteins was unigene #120370. The longest cDNA of this unigene (pcccp1611) (SEQ ID NO: 45) was isolated and sequenced. The insert of the clone pcccp1611 (SEQ ID NO: 45) was found to be 1060 bp long, and to encode a partial ORF sequence of 261 amino acids. Because the full length *P. crispum* protein was 716 amino acids long, it was assumed that the coffee PAL encoded by pcccp1611 (SEQ ID NO: 45) was missing over 455 amino acids at the N terminal end. To recover the missing 5' end, specific primers were designed for use in 5' RACE PCR.

cDNA was prepared from *C. canephora* (BP-409) pericarp RNA (all stages mixed, Table 1), according to the cDNA synthesis Method 4. Using the primers and PCR conditions described in Tables 1-4 and in Example 1, a fragment of approximately 400 bp was obtained. This fragment was cloned in the pCR4-TOPO vector and sequenced. The resulting plasmid (pML19) had an insert sequence (Race1_CcPAL3) of 377 bp (SEQ ID NO: 46). As expected, the insert of pML19 overlapped the 5' end of the sequence in pcccp1611 (SEQ ID NO: 45) (FIG. 4, 107 bp of overlapping sequence), but the sequence Race1_CcPAL3 (SEQ ID NO: 46) was still missing the 5' end of the coding sequence of the coffee PAL3 sequence (SEQ ID NO: 2).

Figure 4A:
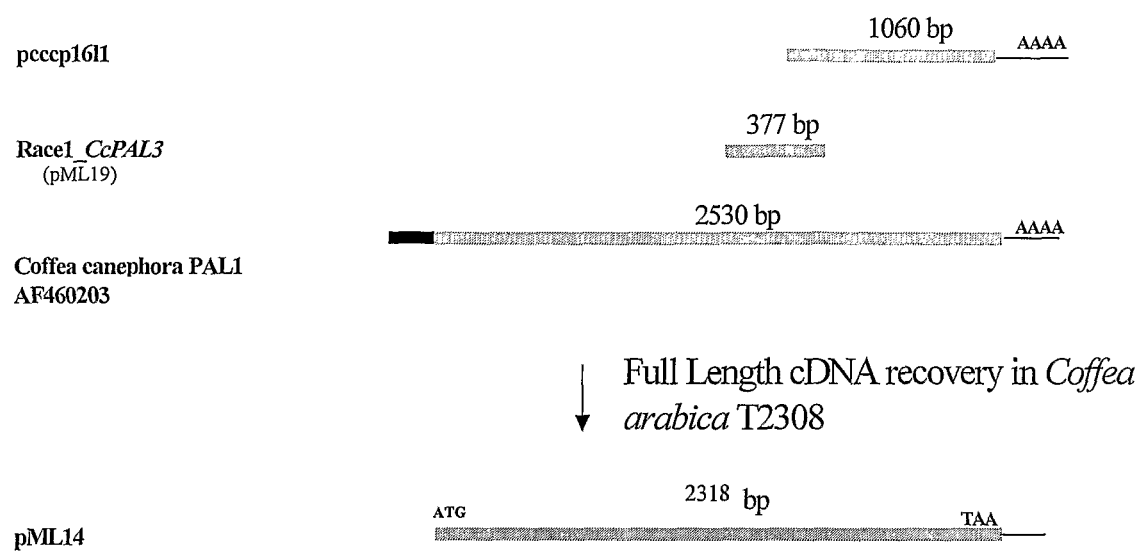
FIG. 4. Characterization of the complete ORF for CaPAL3 (SEQ ID NO: 2) from *Coffea arabica*. A) The full protein-coding region is shown as a hatched bar and the 5' untranslated region and 3' untranslated region are shown as a thick black and a thin black bars, respectively. B) The insert sequence (SEQ ID NO: 2) of pML14 aligned with the cDNA sequences pcccp1611 (SEQ ID NO: 45), Race1_CcPAL3 (SEQ ID NO: 46) and the *Coffea canephora* PAL1 cDNA sequence (GenBank Accession Number AF460203) (SEQ ID NO: 47). The alignment was done using the CLUSTAL W program and manually optimized. Nucleic acids marked in grey match the pML14 (CaPAL3) insert sequence (SEQ ID NO: 2).
Figure 4B:
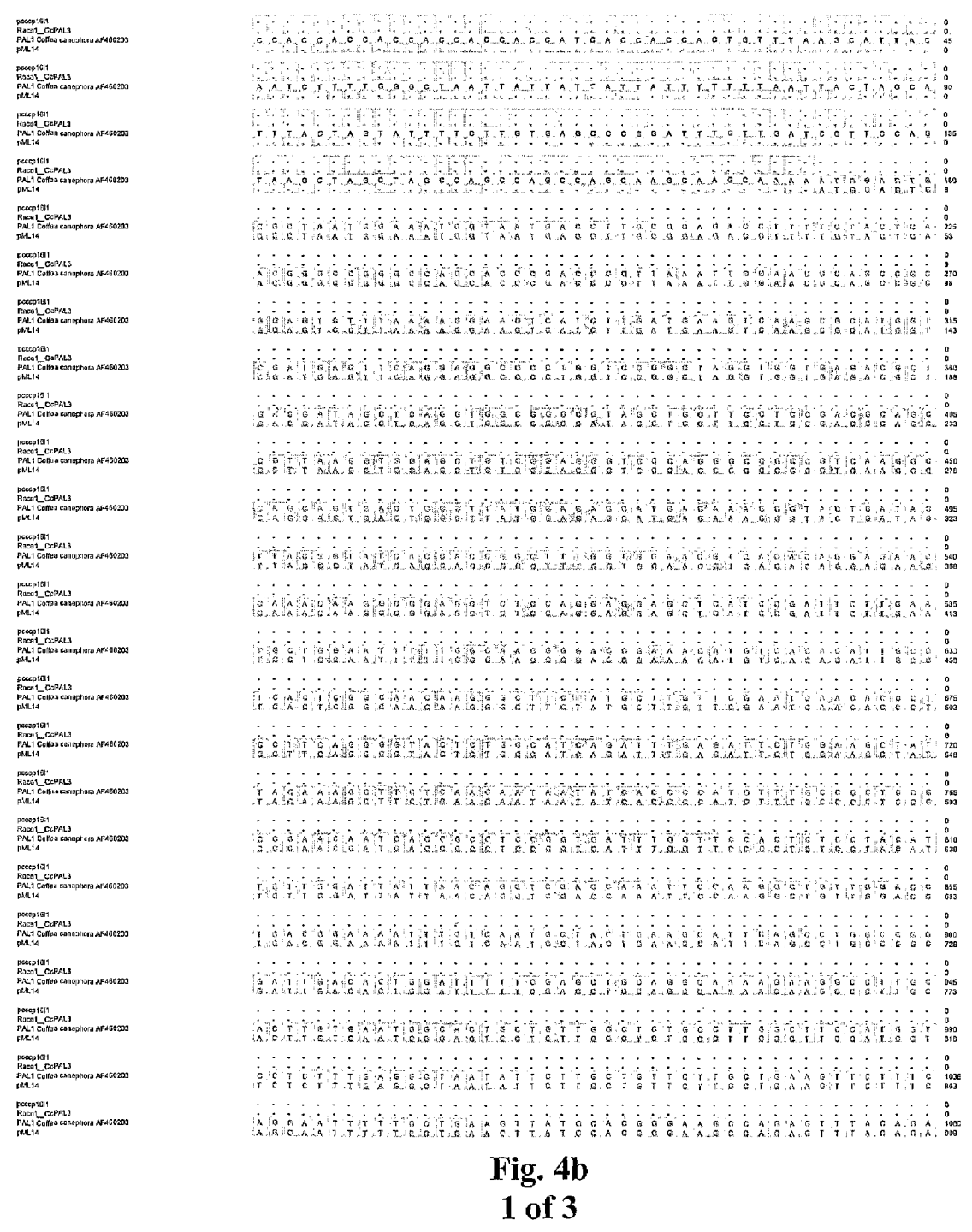
Figure 4B:
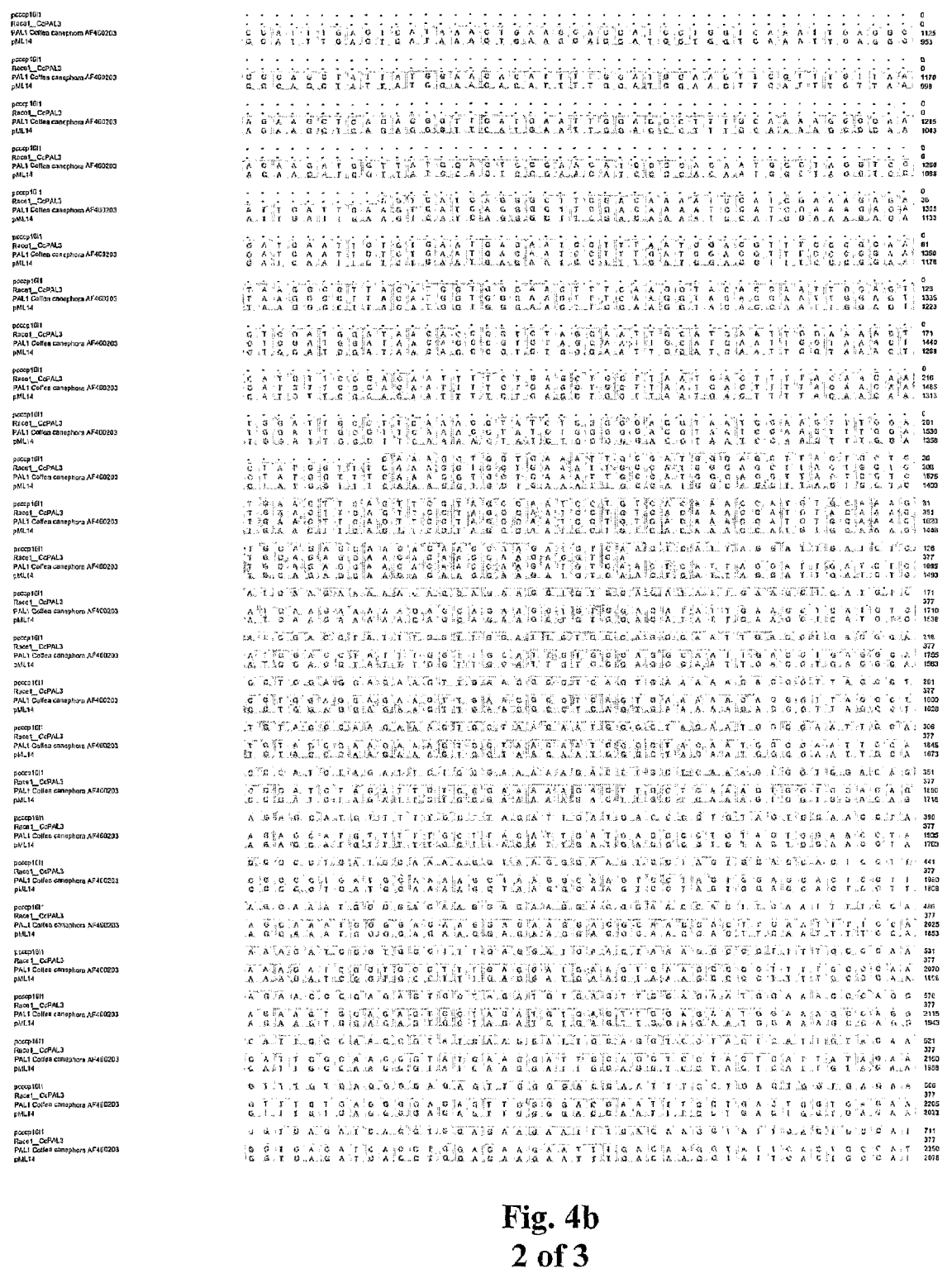
Figure 4B:
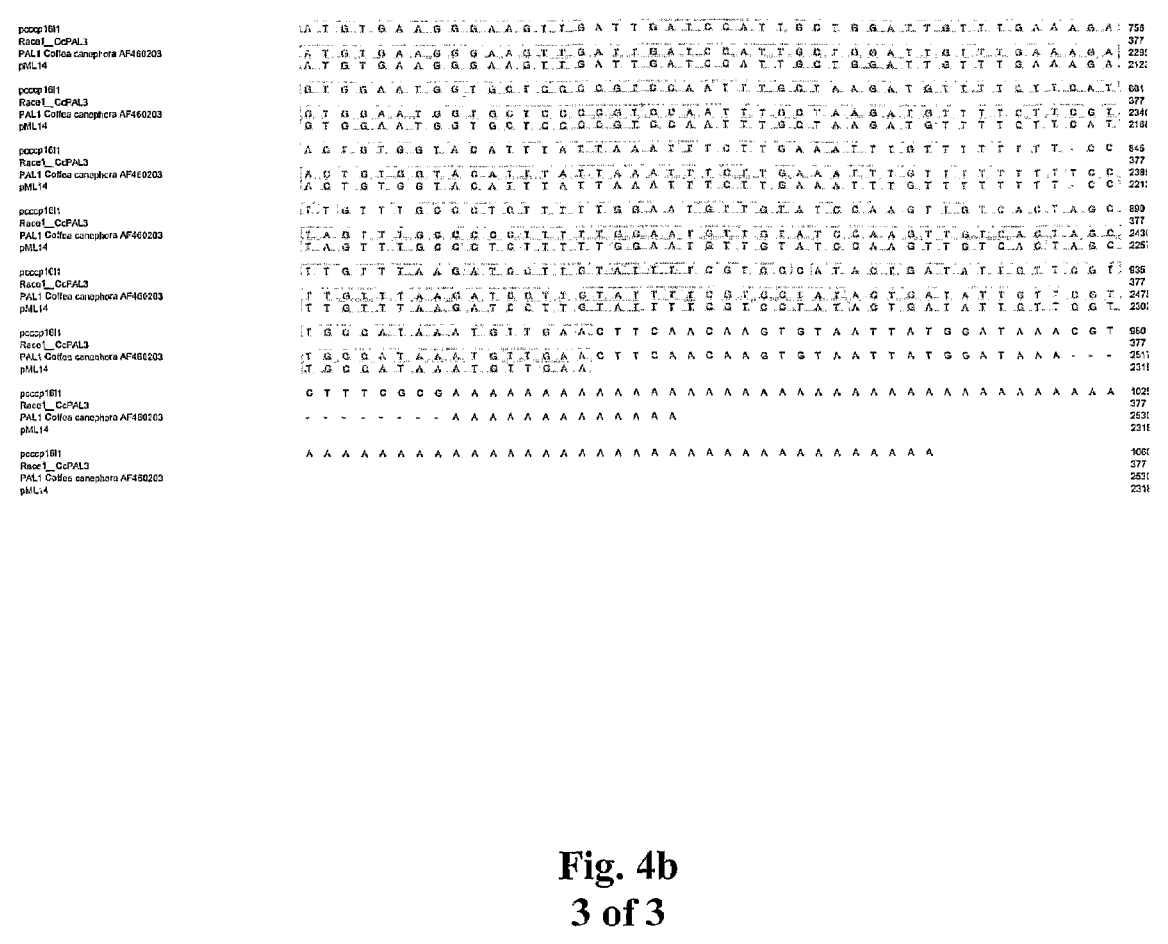

When the 1330 bp contig from pcccp1611 (SEQ ID NO: 45) together and the RACE fragment Race1_CcPAL3 (SEQ ID NO: 46) was aligned with a published *Coffea canephora* PAL sequence (GenBank Accession Number AAN32866) (SEQ ID NO: 48), it was determined that these three sequences were nearly identical, showing 99.2% identity over the regions in common. This fact allowed amplification of the complete ORF of the coffee PAL3 by using the published *Coffea canephora* PAL1 sequence (GenBank Accession Number AAN32866) (SEQ ID NO: 48) to design a 5' specific primer for this gene and a 3' specific primer from the sequence in pcccp1611 plasmid. Using cDNA made by Method 1 from RNA of *C. arabica* (T2308) grain (yellow stage, see Tables 8 and 9) and following PCR conditions described in Example 1 and Table 8, this experiment resulted in the generation of the cDNA sequence CaPAL3 (SEQ ID NO: 2) contained in the plasmid pML14 (FIGS. 4A and 4B). Sequence analysis of the pML14 insert (SEQ ID NO: 2) indicated that this cDNA was 2318 bp long, with a complete ORF of 2154 bp, which encodes a polypeptide (SEQ ID NO: 20) of 717 amino acids having an estimated molecular weight of 77.93 kDa.

The alignment in FIG. 5A demonstrates that sequence of CaPAL3 (pML14) (SEQ ID NO: 2) is different from the new coffee PAL sequences CaPAL1 (SEQ ID NO: 1) and CcPAL2 (SEQ ID NO: 3) presented here (83.1% and 85.1%, respectively). However, this alignment also confirms that CaPAL3 (SEQ ID NO: 2) is almost identical to PAL1 and PAL2 from *Coffea canephora* (both clones have very similar sequences and thus appear to be allelic). This observation indicates that CaPAL3 (SEQ ID NO: 2) is actually a new, potentially *arabica*-specific allele of the coffee PAL 3 gene. It is believed that all three sequences are alleles of the *Coffea* PAL3 gene. The two other previously described partial *arabica* PAL protein sequences (GenBank Accession Numbers AAF27654 and AAF27655) are 99.3% and 95.9% identical to the CaPAL3 sequence (SEQ ID NO: 21) (over the region in common with the publicly available sequences), respectively, indicating that these are alleles of the CaPAL3 product. Alignment of the complete CaPAL3 protein sequence (SEQ ID NO: 21) was also carried out with several biochemically-characterized PAL protein sequences (FIG. 5B). This alignment demonstrates that the CaPAL3 coffee sequence exhibits high similarity with plant PAL proteins, showing 67.6%, 80.2%, 80.3%, 79.6%, 82%, 81.7% and 82.6% identity with *Zea Mays* PAL1 (SEQ ID NO: 50), *Arabidopsis thaliana* PAL1, PAL2, PAL4 (SEQ ID NOs: 51, 52, 53) and the *P. crispum* PAL1, PAL2 and PAL3 (SEQ ID NOs: 54, 55, 56) sequences, respectively. This observation confirms previous claims that this sequence encodes a PAL protein.

EXAMPLE 3

Isolation and Characterization of a *Coffea canephora* cDNA Clone Encoding Cinnamate-4-Hydroxylase (CcC4H)

*Coffea canephora* CcC4H (Full ORF). To find cDNA encoding coffee cinnamate-4-hydroxylase (C4H), two protein sequences encoding biochemically characterized C4H, AtC4H (*Arabidopsis thaliana*, GenBank Accession Number # BAA24355, Mizutani et al., 1997) (SEQ ID NO: 57) and PbC4H (*Populus balsamifera*, GenBank Accession Number #AAG50231, Ro et al., 2001) (SEQ ID NO: 58) served as query sequences for a BLAST search against the Nestlé/Cornell unigene set 5 using the tblastn algorithm.

Using *Arabidopsis thaliana* AtC4H protein sequence, only one unigene (#124550) was found to exhibit a very high level of identity (% identity=77%, e value=0, score=785). The other hits presented too low percent of identity with AtC4H ($\leq$29% identity, e-value$\geq$3e-52, scores$\leq$200) to potentially encode C4H.

The second search with PbC4H (SEQ ID NO: 58) from *Populus balsamifera* uncovered the same best hit #124550 (e value=0, score=869). The longest cDNA representing the 5' end of the unigene #124550 (pccc127h22) that seemed to encode a complete coding sequence of a C4H, was then isolated from the leaves library, sequenced, and named CcC4H (SEQ ID NO: 4). The insert of pccc127h22 was determined to be 1668 bp long, and to encode an ORF (coding) sequence of 1518 bp. The deduced protein sequence (SEQ ID NO: 23) shows a protein of 505 amino acids having a predicted molecular weight of 58.05 kDa.

Figure 6:
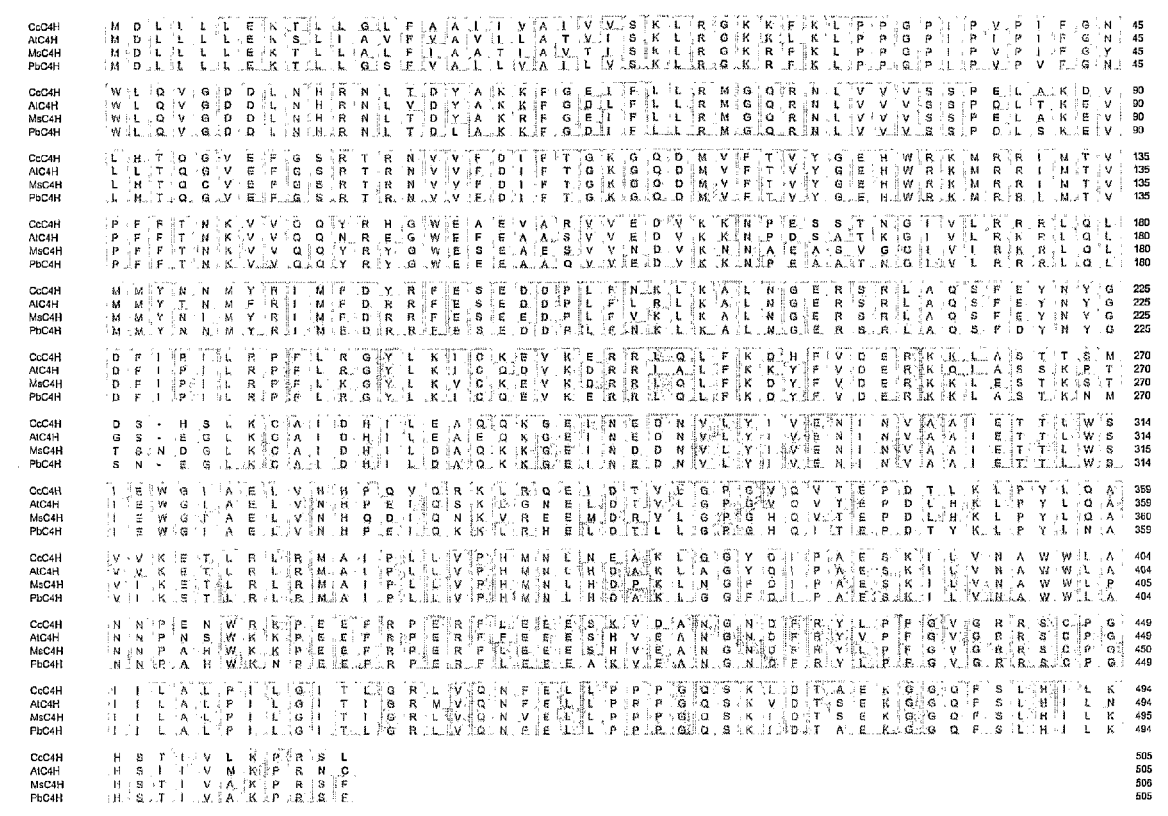

An alignment of the protein sequence (SEQ ID NO: 23) of pccc127h22 with the C4H protein sequences from *A. thaliana* (SEQ ID NO: 57), *P. balsamifera* (SEQ ID NO: 58) and MsC4H (*Medicago sativa*, GenBank Accession Number P37114) (SEQ ID NO: 158) demonstrated that pccc127h22 encoded protein (CcC4H) (SEQ ID NO: 23) shares 85%, 85.8% and 89.9% identity, respectively, with these protein sequences (FIG. 6). The alignment data indicates that the pccc127h22 plasmid contains a full length cDNA (SEQ ID NO: 4) encoding a *C. canephora* cinnamate-4-hydroxylase (CcC4H) (SEQ ID NO: 23). An alignment of the complete coding DNA sequence (5'UTR-ORF-3'UTR) contained in pccc127h22, with the complete coding DNA sequences (5'UTR-ORF-3'UTR) of C4H sequences from *A. thaliana* (D78596) and *P. balsamifera* (AF302495) was performed using ClustalW method in MegAlign software. The alignment demonstrates that the CcC4H DNA sequence (SEQ ID NO: 4) contained in pccc127h22 shares 71% and 75.6% identities with the respective public DNA sequences at DNA level. In this analysis, the complete DNA coding sequences were aligned (i.e., 5' UTR, complete ORF, and 3' UTR sequences were included).

EXAMPLE 4

Isolation and Characterization of *Coffea* cDNA Clones Encoding 4-Coumarate:Coenzyme A Ligases (Cc4CL1, Cc4CL2, and Ca4CL2)

*Coffea canephora* Cc4CL1 consensus (partial ORF). To find cDNA encoding coffee 4-coumarate:coenzyme A ligases, two protein sequences encoding biochemically-characterized 4CL activities served as query sequences for a BLAST search against the Nestlé/Cornell unigene set 5 using the tblastn algorithm: Nt4CL1, *Nicotiana tabacum*, (GenBank Accession Number 024145, Lee et al., 1996) (SEQ ID NO: 67), and At4CL1, *Arabidopsis thaliana*, (GenBank Accession Number Q42524, Ehting et al., 1999) (SEQ ID NO: 63). The first search with the 4CL1 protein sequence from *N. tabacum* revealed 3 unigenes; #119670 (e value=e-151), #128581 (e value=e-102) and #123098 (e value=e-101) that exhibit high levels of homology to Nt4CL1 (SEQ ID NO: 67). The second search with 4CL1 sequence from *A. thaliana* (SEQ ID NO: 63) uncovered the same three unigenes #119670 (e value=e-132), #128581 (e value=2e-71), and #123098 (e value=2e-86).

The longest cDNA representing the 5' end of the unigene #119670 (pcccp27d21) (SEQ ID NO: 59) encoding the partial coding sequence of a 4CL, was isolated from the pericarp library and sequenced. The insert of pcccp27d21 (SEQ ID NO: 59) was found to be 1124 bp long, and to encode a partial ORF of 316 amino acids. Because the full length *N. tabacum* protein (SEQ ID NO: 67) was 547 amino acids long, it was assumed that the coffee 4CL encoded by the cDNA contained in pccp27d21 (SEQ ID NO: 59) was missing over 231 amino acids at the N terminal.

Figure 7A:
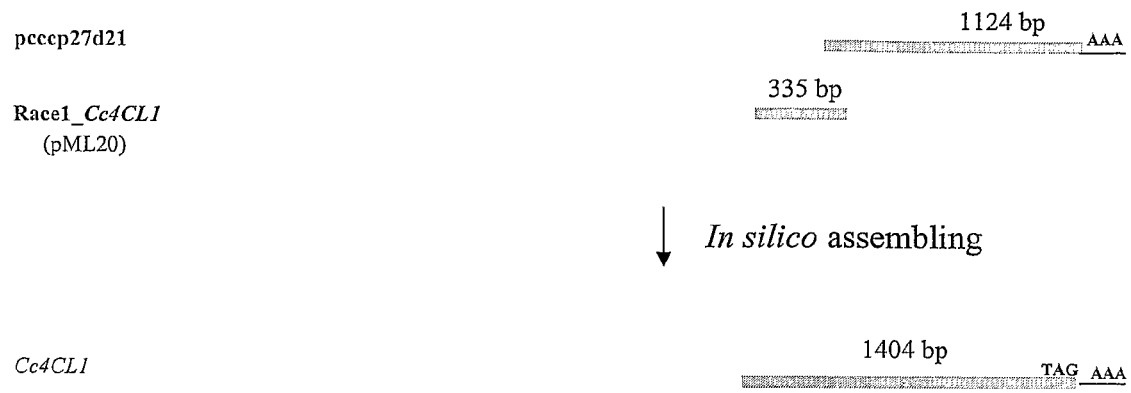
FIG. 7. Characterization of the partial ORF for Cc4CL1 from *Coffea canephora*. A) Generation of an in-silico-assembled partial sequence for Cc4CL1 from *C. canephora*. The partial protein-coding region is shown as a hatched bar and the 3' untranslated region is shown as a thin black line. B) The insert sequence of pcccp27d21 (SEQ ID NO: 59) was aligned with the cDNA sequence Race1_Cc4CL1 (SEQ ID NO: 60) to generate the in-silico partial sequence for Cc4CL1 (SEQ ID NO: 6). The alignment was done using the CLUSTAL W program, and manually optimized.
Figure 7B:
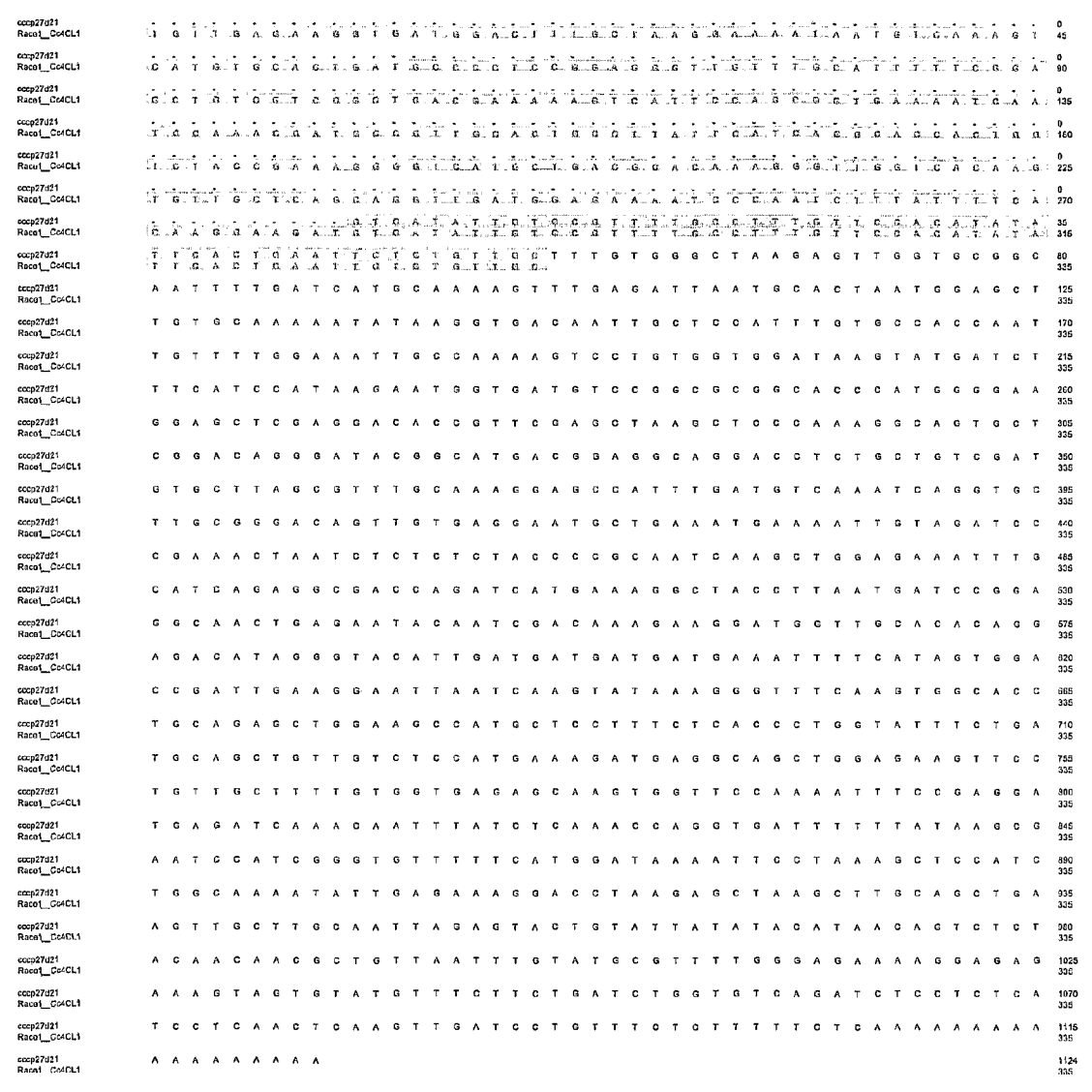

To recover the 5' missing end, specific primers were designed for use in the well established technique of 5' RACE PCR. cDNA was prepared from *C. canephora* (BP-409) pericarp tissue, all stages mixed, (Table 1) (small green, large green, yellow and red) by Method 3 described in Example 1, above. Using the primers and the PCR conditions described in Tables 1-4 and in Example 1, a unique fragment of approximately 350 bp was obtained (estimation by length in gel), cloned in pCR4-TOPO vector (TOPO TA Cloning Kit for Sequencing (Invitrogen), and sequenced using the universal primer T3. The resulting sequence (Race1_Cc4CL1) (SEQ ID NO: 60) was 335 bp long and, as expected, overlapped the 5' end of the sequence in pcccp27d21 (SEQ ID NO: 59) (FIG. 7, 55 bp of overlapping sequence), although the newly isolated Race1_Cc4CL1 (SEQ ID NO: 60) still did not contain the full 5' end of this gene.

The consensus sequence resulting from the alignment of Race1_Cc4CL1 (SEQ ID NO: 60) with sequence contained in pcccp27d21 (SEQ ID NO: 59) was 1404 bp long, and called Cc4CL1 (SEQ ID NO: 6). The longest ORF found in Cc4CL1 (SEQ ID NO: 6) was found to be 1230 bp long and encoded a partial protein sequence of 409 amino acids (SEQ ID NO: 25). Based on length of *Nicotiana tabacum* 4CL1, it is likely another 139 aa at the N terminal must be recovered to obtain the full length Cc4CL1. Additional 5'RACE or an additional primer assisted genome walker will be employed to isolate the full 5' missing end of the Cc4CL1 sequence.

A multiple alignment of the partial Cc4CL1 protein sequence (SEQ ID NO: 25) was done with biochemically-characterized 4CL sequences from *Arabidopsis thaliana* and *Nicotiana tabacum* (SEQ ID NOs: 63, 67), available in GenBank. (FIG. 9). This alignment confirmed the initial annotation of this coffee sequence using BLAST, i.e., the partial ORF of Cc4CL1 (SEQ ID NO: 6) encodes a coffee 4CL protein (SEQ ID NO: 25). The alignment shows 81.9% identity between partial Cc4CL1 sequence (SEQ ID NO: 25) and the Nt4CL2 protein sequence.

*Coffea arabica* Ca4CL2 (complete ORF) and *Coffea canephora* Cc4CL2 (complete ORF). The longest cDNA representing the 5' end of the unigene #123098 (pcccs30w16n14) encoding a partial coding sequence for a 4CL, was isolated from the 30 weeks grain library (30 weeks after flowering) and sequenced. The insert of pcccs30w16n14 was found to be 946 bp long, and to encode a partial ORF sequence of 217 amino acids. Further sequence analysis suggested that the sequences in unigene #128581 (singleton pccc124i21) and in unigene #123098 could actually belong to the same gene. A subsequent alignment of the completely sequenced plasmids pccc124i21 (insert length is 1778 bp) and pcccs30w16n14 sequences confirmed that the sequences of both plasmids could be assembled into a single contig sequence.

The alignment between the DNA sequences encoding the ORF regions contained in these plasmids show the protein sequences are 98.9% identical in the overlapping region, with the differences being due to single nucleotide polymorphisms. This result indicates that the sequences contained in the plasmids pccc124i21 and pcccs30w16n14 represent two alleles of the same gene termed Cc4CL2.

Based on sequences comparisons with other plant 4CL proteins, it was determined that the ORF of pccc124i21 was missing approximately 44 amino acids at the N terminal end. Using the 5' end sequence of the insert in pccc124i21, specific primers were designed for a primer assisted genome walking to isolate the missing 5' end of this gene (primers 4CL2-GW-GSP1 and 4CL2-GW-GSP2 (SEQ ID NOs: 145, 146), Table 7), following the PCR conditions described in Example 1.

A unique PCR fragment of approximately 1100 bases pair (estimation of length in gel) was obtained with the *C. canephora* BP409/EcoRV digested library (sequence obtained called GW1_Cc4CL2) (SEQ ID NO: 62). A second unique PCR fragment of approximately 1550 bases pair (estimation of length in gel) was obtained with the *C. arabica* T2308/StuI digested library (sequence obtained called GW1_Ca4CL2) (SEQ ID NO: 61). These two fragments (GW1_Cc4CL2 and GW1_Ca4CL2) (SEQ ID NOs: 62, 61) were then cloned in pCR4-TOPO vector and sequenced. The fragment GW1_Cc4CL2 (SEQ ID NO: 62) was 1102 bp long and overlapped the sequence contained in pccc124i21 over 579 bp (FIG. 8). The second fragment, GW1_Ca4CL2 (SEQ ID NO: 61), was 1547 bp long and overlapped the sequence contained in pccc124i21 over 571 bp (FIG. 8). Over 800 bp of DNA sequence upstream of the 4CL2 start codon (ATG) was recovered in GW1_Ca4CL2 (SEQ ID NO: 61). This upstream sequence includes the 5' UTR sequence of the 4CL2 gene as well as a significant portion of the promoter sequence for this gene. These newly isolated 5' end 4CL sequences and the sequence in the cDNA pccc124i21 allowed the design of two new primers (see Table 8 and Table 9) capable of specifically amplifying the complete ORF of the coffee 4CL2.

Figure 8A:
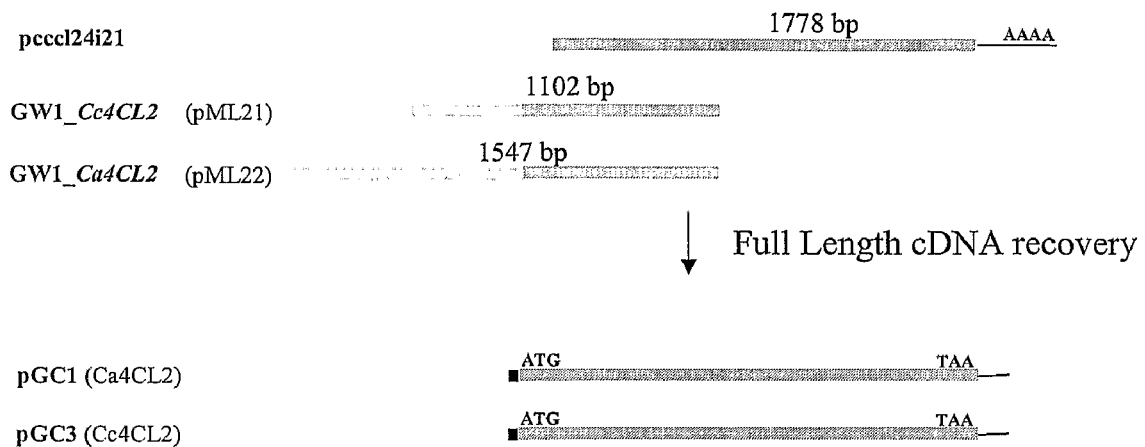
FIG. 8. Isolation and characterization of the complete ORF for Ca4CL2 (SEQ ID NO: 5) from *Coffea arabica* and Cc4CL2 (SEQ ID NO: 7) from *Coffea canephora*. A) Isolation of two cDNA containing the complete ORF sequences of 4CL2 from both *C. arabica* and *C. canephora* (SEQ ID NOs.
Figure 8B:
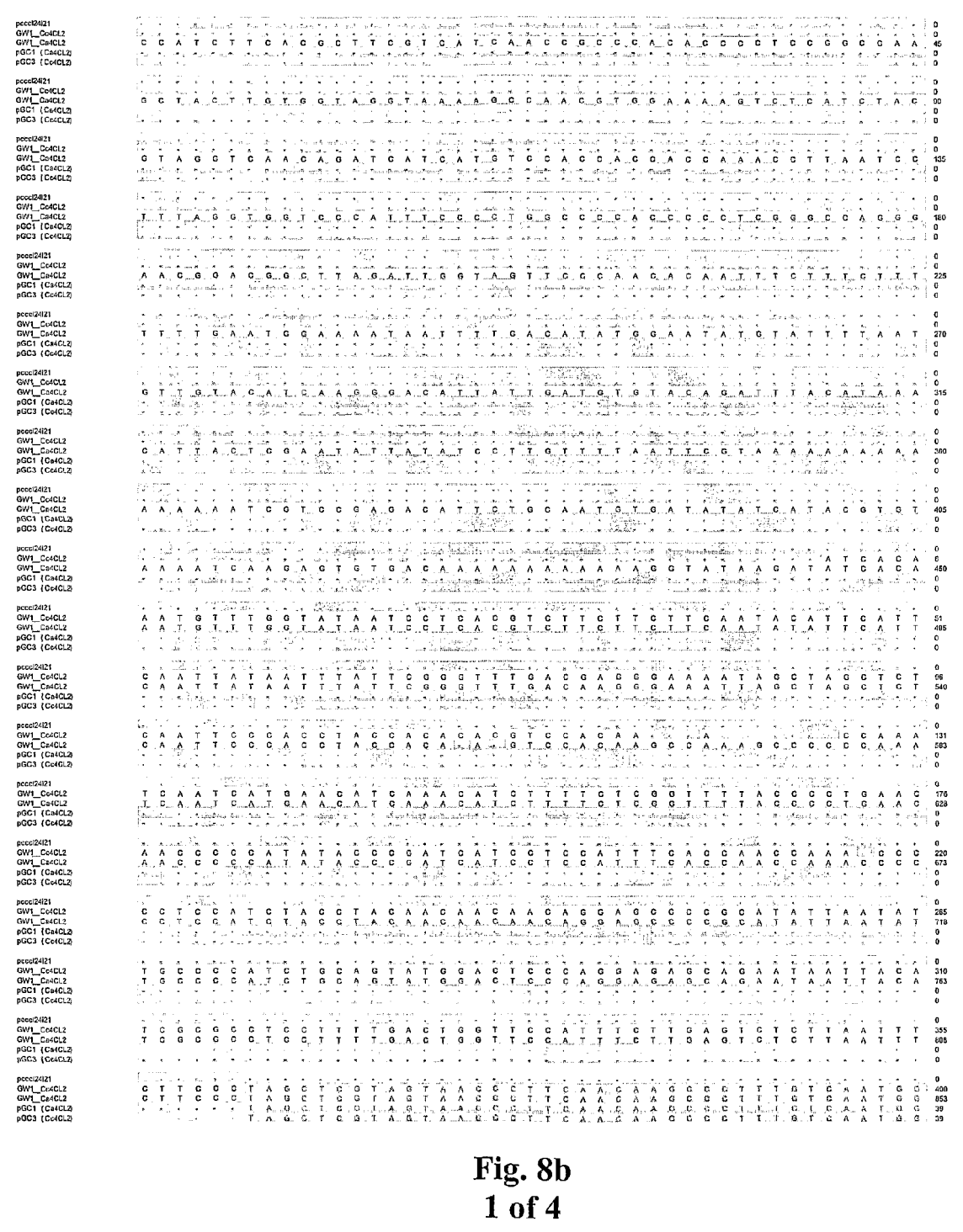
Figure 8B:
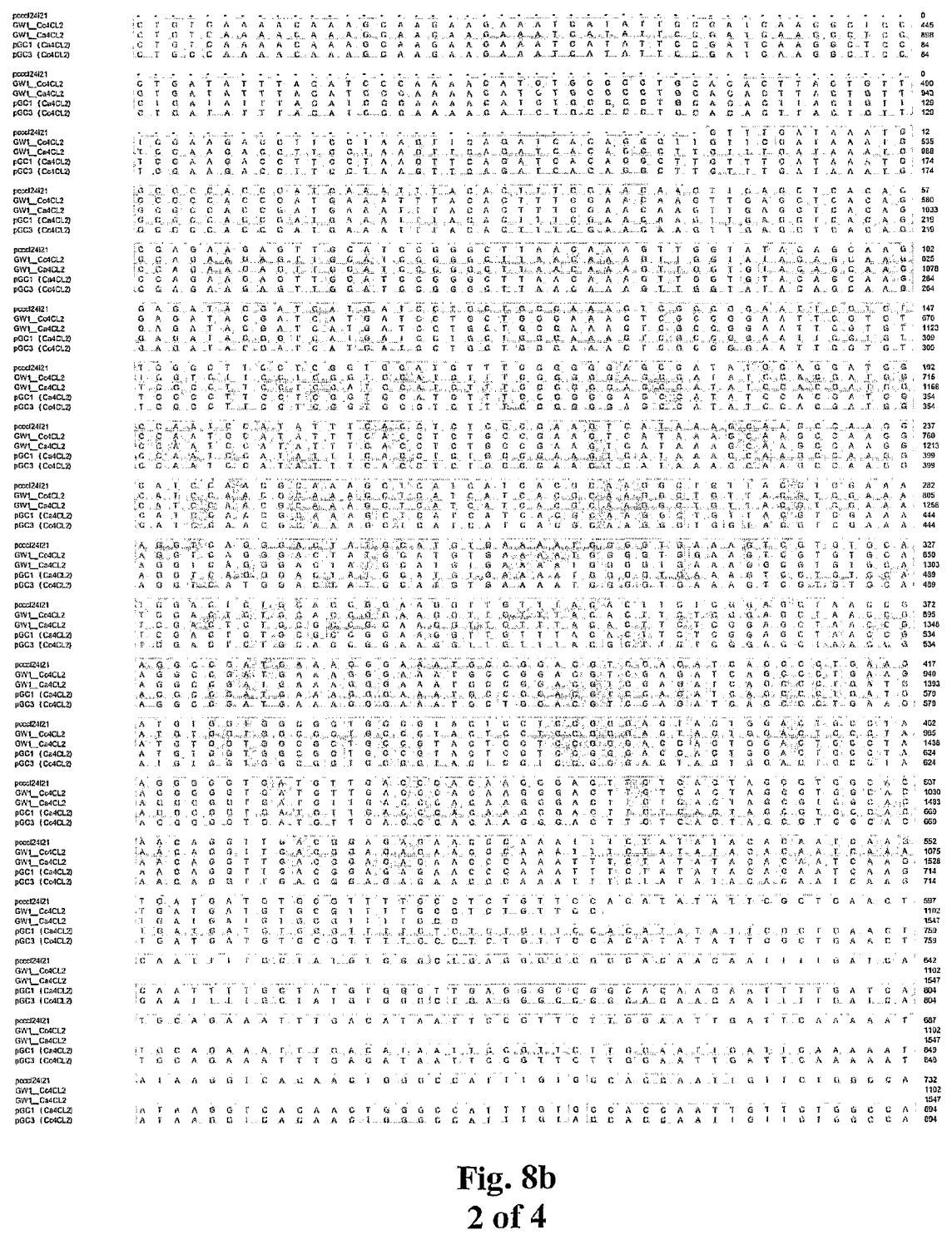
Figure 8B:
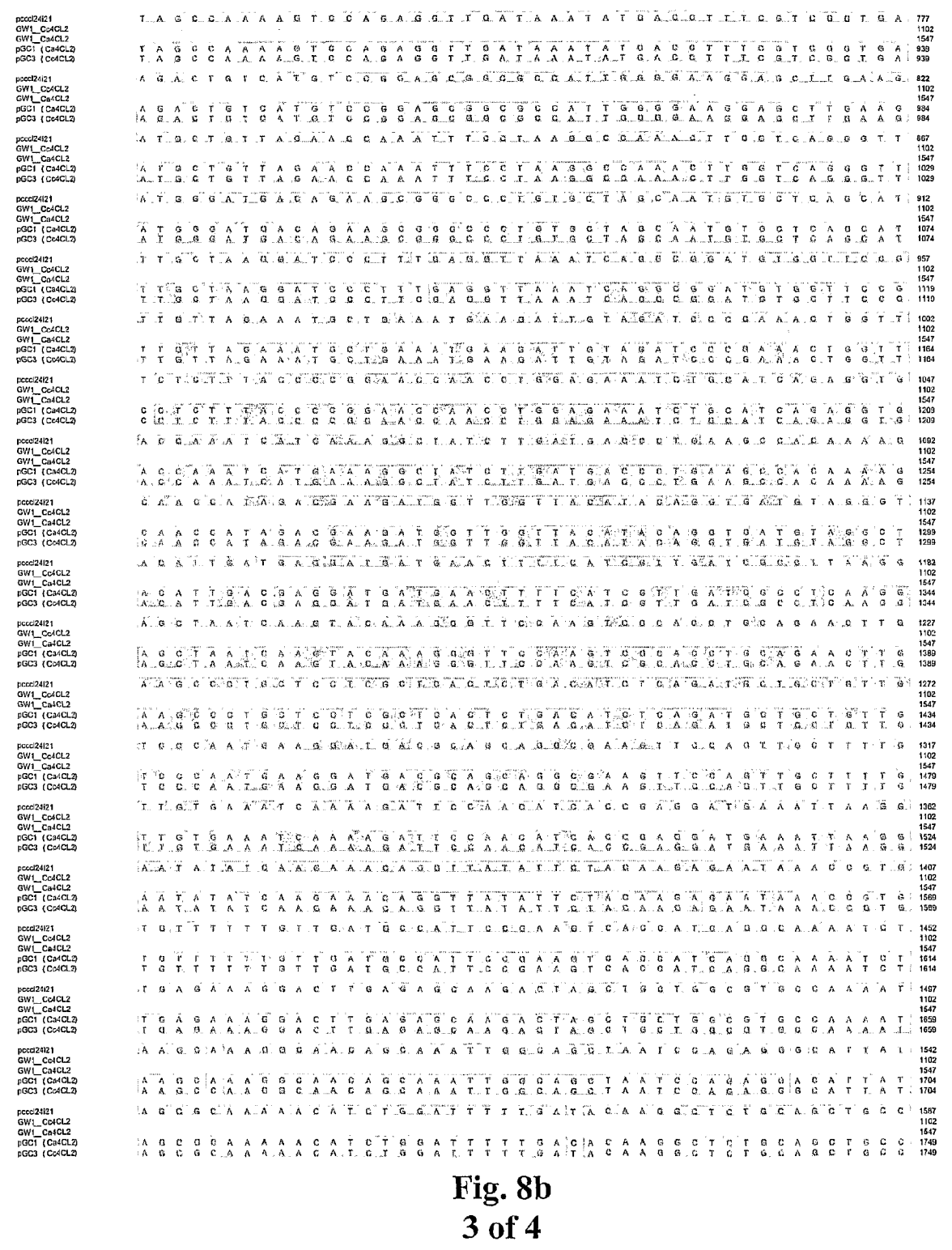
Figure 8B:
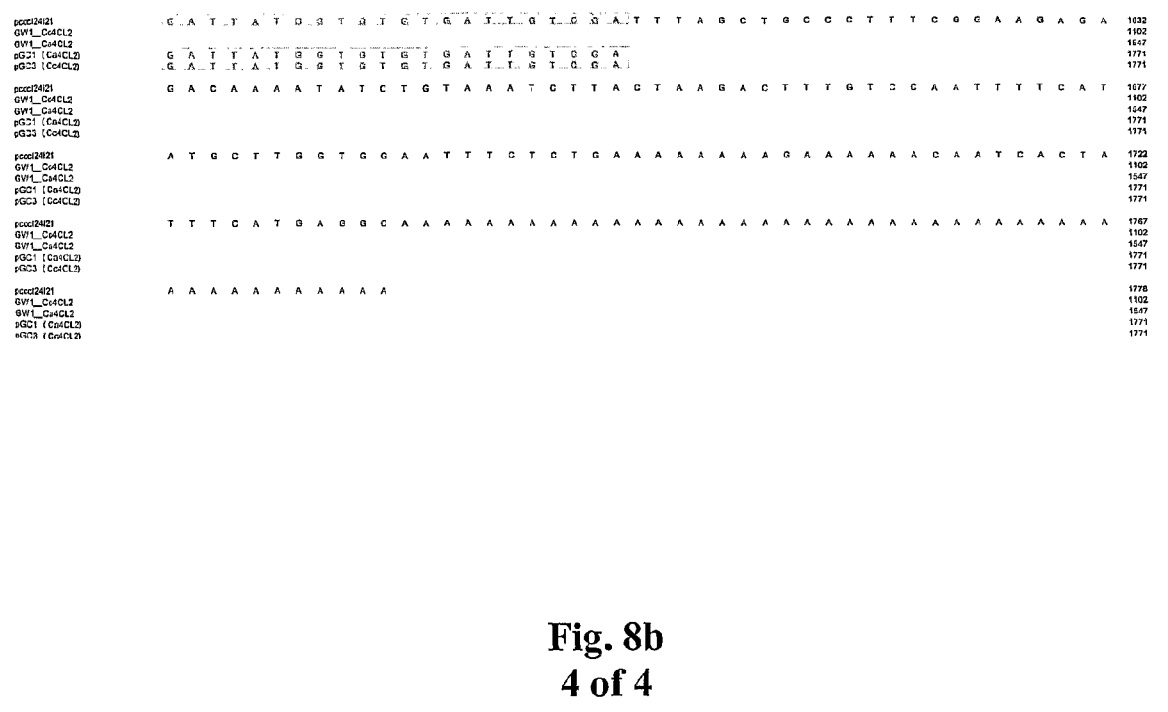

Using cDNA generated by Method 1 from *C. arabica* (T2308) pericarp RNA (yellow stage: see Table 8) and primers and PCR conditions described in Example 1 and Tables 8 and 9, a plasmid named pGC1 was produced containing a fragment of 1771 bp whose sequence was named Ca4CL2 (SEQ ID NO: 5) (FIGS. 8A and 8B). Sequence analysis indicated that pGC1 contained a complete ORF of 1626 bp that encoded a polypeptide (SEQ ID NO: 24) of 541 amino acids having an approximate molecular weight of 59.4 kDa.

Using cDNA generated by Method 1 from *C. canephora* (BP409) pericarp RNA (yellow stage: see Table 8) and primers and PCR conditions described in Example 1 and Tables 8 and 9, a plasmid named pGC3 was produced containing an insert of 1771 bp long whose sequence was called Cc4CL-2 (SEQ ID NO: 7) (FIGS. 8A and 8B). Sequence analysis indicated that pGC3 contained a complete ORF of 1626 bp that encoded a polypeptide (SEQ ID NO: 26) of 541 amino acids having an approximate molecular weight of 59.5 kDa.

A manually-optimized alignment was then carried out between the protein sequences (SEQ ID NOs: 24, 26) encoded by pGC1 (Ca4CL2) and pGC3 (Cc4CL2) (SEQ ID NOs: 5, 7) and biochemically-characterized 4CL sequences from *Arabidopsis thaliana* and *Nicotiana tabacum*, available from GenBank (FIG. 9). This alignment shows identity levels between 54.3% to 81.1% for the two coffee sequences and the other database 4CL sequences. The identity between the *arabica* and *canephora* sequences was determined to be 98.3%, supporting the argument that these sequences are alleles of the same coffee 4CL gene (i.e., 4CL2). The multiple alignment also shows 81.1% identity between the Ca4CL2 and Nt4CL1 protein sequences, and 81% identity between the Cc4CL2 and Nt4CL1 protein sequences. Moreover, the alignment shows that Ca4CL2 and Cc4CL2 (SEQ ID NOs: 5, 7) encode protein different from the Cc4CL1 protein described above, as the multiple alignment shows 77.8% of identity between Ca4CL2 (SEQ ID NO: 24) and Cc4CL1 (SEQ ID NO: 25) and between Cc4CL2 (SEQ ID NO: 26) and Cc4CL1 (SEQ ID NO: 25) proteins.

EXAMPLE 5

Isolation and Characterization of a *Coffea canephora* cDNA Clone Encoding Chalcone Synthase (CcCHS)

To find coffee cDNA encoding chalcone synthase, two protein sequences encoding chalcone synthase (CHS) served as query sequences for a BLAST search against the Nestlé/Cornell unigene set 5 using the tblastn algorithm: HaCHS, *Hypericum androsaemum*, GenBank Accession Number AAG30295 (SEQ ID NO: 69); and LeCHS *Lycopersicon esculentum*, GenBank Accession Number CAA38981 (SEQ ID NO: 70). Using the *Hypericum androsaemum* HaCHS protein sequence, only one unigene (#123889) was found to exhibit a very high level of identity (% identity=90%, e value=0, score=723). The second search with PbC4H from *Lycopersicon esculentum* LeCHS uncovered the same best hit #123889 (% identity=91%, e value=0, score=721).

A cDNA representing the 5' end of the unigene #123889 (pcccp8j10) (SEQ ID NO: 97) was isolated from the pericarp library and sequenced. The insert of pcccp8j10 (SEQ ID NO: 97) was found to be 1397 bp long and to encode a complete ORF sequence of 1176 bp, and was named CcCHS (SEQ ID NO: 8). The deduced protein sequence encodes a protein of 391 amino acids (SEQ ID NO: 27) having a predicted molecular weight of 42.92 kDa. A multiple alignment (ClustalW) of the deduced protein sequence (SEQ ID NO: 27) encoded by pcccp8j10 (SEQ ID NO: 97) with the highly related CHS protein sequences from *Hypericum androsaemum* and *Lycopersicon esculentum* (SEQ ID NOs: 69, 70) and the related characterized stilbene synthases VSS from *Vitis* (GenBank Accession Number AAB19887) (SEQ ID NO: 71) and PsSTS from *Pinus strobes* (GenBank Accession Number CAA87013) (SEQ ID NO: 72) demonstrates that CcCHS shares 90%, 90.5%, 75.7% and 70.8% identity with these protein sequences, respectively (FIG. 10), and supports the argument that pcccp8j10 (SEQ ID NO: 97) encodes a CHS protein rather than a VSS protein.

An alignment of the complete coding DNA sequence (5'UTR-ORF-3'UTR) contained in pcccp8j10 (SEQ ID NO: 97) with the complete coding DNA sequences (5'UTR-ORF-3'UTR) of CHS sequences from *Hypericum androsaemum* (AF315345) and *Lycopersicon esculentum* (X55195) was performed using ClustalW method in MegAlign software. The alignment demonstrates that the CcCHS complete coding sequence contained in pcccp8j10 (SEQ ID NO: 97) shares 72.8% and 70.2% identity with the respective public DNA sequences at DNA level. In this analysis, the complete DNA coding sequences were aligned (i.e., 5' UTR, complete ORF and 3' UTR sequences were included).

EXAMPLE 6

Isolation and Characterization of *Coffea canephora* cDNA Clones Encoding Chalcone Reductases (CcCHR1, CcCHR2A, and CcCHR2B)

To find cDNA encoding chalcone reductases, two protein sequences encoding chalcone reductases (CHR) served as query sequences for a BLAST search against the Nestlé/Cornell unigene set 5 using the tblastn algorithm: SrCHR, *Sesbania rostrata*, GenBank Accession Number CAA11226 (SEQ ID NO: 73); and PlCHR *Pueraria Montana* var. *lobata*, GenBank Accession Number AAM12529 (SEQ ID NO: 74). (Joung et al. (2003)). Using the SrCHR protein sequence from *Sesbania rostrata*, 3 unigenes with high levels of homology were uncovered: unigenes #125260 (e value=e-118), #125256 (e value=e-116) and #125257 (e value=3e-94). The second search with PlCHR from *Pueraria Montana* var. *lobata* uncovered the same 3 unigenes: #125256 (e value=2e-84), #125260 (e value=4e-83), #125257 (e value=1e-66).

*Coffea canephora* CcCHR1 (full ORF). A cDNA representing the 5' end of the unigene #125256 (pcccp24e9) was isolated from the pericarp library and sequenced. The insert of pcccp24e9 was found to be 1271 bp long and to encode a complete ORF sequence of 972 bp, which was named CcCHR1 (SEQ ID NO: 9). The deduced protein sequence reveals a protein of 323 amino acids (SEQ ID NO: 28) having a predicted molecular weight of 36.02 kDa. A manually optimized alignment of the deduced protein sequence encoded by pcccp24e9 was performed with the CHR protein sequences SrCHR from *Sesbania rostrata* (GenBank Accession Number CAA11226) (SEQ ID NO: 73), PlCHR from *Pueraria Montana* var. *lobata* (GenBank Accession Number AAM12529) (SEQ ID NO: 74) and MsCHR from *Medicago sativa* (GenBank Accession Number AAB41555 (SEQ ID NO: 75), biochemical and crystallographic information available Bomati et al. (2005b)). This alignment demonstrates that CcCHR1 protein (SEQ ID NO: 28) shares 60.7% and 48.9% and 48.3% identity with the protein sequences SrCHR, PlCHR and MsCHR (SEQ ID NOs: 73, 74, 75) noted above, respectively, (FIG. 11), and supports the initial annotation of pcccp24d9 as a *C. canephora* chalcone reductase.

*Coffea canephora* CcCHR2A AND CcCHR2B (full ORF). The longest cDNA representing the 5' end of the unigene #125257 (pccc128k6), which appeared to encode a coffee CHR, was isolated from the leaf library and sequenced. The insert of pccc128k6 was found to be 1205 bp long and to encode a nearly complete ORF sequence of 972 bp (only the initial MET appears to be missing). As this sequence was different from CcCHR1 (SEQ ID NO: 8), it was called CcCHR2A (SEQ ID NO: 10). The deduced protein sequence is a polypeptide (SEQ ID NO: 29) of 323 amino acids having a predicted molecular weight of 36.11 kDa. FIG. 11 shows an alignment of the deduced protein sequence (SEQ ID NO: 29) encoded by pccc128k6 (CcCHR2A) (SEQ ID NO: 10) with the CcCHR1 protein from *Coffea canephora* (SEQ ID NO: 28 described above) and CHR protein sequences SrCHR from *Sesbania rostrata* (GenBank Accession Number CAA11226) (SEQ ID NO: 73), PlCHR from *Pueraria Montana* var. *lobata* (GenBank Accession Number AAM12529; activity characterized by Joung et al. (2003) (SEQ ID NO: 74) and MsCHR from *Medicago sativa* (GenBank Accession Number AAB41555) (SEQ ID NO: 75). This alignment shows that the protein encoded by pccc128k6 shares 61.6%, 49.8% and 49.2% identity with the protein sequences SrCHR, PlCHR and MsCHR (SEQ ID NOs: 73, 74, 75), respectively. This alignment also indicates that the ORF in pccc128k6 is nearly complete, missing only the N-terminal amino acid (met) and thus, with the addition of this met, can be considered fall length. It is noted that the CcCHR2A protein sequence (SEQ ID NO: 29) exhibits a higher identity with CcCHR1 (79.5%) than with the publicly available CHR sequences presented in FIG. 11.

The longest cDNA representing the 5' end of the unigene #125260 (pccc126f18) was isolated from the leaf library and sequenced. The insert of pccc126f18 was found to be 1377 bp long, and was also found to contain one unusually short insertion of 24 bp in an otherwise complete ORF. Because this 24 bp insertion is not in frame, and when spliced from the sequence results in a complete ORF, it is believed to be an intron sequence. The ORF generated after in-silico splicing is 987 bp long, and encodes a protein sequence of 328 amino acids having a predicted molecular weight of 36.73 kDa.

Alignment of the spliced insert DNA sequence of pccc126f18 with the insert DNA sequence of pccc128k6 (CcCHR2A) (SEQ ID NO: 10) using ClustalW revealed that these two sequences exhibit 99.1% identity, and therefore are presumably allelic. Accordingly, pccc126f18 was called CcCHR2B (SEQ ID NO: 11). This alignment also shows that within the 1207 bp overlapping sequence, there are only nine single nucleotide differences in the ORF sequence and only 2 single nucleotide differences and a 2 base pair insertion in the 3' UTR of pccc126f18 (SEQ ID NO: 11).

FIG. 11 shows the alignment of the protein sequence (SEQ ID NO: 30) encoded by pccc126f18 (CcCHR2B) (SEQ ID NO: 11) with the CcCHR1 (SEQ ID NO: 28) and the CcCHR2A (SEQ ID NO: 29) protein sequences from *Coffea canephora* (described above) and CHR protein sequences SrCHR, PlCHR and MsCHR (SEQ ID NOs: 73, 74, 75). The alignment demonstrates that CcCHR2B (SEQ ID NO: 30) protein shares 61.3%, 48.9% and 48.3% identity with SrCHR, PlCHR and MsCHR (SEQ ID NOs: 73, 74, 75) protein sequences, respectively, and supports the initial annotation of pccc126f18 as a *C. canephora* chalcone reductase. This multiple alignment also shows that the CcCHR2B (SEQ ID NO: 30) protein has 79.5% and 97.3% identity with CcCHR1 (SEQ ID NO: 28) and CcCHR2A (SEQ ID NO: 29), respectively. The complete coding DNA sequence CcCHR1 (5'UTR-ORF-3'UTR) (SEQ ID NO: 9) contained in pcccp24e9, the partial coding DNA sequence CcCHR2A (partial ORF-3'UTR) (SEQ ID NO: 10) contained in pccc128k6, and the complete CcCHR2B (5'UTR-ORF-intron-ORF-3'UTR) (SEQ ID NO: 11) contained in pccc126f18 were aligned with public Chalcone reductases complete DNA coding sequences (5'UTR-ORF-3'UTR) from *Sesbania rostrata* (AJ223291), *Pueraria Montana* var. *lobata* (AF462632) and *Medicago sativa* (13924) using ClustalW method in MegAlign software. This alignment shows 99.1% identity between CcCHR2A (SEQ ID NO: 10) and CcCHR2B (SEQ ID NO: 11), supporting the hypothesis they are alleles of the same gene. It is interesting to note that there is an unusual 24 bp insertion in the ORF of CcCHR2B (SEQ ID NO: 11) that is absent in all the other sequences in this alignment. The significance of this insertion sequence is not currently known. The CcCHR1 (SEQ ID NO: 9) and CcCHR2B (SEQ ID NO: 11) complete coding sequences share 80.5% identity and the alignment permits the confirmation that they are two different genes. When compared with public sequences, CcCHR1 shows 58.4%, 45.2% and 47.4% identity with SrCHR, PlCHR and MsCHR, respectively, at the DNA level. CcCHR2B shares 54.9%, 43% and 45.5% identity with the complete DNA sequences from *Sesbania rostrata*, *Pueraria Montana* var. *lobata* and *Medicago sativa*, respectively.

EXAMPLE 7

Isolation and Characterization of *Coffea canephora* cDNA Clones Encoding Chalcone Isomerases (CcCHI)

To find cDNA encoding chalcone isomerases, two protein sequences encoding biochemically characterized chalcone isomerases (CHI) served as query sequences for BLAST searches against the Nestlé/Cornell unigene set 5 using the tblastn algorithm (GmCHI-2, *Glycine max* Type I CHI, GenBank Accession Number AAT94360, (Ralston et al. (2005b) (SEQ ID NO: 78); and LjCHI-1, *Lotus corniculatus* var. *japonicus*, Type II CHI, GenBank Accession Number BAC53983 (Shimada et al. (2003)) (SEQ ID NO: 77). Using the GmCHI-2 protein sequence from *Glycine max*, two unigenes were found. The first unigene #124216 exhibited higher level of identity (e value=2e-65) than the second unigene #124635 (e value=4e-18). The second search with LjCHI-1 protein sequence from *Lotus corniculatus* var. *japonicus* (SEQ ID NO: 76), uncovered the same two unigenes; unigene #124216 exhibited higher level of identity (e value=2e-53) than the second unigene #124635 (e value=2e-16).

*Coffea canephora* CcCHI (full ORF). The longest cDNA representing the 5' end of the unigene #124216 (pcccp22k18) was isolated from the pericarp library and sequenced. The insert (SEQ ID NO: 12) of this clone was found to be 926 bp long and to encode a complete ORF sequence of 780 bp. The deduced protein sequence (SEQ ID NO: 31) encoded by this ORF was 259 amino acids (SEQ ID NO: 31) having a predicted molecular weight of 27.88 kDa, and this sequence was named CcCHI (SEQ ID NO: 31). A manually optimized alignment of the deduced protein sequence (SEQ ID NO: 31) encoded by pcccp22k18 (CcCHI) (SEQ ID NO: 12) was performed with the CHI protein sequences PhCHI from *Petunia×hybrida* (PIR ID: ISPJA1) (SEQ ID NO: 76), LjCHI-2 (Type I CHI, GenBank Accession Number BAC53984) (SEQ ID NO: 77), from *Lotus corniculatus* var. *japonicus*, and GmCHI-2 (Type I CHI, GenBank Accession Number AAT94360) (SEQ ID NO: 78) from *Glycine max*, available in public databanks (FIG. 12A).

This alignment demonstrates that the CcCHI protein (SEQ ID NO: 31) shares 62.5%, 63.4% and 57.7% identity with the Type I CHI protein sequences PhCHI, LjCHI-2 and GmCHI-2, (SEQ ID NOs: 76, 77, 78) respectively, and supports the annotation of the polypeptide (SEQ ID NO: 31) encoded by pcccp22k18 (SEQ ID NO: 12) as a *C. canephora* chalcone isomerase. Comparison of CcCHI (SEQ ID NO: 31) with the well characterized Type I and Type II CHI protein sequences in the database using an optimal alignment revealed that CcCHI was closer to the Type I CHI than Type II CHI sequences.

An alignment of the complete coding DNA sequence (5'UTR-ORF-3'UTR) contained in pcccp22k18 with the complete coding DNA sequence GmCHI-2 (5'UTR-ORF-3'UTR) from *Glycine max* (AY595415) was performed using ClustalW method in MegAlign software. The alignment demonstrates that the CcCHI complete coding sequence contained in pcccp22k18 shares 57.2% identity with the DNA sequence GmCHI-2.

*Coffea canephora* CcCHI-like protein (full ORF). One of the longest 5' end clones from unigene #124635 (pcccp12o15) was isolated from the pericarp library and sequenced. The insert of pcccp12o15 (SEQ ID NO: 13) was found to be 1073 bp long and to encode a complete ORF of 642 bp. The deduced protein sequence (SEQ ID NO: 32) is a protein of 213 amino acids having a predicted molecular weight of 23.82 kDa, and this sequence was named CcCHI-like (SEQ ID NO: 32). An optimized alignment of the deduced protein sequence (SEQ ID NO: 32) encoded by pcccp12o15 (SEQ ID NO: 13) was performed with full length CHI protein sequences GmCHI-4A from *Glycine max* (GenBank Accession Number AAT94362) (SEQ ID NO: 79) and GmCHI-1A from *Glycine max* (GenBank Accession Number AAT94358) (SEQ ID NO: 80) (FIG. 12B). This alignment shows CcCHI-like (SEQ ID NO: 32) shares 64.3% identity with GmCHI-4A (SEQ ID NO: 79) and 29.1% identity with GmCHI-1A (SEQ ID NO: 80).

Using Clustalw Method in MegAlign software, the complete coding DNA sequence (5'UTR-ORF-3'UTR) contained in pcccp12o15 (SEQ ID NO: 13) was aligned with the complete coding DNA sequences (5'UTR-ORF-3'UTR) GmCHI-4A (AY595417) and GmCHI-1A (AY595413) from *Glycine max*. The alignment shows that the CcCHI-Like sequence shares 55.8% and 45.2% identity with GmCHI-4A and GmCHI-1A, respectively, at the DNA level. Thus, the CcCHI-Like complete coding sequence is more closed to GmCHI-4A than to GmCHI-1A. It is also interesting to note that CcCHI-Like full protein shares 64.3% identity at protein level with GmCHI-4A, whereas their respective DNA sequences share lower level identity (55.8%). In contrast, CcCHI-Like full protein shares 29.1% identity at protein level with GmCHI-1A, whereas their respective DNA sequences have a higher level of identity (45.2%).

EXAMPLE 8

Isolation and Characterization of *Coffea canephora* cDNA Clone Encoding Flavanone 3-Hydroxylase (CcF3H)

To find cDNA encoding flavanone 3-hydroxylase, two protein sequences encoding partially characterized flavanone 3-hydroxylases (F3H) served as query sequences for a BLAST search against the Nestlé/Cornell unigene set 5 using the tblastn algorithm (AtF3H; *Arabidopsis thaliana*, GenBank Accession Number #AAC68584, knock-out mutants done by Wissman et al, (1998); and GmF3H, *Glycine max*, GenBank Accession Number #AAT94365. Using the GmF3H protein sequence from *Glycine max*, only one unigene (#123808) was found to exhibit a high level of identity (e value=e-142). The second search with the AtF3H protein sequence from *Arabidopsis thaliana* uncovered the same best Unigene hit #123808 (e value=e-145).

A cDNA representing the 5' end of the unigene #123808 (pcccp5120) was isolated from pericarp library and sequenced. The insert of pcccp5120 was found to be 1286 bp long and to encode a complete ORF of 1092 bp (SEQ ID NO: 14). This sequence was named CcF3H (SEQ ID NO: 14). The deduced ORF encodes a protein (SEQ ID NO: 33) of 363 amino acids having a predicted molecular weight of 40.88 kDa. An alignment of the deduced protein sequence (SEQ ID NO: 33) encoded by pcccp5120 (SEQ ID NO: 14) was made with the F3H protein sequences from *Glycine max* and *Arabidopsis thaliana* cited above. This alignment demonstrates that the CcF3H protein sequence of pcccp5120 has 82.4% and 81.8% identity with these protein sequences, respectively (FIG. 13A), supporting the annotation of pcccp5120 (SEQ ID NO: 14) as a coffee flavanone 3-hydroxylase.

An alignment of the complete CcF3H coding DNA sequence (5'UTR-ORF-3'UTR) contained in pcccp5120 was performed using ClustalW (MegAlign software) with the complete coding DNA sequence of GmF3H (5'UTR-ORF-3'UTR) from *Glycine max* (AY595420). The alignment demonstrates that the CcF3H complete coding sequence shares 70.1% identity with the public complete coding DNA sequence for GmF3H.

EXAMPLE 9

Isolation and Characterization of a *Coffea canephora* cDNA Clone Encoding Flavonoid 3'15'-Hydroxylase (CcF3'5'H)

To find cDNA encoding coffee flavonoid 3',5'-hydroxylase (F3'5'H), two protein sequences encoding biochemically-characterized flavonoid 3',5'-hydroxylase served as query sequences for a BLAST search against the Nestlé/Cornell unigene set 5 using the tblastn algorithm: CrF3'5'H, *Catharanthus roseus*, GenBank Accession Number CAA09850 (SEQ ID NO: 83), enzyme activity characterized by Kaltenbach et al. (1999); and GtF3'5'H, *Gentiana triflora*, GenBank Accession Number Q96581 (SEQ ID NO: 84), enzyme activity characterized by Tanaka et al. (1996)). Using CrF3'5'H protein sequence from *Catharanthus roseus* only one unigene (#130482) was found to exhibit significant homology (over 60% identity). The second search with GtF3'5'H protein sequence from *Gentiana triflora* uncovered the same unigene hit #130482 (over 58% identity).

The single cDNA representing unigene #130482 (pcccwc22w23n18) (SEQ ID NO: 15) was isolated from the 22 weeks whole cherry library and fully sequenced. The sequence obtained for pcccwc22w23n18 (SEQ ID NO: 15) is 1350 bp long, and contains a partial ORF. Two unusual features can be seen in this sequence. First, the premier 78 bp of this cDNA (5' end) appears to contains an intron sequence because this sequence does not match the homologous proteins, and has no homologs in the GenBank database. Second, the main (partial) ORF contains a stop codon that leads to a break in this ORF. It is believe that this stop codon is due to a mutation (TGA) induced during the production of this cDNA clone. This proposed explanation will be verified in the future by re-amplifying this region of the sequence, and can be done simultaneously with the recovery of the missing 5' sequence by 5' RACE PCR. In the current sequence this TGA is replaced by TGN in the sequence.

The partial ORF of pcccwc22w23n18 (SEQ ID NO: 15) is 552 bp long and encodes a polypeptide sequence of 183 amino acids (SEQ ID NO: 34). This sequence was named CcF3'5'H (SEQ ID NO: 15). Based on an alignment with the complete ORF of CrF3'5'H (512 aa), it was assumed that the CcF3'5'H protein was missing over 331 amino acids at the N terminal end. An alignment of the 183 amino acids ORF in pcccwc22w23n18 (CcF3'5'H) (SEQ ID NO: 15) with the same region of the F3'5'H protein sequences from *Catharanthus roseus* (CrF3'5'H) (SEQ ID NO: 83) and *Gentiana triflora* (GtF3'5'H) (SEQ ID NO: 84) (FIG. 13B) strongly indicates that this coffee ORF represent a coffee F3'5'H because it shares 67.8% and 60.7% identity with CrF3'5'H and GtF3'5'H protein sequences, respectively. In comparison, the complete ORF's of CrF3'5'H and GtF3'5'H are 74% identical. This partial sequence will enable the cloning of the remaining portion of the coding sequence of CcF3'5'H upon generation of specific DNA primers from the DNA of pcccwc22w23n18 (SEQ ID NO: 15), and using these primers in the well-known techniques of 5' RACE and primer-assisted genome walking.

EXAMPLE 10

Isolation and Characterization of a *Coffea canephora* cDNA Clone Encoding Dihydroflavonol-4-Reductase (CcDFR)

To find cDNA encoding a coffee dihydroflavonol-4-reductase, two protein sequences encoding biochemically characterized dihydroflavonol-4-reductases (DFR) served as query sequences for a BLAST search against the Nestlé/Cornell unigene set 5 using the tblastn algorithm: MtDFR1 and MtDFR2 from *Medicago truncatula*, GenBank Accession Numbers AAR27014 and AAR27015 (SEQ ID NOs:), respectively, activities characterized by Xie et al. (2004). Using the MtDFR1 protein sequence from *Medicago truncatula*, only one unigene (#122897) was found to exhibit a high level of identity (e value=e-133). The second search with MtDFR2 protein sequence from *Medicago truncatula* uncovered the same best unigene hit #122897 (e value=e-137).

The longest cDNA representing unigene #122897 (pcccp5115) was isolated from the pericarp library and sequenced. The insert of pcccp5115 (SEQ ID NO: 16) was found to be 1398 bp long and to encode an ORF sequence of 1110 bp. This sequence was named CcDFR (SEQ ID NO: 16). The deduced polypeptide (SEQ ID NO: 35) is 369 amino acids long and has a predicted molecular weight of 40.91 kDa. An alignment of the protein sequence (SEQ ID NO: 35) encoded by pcccp5115 (SEQ ID NO: 16) with the protein sequences MtDFR1 and MtDFR2 from *Medicago truncatula* (#AAR27014 and #AAR27015, (SEQ ID NOs: 85, 86) respectively) demonstrates that polypeptide (SEQ ID NO: 35) encoded by pcccp5115 (CcDFR) (SEQ ID NO: 16) shares 65.2% and 67.6% identity with those protein sequences, respectively (FIG. 14). This alignment data indicates that pcccp5115 plasmid contains a full length cDNA encoding a *C. canephora* dihydroflavonol-4-reductase (CcDFR).

Using the ClustalWMethod in the MegAlign software, the complete coding DNA sequence (5'UTR-ORF-3'UTR) of CcDFR contained in pcccp5115 was aligned with the complete coding DNA sequence (5'UTR-ORF-3'UTR) of MtDFR1 from *Medicago truncatula* (AY389346). CcDFR and MtDFR1 are 59.4% identical

EXAMPLE 11

Isolation and Characterization of *Coffea canephora* cDNA Encoding Leucoanthocyanidin Dioxygenase (CcLDOX)

To find cDNA encoding a coffee leucoanthocyanidin dioxygenase, the protein sequence encoding biochemically characterized LDOX (also known as Anthocyanidin Synthase (ANS)) from *Perilla frutescens* PfANS served as query sequence for a BLAST search against the Nestlé/Cornell unigene set 5 using the tblastn algorithm (PfANS, from *Perilla frutescens*, GenBank Accession Number #O04274 (SEQ ID NO: 88), activity characterized by Saito et al. (1999)). Using the PfANS protein sequence, two unigenes were found to exhibit significant homologies; unigene #131577 (e value=2e-73) and unigene #122116 (e value=7e-46).

*Coffea canephora* CcLDOX (full ORF). The single cDNA representing unigene #131577 (pccc121b21) was isolated from the leaf library and sequenced. The insert of pccc121b21 (SEQ ID NO: 17) was found to be 1430 bp long and to encode a complete ORF sequence of 1128 bp. This sequence was called CcLDOX (SEQ ID NO: 17). The deduced protein sequence is a protein of 375 amino acids (SEQ ID NO: 36) having a predicted molecular weight of 42.52 kDa.

Figure 15A:
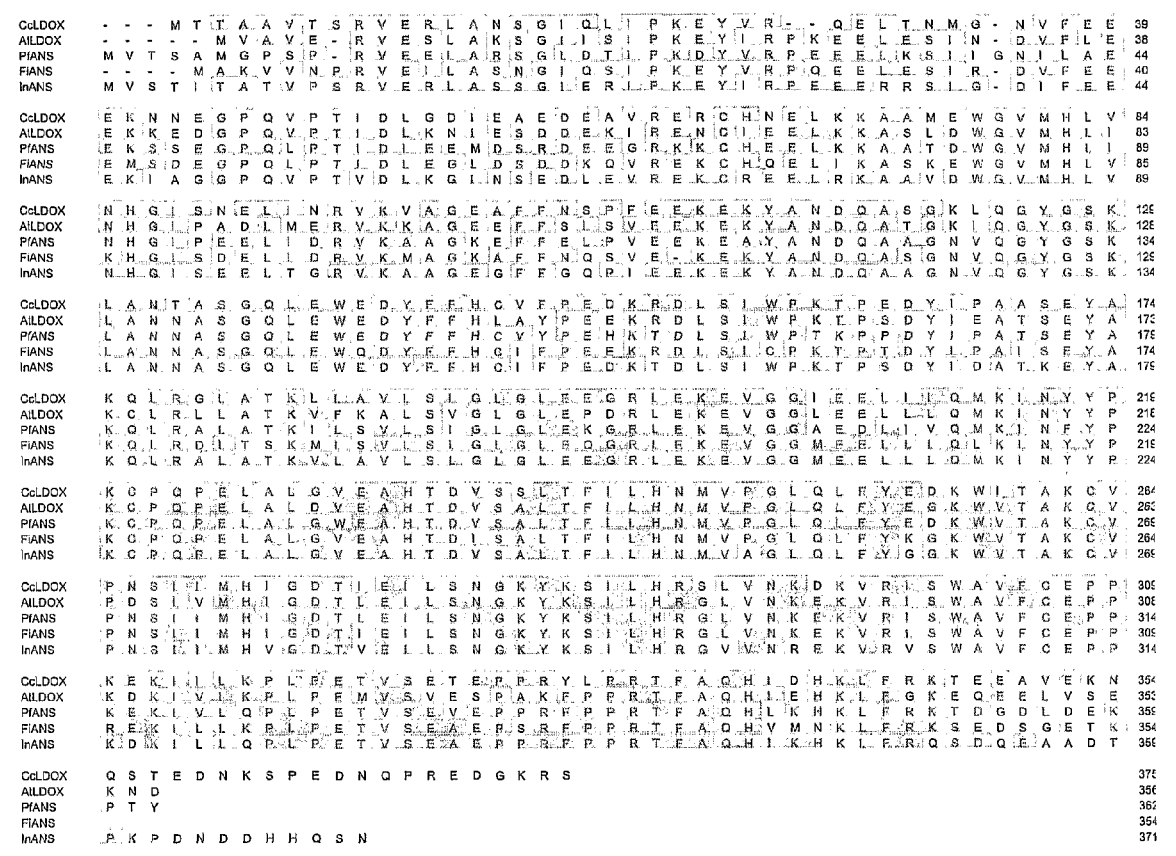

FIG. 15A shows an optimized alignment of the protein sequence (SEQ ID NO: 36) encoded by pccc121b21 (CcLDOX) (SEQ ID NO: 17) with the protein sequences of AtLDOX from *Arabidopsis thaliana* (#CAD91994) (SEQ ID NO: 87), PfANS from *Perilla frutescens* (#O04274) (SEQ ID NO: 88), FiANS from *Forsythiaxintermedia* (#CAA73094) (SEQ ID NO: 89) and InANS from *Ipomoea nil* (BAB71810) (SEQ ID NO: 90). This alignment demonstrates that the CcLDOX protein (SEQ ID NO: 36) shares 69.3%, 70.7%, 72.3% and 73.1% identity with these protein sequences (SEQ ID NOs: 87, 88, 89, 90), respectively. This alignment data indicates that the pccc121b21 plasmid contains a full length cDNA (SEQ ID NO: 17) encoding a *C. canephora* leucoanthocyanidin dioxygenase (CcLDOX) (SEQ ID NO: 36).

When the sequence for the singleton cDNA representing unigene #122116 (pcccp14i24, pericarp library) was obtained, it was observed that this sequence could be assembled with the insert sequence of pccc121b21 into a unique contig that had an overlapping region of 588 bp. Only two single nucleotide differences were observed in this overlapping region, and they were localized in 3'UTR. Based on these observations, it was concluded that these two cDNA represent allelic sequences of CcLDOX. The insert of pcccp14i24 is 659 bp long and contains a partial ORF of 321 bp coding for 106 amino acids.

The complete coding DNA sequence CcLDOX (5'UTR-ORF-3'UTR) contained in pccc121b21 was aligned with the complete coding DNA sequence (5'UTR-ORF-3'UTR) of PfANS from *Perilla frutescens* (AB003779) using ClustalW method in MegAlign software. This alignment shows there is 65.5% identity between CcLDOX and the well characterized public sequence from *Perilla frutescens*.

EXAMPLE 12

Isolation and Characterization of a *Coffea canephora* cDNA Clone Encoding Leucoanthocyanidin Reductase (CcLAR)

To find cDNA encoding a coffee leucoanthocyanidin reductase, the protein sequence encoding a biochemically characterized leucoanthocyanidin reductase (LAR) served as query sequence for a BLAST search against the Nestlé/Cornell unigene set 5 using the tblastn algorithm: DuLAR, *Desmodium uncinatum*, GenBank Accession Number CAD79341; activity characterized by Tanner et al. (2003). Using the protein sequence DuLAR, one unigene #132429 was found to exhibit a high level of homology (e-value=3e-45). Currently, the only sequence data for the singleton cDNA representing unigene #132429 (pccc121e8) is the EST DNA sequence in the Nestlé/Cornell database. The available sequence for the insert of pccc121e8 is 648 bp long and encodes the N-terminal region of an ORF. This partial ORF is 561 bp long, and codes for 187 amino acids. The sequence has been named CcLAR.

Figure 15B:
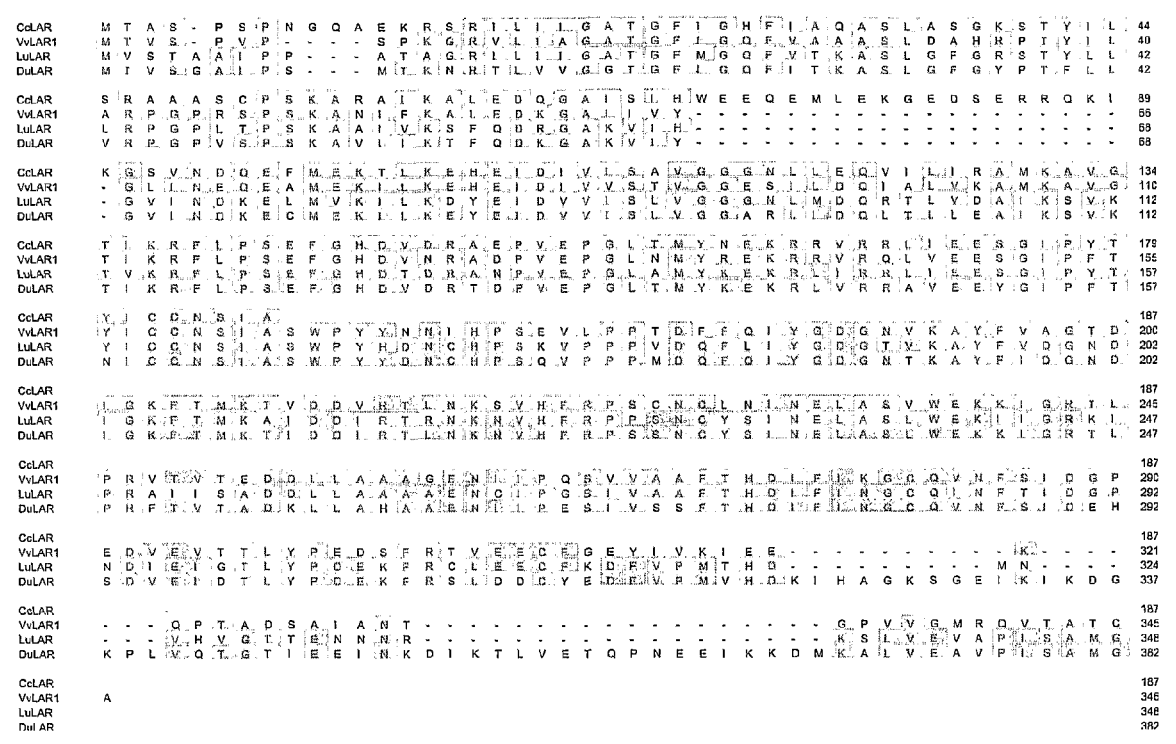

FIG. 15B shows an alignment of the available protein sequence (SEQ ID NO: 37) encoded by pccc121e8 (CcLAR) (SEQ ID NO: 18) with the full protein sequences VvLAR from *Vitis vinifera* (GenBank Accession Number CAI26309) (SEQ ID NO: 91), LuLAR from *Lotus uliginosus* (GenBank Accession Number AAU45392) (SEQ ID NO: 92), and DuLAR from *Desmodium uncinatum* (GenBank Accession Number Q84V83) (SEQ ID NO: 93). This alignment demonstrates that the available protein sequence (SEQ ID NO: 37) of pccc121e8 (CcLAR) (SEQ ID NO: 18) represents the 5' region of the protein, and that it shares 59.9%, 55.6% and 54% identity with the foregoing protein sequences, respectively. This alignment data indicates that the plasmid pccc121e8 (SEQ ID NO: 18) represents a *C. canephora* leucoanthocyanidin reductase (CcLAR) (SEQ ID NO: 37), and potentially encodes a complete cDNA for this gene.

EXAMPLE 13

Isolation and Characterization of a *Coffea canephora* cDNA Clone Encoding Anthocyanin Reductase (CcANR)

To find cDNA encoding a coffee anthocyanidin reductase, a protein sequence encoding the biochemically characterized anthocyanidin reductase from *Medicago truncatula*, served as the query sequence for a BLAST search against the Nestlé/Cornell unigene set 5 using the tblastn algorithm: MtANR; GenBank Accession Number, AAN77735, activity characterized by Xie et al. (2003b). The ANR protein of *Medicago* is encoded by the BAN gene.

Using the MtANR protein sequence from *Medicago truncatula* as the search query, only one unigene (#122851) was found to exhibit a high level of homology (e value=e-108). Currently, the only sequence data for the longest cDNA representing unigene #122851 (pcccwc22w14g7) is the EST DNA sequence from the whole cherries library in the Nestlé/Cornell database. The available sequence data for the insert of pcccwc22w14g7 from the Cornell database was found to be 1048 bp long and to encode a complete ORF sequence of 1014 bp. The deduced protein (SEQ ID NO: 38) is 337 amino acids long, having a predicted molecular weight of approximately 36.33 kDa. The sequence was named CcANR (SEQ ID NO: 38).

The CcANR protein sequence (SEQ ID NO: 38) was aligned with the protein sequences MtANR (*Medicago truncatula*, GenBank Accession Number AAN77735) (SEQ ID NO: 94), AtANR (*Arabidopsis thaliana*, GenBank Accession Number AAF23859 (SEQ ID NO: 95), encoded by AtBAN gene GenBank Accession Number AF092912, activity characterized by Xie et al. (2003c)); and CsLAR (*Camellia sinensis*, GenBank Accession Number AAT68773) (SEQ ID NO: 96). This alignment showed that the coffee ANR protein (pccc121e8, CcANR) (SEQ ID NO: 38) shares 71.5%, 63.2% and 77.4% identity with the other ANR protein sequences, respectively (FIG. 15c). This alignment data indicates that the pcccwc22w14g7 (SEQ ID NO: 19) plasmid encodes a *C. canephora* anthocyanidin reductase (CcANR) (SEQ ID NO: 38).

Using ClustalW (MegAlign software), the complete ORF DNA sequence contained in pcccwc22w14g7 was aligned with the complete ORF DNA sequences of MtBAN (AY184243) from *Medicago truncatula* and AtBAN (AF092912) from *Arabidopsis thaliana*, that encode well-characterized Anthocyanidin reductases MtANR and AtANR. The alignment shows that the coffee pcccwc22w14g7 ORF has 71.8% and 63.4% identity with the respective public DNA sequences MtBAN and AtBAN, at the DNA level.

EXAMPLE 14

Northern Blot and RT-PCR Analysis of the Expression of CHS, CHI, DFR and F3H in Grains Pericarp, and Other Tissues of *Coffea arabica*

Northern blot analysis of the expression of the CHS, CHI, DFR, and F3H genes is shown in FIG. 16. The data presented indicates that the CHS gene is most strongly expressed in the late pericarp (yellow and red stages), weakly expressed in flowers and leaves, and very weakly expressed in roots and stems.

CHS expression was not detected by northern blotting in the grain at any stage, or in the root and stem. This expression pattern was confirmed by using RT-PCR except expression in stems and roots (FIG. 17). By Northern blotting, CHI was found to be expressed only in the late stages of pericarp development. No CHI expression was detected by Northern blotting in roots, stems, leaf, early pericarp tissue, or in any of the grain samples. Using the more sensitive RT-PCR technique however, low levels of CHI transcripts could now be detected in the leaf, stem, and root. The results from the RT-PCR suggest that CHI could also be very weakly expressed in the last three stages of grain development.

Expression of the CHI-like gene was also analysed by RT-PCR (FIG. 17). This experiment showed that the CHI-like gene is weakly expressed in the root, stem, leaf, late pericarp (yellow and red), and possibly very weakly in the first three stages of grain development (small green, large green, and yellow). No expression was observed in the early pericarp (small and large green) or red grain samples.

A similar expression pattern to CHI was observed for the DFR gene by Northern blotting, i.e., a high level of DFR transcripts were detected during the late stages of pericarp development/maturation, and no expression was detected in the other tissues. Northern blot analysis shows that the F3H gene is also very strongly expressed in the later pericarp developmental/maturation stages. Very high levels of expression of F3H is observed in the flowers, and unlike CHI and DFR, a lower, but significant level of expression was also detected for F3H at all stages in the grain, in the two early stage of pericarp (small green and large green), as well as in the root, stem and leaf.

EXAMPLE 15

Expression of Early Phenylpropanoid and Flavonoid Genes

The number of ESTs associated with a particular unigene gives an estimation of the expression level of the associated gene in each library (in each tissue). Therefore, an examination of the number of ESTs within the different unigenes of the phenylpropanoid and flavonoid genes discussed above can give a broad overview of the expression of these genes. All the unigenes discussed herein, and the number of ESTs in each library for these unigenes, are provided in Table 10.

each tissue sample was determined by normalizing the transcript level of this sample versus the rpl39 transcript level in that tissue.

The expression of PAL1 is very low in the grain at all four stages tested, with the levels being similar for *arabica* and robusta (RQ's 0.02-0.05), except at the mature red stage where the levels of PAL1 seem to be higher in *arabica* (0.28) relative to robusta (0.03). In the pericarp, PAL1 appears to be more highly expressed in robusta relative to *arabica*, and the transcript levels in the robusta pericarp seem to peak at the large green stage (RQ 0.51 for robusta), and then fall off slightly. A relatively low level of PAL1 transcripts are also observed in the roots (arabica RQ 0.20 and robusta RQ 0.11), and stems (*arabica* RQ 0.09 and robusta RQ 0.23) of both *arabica* and robusta. Interestingly, the leaf tissue showed very significant differences in PAL1 expression, with an RQ of 0.73 observed for *arabica* and an RQ of only 0.04 for robusta. A large difference in PAL1 transcript levels is also observed in the flowers, with *arabica* exhibiting a much higher RQ (16.33) than robusta RQ (0.89).

TABLE 10

In silico distribution of ESTs in the unigenes.

| Gene | #Unigene Number | EST/cDNA Name | cccl | cccp | cccwc22w | cccs18w | cccs30w | cccs46w |
|---|---|---|---|---|---|---|---|---|
| CcPAL1 | #121018 | cccwc22w18n3 (partial) |  | 5 | 16 |  | 3 |  |
| CaPAL1 |  | pML8 (full) |  |  |  |  |  |  |
| CcPAL2 | #119778 | cccl25c13, cccp19k7 (partial) | 1 | 1 |  |  |  |  |
| CcPAL3 | #120370 | cccp16l1 (partial) | 1 | 2 |  | 1 |  |  |
| CaPAL3 |  | pML14 (full) |  |  |  |  |  |  |
| CcC4H | #124550 | cccl27h22 (full) | 2 | 5 | 5 |  |  | 2 |
| Cc4CL1 | #119670 | cccp27d21 (partial) | 1 | 3 |  |  | 1 |  |
| Cc4CL2 | #128581 | cccl24i21 (partial) |  |  |  |  |  |  |
| Ca4CL2 |  | pGC1 (full) | 1 |  |  |  |  |  |
| Cc4CL2 |  | pGC3 (full) |  |  |  |  |  |  |
| CcCHS | #123889 | cccp8j10 (full) | 5 | 9 | 3 |  |  |  |
| CcCHR1 | #125256 | cccp24e9 (full) | 18 | 2 | 2 |  | 2 |  |
| CcCHR2A | #125257 | cccl28k6 (nearly full) | 5 |  |  |  |  |  |
| CcCHR2B | #125260 | cccl26f18 (full) | 7 |  |  |  |  |  |
| CcCHI | #124216 | cccp22k18 (full) |  | 2 | 4 |  |  |  |
| CcCHI-like | #124635 | cccp12o15 (full) |  | 2 | 4 |  | 3 |  |
| CcF3H | #123808 | cccp5l20 (full) | 1 | 2 | 3 |  |  | 21 |
| CcF3'5'H | #130482 | cccwc22w23n18 (partial) |  |  | 1 |  |  |  |
| CcDFR | #122897 | cccp5l15 (full) | 1 | 19 | 2 |  |  |  |
| CcLDOX | #131577 | cccl21b21 (full) |  |  |  |  |  |  |
|  | #122116 | cccp14i24 (full, 100% identity with Unigene #131577 in CDS) | 1 | 1 |  |  |  |  |
| CcLAR | #132429 | cccl21e8 (full) | 1 |  |  |  |  |  |
| CcANR | #122851 | cccwc22w14g7 (full) |  |  | 2 |  |  |  |

In silico distribution of ESTs in the unigenes containing the partial CcPAL1, partial CcPAL2, partial CcPAL3, full length CcC4H, partial Cc4CL1, partial Cc4CL2, full length CcCHS, full length CcCHR1, quasi-full length CcCHR2A, full length CcCHR2B, full length CcCHI, full length CcCHI-like, full length CcF3H, partial CcF3'5'H, full length CcDFR, full length CcLDOX, full length CcLAR, and the full length CcANR *Coffea canephora* cDNA. For each unigenes the name(s) of the representative EST(s) that are partially or fully sequenced is indicated. Parentheticals denote if the 5' end coding sequence of the EST is full or partial. PAL1, PAL3 and 4CL2 genes were found in unigenes that contained only their partial coding sequences, but further experiments permitted isolation of the full length sequence in arabica or robusta.

Expression of PAL1, PAL2, and PAL3. Overall, the data in Table 10 suggests that CcPAL1 may be the most expressed of the three PAL genes, and that it is most highly expressed in whole small green cherries (grain and pericarp). In order to obtain more accurate data on the expression of these three genes, specific primers and TAQMAN probe sets (Table 6) were prepared for each gene, and used to measure the transcript levels for each PAL gene in several different coffee tissues of *arabica* and robusta. (FIG. 18). The different cDNA used for these experiments were prepared by Method 1 with RNA isolated from roots, stems, leaves, flowers, and from the grain and pericarp tissues isolated from 4 different stages of development of *arabica* (T2308) and robusta (BP409) coffee cherries as described in Example 1 above. The RQ value for The TAQMAN expression data for PAL2 shows that transcripts for this gene are barely detectable in both *arabica* and robusta grain for all stages tested, with the exception of the small green robusta grain, which is known to be at an earlier stage than the small green *arabica* grain used in the experiments presented here. (Hinniger et al. manuscript submitted for publication; co-pending U.S. Provisional Application No. 60/696,890). In contrast, PAL2 is clearly expressed in the cherry pericarp from the large green stage, with robusta showing higher levels of expression than *arabica* at the large green and red stages. PAL2 is also highly expressed in the pericarp at the small green stage of robusta (RQ of 4.09), whereas no expression is detected in the pericarp of the *arabica* tissue at this physically defined stage. This expression difference is consistent with the earlier developmental stage of the robusta small green grain sample.

The high level of PAL2 expression in the pericarp of robusta at the small green stage (RQ of 4.09) suggests that expression of this gene could be important for the significant expansion of the pericarp tissue that occurs during, and just after, this period. Expression of PAL2 was not detected in the robusta root (low expression in *arabica* root), and was not detected in the robusta and *arabica* stem tissue. PAL2 transcripts were detected at relatively high levels in the *arabica* leaf and flower tissues, but not in these tissues in robusta.

The TAQMAN data for PAL3 shows that this gene is expressed at relatively low levels in the grain (RQ 0.09 for large green robusta grain) (FIG. 18). The more immature small green grain of robusta shows a higher level of expression relative to the *arabica* small green grain (RQ 0.81 versus RQ 0.04). The mature *arabica* grain has a higher level of PAL3 expression than the mature robusta grain (RQ 0.72 versus RQ 0.16). In the pericarp, PAL3 expression is very low for *arabica* in the small green and large green stages, but increases somewhat in the last two stages. In contrast, although PAL3 expression levels are low in robusta, these levels appear to be more similar at all the developmental stages examined. In stems, PAL3 expression was relatively high in robusta (RQ 0.24), but relatively very low in *arabica* (RQ 0.03). In contrast, in the leaf, the levels of PAL3 were higher in *arabica* than robusta (RQ 2.57 versus RQ 0.03). In the flower samples, a slightly higher level of PAL3 transcripts were observed in *arabica* versus robusta. The fact that each of the three PAL genes are expressed at different levels in the *arabica* and robusta leaf and flower samples indicates that the these two tissues are expressed at different developmental stages and their expression may be controlled differently depending on the environmental stress imposed.

Expression of C4H. The number of ESTs for C4H suggests that this gene is expressed in all the tissues examined (leaf, seed, pericarp; Table 10). This observation was confirmed using a TAQMAN assay for this gene (FIG. 18). In the robusta grain, transcripts for C4H are low in the small green stage (RQ=0.40), and then appear to fall progressively to a very low level in the mature grain stage (RQ=0.03). In the *arabica* grain, transcripts for C4H are generally higher than in the robusta gain, especially at the mature red stage. The one exception is in the yellow stage where the *arabica*/robusta levels seem relatively similar. In the *arabica* pericarp, relatively similar levels of C4H transcripts are observed at all stages. In contrast, the C4H transcript levels vary more in the different stages of robusta pericarp, with small green and large green stages having significantly higher levels of C4H transcripts than the large green *arabica* pericarp. In the yellow and mature (red) arabica pericarp, the levels of C4H transcripts are much more similar to those seen in the robusta samples. Similar levels of C4H transcripts are also observed in the roots of *arabica* and robusta, although in the stems, there is a significantly higher level of C4H transcripts in robusta relative to *arabica*. In the leaf and flower samples, higher levels of C4H transcripts are observed in the *arabica* sample relative to the robusta sample.

Expression of 4CL1 and 4CL2. The number of ESTs for the 4CL unigenes indicate that these two genes are expressed at relatively similar levels in at least some robusta tissues. For more information on the expression of these genes, specific TAQMAN assays were developed for each gene. The QRT-PCR results obtained for these two genes are presented in FIG. 18.

In robusta, relatively low levels of 4CL1 transcripts are detected in nearly all the tissues except in the pericarp at the large green (0.08 of RQ) and yellow stages (0.04 of RQ), where slightly higher levels of transcripts were detected, and the roots and leaves where no significant levels of 4CL1 expression were detected. Using the 4CL1 set of TAQMAN probes, 4CL1 expression was only detected at low levels in the roots (0.01 of RQ) of *arabica*. The fact that expression can be detected in at least one *arabica* sample suggests that this 4CL1 allele exists in the *arabica* genome, but that the expression of this gene is very different between the robusta and *arabica* varieties presented herein.

The QRT-PCR results obtained for 4CL2 indicate that this gene shows a variable expression pattern in robusta, with nearly undetectable levels in the small green grain (0.01), roots (0.01), stem (0.07), and leaf samples (0.06) (FIG. 18). Slightly higher levels are seen in robusta for the large green grain (0.59), red (mature) grain (0.65), for the large green (0.65), yellow (0.95), and red pericarp (0.88). In contrast, the transcript level is lower in yellow grain (0.12) and in the flowers (0.19). A spike of 4CL2 expression in robusta was detected in the small green pericarp tissue (RQ=3.49), and this may be associated with the fact that these cherries are at an earlier developmental stage than the visually comparable *arabica* cherries used in this experiment (as indicated by the absence of endosperm specific transcripts in the small green robusta cherries. See copending U.S. Provisional Application No. 60/696,445). For some *arabica* tissues, the expression of 4CL2 is relatively similar to that observed in robusta. For example, 4CL2 expression is detected at similar low levels in *arabica* large green (0.19), yellow (0.23), and red grain (0.38) samples and in *arabica* yellow (0.27) and red pericarp samples (RQ 0.27), and at very low levels in the stem samples (RQ=0.114). In contrast to robusta, however, 4CL2 expression is slightly detected in *arabica* small green pericarp (0.02) (approximately equivalent to large green *arabica* pericarp), and the expression of 4CL2 is significantly higher in leaves (RQ 1.86) and flowers (RQ 4.84) of the *arabica* samples relative to the robusta samples.

EXAMPLE 16

Production of the Ca4CL2 and Cc4CL2 Proteins in *E. Coli*

To verify that the Ca4CL2 and Cc4CL2 cDNAs (SEQ ID NOs:) can be used to produce functional Ca4CL2 and Cc4CL2 proteins (SEQ ID NOs:), the ORFs for these cDNA were cloned into an *E. coli* expression vector and overexpressed.

In order to over-express the proteins Ca4CL2 and Cc4CL2 (SEQ ID NOs:) encoded by pGC1 and pGC3 the ORF sequences were sub-cloned using PCR into the expression vector pET28a+ (Invitrogen). To facilitate this cloning reaction, restrictions sites were added at the ends by PCR (primers and PCR conditions shown in Table 11). A BglII site was generated immediately 5' to the ATG codons, and a HindIII site was added just after the stop codon. The PCR reactions were performed in 50 µl reactions as follows: 2 µl of pGC1 or pGC3 plasmid (1/50 diluted), 5 µL 10×PCR buffer (La PCR Buffer II $Mg^{++}$ plus), 300 nM of each gene specific primer (Table 11), 200 µM each dNTP, and 0.5 U of DNA polymerase Takara LA Taq (Cambrex Bio Science). After denaturing at 94° C. for 5 min, the amplification consisted of 25 cycles of 1 min at 94° C., 1 min at 55° C. (Table 11) and 2 min 30 at 72° C. for elongation. An additional final step of elongation was carried out at 72° C. for 7 min. The specific PCR products generated were purified on an agarose gel and extracted using the Qiagen MiniElute kit according to the manufacturers protocol, with the DNA ending in a final volume of 12 µl. Five microliters of each purified PCR product was then digested at 37° C. overnight with 5 units of BglII and HindIII restriction enzymes in the appropriate buffer. The plasmid pET28a+ was also digested with BamHI and HindIII under the same conditions (BamHI and BglII generate compatible sites). Afterward, digestion products were purified on agarose gels and extracted using Qiagen MiniElute kit. Next, 1 µl of each digestion product was ligated with 1 µl of the digested plasmid pET28a+ using T4 DNALigase (Promega) overnight at 16° C. Top10 competent cells (Invitrogen) were then transformed with 1 µl of each ligation mixture according the manufacturers protocol. Screening of colonies for those with the appropriate inserts was performed by PCR using the same primers employed to clone the ORF. Selected plasmids were then purified and the 4CL2 inserts were sequenced. The pET28a+ plasmid containing the Ca4CL2 sequence was named pGC5 and the pET28a+ plasmid containing the Cc4CL2 sequence was named pGC8. Finally, expression competent cells B121AI were transformed according to manufacturer's protocol (Invitrogen) with pGC5 or pGC8 in order to produce the protein.

For protein expression, a pre-culture of each recombinant B112AI cells containing either Ca4CL2 or Cc4CL2 was grown over night at 37° C. in 5 ml of LB medium containing 50 µg/ml of kanamycin. One milliliter of each pre-culture was then used to inoculate two cultures (50 ml of LB medium with 50 µg/ml of kanamycin), and cells grown until the OD 600 nm reached 0.6. The induction of expression was then performed with 1.5 mM of IPTG and 0.2% of L-arabinose and the cultures were grown for a further 4 h at 37° C. A control culture was also established for each transformed strain that was not subject to induction by IPTG. After the induction treatment, the cells were pelleted, and then resuspended in four ml of lysis buffer (50 mM Tris-HCl pH 7.9, 300 mM NaCl, 10% Glycerol, 1% Triton X100, imidazole 20 mM). Lysis was carried out by three cycles of freeze/thaw (−180° C./42° C.) and sonication (Bioblock scientific 88155) during one minute. The lysed cells were centrifuged (30 min 10,000 g), and the supernatant was applied to a Ni-Nta media (Ni-Nta superflow, Qiagen) for 1 hour. The medium was then transferred on a chromatography column (Invitrogen), and then washed twice with 4 ml of washing buffer (50 mM Tris HCl pH 7.9, 300 mM NaCL, 20 mM imidazole, 10% Glycerol). The his-tagged protein was eluted in five distinct fi-actions of 0.5 ml elution buffer (50 mM Tris HCl pH 7.9, 300 mM NaCL, 10% Glycerol, 250 mM imidazole). After pooling fractions containing the protein band of interest, the pooled fractions were dialyzed over night against 4 L of 100 mM Tris HCl pH 7.5 2.5 mM MgCl2, 10% Glycerol using Silde A lyser 3.5K cassette (Pierce). The production of the recombinant proteins and their purification was followed by analysis on 12% SDS-PAGE gel (Novex NuPage precast Gel Invitrogen).

Results are shown in FIG. 19. As can be seen, both recombinant overexpression vectors pGC5 and pGC8 produced proteins of the expected size when the corresponding bacterial cultures were subjected to induction with IPTG. The size of recombinant proteins were estimated from the gel (FIG. 19A) to be between 60 and 65 kDa, values close to the predicted sizes of the fusion proteins HisTag-Ca4CL2 and HisTag-Cc4CL2 (approximately 62.7 Kda).

TABLE 11

List of specific primers and PCR conditions used to sub-clone Ca4CL2 and Cc4CL2.

| Gene | Gene Specific primer | Primer sequence | Annealing temperature | Number of cycles |
|---|---|---|---|---|
| Ca4CL2 | Ca4CL2-Bgl2[1] | 5' GAAGATCTGCTGTCAAAACAAAGCAAGAAG 3' | 55° C. | 25 |
| | Cx4CL2-Hind3[2] | 5' CCCAAGCTTTTATTTTGGCACGCCAGCAGC 3' | | |
| Cc4CL2 | Cc4CL2-Bgl2[3] | 5' GAAGATCTGCTGCCAAAACAAAGCAAGA 3' | 55° C. | 25 |
| | Cx4CL2-Hind3[4] | 5' CCCAAGCTTTTATTTTGGCACGCCAGCAGC 3' | | |

[1,2,3,4] = SEQ ID NOs: 154, 155, 156, 157, respectively.

REFERENCES

Bazzano L A, He J, Ogden L G, Loria C M, Vupputuri S, Myers L, Whelton P K (2002) Fruit and vegetable intake and risk of cardiovascular disease in US adults: the first National Health and Nutrition Examination Survey Epidemiologic Follow-up Study. *Am. J. of Clin. Nutr.* 76: 93-99.

Bomati E, Austin M, Bowman M, Dixon R, Noel J (2005) Structural Elucidation of Chalcone Reductase and implications for deoxychalcone biosynthesis. *J. Biol. Chem.* 280:30496-503.

Bovy A, de Vos R, Kemper M, Schijlen E, Pertejo M, Muir S, Collins G, Robinson S, Verhoeyen M, Hughes S, Santos-Buelga C, Van Tunen A (2002) High-flavonol tomatoes resulting from the heterologous expression of the maize transcription factor genes LC and C1. *Plant Cell* 14: 2509-2526.

Christensen A B, Gregersen P L, Olsen C E, Collinge D B. (1998) A flavonoid 7-O-methyltransferase is expressed in barley leaves in response to pathogen attack. *Plant Mol. Biol.* 36:219-27.

Clifford M N (2004) Diet-derived Phenols in plasma and tissues and their implications for health. *Planta Medica* 70: 1103-1114.

Cos P, DeBruyne T, Hermans N, Apers S, Berghe D, Vlietinck A (2005) Proanthocyanidins in health care: current and new trends. *Curr. Med. Chem.* 11: 1345-1359.

Daglia M, Racchi M, Papetti A, Lanni C, Govoni S, Gazzani G (2004) In vitro and ex vivo antihydroxyl radical activity of green and roasted coffee. *J. of Agric. Food Chem.* 52: 1700-1704.

DeWhalley C V, Rankin S M, Hoult J R S et al. (1990) Flavonoids inhibit the oxidative modification of low density lipoproteins by macrophages. *Biochem. Pharmac.* 39:1743-1750.

Dixon R, Paiva N (1995) Stress-induced phenylpropanoid metabolism. *Plant Cell* 7: 1085-1097.

Dixon R, Steele C (1999) Flavonoids and isoflavonoids—a gold mine for metabolic engineering. *Trends Plant Sci.* 4: 394-400.

Dixon R A (2005) Engineering of plant natural product pathways. *Curr. Op. Plant Biol.* 8: 329-336.

Dixon R, Xie D, and Sharma S. (2005b) Proanthocyanidins—a final frontier in flavonoid research? *New Phytol.* 165:9-28.

Duarte J, Jimenez R, O'Valle F, Galisteo M, Perez-Palencia R, Vargas F, Perez-Vizcaino F, Zarzuelo A, Tamargo J (2002) Protective effects of the flavonoid quercetin in chronic nitric oxide deficient rats. *J. Hypertension.* 20:1843-1854.

Duthie G, Crozier A (2000) Plant-derived phenolic antioxidants. *Curr. Op. Lipidol.* 11: 43-47.

Frankel E N, Kanner J, German J B et al. (1993) Inhibition of oxidation of human low-density lipoprotein by phenolic substances in red wine. *Lancet.* 341:454-457.

Frydman A, Weisshaus O, Bar-Peled M, Huhman D, Sumner L, Marin F, Lewinsohn E, Fluhr R, Gressel J, and Eyal Y. (2004) Citrus fruit bitter flavors: isolation and functional characterization of the gene Cm1,2RhaT encoding a 1,2 rhamnosyltransferase, a key enzyme in the biosynthesis of the bitter flavonoids of citrus. *Plant J.* 40:88-100.

Garcia-Saura M F, Galisteo M, Villar I C, Bermejo A, Zarzuelo A, Vargas F, Duarte J (2005) Effects of chronic quercetin treatment in experimental renovascular hypertension. *Mol. Cell. Biochem.* 270: 147-155.

Go M, Wu X, Liu X (2005) Chalcones: an update on cytotoxic and chemoprotective properties. *Curr. Med. Chem.* 12: 481-499.

Grassi D, Lippi C, Necozione S, Desideri G, Ferri C (2005) Short-term administration of dark chocolate is followed by a significant increase in insulin sensitivity and a decrease in blood pressure in healthy persons. *Am. J. of Clin. Nutr.* 81: 611-614.

Gupta S, Hastak K, Ahmad N, Lewin J S, Mulditar H (2001) Inhibition of prostate carcinogenesis in TRAMP mice by oral infusion of green tea polyphenols. *Proc. Natl. Acad. Sci. USA.* 98:10350-10355.

Hamberger B, Hahlbrock K (2004) The 4-coumarate: CoA ligase gene family in *Arabidopsis thaliana* comprises one rare, sinapate-activating and three commonly occurring isoenzymes. *Proc. Natl. Acad. of Sci. U.S.A.* 101: 2209-2214.

Hertog M G, Feskens E J, Hommna P C, et al. (1993) Dietary antioxidant flavonoids and risk of coronary heart disease: the Zutphen elderly study. *Lancet* 342:1007-1011.

Hertog M G, Feskens E J, Hommna P C, Katan M B, Kromhout D (1994) Dietary antioxidant flavonoids and cancer risk in the Zutphen elderly study. *Nutr. Cancer* 22:175-184.

Hu W, Kawaoka A, Tsai C, Lung J, Osakabe K, Ebinuma H., Chiang V (1998) Compartmentalized expression of two structurally and functionally distinct 4-coumarate:CoA ligase genes in aspen (*Populus tremuloides*). *Proc. Natl. Acad. Sci. U.S.A.* 95: 5407-5412.

Huang M T, Lysz T, Ferraro T, et al. (1991) Inhibitory effects of curcumin on in vitro lipoxygenase and cyclooxygenase activities in mouse epidermis *Cancer Res.* 51:813-819.

Ishimi Y, Miyaura C, Ohmura M, Onoe Y, Sato T, Uchiyama Y, Ito M, Wang X, Suda T, Ikegami S (1999) Selective effects of genistein, a soybean isoflavone, on B-lymphopoiesis and bone loss caused by estrogen deficiency. *Endocrinol.* 140: 1893-1900.

Jang M, Cai L, Udeani G, Slowing K, Thomas C, Beecher C, Fong H, Fernsworth N, Kinghom D, Mehta R, Moon R, Pezzuto J (1997) Cancer chemopreventative activity of resveratrol, a natural product derived from grapes. *Science* 275: 218-220.

Johnson E T, Ryu S, Yi H K, Shin B, Cheong H, Choi G (2001) Alteration of a single amino acid changes the substrate specificity of dihydroflavonol 4-reductase. *Plant J.* 25: 325-333.

Joung J Y, Kasthuri G M, Park J Y, Kang W J, Kim H S, Yoon B S, Joung H, Jeon J H (2003) An overexpression of chalcone reductase of *Pueraria montana* var. *lobata* alters biosynthesis of anthocyanin and 5'-deoxyflavonoids in transgenic tobacco. *Biochem. Biophys. Res. Commun.* 303:326-331

Kaltenbach M, Schroder G, Schmelzer E, Lutz V, Schroder J (1999) Flavonoid hydroxylase from *Catharanthus roseus*: cDNA, heterologous expression, enzyme properties and cell-type specific expression in plants. *Plant J.* 19:183-193

Kobayashi H, Naciri-Graven Y, Broughton W J, Perret X (2004) Flavonoids induce temporal shifts in gene-expression of nod-box controlled loci in *Rhizobium* sp. NGR234. *Mol. Microbiol.* 51: 335-347.

Kotkar H M, Mendki P S, Sadan S V, Jha S R, Upasani S M, Maheshwari V L. (2002) Antimicrobial and pesticidal activity of partially purified flavonoids of *Annona squamosa*. *Pest Manag. Sci.* 58:33-7.

Lahtinen M, Salminen J P, Kapari L, Lempa K, Ossipov V, Sinkkonen J, Valkama E, Haukioja E, Pihlaja K. (2004) Defensive effect of surface flavonoid aglycones of *Betula pubescens* leaves against first instar *Epirrita autumnata* larvae. *J. Chem. Ecol.* 30:2257-68.

Lamartiniere C, Cotroneo M, Fritz W, Wang J, Mentor-Marcel R, Elgavish A (2002) Genistein chemoprevention: timing and mechanisms of action in murine mammary and prostate. *J. Nutr.* 132: 552S-558S.

Lattanzio V, Arpaia S, Cardinali A, Di Venere D, Linsalata V. (2000) Role of endogenous flavonoids in resistance mechanism of *Vigna* to aphids. *J. Agric. Food Chem.* 48:5316-20.

Lee D, Douglas C J (1996) Two divergent members of a tobacco 4-coumarate:coenzyme A ligase (4CL) gene family. cDNA structure, gene inheritance and expression, and properties of recombinant proteins. *Plant Physiol.* 112: 193-205.

Lesschaeve I and Noble A. (2005) Polyphenols: factors influencing their sensory properties and their effects on food and beverage preferences. *Am. J. Clin. Nutr.* 81 (1 Suppl): 300S-335S.

Lindermayr C, Mollers B, Fliegmann J, Uhlmann A, Lottspeich F, Meimberg H, Ebel J (2002) Divergent members of a soybean (*Glycine max* L.) 4-coumarate: coenzyme A ligase gene family—Primary structures, catalytic properties, and differential expression. *Eur. J. Biochem.* 269: 1304-1315.

Marraccini P., Deshayes A., Pétiard V. and Rogers W. J. (1999) Molecular cloning of the complete 11S seed storage protein gene of *Coffea arabica* and promoter analysis in the transgenic tobacco plants. *Plant Physiol. Biochem.* 37:273-282.

Marraccini P, Courjault C, Caillet V, Lausanne F, LePage B, Rogers W, Tessereau S, and Deshayes A. (2003) Rubisco small subunit of *Coffea arabica*: cDNA sequence, gene cloning and promoter analysis in transgenic tobacco plants. *Plant Physiol. Biochem.* 41:17-25.

Monagas M, Bartolome B, and Gomez-Cordoves C, (2005) Updated knowledge about the presence of phenolic compounds in wine. *Crit. Rev. Food Sci. Nutr.* 45:85-118.

Onyilagha J C, Lazorko J, Gruber M Y, Soroka J J, Erlandson M A. (2004) Effect of flavonoids on feeding preference and development of the crucifer pest *Mamestra configurata* Walker. *J. Chem. Ecol.* 30:109-24.

Peters D J, Constabel C P (2002) Molecular analysis of herbivore-induced condensed tannin synthesis: cloning and expression of dihydroflavonol reductase from trembling aspen (*Populus tremuloides*). *Plant J.* 32: 701-712.

Raes J, Rohde A, Christensen J H, Van de Peer Y, Boerjan W (2003) Genome-wide characterization of the lignification toolbox in *Arabidopsis*. *Plant Physiol.* 133: 1051-1071

Ralston L, Subramanian S, Matsuno M, Yu O (2005) Partial reconstruction of flavonoid and isoflavonoid biosynthesis in yeast using soybean type I and type II chalcone isomerases. *Plant Physiol.* 137: 1375-1388.

Ramirez-Coronel M, Marnet N, Kolli V, Roussos S, Guyot S, Augor C (2004) Characterization and estimation of proanthocyanidins and other phenolics in coffee pulp (*Coffea arabica*) by thiolysis-high performance liquid chromatography. *J. Agric. Food Chem.* 52: 1344-1349.

Rice-Evans C (2001) Flavonoid Antioxidants. *Curr. Med. Chem.* 8:797-807.

Rogers J., Michaux S., Bastin M., Bucheli P. (1999) Changes to the content of sugars, sugar alcohols, myo-inositol, carboxylic acids and inorganic anions in developing grains from different varieties of Robusta (*Coffea canephora*) and Arabica (*C. arabica*) coffees *Plant Science.* 149: 115-123.

Rohde A, Morreel K, Ralph J, Goeminne G, Hostyn V, De Rycke R, Kushnir S, Van Doorsselaere J, Joseleau J P, Vuylsteke M, Van Driessche G, Van Beeumen J, Messens E, Boerjan W (2004) Molecular phenotyping of the pal1 and pal2 mutants of *Arabidopsis thaliana* reveals far-reaching consequences on and carbohydrate metabolism. *Plant Cell* 16: 2749-2771.

Saito K, Kobayashi M, Gong Z, Tanaka Y, Yamazaki M (1999) Direct evidence for anthocyanidin synthase as a 2-oxoglutarate-dependent oxygenase: molecular cloning and functional expression of cDNA from a red form a of *Perilla frutescens. Plant J.* 17:181-189

Schneider K, Hovel K, Witzel K, Hamberger B, Schomburg D, Kombrink E, Stuible H P (2003) The substrate specificity-determining amino acid code of 4-coumarate: CoA ligase. *Proc. Natl. Acad. Sci. U.S.A.* 100: 8601-8606.

Setchell K, Cassidy A (1999) Dietary isoflavones: biological effects and relevance to human health. *J. Nutr.* 129: 758S-767S.

Shimada N, Aoki T, Sato S, Nakamura Y, Tabata S, Ayabe S (2003) A cluster of genes encodes the two types of chalcone isomerase involved in the biosynthesis of general flavonoids and legume-specific 5-deoxy(iso)flavonoids in *Lotus japonicus. Plant Physiol.* 131: 941-951

Sivakumaran S, Molan A, Meagher L, Kolb B, Foo L, Lane G, Attwood G, Fraser K, Tavendale M (2004) Variation in antimicrobial action of proanthocyanidins from *D. rectum* against lumen bacteria. *Phytochem.* 65: 2485-2497.

Sugihara N, Arakawa T, Ohnishi M, Furono K (1999) Anti- and pro-oxidative effects of flavonoids on metal-induced lipid hydroperoxide-dependent lipid peroxidation in cultured hepatocytes loaded with alpha-linoleic acid. *Free Rad. Biol. Med.* 27: 1313-1323.

Tanaka Y, Yonekura K, Fukuchi-Mizutani M, Fukui Y, Fujiwara H, Ashikari T, Kusumi T (1996) Molecular and biochemical characterization of three anthocyanin synthetic enzymes from *Gentiana triflora. Plant Cell Physiol.* 37:711-716

Tanner G J, Francki K T, Abrahams S, Watson J M, Larkin P J, Ashton A R (2003) Proanthocyanidin biosynthesis in plants. Purification of legume leucoanthocyanidin reductase and molecular cloning of its cDNA. *J. Biol. Chem.* 278: 31647-31656

Wellmann F, Matern U, Lukacin R (2004) Significance of C-terminal sequence elements for Petunia flavanone 3 beta-hydroxylase activity. *Febs Letters* 561: 149-154.

Winkel-Shirley B (2002) Biosynthesis of flavonoids and effects of stress. *Curr. Op. Plant Biol.* 5: 218-223.

Wood J G, Rogina B, Lavu S, Howitz K, Helfand S L, Sinclair D, Tatar M (2004) Sirtuin activators delay aging by mimicking calorie restriction in yeast and metazoans. *J. Nutr.* 134: 3518S-3519S.

Xie D Y, Jackson L A, Cooper J D, Ferreira D, Paiva N L (2004) Molecular and biochemical analysis of two cDNA clones encoding dihydroflavonol-4-reductase from *Medicago truncatula. Plant Physiol.* 134: 979-994.

Xie D Y, Sharma S B, Paiva N L, Ferreira D, Dixon R A (2003) Role of anthocyanidin reductase, encoded by BANYULS in plant flavonoid biosynthesis. *Science* 299: 396-399.

Yamagishi M, Natsume M, Osakabe N et al. (2002) Effects of cacao liquor proanthocyanidins on PhIP-induced mutagenesis in vitro, and in vivo mammary and pancreatic tumorigenesis in female Sprague Dawley rats. *Cancer Lett.* 185:123-130.

Yamane T, Nakatani H, Kikuoka N et al. (1996) Inhibitory effects and toxicity of green tea polyphenols for gastrointestinal carcinogenesis. *Cancer* 77 (8 Suppl): 1662-1667.

Yan L J, Droy-Lefaix M T, Packer L (1995) *Ginko biloba* extract (EGb 761) protects human low density lipoproteins against oxidative modification mediated by copper. *Biochem. Biophys. Res. Comm.* 212:360-366.

Yang C S, Yang G Y, Landau J M, Kim S, Liao J. (1998) Tea and tea polyphenols inhibit cell hyperproliferation, lung tumorigenesis, and tumor progression. *Exp. Lung Res.* 2:629-639

Yen W-J, Wang B-S, Chang L-W, Duh P-D (2005) Antioxidant properties of roasted coffee residues. *J. Agric. Food Chem.* 53: 2658-2663.

Yilmaz Y, Toledo R T (2004) Health aspects of functional grape seed constituents. *Trends Food Sci. Technol.* 15: 422-433.

Yoshimoto T, Furrkawa M, Yamamoto S et al. (1983) Flavonoids: Potent inhibitors of arachidonate 5-lipoxygenase. *Biochem Biophys. Res. Comm.* 116:612-618.

Yu O, Jung W, Shi J, Croes R, Fader G, McGonigle B, Odell J (2000) Production of the isoflavones genistein and diadzein in non-legume dicot and monocot tissues. Plant Physiology 124: 781-794

What is claimed:

1. A nucleic acid molecule isolated from coffee (*Coffea* spp.), having a coding sequence that encodes a phenylalanine ammonia lyase, wherein the phenylalanine ammonia lyase comprises an amino acid sequence at least 95% identical to SEQ ID NO: 20 or 22 or comprises an amino acid sequence identical to SEQ ID NO: 21.

2. The nucleic acid molecule of claim 1, wherein the phenylalanine ammonia lyase has an amino acid sequence identical to SEQ ID NO:20.

3. The nucleic acid molecule of claim 1, wherein the phenylalanine ammonia lyase has an amino acid sequence identical to SEQ ID NO:21.

4. The nucleic acid molecule of claim 1, wherein the phenylalanine ammonia lyase has an amino acid sequence identical to SEQ ID NO:22.

5. The nucleic acid molecule of claim 1, wherein the coding sequence is an open reading frame of a gene, or a mRNA, or a cDNA.

6. A vector comprising the coding sequence of the nucleic acid molecule of claim 1.

7. The vector of claim 6, which is an expression vector selected from the group of vectors consisting of plasmid, phagemid, cosmid, baculovirus, bacmid, bacterial, yeast and viral vectors.

8. The vector of claim 7, wherein the coding sequence of the nucleic acid molecule is operably linked to a constitutive promoter, an inducible promoter or a tissue-specific promoter.

9. The vector of claim 8, wherein the tissue specific promoter is a seed specific promoter.

10. The vector of claim 9, wherein the seed specific promoter is a coffee seed specific promoter.

11. A host cell transformed with the vector of claim 7.

12. The host cell of claim 11, which is a plant cell selected from the group of plants consisting of coffee, tobacco, *Arabidopsis*, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, petunia, zinnia, and turfgrasses.

13. A fertile plant produced from the plant cell of claim 12, said plant comprising said vector.

14. A method of modulating flavor or aroma of coffee beans, comprising modulating production or activity of one or more phenylalanine ammonia lyase enzymes within coffee seeds by introducing into a coffee plant a nucleic acid molecule encoding a phenylalanine ammonia lyase enzyme operably linked to a promoter in the sense or antisense orientation, wherein the phenylalanine ammonia lyase comprises an amino acid sequence at least 95% identical to SEQ ID NO: 20 or 22 or comprises an amino acid sequence identical to SEQ ID NO: 21.

15. The method of claim 14, comprising increasing production or activity of the one or more phenylalanine ammonia lyase enzymes, wherein the nucleic acid molecule encoding a phenylalanine ammonia lyase enzyme is operably linked to a promoter in the sense orientation.

16. The method of claim 14, comprising decreasing production or activity of the one or more phenylalanine ammonia lyase enzymes.

17. The method of claim 15, comprising increasing expression of one or more endogenous genes encoding phenylalanine ammonia lyase enzymes within the coffee seeds.

18. The method of claim 16, wherein the nucleic acid molecule inhibits the expression of one or more genes encoding the phenylalanine ammonia lyase enzymes.

* * * * *

SEQUENCE LISTING

<160> NUMBER OF SEQ ID NOS: 157

<210> SEQ ID NO 1
<211> LENGTH: 2344
<212> TYPE: DNA
<213> ORGANISM: Coffea arabica

<400> SEQUENCE: 1

```
caccactgct actgcttcag ttcctttat cacttgcttt acatgaatta agtcgatact      60
cttccttgaa tacctagcga ttagtttcgt ggtgacctat ctagcacgtc tagccatttt    120
tctgtttcgg tggcatcaat cctgagcaga gaaagctgca agatggaaaa tggtcatgac    180
gaaggcgtga agtctcgga gttttgcttg aaatcagatc ctctgaactg gggagtggca    240
gctgagtcac tgatgggaag tcatttggac gaagtgaagc gcatggtagc tgagtttagg    300
aagccggtgg taaagctcgg cggtgagagc ttgaccgttg ctcaggtggc cgcgattgcc    360
gccaaaggtg atcagggtgt gaaggtggag ctggcggagg acgcaagggc tggggtgaag    420
gcaagcagcg actgggtgat ggagagtatg aacaaaggca ctgatagtta cggagttacc    480
actgggtttg gtgccacttc acacaggcgg accaatcaag gcggtgccct tcagaaggag    540
cttattagat ttctgaacgc gggaatcttc ggaaacggca cggaaacttg ccacatgctg    600
ccacactcag caacaagggc agcgatgctt gtaagaatca cacccttct tcaaggttat    660
tccgggatca gattcgaaat cttggaagcc atcaccactt tccttaacca caacatcacc    720
ccatgcttgc ctcttcgcgg tacaatcact gcctctggtg atcttgtccc cttgtcctac    780
attgccggtt tactaaccgg ccgccccaac tccaaggccg ttgggcccaa cggagaagct    840
ttcaatgccg aagaagcatt tcgccttgct ggcctcagcg gtggctttt cctgctgcag    900
cctaaagaag gccttgctct tgttaacgga acagcagttg gttctggctt ggcctctatt    960
gttctatttg aggctaacgt gcttgctgtc ttatctgtag tgctgtcagc aatctttgct   1020
gaagtgatga atggcaagcc tgagttcacc gatcatttga cgcataagtt gaagcatcat   1080
ccgggccaaa ttgaggccgc ggctatcatg gagcatatct tggatggaag ctcttacgtc   1140
aaggctgctc aaaagttgca tgagttggat cccctgcaaa agccaaagca ggaccgatac   1200
gctctcagga cgtctccgca gtggctgggt ccacaaatcg aagttattcg tgcagcaaca   1260
aaaatgattg agagggagat caattcagtt aatgataacc ctctcattga tgtgtccagg   1320
aacaaggcct acatggtgg caacttccag ggtaccccta ttggagtgag catggacaac   1380
gctcgactgg ccattgcatc tattggcaaa ctgatgtttg ctcaattttc cgagcttgtt   1440
aatgattact acaacaatgg gttgccgtcc aatctctctg gaggaaggaa tccaagtttg   1500
gactatggat tcaagggagc tgagattgct atggctgcat actgttctga actccagtat   1560
ttggcaatc cagtgaccaa ccatgtccag agtgccgagc aacacaacca agacgtcaac   1620
tccttgggat taatctcttc aagaaaaacg gcagaagcca ttgatatctt gaagcttatg   1680
tcatccactt atttggtggc actttgtcaa gcaatcgatt tgaggttttt ggaagaaaac   1740
ttgaaaaatg ctgttaagaa tattgtcagc caagtggcaa agcgaactct gacaatgggt   1800
gctaatggag aactgcatcc ttcacggttt tgtgagaagg atttgctcag agtggtggac   1860
cgcgaatacg ccttttgccta tgtggatgac ccttgcagcg ctacctatcc attaatgcaa   1920
aagttaaggc aagtgctcgt ggatcatgcg ttgaagaatg gtgatcagga gaagaacgtc   1980
aacacctcca tcttccaaaa gattgctgca tttgaagatg aactgaaggc tgtcctacca   2040
aaagaagtgg agagtgccag aagcgctgtg gagagtggaa atccagcaat ccctaatcgg   2100
ataagggagt gcagatctta cccattgtac aagttcgttc gagaagtgtt ggggacagga   2160
ctgctgactg gagagaaagc tcagtcacct ggtgaggtgt tcgaccaggt gttcacagca   2220
atgagcaagg gcagattgt agatcctttg ttggaatgtc tccaagaatg gaatggtgct   2280
cctctcccaa tctgttgatt tactttcatc cattcaaaca tttgtttatc aaatccttca   2340
```

```
atgt                                                                    2344

<210> SEQ ID NO 2
<211> LENGTH: 2318
<212> TYPE: DNA
<213> ORGANISM: Coffea arabica

<400> SEQUENCE: 2
atggagtgcg ctaatggaaa tgtaatgac cttgcggaga cctttttgtac tcaacgggcc         60 gggccagcac ccgacccgtt aaattggaac gcagccgcgg agtccttaaa aggaagtcat        120
cttgatgaag tcaagcgcat ggtcgatgag ttcaggaggc ccctggtccg gctaggtggt        180
gagacgctga cgatagctca ggtggcggcc atagctgctt cctccgacgc agcggttaag        240
gtggagctgt cggagggtgc cagggccggc gtcaaggcca gcagtgactg ggttatggag        300
agcatgagaa agggtactga tagttacggt atcaccaccg gctttggtgc aacgtcacac        360
aggagaacca aacaaggcgg agctctccag gaggagctca tccgattctt gaatgctgga        420 attttttggca acgggaccga acatgtcac acattgcctc actcggcaac aagggcttct        480
atgcttgttc gaatcaacac cctccttcag gggtactctg gcatcagatt tgagattctg        540
gaagctatta caaagcttct caacaataat atcaccccat gtttgcccct ccgcggaacg        600
atcaccgcct ccggtgattt ggttccgctc tcctacattg ttggattatt aacaggtcga        660
ccaaattcca aggctgttgg acctgacgga aaatttgtca atgctactga agcattcagc        720
ctggcgggga ttgacactgg attttttcgag ctgcaggcaa agaaggcct tgcacttgtg        780 aatggcactg ctgttggctc tgccttggct tccatggttc tctttgaggc taatattctt        840
gctgttcttg ctgaagttct ttcaggaatt tttgctgaag ttatgcacgg gaagccagag        900
tttacagacc atttgactca taaactgaag caccatcctg gtcaaattga ggccgcagct        960
attatggaac acatttttgga tggaagttca tttgttaaag aagctcagag ggttcatgaa       1020
ttcgacccct tgcaaaagcc caaacaagat cgttatgcac tccgaacatc cccacaatgg       1080
ctaggtccat tgattgaagt catcagggct tcgacaaaat ccatcgaaag agagatcaat       1140
tctgtgaatg acaatccttt gatcgacgtt tcccggaata aggccttaca tggtgggaac       1200
ttccaaggta caccaattgg agtctcgatg gataacaccc gtctggcaat tgcatcaatt       1260
ggtaaactca tgttcgcaca attttctgag ctggttaatg acttttacaa caatggattg       1320
ccttcaaaac tatctggggg acgtaatcca agtttggact atggtttcaa aggtgctgaa       1380
attgccatgg cagcttactg ctctgaactt cagttcctag ccaatcctgt cacaaaccat       1440
gtgcaaagtg cagagcaaca caaccaagat gtcaactcat taggattgat ctcatcaaga       1500
aaaacagcag aagctgtgga catattgaag ctcatgtcat cgacctattt ggttgcattg       1560
tgccaggcaa ttgacctgag gcacctggag gagaacttga aggcctcagt gaaaaacacg       1620
gttagccttg tagccaagaa agtgctaaca atgggctaca atggcgaatt gcacccatct       1680
agattctgcg aaaaagactt gctcaaagtg tggacagag agcatgtttt tgcttacatt       1740
gatgacccct gtagtggaac ctaccccctg atgcaaaagc taaggcaagt cctagtggag       1800
cactccttag caaatgggga caaggagaag gacgcaacca cttcaatttt ccaaaagatc       1860
ggtgcctttg aggatgaact aaaggccctt ttgcccaaag aagtgagag tgctagatgt       1920 gagttggaga atggaaagcc aggcattgcc aaccgtatca aggattgcag gtcctactca       1980
ttgtacaagt ttgtgagggg agagttgggg accaatttcc tgactggtga aaggtgaga       2040 tcacctggag aagaatttga caaggtattc actgccatat gtgaagggaa gttgattgat       2100
```

```
ccattgctgg attgtttgaa agagtggaat ggtgctcccc gtccaatttg ctaagatgtt    2160
ttcttcatac tgtggtacat ttattaaatt tcttgaaatt tgttttttt  cctagtttgc    2220 cctcttttg  gaatgttgta tccaagttgt cactagcttg tttaagatcc ttgtattttc    2280
gtcctatact gatattgttc gttgccataa atgttgaa                           2318

<210> SEQ ID NO 3
<211> LENGTH: 3476
<212> TYPE: DNA
<213> ORGANISM: Coffea canephora

<400> SEQUENCE: 3
aaagaacagt taaattctca aatgcagcaa ataatttgaa acggaggagg aagtaagtat     60
acacgaagcg acagggtagg aaaaaggagg gtgactggtt gggttcaaag agttgataag    120
ttattggttg tgttttattg ccgaggggga attgtttgtt gtcaggcaaa cagttaaagg    180
gaaaaagcaa gagggttgct ttcagagggg tggtaaataa ttaagaggat gggacaaaga    240
gtaaaagaat ccttcctgat ttcctccctc tttatgtcat tacatcgatt tcagcctttt    300
tctaagtgtg tttgctttgc ttgtaaatac tgtttttgt  ttttggtttg taaagtaggg    360
tctttactct ttatggacca aattgttagg tacgttgctt aaccaataat gagaacttgt    420
tgcccaacaa aacagggaca gctttataaa gttctgcttg attatctctt ttgacttgca    480
ttcttgtcca ggatttcttg gaaatttcat cagcatgctg tctaatcttg tagcggttcc    540
gtaccttcca gattccctat atatagaata tagaatttat cgtgtcgaga aaaaaagaa     600 aagagagaac ttttgtcaa  aaagatgaa  taagttaggc gcattgccta ttttatttta    660 ttttatttt  ttgctaggag tcttctaat  acagttcatt gggaaaaaaa acaaaaagat    720
ggaatataga agaaaaaaaa atttattgct agtacagtta gatactccac aaggtgggac    780
gacaatttat tgctagtagg gaaaacaatt ttcgttttct tgtagtcgca caaggtggga    840
gggacacttg aaggggcgcc cggaggggaa gaaaggaagt agtactatct tctacctaac    900
cccactttga ctgtaggcga gatcgccccc agcgagcatt atcaaagctt gtatccttga    960
gcagggctgc tctgcaaagc taggagtagt tggctaaatt gggacactac cttctgttga   1020
aaaaaaaaat aaaaaacaac taaaaactaa agtagtagg  cgggatagcc catcataata   1080
tagccgattt tgttgcctaa ataaaattga aaacccacac ttttgcttaa aagctgcttt   1140
tttttttttt ttttttttgt ggttaactga ttgaccttta tcccatccct gagggcatgg   1200
gttctgtgtt gattggacca tagttatgaa gagccaacat ggcctatccc tgaaaattaa   1260
atgtcatggc agaattgttg ccctatcatt aatgtcatag aaaaaaaata ccatgctctt   1320
ggacatttgt agcgtgaaat atttatgaaa ttattaatat gttaattagt gtaaatcaat   1380
tttgtaaagc caccgaaaaa gaaactattt gacccaatgc tgttgaaaaa tcaggttctt   1440
gaatgctgga atttttggaa atggaacaga gtcaggtcac acgttgccac attctgcgac   1500
gagggctgca atgctagtga ggatcaacac ccttctacag gggtattcgg ggatcagatt   1560
tgagatatta gaagctctta caaagcttct caatcacaac atcactccgt gtttgcctct   1620
ccgtggcacg atcactgcct ctggcgattt ggttcctctg tcatacattg ccggactgtt   1680
gaccggccgt cctaattcta ggtgtgttgg gcccaatggt cggtcccttg atgccacgga   1740
ggcatttcag attgctggga tgaattccgg gttctttgag ttgcagccta aggagggtct   1800
agcactggtt aatggcacgg ctgttgggtc gggtttggcc tccatggttc tatttgaggc   1860
aaatttattg gtaatcttat ctgaagtttt ttcagcaatt tttgctgaag ttatgcacgg   1920
```

| | |
|---|---|
| gaaaccggag ttcattgatc atttgatgca taaactgaag caccaccctg gtcagataga | 1980 |
| agccgcagcc ataatggaac acattttaga tggcagttcc tatgtcaagg cagcaaaggc | 2040 |
| attgcatgaa acggatcccc tccagaagcc taaacaggat agatatgcac ttcgtacttc | 2100 |
| accacagtgg ctaggacccc tgattgaagt tattagatca tcgacaaaat cgattgaacg | 2160 |
| ggagatcaat tctgtcaatg acaacccttt gattgacgtg tcgagaaaca agccttgca | 2220 |
| tggagggaat tttcagggga ctccaattgg tgtgtcaatg acaacacca gattagctat | 2280 |
| agcgtccata gggaaactca tgtttgctca attttctgag ctcgtcaatg atttctacaa | 2340 |
| taatggcttg ccttctaatc tatctggagg aagaaatcct agcttggatt atgggttcaa | 2400 |
| aggcgccgaa attgcaatgg ccgcctattg ttctgagctt caattttttgg ccaaccctgt | 2460 |
| cacaaatcat gtacagagtg ccgagcaaca caatcaggat gttaactctt taggattgat | 2520 |
| ttcttctaga aaagcagctg aagcagtaga catcttgaaa ctgatgtctt caacttacct | 2580 |
| agtggcactt tgtcaggcaa ttgatctgag gcatttggag gaaaatttga aaaacgctgt | 2640 |
| caagagcaca gttcaccaag tcgctaaaaa ggttctgacc acaggcatca atggggagct | 2700 |
| tcatccttca agattctgtg aaaaagattt acttaaagtg gttgagcgtg aatacgtgtt | 2760 |
| tacatacata gatgatcctt gcagtgcaac ttatccactg atgcaaaagc taaggcaagt | 2820 |
| ccttgttgat catgccctga tcaacaatga ggacctaaat ccgaacactt cgattttcct | 2880 |
| caaagttgga gcttttgaag aagagctgaa gacccttttg ccaatagaag ttgaaagtgc | 2940 |
| aagaaatgca tgtgaaagtg gtaatcctgc agtcccaaat aggatcaaga atgcaggtc | 3000 |
| ttacccttta tacaaatttg tgagggaaga tttggcgact ggattcttga caggagaaaa | 3060 |
| ggcaaagtca cctggagagg aatttgataa ggttttctcc gcaatttgtg atggtaagat | 3120 |
| ggtcgatcca ttgctcgagt gtctcaaaga ttggaatggt gctccgctac ccttgtgtta | 3180 |
| aatgccactc cacggcacgt tgagcagatt ttagctgttg tactcggtga aggccgacag | 3240 |
| aagagcaggc ttccttgagg aatattttgt tttactgtag tagcaaactg ttttttctcta | 3300 |
| cttttttttt tttttttttt ttggtgttgt tgttgtcaat tatcaccatc tactcctact | 3360 |
| tccatctatt attttttctct atcttttttgt ctctcgtgat ttatgtacag ataaattatt | 3420 |
| gtaatttgtt gggatttctc aaattttgtg aggatttgaa tcaaaaaaaa aaaaaa | 3476 |

<210> SEQ ID NO 4
<211> LENGTH: 1668
<212> TYPE: DNA
<213> ORGANISM: Coffea canephora

<400> SEQUENCE: 4

| | |
|---|---|
| cactcaacca aaccaaacct cccactcctc cacaccgtca tggatcttct cctgctagag | 60 |
| aagaccctct tgggactgtt tgcagccatc atagttgcca tcgttgtttc taaattacgg | 120 |
| ggcaagaaat tcaagctgcc tccaggccca atcccagttc ccattttcgg aaactggtta | 180 |
| caagttggtg atgatttgaa ccaccgcaac ctcactgact acgccaagaa atttggagaa | 240 |
| atcttccttc tgagaatggg ccagcgcaat cttgtggtgg tatcgtcccc tgaacttgcc | 300 |
| aaagacgtct tgcacaccca gggggtggag ttcggctccc gcaccagaaa tgtggtgttt | 360 |
| gatatattca ccggcaaagg ccaggatatg gtcttcaccg tctacggcga gcattggagg | 420 |
| aagatgagaa ggattatgac tgtcccctttt ttcactaaca aagttgttca gcagtacagg | 480 |
| cacggttggg aggcagaggt tgcccgtgtc gtggaggatt taagaagaa ccctgaatcc | 540 |
| tccaccaatg ggattgtctt gaggaggagg ttgcagctca tgatgtacaa taatatgtac | 600 |

| | |
|---|---|
| cgaatcatgt tgattaccg atttgagagc gaggatgatc ctctgtttaa caagcttaag | 660 |
| gctttgaacg gagagaggag taggctggct cagagcttcg aatataatta cggtgatttc | 720 |
| attcccatct tgaggccttt cttgaggggt tacttgaaga tctgtaagga ggttaaggag | 780 |
| aggaggctgc agctgttcaa ggatcacttc gttgacgaaa ggaagaagct tgcaagcaca | 840 |
| acaagcatgg atagccacag cctaaaatgt gccattgatc atattcttga agcacagcag | 900 |
| aagggagaga ttaacgagga caatgtcctt tacattgtgg aaaacatcaa tgttgccgct | 960 |
| attgagacaa cgttgtggtc aattgaatgg ggcattgcgg agttggtaaa ccacccacaa | 1020 |
| gtccagagga aactgcgaca ggagattgat accgtgcttg acctggtgt gcaagtcact | 1080 |
| gaacccgaca ccctcaaact accatacctt caggctgtgg tcaaggagac cctccgactt | 1140 |
| cgaatggcaa ttcctctttt ggtgcctcac atgaacctca atgaagccaa gctgggcggg | 1200 |
| tatgatattc ctgccgagag caagattttg tcaacgcttg gtggctcgc aaacaaccca | 1260 |
| gagaactgga ggaagccaga ggagttcaga ccagagaggt ttttggaaga ggagtctaag | 1320 |
| gttgatgcca atggcaacga cttccggtat cttccattcg tgttggtag gagaagctgc | 1380 |
| cctggaatca tccttgcatt gccaattctt ggtatcactt tgggacgctt ggtgcagaat | 1440 |
| tttgagctgt tgcctcctcc agggcaatcc aagattgata ctgcagaaaa gggtggacaa | 1500 |
| ttcagtctgc acattttgaa gcattccacc attgtcttga agccaagatc cctctagacg | 1560 |
| tgattgtaat tgtgtgatga aatcggttta ttgcaaattg cattaaaata aaaaaaaaa | 1620 |
| aaaaaaaaa aaaaaaaaa aaaaaaaaa aaaaaaaaa aaaaaaa | 1668 |

<210> SEQ ID NO 5
<211> LENGTH: 1771
<212> TYPE: DNA
<213> ORGANISM: Coffea arabica

<400> SEQUENCE: 5

| | |
|---|---|
| tagctcgtag taacccttca acaagcccctt tgtcaatggc tgtcaaaaca aagcaagaag | 60 |
| aaatcatatt ccgatcaagg ctccctgata tttacatccc aaaacatctg ccctgcaca | 120 |
| cttactgttt cgaagaccett cctaagttca gatcacaggc ttgtttgata aatggcgcca | 180 |
| ccgatgaaat ttcactttc gaacaagttg agctcacagc cagaagagtt gcatccgggc | 240 |
| ttaacaaagt tggtgtacag caaggagata cggtcatgat cctgctgcca aactcgccgg | 300 |
| aattcgtgtt cgccttcctc ggtgcatctt tccggggagc catatccacg atggccaatc | 360 |
| catatttcac ctctgccgaa gtcataaagc aagccaaggc atccaacgca aagctcatca | 420 |
| tcacgcaagg ctgttacgtc gaaaaggtca gggactatgc atgtgaaaat ggggtgaaag | 480 |
| tcgtgtgcat cgactctgcg ccggaaggtt gtttacactt ctcggagcta accgaggccg | 540 |
| atgaaaggga aatgccggac gtcgagatca gccctgatga tgtggtggcg ctgccgtact | 600 |
| cctccgggac cactggactg cctaaggggg tgatgttgac ccacaaggga cttgtcacta | 660 |
| gcgtggcaca acaggttgac ggagagaacc caaatttcta tatacacaat caagtgatga | 720 |
| tgtgcgtttt gtctctgttc cacatatatt cgctgaactc aatttttgcta tgtgggttga | 780 |
| gggccggcac aacaattttg atcatgcaga aatttgacat aattccgttc ttggaattga | 840 |
| ttcaaaaata taaggtcaca actgggccat tgtgccacc aattgttctg gccatagcca | 900 |
| aaagtccaga ggttgataaa tatgaccttt cgtcggtgaa gactgtcatg tccggagcgg | 960 |
| cgccattggg gaaggagctt gaagatgctg ttagaaccaa atttcctaag gccaaacttg | 1020 |
| gtcagggtta tgggatgaca gaagcggcc ctgtgctagc aatgtgctca gcatttgcta | 1080 |

```
aggatccctt tgaggttaaa tcaggcggat gtggttccgt tgttagaaat gctgaaatga    1140
agattgtaga tcccgaaact ggttcctctt tacccggaa ccaacctgga gaaatctgca     1200
tcagaggtga ccaaatcatg aaaggctatc ttgatgaccc tgaagccaca aaagcaacca    1260
tagacgaaga tggttggtta catacaggtg atgtaggcta cattgacgag gatgatgaac    1320
ttttcatcgt tgatcgcctc aaggagctaa tcaagtacaa agggttccaa gtcgcacctg    1380
cagaacttga agccctgctc ctcgctcact ctgacatctc agatgctgct gttgtcccaa    1440
tgaaggatga cgcagcaggc gaagttccag ttgcttttgt tgtgaaatca aaagattcca    1500
acatcaccga ggatgaaatt aaggaatata tcaagaaaca ggttatattc tacaagagaa    1560
taaaccgtgt gttttttgtt gatgccattc cgaagtcacc atcaggcaaa atcttgagaa    1620
aggacttgag agcaagacta gctgctggcg tgccaaaata agcaaggca acagcaaatt     1680 ggcagctaat ccagaggaca ttatagcgca aaaacatctg gattttgac acaaggctct      1740 gcagctgccg attatggtgt gtgattgtcg a                                    1771

<210> SEQ ID NO 6
<211> LENGTH: 1404
<212> TYPE: DNA
<213> ORGANISM: Coffea canephora

<400> SEQUENCE: 6
tgttgagaag gtgatggact tgctaagga aataatgtc aaagtcatgt gcactgatgc       60
ccctccggag ggttgtttgc attttcgga gctgtcgtcg gctgacgaaa agtcattcc       120 agcggtgaaa atcaatccaa acgatgccgt tgcactgcct tattcatcag gcaccactgg    180
tctaccgaaa ggggtcatgc tgacgcacaa agggttggtc acaagtgttg ctcagcaggt    240
tgatggagaa atcccaatc tttatttca caaggaagat gtgatattgt gcgttttgcc      300
tttgttccac atatattcac tgaattctgt gttgctttgt gggctaagag ttggtgcggc    360
aattttgatc atgcaaaagt ttgagattaa tgcactaatg gagcttgtgc aaaaatataa    420
ggtgacaatt gctccatttg tgccaccaat tgttttggaa attgccaaaa gtcctgtggt    480
ggataagtat gatctttcat ccataagaat ggtgatgtcc ggcgcggcac ccatggggaa    540
ggagctcgag gacaccgttc gagctaagct cccaaaggca gtgctcggac agggatacgg    600
catgacggag gcaggacctc tgctgtcgat gtgcttagcg tttgcaaagg agccatttga    660
tgtcaaatca ggtgcttgcg ggacagttgt gaggaatgct gaaatgaaaa ttgtagatcc    720
cgaaactaat ctctctctac cccgcaatca agctggagaa atttgcatca gaggcgacca    780
gatcatgaaa ggctaccta atgatccgga ggcaactgag aatacaatcg acaaagaagg    840
atggttgcac acaggagaca tagggtacat tgatgatgat gatgaaattt tcatagtgga    900
ccgattgaag gaattaatca agtataaagg gtttcaagtg gcacctgcag agctggaagc    960
catgctcctt tctcaccctg gtatttctga tgcagctgtt gtctccatga agatgaggc    1020 agctggagaa gttcctgttg cttttgtggt gagagcaagt ggttccaaaa tttccgagga    1080
tgagatcaaa caatttatct caaaccaggt gattttttat aagcgaatcc atcgggtgtt    1140
tttcatggat aaaattccta agctccatc tggcaaaata ttgagaaagg acctaagagc    1200
taagcttgca gctgaagttg cttgcaatta gagtactgta ttatatacat aacagtctct    1260
acaacaacgc tgttaatttg tatgcgtttt gggagaaaag gagagaaagt agtgtatgtt    1320
tcttctgatc tggtgtcaga tctcctctca tcctcaactc aagttgatcc tgtttctctt    1380
tttctcaaaa aaaaaaaaaa aaaa                                          1404
```

<210> SEQ ID NO 7
<211> LENGTH: 1771
<212> TYPE: DNA
<213> ORGANISM: Coffea canephora

<400> SEQUENCE: 7

```
tagctcgtag taacccttca acaagcccctt tgtcaatggc tgccaaaaca aagcaagaag      60
aaatcatatt ccgatcaagg ctccctgata tttacatccc aaaacatctg ccctgcaca      120
cttactgttt cgaagacctt cctaagttca gatcacaggc ttgtttgata aatggcgcca     180
ccgatgaaat ttcacttttc gaacaagttg agctcacagc cagaagagtt gcatccgggc     240
ttaacaaagt tggtatacag caaggagata cgatcatgat cctgctgcca aactcgccgg     300
aattcgtgtt cgccttcctc ggtgcgtctt tccggggagc catatccacg atggccaatc     360
catatttcac ctctgccgaa gtcataaagc aagccaaggc atccaacgca aagctcatca     420
tcacgcaagg ctggtacgtc gaaaaggtca tggactatg atgtgaaaat ggggtgaaag     480
tcgtgtgcat cgactctgca ccggaaggtt gtttacgctt ctcggagcta accgaggccg     540
atgaaaggga aatgctggac gtcgagatca gccctgaaga tgtggtggcg ctgccgtact     600
cctccgggac tactggactg cctaagggggg tgatgttgac ccacaaggga cttgtcacta     660
gcgtggcaca acaggttgac ggagagaacc caaatttcta tatacacaat caagtgatga     720
tgtgcgtttt gcctctgttc cacatatatt cgctgaactc aattttgcta tgtgggctga     780
gggccggcac aacaatttg atcatgcaga aatttgacat aattccgttc ttggaattga     840
ttcaaaaata taaggtcaca actgggccat ttgtaccacc aattgttctg gccatagcca     900
aaagtccaga ggttgataaa tatgacccttt cgtcggtgaa gactgtcatg tccggagcgg     960
cgccattggg gaaggagctt gaagatgctg ttagaaccaa atttcctaag gccaaacttg    1020
gtcagggtta tgggatgaca gaagcgggcc ctgtgctagc aatgtgctca gcatttgcta    1080
aggatccctt cgaggttaaa tcaggcggat gtggttccgt tgttagaaat gctgaaatga    1140
agattgtaga tcccgaaact ggttcctctt taccccggaa ccaacctgga gaaatctgca    1200
tcagaggtga ccaaatcatg aaaggctatc ttgatgaccc tgaagccaca aaagcaacca    1260
tagacgaaga tggttggtta catacaggtg atgtaggcta cattgacgag atgatgaac    1320
ttttcatcgt tgatcgcctc aaggagctaa tcaagtacaa agggttccaa gtcgcacctg    1380
cagaacttga gccctgctc ctcgctcact ctgacatctc agatgctgct gttgtcccaa    1440
tgaaggatga cgcagcaggc gaagttccag ttgctttttgt tgtgaaatca aaagattcca    1500
acatcaccga ggatgaaatt aaggaatata tcaagaaaca ggttatattc tacaagagaa    1560
taaaccgtgt gttttttgtt gatgccattc cgaagtcacc atcaggcaaa atcttgagaa    1620
aggacttgag agcaagacta gctgctggcg tgccaaaata agccaaggca acagcaaatt    1680
ggcagctaat ccagagggca ttatagcgca aaaacatctg gattttgat acaaggctct    1740
gcagctgccg attatggtgt gtgattgtcg a                                   1771
```

<210> SEQ ID NO 8
<211> LENGTH: 1397
<212> TYPE: DNA
<213> ORGANISM: Coffea canephora

<400> SEQUENCE: 8

```
cggagctaca aagctagcag ctacctgcaa aactctacgt accttaattt ttctctttt      60
ccgagcaaaa atggttaccg tcgaggaagt taggagggct caaagggccg aaggaccggc     120
```

```
gacgatcatg gccatcggaa cagctacgcc accaaattgt gtcgagcaaa gcacttatcc     180
ggattattat tttcgcatta ctgatagtga gcataagact gagctcaaag aaaagtttaa     240
gcgcatgtgt gacaaatcca tgattaagaa gcgctacatg tacttgacag aggaaatctt     300
gaaggaaaat cccaatattt gtgcttacat ggcaccctca ctagatgcta ggcaagacat     360
ggtggttgtt gaagtaccaa aactgggcaa agaagcagcc caaaaggcca ttaaggaatg     420
gggtcagccc aagtccaaga tcacccatct agtcttctgt accaccagtg gtgtggacat     480
gcctggagca gactatcagc tcaccaaact cttgggcctt cgcccgtccg tcaagcgcct     540
catgatgtac caacagggtt gttttgccgg tgggacggtc ctccggctag ccaaggacct     600
ggctgagaac aacaaaggtg cccgtgtcct cgtcgtctgc tcagaaatca ctgcagttac     660
attccgtggc ccaagtgatt cgcatttgga tagccttgta ggccaagccc tgtttggaga     720
tggggcagct gccatcatta tcggcgccga tcccgttccc gaagttgaga ggcccttgtt     780
tgagctcgtt acagcagccc aaaccattct tccagacagt cacggggcta tcgacggcca     840
tcttcgtgag gttgggctta cgttccatct tctcaaggat gttcccgggt taatctccaa     900
gaacattgaa aagagcctga agaagcatt  tgagcctctc ggtatttctg attggaactc     960
actcttctgg attgcacatc ctggtgggcc tgcaatttta gaccaggtgg agcaaaaact    1020
ggctcttaaa cccgaaaaat tacgggctac taggcatgtg ctgagtgagt atggaaatat    1080
gtcaagtgcc tgtgtcgtgt tcattcttga cgagatgaga aaggcctcag ccaaggatgg    1140
attcaacacc acaggggaag gcttagactg gggtgtgctc tttggttttg ggcctggact    1200
cacagttgag acagtggttc ttcacagcgc cacgattcaa aagtaatcat gtttgaatct    1260
ttcaatgaat attccaaatc tgtattacta tggagtacta agtaatttt tttttatgtg    1320 tgccttaagt ttatgtaaca atcatgatga caataaggtg ttacaccttg ttctggcaaa    1380
aaaaaaaaaa aaaaaaa                                                   1397

<210> SEQ ID NO 9
<211> LENGTH: 1271
<212> TYPE: DNA
<213> ORGANISM: Coffea canephora

<400> SEQUENCE: 9
agaccatgga aaagctgga  gaaacaatcc cagaaatagt gttaaataca ggccacaaaa      60
tgccattggt ggggtttgga tgtgcagctc agcctttgcc accatcagaa caactagtat     120
caacttttat tgatgcaatg gagattggat acaggcattt tgatacagca gcatgttatg     180
gcactgagga agctcttggt aaagctgtgg ctaaagcact agagattgga ttaattaaga     240
gcagggatga attgttcatc acttctaaac tttggtgtac tgatgctgat catgaccttg     300
ttctgcccgc cctcaaacaa actcttggga agttggggct agagtatttg gatctttatt     360
tgattcactg gcctctgagg ctaaagcagg gtactgagat gctcaatttc accaaagatg     420
caattctccc ttttgacatg catggaacgt ggaaggccat ggaagaatgc agcaaattgg     480
gcttgacaaa gtctataggt ttgagcaact tcacctgtga aaaaatctcc aaactccaag     540
aaagtgctac catccttcca gcagttaatc aggtggagat gaatgttggt tggcagcagc     600
gaaaattggt accatttgcc aaagagaaag gaattcacat aagtgcttgg tctcctcttg     660
gaggttatgg tacttcttgg ggtagcaatg cagtcatgga gagtccaatc atcaaaaata     720
ttgctgactc aagaaacaag accgtggcag aggtggcatt gagatgggta tatctgcaag     780
gagcaagcgt cattgtgaag agcttcagca aggaaaggat gaaacagaac ctccaagtat     840
```

| | | |
|---|---|---|
| ttgattggga actcaccaag gaagaaatgg atcaaattct gcagattcct cagcgtagag | 900 | |
| cccctggaac ggaagcgctt gttgatccaa cagggccata caaatctttg gaggaatttt | 960 | |
| gggatggcga cgtctgaatt tctggacaat gtgaacttca actctaccat gatgatcaac | 1020 | |
| attattccaa tcctgttggg gtattctcaa atcaaatagg gaagcagccg aacccaacat | 1080 | |
| cgtagtgact tatcttttac caaaacacca tagtaggttt gattatcagt tgtcaattgt | 1140 | |
| cggattgttt aatatatcat atataaagat ttaaaaacaa ataaataatc aacaggaaaa | 1200 | |
| agaaataaaa tgattatgta gagagtaaaa aaaaaaaaaa aaaaaaaaaa aaaaaaaaaa | 1260 | |
| aaaaaaaaaa a | 1271 | |

<210> SEQ ID NO 10
<211> LENGTH: 1205
<212> TYPE: DNA
<213> ORGANISM: Coffea canephora

<400> SEQUENCE: 10

| | | |
|---|---|---|
| ggaaaaagtt gaacaagaaa tccctgaaat agcagtatta aattcgggcc acaaaatgcc | 60 | |
| agtggcgggc ttaggatgtg ccgcacatcc tttgccacca ttagagcaat tagtaacaac | 120 | |
| ttttattgat gcaatggaga ttggatacag gcatttcgat acagcagcat gctatggcac | 180 | |
| agaggaggcc cttggtagag ctgtggctaa agcactagag attggattaa ttaagagcag | 240 | |
| ggatgaattg ttcatcactt ctaaactttg gtgcactgat gctgatcatg accttgttca | 300 | |
| gcctgccctc aaacaaactc tgggaagtt ggggctggag tatttggatc tttatttggt | 360 | |
| tcactggcca gtaagggtaa agcacggtgc tgagaagttc aatttcgcca agatgaaat | 420 | |
| tctccctttt gatatccatg gaacgtggca ggccatggaa ggatgcacca aattaggttt | 480 | |
| gacaaagtcc atcggtctga gcaacttcac ttgtgagaaa atctgcaaac tcctagaaat | 540 | |
| tgctaccatc cctccagcag ttaatcaggt ggagatgaat gttggctggc agcagagaaa | 600 | |
| attggtgcca tttgcaaaag acagagggat tcgtatatgt gcctggtctc ctcttgcatc | 660 | |
| ttatggtggt ctttggggca acagtgcagt catggagaat ccagtgctca aggatattgc | 720 | |
| tgcctcaaaa agcaagtccg tggcacaggt tgctttgcga tggatatatc agcaaggagc | 780 | |
| aagctttgtt gcgaagagct tcaacaagga aaggatgaaa caaaacctcc aaatatttga | 840 | |
| ttgggaactc accaaggaag aaatggatca aattctgcag attcctcagc ggagaggctt | 900 | |
| tgctggggaa gtgtttgttc atccaaccgg gccatacaaa tcggtcgagg aactttggga | 960 | |
| tggcgacacc tgaatttatc cttgtttgta aaataaatca agattagaag tatttattta | 1020 | |
| tttactcact agttttattg gagtcaagtt tttagtagtt gtgttattta atttagaagt | 1080 | |
| acgtattttg tttggtgatt gttgatgcaa gtctggtagg ttataaacag gatgtcatgg | 1140 | |
| tttctgagag attccaacaa gatgatatct agttgattgg taacttcaaa aaaaaaaaa | 1200 | |
| aaaaa | 1205 | |

<210> SEQ ID NO 11
<211> LENGTH: 1377
<212> TYPE: DNA
<213> ORGANISM: Coffea canephora

<400> SEQUENCE: 11

| | | |
|---|---|---|
| acttttcat caagtggaga tgagataaga taattgacta gacagaaact tcttgtataa | 60 | |
| agttcttgca tctttctcca ttgatttcca ttggtaaaat catgcctgag acaatggaaa | 120 | |
| aagttgaaca aaaaatccct gaaatagcag tattaaattc gggccacaaa atgccagtgg | 180 | |

```
cgggcttagg atgtgccgca catcctttgc caccatcaga acaattagta acaactttta    240
ttgatgcaat ggagattgga tacaggcatt tcgatacagc agcatgctat ggcacagagg    300
aggcccttgg tagagctgtg gctaaagcac tagagattgg attaattaag agcagggatg    360
aattgttcat cacttctaaa ctttggtgta ctgatgctga tcatgacctt gttctgcctg    420
ccctcaaaca aactcttggt ttggaataac tctacttcgg taggaagttg gggctggagt    480
atttggatct ttatttggtt cactggccag taagggtaaa gcacggtgct gagaagttca    540
atttcgccaa agatgaaatt ctcccttttg atatccatgg aacgtggcag gccatggaag    600
aatgcaccaa attaggtttg acaaagtcca tcggtctgag caacttcact tgtgagaaaa    660
tctgtaaact cctagaaatt gctaccatcc ctccagcagt taatcaggtg gagatgaatg    720
ttggttggca gcagagaaaa ttggtgccat ttgcaaaaga cagagggatt cgtatatgtg    780
cctggtctcc tcttgcatct tatggtggtc tttggggcaa cagtgcagtc atggagaatc    840
cagtgctcaa ggatattgct gcctcaaaaa gcaagtccgt ggcacaggtt gctttgcgat    900
ggatatatca gcaaggagca agctttgttg cgaagagctt caacaaggaa aggatgaaac    960
aaaacctcca aatatttgat tgggaactca ccaaggaaga aatggatcaa attctgcaga   1020
ttcctcagcg gagaggcttt gctggggaag tgtttgttca tccaacaggg ccatacaaat   1080
cggtcgagga actttgggat ggcgacacct gaatttatcg ttgtttgtaa aataaatcaa   1140
gattagaagt atttatttat ttttactcac tagtttattt ggagtcaagt ttttagtagt   1200
tgtgttattt aatttagaag tacgtatttt gtttggtgat tgttgatgca agtctggtag   1260
gttataaaca ggatgtaatg gtttctgaga gattccaaca agatgatatc tagttgattg   1320
gtaacttcaa aaaaaaaaaa aaaaaaaaaa aaaaaaaaaa aaaaaaaaaa aaaaaaa      1377

<210> SEQ ID NO 12
<211> LENGTH: 926
<212> TYPE: DNA
<213> ORGANISM: Coffea canephora

<400> SEQUENCE: 12
caattcttca aaggtgccgc gaaatctctg agtgctagtt acaatatgtc cctctcgctc     60
tccgttggtg aagttcatgt tgacggccac gttttccctc cggccgcgaa gaagcctcct    120
ggctctgatc aaaactttt tctggggaggc gcaggggcac gaggattgga aattgaaggc    180
aagtttatta aattcacggc tattggagtt tacatggagg agaccgccat cccgtcactg    240
gccgttaagt ggaagggcaa gactgctgag gaattaacgg aatccgttga gttcttcaga    300
gacatcgtta caggtccctt tgagaaattt ataagggtga cgatgatctt gcccttaacg    360
ggtaggcaat actcagagaa ggttgccgaa aattgctctg cttattggaa agcagttgga    420
atttacactg atgcagaggg taaagccatt gaaatgttcc ttgacatctt ccagaatgag    480
tccttcccac ctggagcctc tattctgttc acccagtcac ctctgggatc attaacgatt    540
agcttctcga aggatagttc aatacctgag gtcagcaatg cagttgtgga gaacaagcta    600
ctgtcagaag cggtgttgga gtccataatt ggcaaaaatg gtgtttcacc tgacacaaag    660
aagagtttgg caatacgttt atcagaatta ctgaaagtgt tgacaataa taataataat    720 gtcactgctg ataataagaa acttgaggcc gacgggcta ttgctgcgga gccccgggc    780 gaaaagcagg ttaatggcgt gcaagttcca gtacaggtac cttaagctga atgtaattgt    840
cctggaactt tctattgcat tctgcttggg aagagtataa atgaactctc tttccacgtc    900
ttcttgtaaa aaaaaaaaaa aaaaaa                                         926
```

<210> SEQ ID NO 13
<211> LENGTH: 1073
<212> TYPE: DNA
<213> ORGANISM: Coffea canephora
<220> FEATURE:
<221> NAME/KEY: misc_feature
<222> LOCATION: (472)..(472)
<223> OTHER INFORMATION: n is a, c, g, or t

<400> SEQUENCE: 13

```
gtctatataa cctctcttcg atttccgttg aattagtagt aaccagcaac actagattgt      60
tctctgccaa taaagagtct gccgcaggtt tctttcgcaa taattttcag atgggaactg     120
aagtagtgaa ggtggatgaa attccctttc ctctccaagt caccccttct accaccaagc    180
cactatcttt gctaggccat ggtataactg acattgagat tcacttcctt caaattaaat    240
tcactgcaat cggggtttat atggattccg aaattgtcac ctatttacaa caatggaagg    300
gcaagaagtg cactgatctt gcagaagacg atgacttctt tgaggctata atttctgccc    360
ccgtggacaa gtttctgaga atcgtagtga ttaaagagat caagggctcg caatatggcg    420
tgcagctaga aagcgcggtg agggatcgac ttgcagctga tgatagatat gnagatgagg    480
aggaagcagc tcttgaggaa cttattgagt ttttccaacc taaatatttc aagaaagatt    540
ctatcttgac atattatttc cctgccggtt cttctgcctc cgctgagatt gcattcacaa    600
cagagggaaa agaggaatca agataaagg tggagaatgc aaacgtggtt gagacgatca    660
agaaatggta cctgggtgga accagagggg tgtcacagac caccatctcc tccttagcca    720
atactcttgc tgccgagtta tctaaagaat gagaagttaa acgtctagtg cctgggcttg    780
gaatcttggt ctgtactttc tacgacgatg gtgttacctg gtgttgggat tcatggtctt    840
cctaatttaa tagtaaattc tacttcatct cttttacttg tcgactatta aaccggttga    900
aaccctctgt actattgctg ttatggatcc cttttagcca attgtgacct acgatctgaa    960
tattttaaga aggtggagac acggttcttc gattaccaaa aaaaaaaaa aaaaaaaaa     1020
aaaaaaaaa aaaaaaaaa aaaaaaaaa aaaaaaaaa aaaaaaaaa aaa               1073
```

<210> SEQ ID NO 14
<211> LENGTH: 1286
<212> TYPE: DNA
<213> ORGANISM: Coffea canephora

<400> SEQUENCE: 14

```
cgccgataat taattcatcg tatcgagtgt gggcaaaaca agaaagaaag ctgacaaact      60
gaaacagtga gacagatggc tccctcaact ctcacagctc tagcagagga gaagacgctt     120
cagtcaagtt tcatcaggga tgaagatgaa cgtcccaaag tggcctacaa ccaattcagc    180
aatgagattc ctatcatttc tttaaagggt cttgatgaca ctgacggtgc aagacctgaa    240
atttgtaaaa agattgtgga agcctgcgaa gactggggga ttttccaggt tattgatcat    300
ggggttgatg acaaactcat ttctgacatg acccgcctcg ctagagaatt cttcgctttg    360
ccacctgaag agaagctccg attcgatatg tcaggcggca agaaggggg atttatcgtc    420
tcaagccatc tacagggtga aactgtgcaa gactggcgtg agattgtgac atattttcc    480
tatccaattc gggcaaggga ttactcaagg tggccagaca ggcagaggc atggagggcc    540
gtgacagaga aatatagtga agagttgatg gagctggcat gtaaactgtt ggaggtattg    600
tcagaggcaa tgggattgga aaaggaagcc ttaactaatg catgtgtgga catggaccaa    660
aaagttgtgg tgaacttta cccaaagtgt ccacagcctg acctcacatt gggcctcaaa    720
```

```
cgccacaccg accctggaac catcactctc ttgttacagg accaagttgg tggacttcag      780
gccaccaggg acggtggcaa gacctggatt accgtccagc ctgttgaagg tgcttttgtt      840
gttaaccttg gtgaccatgg ccattacttg agcaacggga ggttcaagaa cgcagatcat      900
caggctgtgg taaactcaaa ttgtagcagg ttgtccatag ccacatttca gaacccggca      960
ccagaggcaa ctgtgtatcc actgaagatc cgtgagggtg agaaggcggt gcttgatgct     1020
cccatgacct tttcagagat gtacaggaag aaaatgagca aggaccttga gcttgcgagg     1080
ctgaagaagc tggccaagga gcaagagttg caagcagttg agaaagccaa gttggaggcc     1140
aagcccattg acgagatttt tgcttgaaac ctcatagttt gttgtttcac tactattact     1200
acttgtttgt gttatgcatt ctcaaaatta gtgttgtgga tttcatgaat aagaatgtat     1260
gttgccagaa gcaaaaaaaa aaaaaa                                           1286

<210> SEQ ID NO 15
<211> LENGTH: 1350
<212> TYPE: DNA
<213> ORGANISM: Coffea canephora
<220> FEATURE:
<221> NAME/KEY: misc_feature
<222> LOCATION: (132)..(132)
<223> OTHER INFORMATION: n is a, c, g, or t

<400> SEQUENCE: 15
gttcctttga aggtagaatg ttgttaatca attgcaataa aaaatttaa gattcacgta       60
tttagatgga tagagtgagc acaagaggag atggatagag tcactggtag aaaccgaaga     120
attgttgatt gncttgagtc ggatatacct aagcttcgat acctccaagc tatatgcaaa     180
gaagcatttt ggaagcacct ttctgcaccg ctaaatcttc ctcgaattgc atctcaagca     240
tgtgaagtaa atgggtactg catacccaag aacactggac ttagcgtgaa tatttgggca     300
attggaagag atcctgatgt gtgggaaaat ccactagatt tccaccctga taggtttctt     360
agcggaaaac atgcaaaact tgaccccca cccccagtaa atgatttcga gttgtttcat     420
tccatttggg gcctggagga gaatttgtgc tggagccaga aagtgggtag tgctagtgtg     480
gaatacgtac tagggacgtt ggtgcactca ttcgactgga aactgcctgc tgaagtgatt     540
gagttgaaca tggaggaaag ttttggtttg gctgtgcctc ttaaagccaa ggttagtcca     600
agactggctc taaattctta ttcagcttaa gctcctttgc ccgtgtccaa gattttcaaa     660
caatcagtct tttgaatttt gaatgagtac gaatttgata ggtaggaata gacaggctaa     720
gagatttaac cacccaagat ctctcttctt cgagaagcga atggcccaat caagaatagt     780
ttgtgttgcg gcctcacttc gatgcaattt tggttcgaaa tcgtgtaagc acaagaagaa     840
ggaaagcaca aagaggatcg aggctttccc tccggtgtcg agtgcgactc cgatagatac     900
ctaaattagc ttctgaggtg ttaggaaact cggttaagga gagttctgat gatttcttgt     960
tacctgttat ccaggaggag agggatattt gtattgggtg agaagaggtg cccatcaatt    1020
ttgtatactt gtcatgaatg tgtctgccta attgcgaaga ttcaatttca taagcaggac    1080
acaacatgaa ccacactcat ttactgttta ctgaagctcc gtctgtccat tgttgccgca    1140
ccaaatcaga tggttgtaca ttgcaaggga agacgcatga tcatttgaca tccaaaattt    1200
tttccaatac tagtaatagt ttacatgctt tgcacgtgat tataatgttc taaaatatat    1260
tcttctttag atactacttt tttttttttt ttgtaaaatt ttgatcatca acattataat    1320
acagtatttt tatgttaaaa aaaaaaaaaa                                     1350
```

```
<210> SEQ ID NO 16
<211> LENGTH: 1398
<212> TYPE: DNA
<213> ORGANISM: Coffea canephora

<400> SEQUENCE: 16
cttttcttct gcatatataa tagccattag agtttcccgc ttgattttc atctcctacc      60
tttcttgaaa tggaaggaga tattgcaacc tctgccgcgg caaagggcac cgtttgtgtc    120
acgggagccg ctggtttcat cggatcatgg cttgttatga gacttcttga acgtggctat    180
gttgtccggg ccactgtccg ggatccaggg aatatgaaga agtaaaaca tttgctagat    240
ttgcccaagg ccagcacgca tttgacgctg tggaaggcgg acatgacgga agaaggaagt    300
ttcgatgaag ccactcaagg ctgcgaaggg gtgtttcatg tggccacacc catggatttc    360
gactctaaag accctgagaa cgaaataatc aagccaacga tcaatgggc tttaaacatc     420
ataagatcat gtgtcaaggc aaaaactgtc aagaggctgg tttacacttc atctgctgga   480
accgtcaacg ttcaagaaca ccaacagccc gtctacgacg agaccaactg gagtgatttg    540
gactttatat attcgacaaa gatgacagga tggatgtatt tcgtttctaa gcttttggct    600
gagaaagaag cctgggaggt ctcgaaacag agcaacattg atttcataag cataatacca    660
acgctagtcg taggtccatt catcatgcct acattcccac ccagcctaat aactgcactt    720
tccttgatca ctgggaatga agctcactac tcaattatta ggcaaggcca gttcgtccat    780
gtggatgatc tttgtgaggc ccatatattc ttgtacgagg atcctaccgc cgaaggaaga    840
tacatctgct cttctcatga tgccactatt catgatttgg caaaattgat cgcggagaaa    900
tggccagagt actctatccc cgagttaaag ggcgtagaca aggacatacc cgtggttccc    960
tttcttccaa gaagttggt aggcaagggc ttccaatata agtacacctt ggaggacatg   1020
tttcgggcgg ccattgacac atgccgtgaa aagggattgc tcccctattc tactcaaacc   1080
catgaaaatg gaaagaaaa agaaccactt cctgttgcta acaaggacca ggcgagcggc   1140
caagtcaacg ccccacttcc agattccgca gaaaaatagc accattgact ttttttaagt   1200
acaagaataa agatggagag ggcgacaagg caaagcgttt ttcagcggtt tatattcatt   1260
tctgagctat catcacacga ggatgatgaa gcagtgtgct gcttttgtaa catttggcaa   1320
ttttaattca atcaaagtca tctatgagtt gcgcggtttt gctgttgaaa aaaaaaaaa   1380
aaaaaaaaa aaaaaaaa                                                 1398

<210> SEQ ID NO 17
<211> LENGTH: 1430
<212> TYPE: DNA
<213> ORGANISM: Coffea canephora

<400> SEQUENCE: 17
caggctttag atatacctg ttaaatagaa aaagcgatat caaaagtagg taatcgggta      60
gagtaacata caggaaaaat gaccactgct gcggtgactt caagagttga gaggttggcc    120
aacagtggga ttcaattaat accaaaagag tatgtgaggc aagagctgac gaacatgggt    180
aacgtctttg aggaagagaa aaacaacgaa gggcctcagg tgccaaccat tgatttgggg    240
gacattgaag cagaggacga agctgttcgt gagagatgtc acaacgagtt gaagaaggct    300
gccatggagt ggggagtgat gcaccttgtc aaccatggca tatcaaatga gctcattaat    360
cgagtcaagg ttgctggaga ggccttcttc aattcaccct tgaggaaaaa ggagaagtat    420
gccaatgatc aggcatcagg caaactgcaa ggatacggca gcaaactagc aaacactgcc    480
agtggtcagc ttgaatggga ggactacttt ttccattgtg ttttcccga ggacaagcgg     540
```

```
gatttgtcga tttggcccaa gactccagaa gactatatcc ctgcagcgag tgagtatgca      600
aagcaattga ggggcttggc aaccaagcta ttagctgtgc tgtctcttgg cttgggatta      660
gaagaaggca ggctagaaaa ggaagttggt ggtatcgaag agttaattct gcaaatgaag      720
attaactact accccaaatg ccctcaaccg gagctagcat tgggtgttga agctcacact      780
gatgtcagtt ctctgacttt catccttcac aatatggtgc ctggcctgca attgttctat      840
gaggacaagt ggattactgc caaatgtgtc cccaattcca ttatcatgca cattggggac      900
accattgaga ttctaagcaa tggaaaatac aagagcattc ttcatagaag ccttgtgaac      960
aaagacaaag taagaatctc ttgggcagtt ttctgtgaac caccaaagga gaagatcatc     1020
ctcaaaccac tgcctgagac agtttcagag actgagcccc ctcgctacct gcctcgaacg     1080
tttgcgcagc atattgacca taaactgttc aggaaaaccg aggaagctgt tgaaaaaaat     1140
caatccactg aggacaataa atctcctgaa gacaatcaac ctcgtgaaga tggtaaacgt     1200
tcgtgaatgg agatccctcc tactttttct gctaatccaa gttgcaccaa gctaattaat     1260
aaccttttct acttgttctc gtttgggagt ccggtttgca actggttcaa gcgccatttt     1320
gctgtgtttc attattcctt gaagttggtc cttatgtcct ctaaagttat tacgtgcttt     1380
gctttgcatc gaataaaatc atgtatttat taaaaaaaaa aaaaaaaaa                 1430

<210> SEQ ID NO 18
<211> LENGTH: 648
<212> TYPE: DNA
<213> ORGANISM: Coffea canephora

<400> SEQUENCE: 18
gacgctattg ctttagttac aaaatttcag ctcatatttc tctctctact ggggccaaag       60
gcgaaggctt aattaagccg aaaaaatgac tgcgtctcct tctccgaatg acaagcaga      120 aaagagaagc agaatcttga tcatcggagc tacaggtttt attggtcact ttattgcaca     180
agcaagtctt gcttccggta agtcaaccta tattctcagc cgggcagctg cctcttgccc     240
ttctaaggcc agagccatca aagctttgga ggatcaagga gccattagta ttcattggga     300
agaacaggaa atgctggaaa agggagaaga ttctgagagg aggcaaaaaa ttaagggttc     360
tgtcaatgac caagaattca tggaaaagac tttgaaagag catgagatag acatagttat     420
atcagctgtc ggtggaggca atttactaga gcaagttatc ctcatccgtg ccatgaaggc     480
tgttggtact attaagagat tcttgccctc cgagtttggg catgatgtgg acagagcgga     540
gccagtggag ccagggctga ccatgtacaa tgaaaaacga gagtccgaa ggttgattga      600 ggaatcagga ataccatata cttacatttg ctgcaactca attgcttc                  648

<210> SEQ ID NO 19
<211> LENGTH: 1048
<212> TYPE: DNA
<213> ORGANISM: Coffea canephora

<400> SEQUENCE: 19
aatctatagg aatagaactg atggcagctc aagcaattga actgaagaaa gcctgtgtta       60
tcggtggcag tggattttg gcatcatttc tggtgaagct attgctccag aaagggtatg      120
cagtgaatac aaccgttcgg gatcctggta atcagaaaaa gataactcac ctattggcac     180
tacagagttt gggagactta aaagtttta aagcagatct tacagatgaa gcaagctttg      240
atgcccctgt gcaggctgt gaccttgtct ttcatgtggc cgcccagtc aactttgcct       300 ctgaggatcc agagaatgat atgataaaac cggcaattca aggagttgtc aatgttctaa     360
```

```
aagcttgcgt aaaagctgga tcagtgaaac gcgtaatttt tacctcctca gctgcagctg      420
taaccatcaa cgaaattaag ggtacagggc tgattatgga tgaagggaac tggacagatg      480
ttgagtttct gagttctgca aaaccaccta cttgggggta tcctgtctcc aagactctag      540
ctgaaaagga agcttggaaa tttgctgaag agaagaagat tgatctcatt accgtcattc      600
caagtctcat tgctggtcct cccctgacac cagacgttcc ctccagcgtc aatcttgcga      660
tgtccttgat cacaggaaac gagttcctca ttaatggctt gaaagggatg cagatgctcg      720
caggatcaat ctccattaca catgtggaag atgtctgtga agcccacatt ttttttggctg      780 agaaaaaatc ggcttccggt cgttacattt gctgcgctgc caatactagt gttcctgacc      840
tcgcaaactt tctgagtaaa agatacccag actacaaaat cccaacagaa tttgaaggtt      900
ttccatccaa agcaaagttg atcatctcat cagagaagct tatcaaagag ggtttcaatt      960
ttaagcatgg aattgaggac atttatgatg acgcccttgc ttatttcaag gctaagggtt     1020
tattgcagca ttgaagactt ttttttttt                                      1048
```

<210> SEQ ID NO 20
<211> LENGTH: 711
<212> TYPE: PRT
<213> ORGANISM: Coffea arabica

<400> SEQUENCE: 20

```
Met Glu Asn Gly His Asp Glu Gly Val Lys Val Ser Glu Phe Cys Leu
1               5                   10                  15

Lys Ser Asp Pro Leu Asn Trp Gly Val Ala Ala Glu Ser Leu Met Gly
            20                  25                  30

Ser His Leu Asp Glu Val Lys Arg Met Val Ala Glu Phe Arg Lys Pro
        35                  40                  45

Val Val Lys Leu Gly Gly Glu Ser Leu Thr Val Ala Gln Val Ala Ala
    50                  55                  60

Ile Ala Ala Lys Gly Asp Gln Gly Val Lys Val Glu Leu Ala Glu Asp
65                  70                  75                  80

Ala Arg Ala Gly Val Lys Ala Ser Ser Asp Trp Val Met Glu Ser Met
                85                  90                  95

Asn Lys Gly Thr Asp Ser Tyr Gly Val Thr Thr Gly Phe Gly Ala Thr
            100                 105                 110

Ser His Arg Arg Thr Asn Gln Gly Gly Ala Leu Gln Lys Glu Leu Ile
        115                 120                 125

Arg Phe Leu Asn Ala Gly Ile Phe Gly Asn Gly Thr Glu Thr Cys His
    130                 135                 140

Met Leu Pro His Ser Ala Thr Arg Ala Ala Met Leu Val Arg Ile Asn
145                 150                 155                 160

Thr Leu Leu Gln Gly Tyr Ser Gly Ile Arg Phe Glu Ile Leu Glu Ala
                165                 170                 175

Ile Thr Thr Phe Leu Asn His Asn Ile Thr Pro Cys Leu Pro Leu Arg
            180                 185                 190

Gly Thr Ile Thr Ala Ser Gly Asp Leu Val Pro Leu Ser Tyr Ile Ala
        195                 200                 205

Gly Leu Leu Thr Gly Arg Pro Asn Ser Lys Ala Val Gly Pro Asn Gly
    210                 215                 220

Glu Ala Phe Asn Ala Glu Glu Ala Phe Arg Leu Ala Gly Leu Ser Gly
225                 230                 235                 240

Gly Phe Phe Leu Leu Gln Pro Lys Glu Gly Leu Ala Leu Val Asn Gly
                245                 250                 255
```

```
Thr Ala Val Gly Ser Gly Leu Ala Ser Ile Val Leu Phe Glu Ala Asn
            260                 265                 270

Val Leu Ala Val Leu Ser Val Leu Ser Ala Ile Phe Ala Glu Val
        275                 280                 285

Met Asn Gly Lys Pro Glu Phe Thr Asp His Leu Thr His Lys Leu Lys
    290                 295                 300

His His Pro Gly Gln Ile Glu Ala Ala Ala Ile Met Glu His Ile Leu
305                 310                 315                 320

Asp Gly Ser Ser Tyr Val Lys Ala Ala Gln Lys Leu His Glu Leu Asp
                325                 330                 335

Pro Leu Gln Lys Pro Lys Gln Asp Arg Tyr Ala Leu Arg Thr Ser Pro
            340                 345                 350

Gln Trp Leu Gly Pro Gln Ile Glu Val Ile Arg Ala Ala Thr Lys Met
        355                 360                 365

Ile Glu Arg Glu Ile Asn Ser Val Asn Asp Asn Pro Leu Ile Asp Val
    370                 375                 380

Ser Arg Asn Lys Ala Leu His Gly Gly Asn Phe Gln Gly Thr Pro Ile
385                 390                 395                 400

Gly Val Ser Met Asp Asn Ala Arg Leu Ala Ile Ala Ser Ile Gly Lys
                405                 410                 415

Leu Met Phe Ala Gln Phe Ser Glu Leu Val Asn Asp Tyr Tyr Asn Asn
            420                 425                 430

Gly Leu Pro Ser Asn Leu Ser Gly Gly Arg Asn Pro Ser Leu Asp Tyr
        435                 440                 445

Gly Phe Lys Gly Ala Glu Ile Ala Met Ala Ala Tyr Cys Ser Glu Leu
    450                 455                 460

Gln Tyr Leu Gly Asn Pro Val Thr Asn His Val Gln Ser Ala Glu Gln
465                 470                 475                 480

His Asn Gln Asp Val Asn Ser Leu Gly Leu Ile Ser Ser Arg Lys Thr
                485                 490                 495

Ala Glu Ala Ile Asp Ile Leu Lys Leu Met Ser Ser Thr Tyr Leu Val
            500                 505                 510

Ala Leu Cys Gln Ala Ile Asp Leu Arg Phe Leu Glu Glu Asn Leu Lys
        515                 520                 525

Asn Ala Val Lys Asn Ile Val Ser Gln Val Ala Lys Arg Thr Leu Thr
    530                 535                 540

Met Gly Ala Asn Gly Glu Leu His Pro Ser Arg Phe Cys Glu Lys Asp
545                 550                 555                 560

Leu Leu Arg Val Val Asp Arg Glu Tyr Ala Phe Ala Tyr Val Asp Asp
                565                 570                 575

Pro Cys Ser Ala Thr Tyr Pro Leu Met Gln Lys Leu Arg Gln Val Leu
            580                 585                 590

Val Asp His Ala Leu Lys Asn Gly Asp Gln Glu Lys Asn Val Asn Thr
        595                 600                 605

Ser Ile Phe Gln Lys Ile Ala Ala Phe Glu Asp Glu Leu Lys Ala Val
    610                 615                 620

Leu Pro Lys Glu Val Glu Ser Ala Arg Ser Ala Val Glu Ser Gly Asn
625                 630                 635                 640

Pro Ala Ile Pro Asn Arg Ile Arg Glu Cys Arg Ser Tyr Pro Leu Tyr
                645                 650                 655

Lys Phe Val Arg Glu Val Leu Gly Thr Gly Leu Leu Thr Gly Glu Lys
            660                 665                 670

Ala Gln Ser Pro Gly Glu Val Phe Asp Gln Val Phe Thr Ala Met Ser
```

```
                       675                 680                 685
Lys Gly Gln Ile Val Asp Pro Leu Leu Glu Cys Leu Gln Glu Trp Asn
            690                 695                 700

Gly Ala Pro Leu Pro Ile Cys
705                 710

<210> SEQ ID NO 21
<211> LENGTH: 717
<212> TYPE: PRT
<213> ORGANISM: Coffea arabica

<400> SEQUENCE: 21

Met Glu Cys Ala Asn Gly Asn Gly Asn Asp Leu Ala Glu Thr Phe Cys
1               5                   10                  15

Thr Gln Arg Ala Gly Pro Ala Pro Asp Pro Leu Asn Trp Asn Ala Ala
            20                  25                  30

Ala Glu Ser Leu Lys Gly Ser His Leu Asp Glu Val Lys Arg Met Val
        35                  40                  45

Asp Glu Phe Arg Arg Pro Leu Val Arg Leu Gly Gly Glu Thr Leu Thr
    50                  55                  60

Ile Ala Gln Val Ala Ala Ile Ala Ala Ser Asp Ala Ala Val Lys
65                  70                  75                  80

Val Glu Leu Ser Glu Gly Ala Arg Ala Gly Val Lys Ala Ser Ser Asp
                85                  90                  95

Trp Val Met Glu Ser Met Arg Lys Gly Thr Asp Ser Tyr Gly Ile Thr
            100                 105                 110

Thr Gly Phe Gly Ala Thr Ser His Arg Arg Thr Lys Gln Gly Gly Ala
        115                 120                 125

Leu Gln Glu Glu Leu Ile Arg Phe Leu Asn Ala Gly Ile Phe Gly Asn
    130                 135                 140

Gly Thr Glu Thr Cys His Thr Leu Pro His Ser Ala Thr Arg Ala Ser
145                 150                 155                 160

Met Leu Val Arg Ile Asn Thr Leu Leu Gln Gly Tyr Ser Gly Ile Arg
                165                 170                 175

Phe Glu Ile Leu Glu Ala Ile Thr Lys Leu Leu Asn Asn Asn Ile Thr
            180                 185                 190

Pro Cys Leu Pro Leu Arg Gly Thr Ile Thr Ala Ser Gly Asp Leu Val
        195                 200                 205

Pro Leu Ser Tyr Ile Val Gly Leu Leu Thr Gly Arg Pro Asn Ser Lys
    210                 215                 220

Ala Val Gly Pro Asp Gly Lys Phe Val Asn Ala Thr Glu Ala Phe Ser
225                 230                 235                 240

Leu Ala Gly Ile Asp Thr Gly Phe Phe Glu Leu Gln Ala Lys Glu Gly
                245                 250                 255

Leu Ala Leu Val Asn Gly Thr Ala Val Gly Ser Ala Leu Ala Ser Met
            260                 265                 270

Val Leu Phe Glu Ala Asn Ile Leu Ala Val Leu Ala Glu Val Leu Ser
        275                 280                 285

Gly Ile Phe Ala Glu Val Met His Gly Lys Pro Glu Phe Thr Asp His
    290                 295                 300

Leu Thr His Lys Leu Lys His His Pro Gly Gln Ile Glu Ala Ala Ala
305                 310                 315                 320

Ile Met Glu His Ile Leu Asp Gly Ser Ser Phe Val Lys Glu Ala Gln
                325                 330                 335

Arg Val His Glu Phe Asp Pro Leu Gln Lys Pro Lys Gln Asp Arg Tyr
```

```
                       340                 345                 350
Ala Leu Arg Thr Ser Pro Gln Trp Leu Gly Pro Leu Ile Glu Val Ile
            355                 360                 365

Arg Ala Ser Thr Lys Ser Ile Glu Arg Glu Ile Asn Ser Val Asn Asp
            370                 375                 380

Asn Pro Leu Ile Asp Val Ser Arg Asn Lys Ala Leu His Gly Gly Asn
385                 390                 395                 400

Phe Gln Gly Thr Pro Ile Gly Val Ser Met Asp Asn Thr Arg Leu Ala
                405                 410                 415

Ile Ala Ser Ile Gly Lys Leu Met Phe Ala Gln Phe Ser Glu Leu Val
            420                 425                 430

Asn Asp Phe Tyr Asn Asn Gly Leu Pro Ser Lys Leu Ser Gly Gly Arg
            435                 440                 445

Asn Pro Ser Leu Asp Tyr Gly Phe Lys Gly Ala Glu Ile Ala Met Ala
            450                 455                 460

Ala Tyr Cys Ser Glu Leu Gln Phe Leu Ala Asn Pro Val Thr Asn His
465                 470                 475                 480

Val Gln Ser Ala Glu Gln His Asn Gln Asp Val Asn Ser Leu Gly Leu
                485                 490                 495

Ile Ser Ser Arg Lys Thr Ala Glu Ala Val Asp Ile Leu Lys Leu Met
            500                 505                 510

Ser Ser Thr Tyr Leu Val Ala Leu Cys Gln Ala Ile Asp Leu Arg His
            515                 520                 525

Leu Glu Glu Asn Leu Lys Ala Ser Val Lys Asn Thr Val Ser Leu Val
            530                 535                 540

Ala Lys Lys Val Leu Thr Met Gly Tyr Asn Gly Glu Leu His Pro Ser
545                 550                 555                 560

Arg Phe Cys Glu Lys Asp Leu Leu Lys Val Val Asp Arg Glu His Val
                565                 570                 575

Phe Ala Tyr Ile Asp Asp Pro Cys Ser Gly Thr Tyr Pro Leu Met Gln
            580                 585                 590

Lys Leu Arg Gln Val Leu Val Glu His Ser Leu Ala Asn Gly Asp Lys
            595                 600                 605

Glu Lys Asp Ala Thr Thr Ser Ile Phe Gln Lys Ile Gly Ala Phe Glu
610                 615                 620

Asp Glu Leu Lys Ala Leu Leu Pro Lys Glu Val Glu Ser Ala Arg Cys
625                 630                 635                 640

Glu Leu Glu Asn Gly Lys Pro Gly Ile Ala Asn Arg Ile Lys Asp Cys
                645                 650                 655

Arg Ser Tyr Ser Leu Tyr Lys Phe Val Arg Gly Glu Leu Gly Thr Asn
            660                 665                 670

Phe Leu Thr Gly Glu Lys Val Arg Ser Pro Gly Glu Glu Phe Asp Lys
            675                 680                 685

Val Phe Thr Ala Ile Cys Glu Gly Lys Leu Ile Asp Pro Leu Leu Asp
            690                 695                 700

Cys Leu Lys Glu Trp Asn Gly Ala Pro Arg Pro Ile Cys
705                 710                 715

<210> SEQ ID NO 22
<211> LENGTH: 583
<212> TYPE: PRT
<213> ORGANISM: Coffea canephora

<400> SEQUENCE: 22

Ile Arg Phe Leu Asn Ala Gly Ile Phe Gly Asn Gly Thr Glu Ser Gly
```

-continued

```
            1               5                  10                 15
          His Thr Leu Pro His Ser Ala Thr Arg Ala Ala Met Leu Val Arg Ile
                        20                 25                 30

Asn Thr Leu Leu Gln Gly Tyr Ser Gly Ile Arg Phe Glu Ile Leu Glu
                        35                 40                 45

Ala Leu Thr Lys Leu Leu Asn His Asn Ile Thr Pro Cys Leu Pro Leu
                        50                 55                 60

Arg Gly Thr Ile Thr Ala Ser Gly Asp Leu Val Pro Leu Ser Tyr Ile
           65                 70                 75                 80

Ala Gly Leu Leu Thr Gly Arg Pro Asn Ser Arg Cys Val Gly Pro Asn
                        85                 90                 95

Gly Arg Ser Leu Asp Ala Thr Glu Ala Phe Gln Ile Ala Gly Met Asn
                        100                105                110

Ser Gly Phe Phe Glu Leu Gln Pro Lys Glu Gly Leu Ala Leu Val Asn
                        115                120                125

Gly Thr Ala Val Gly Ser Gly Leu Ala Ser Met Val Leu Phe Glu Ala
                        130                135                140

Asn Leu Leu Val Ile Leu Ser Glu Val Phe Ser Ala Ile Phe Ala Glu
          145                150                155                160

Val Met His Gly Lys Pro Glu Phe Ile Asp His Leu Met His Lys Leu
                        165                170                175

Lys His His Pro Gly Gln Ile Glu Ala Ala Ile Met Glu His Ile
                        180                185                190

Leu Asp Gly Ser Ser Tyr Val Lys Ala Ala Lys Ala Leu His Glu Thr
                        195                200                205

Asp Pro Leu Gln Lys Pro Lys Gln Asp Arg Tyr Ala Leu Arg Thr Ser
                        210                215                220

Pro Gln Trp Leu Gly Pro Leu Ile Glu Val Ile Arg Ser Ser Thr Lys
          225                230                235                240

Ser Ile Glu Arg Glu Ile Asn Ser Val Asn Asp Asn Pro Leu Ile Asp
                        245                250                255

Val Ser Arg Asn Lys Ala Leu His Gly Gly Asn Phe Gln Gly Thr Pro
                        260                265                270

Ile Gly Val Ser Met Asp Asn Thr Arg Leu Ala Ile Ala Ser Ile Gly
                        275                280                285

Lys Leu Met Phe Ala Gln Phe Ser Glu Leu Val Asn Asp Phe Tyr Asn
                        290                295                300

Asn Gly Leu Pro Ser Asn Leu Ser Gly Gly Arg Asn Pro Ser Leu Asp
          305                310                315                320

Tyr Gly Phe Lys Gly Ala Glu Ile Ala Met Ala Ala Tyr Cys Ser Glu
                        325                330                335

Leu Gln Phe Leu Ala Asn Pro Val Thr Asn His Val Gln Ser Ala Glu
                        340                345                350

Gln His Asn Gln Asp Val Asn Ser Leu Gly Leu Ile Ser Ser Arg Lys
                        355                360                365

Ala Ala Glu Ala Val Asp Ile Leu Lys Leu Met Ser Ser Thr Tyr Leu
                        370                375                380

Val Ala Leu Cys Gln Ala Ile Asp Leu Arg His Leu Glu Glu Asn Leu
          385                390                395                400

Lys Asn Ala Val Lys Ser Thr Val His Gln Val Ala Lys Lys Val Leu
                        405                410                415

Thr Thr Gly Ile Asn Gly Glu Leu His Pro Ser Arg Phe Cys Glu Lys
                        420                425                430
```

```
Asp Leu Leu Lys Val Val Glu Arg Glu Tyr Val Phe Thr Tyr Ile Asp
            435                 440                 445

Asp Pro Cys Ser Ala Thr Tyr Pro Leu Met Gln Lys Leu Arg Gln Val
    450                 455                 460

Leu Val Asp His Ala Leu Ile Asn Asn Glu Asp Leu Asn Pro Asn Thr
465                 470                 475                 480

Ser Ile Phe Leu Lys Val Gly Ala Phe Glu Glu Leu Lys Thr Leu
                485                 490                 495

Leu Pro Ile Glu Val Glu Ser Ala Arg Asn Ala Cys Glu Ser Gly Asn
            500                 505                 510

Pro Ala Val Pro Asn Arg Ile Lys Lys Cys Arg Ser Tyr Pro Leu Tyr
            515                 520                 525

Lys Phe Val Arg Glu Asp Leu Ala Thr Gly Phe Leu Thr Gly Glu Lys
530                 535                 540

Ala Lys Ser Pro Gly Glu Glu Phe Asp Lys Val Phe Ser Ala Ile Cys
545                 550                 555                 560

Asp Gly Lys Met Val Asp Pro Leu Leu Glu Cys Leu Lys Asp Trp Asn
                565                 570                 575

Gly Ala Pro Leu Pro Leu Cys
            580

<210> SEQ ID NO 23
<211> LENGTH: 505
<212> TYPE: PRT
<213> ORGANISM: Coffea canephora

<400> SEQUENCE: 23

Met Asp Leu Leu Leu Glu Lys Thr Leu Gly Leu Phe Ala Ala
1               5                   10                  15

Ile Ile Val Ala Ile Val Ser Lys Leu Arg Gly Lys Lys Phe Lys
                20                  25                  30

Leu Pro Pro Gly Pro Ile Pro Val Pro Ile Phe Gly Asn Trp Leu Gln
            35                  40                  45

Val Gly Asp Asp Leu Asn His Arg Asn Leu Thr Asp Tyr Ala Lys Lys
50                  55                  60

Phe Gly Glu Ile Phe Leu Leu Arg Met Gly Gln Arg Asn Leu Val Val
65                  70                  75                  80

Val Ser Ser Pro Glu Leu Ala Lys Asp Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
130                 135                 140

Gln Tyr Arg His Gly Trp Glu Ala Glu Val Ala Arg Val Val Glu Asp
145                 150                 155                 160

Val Lys Lys Asn Pro Glu Ser Ser Thr Asn Gly Ile Val Leu Arg Arg
                165                 170                 175

Arg Leu Gln Leu Met Met Tyr Asn Asn Met Tyr Arg Ile Met Phe Asp
            180                 185                 190

Tyr Arg Phe Glu Ser Glu Asp Asp Pro Leu Phe Asn Lys Leu Lys Ala
        195                 200                 205

Leu Asn Gly Glu Arg Ser Arg Leu Ala Gln Ser Phe Glu Tyr Asn Tyr
210                 215                 220
```

Gly Asp Phe Ile Pro Ile Leu Arg Pro Phe Leu Arg Gly Tyr Leu Lys
225                 230                 235                 240

Ile Cys Lys Glu Val Lys Glu Arg Arg Leu Gln Leu Phe Lys Asp His
            245                 250                 255

Phe Val Asp Glu Arg Lys Lys Leu Ala Ser Thr Thr Ser Met Asp Ser
                260                 265                 270

His Ser Leu Lys Cys Ala Ile Asp His Ile Leu Glu Ala Gln Gln Lys
            275                 280                 285

Gly Glu Ile Asn Glu Asp Asn Val Leu Tyr Ile Val Glu Asn Ile Asn
290                 295                 300

Val Ala Ala Ile Glu Thr Thr Leu Trp Ser Ile Glu Trp Gly Ile Ala
305                 310                 315                 320

Glu Leu Val Asn His Pro Gln Val Gln Arg Lys Leu Arg Gln Glu Ile
                325                 330                 335

Asp Thr Val Leu Gly Pro Gly Val Gln Val Thr Glu Pro Asp Thr Leu
                340                 345                 350

Lys Leu Pro Tyr Leu Gln Ala Val Lys Glu Thr Leu Arg Leu Arg
            355                 360                 365

Met Ala Ile Pro Leu Leu Val Pro His Met Asn Leu Asn Glu Ala Lys
370                 375                 380

Leu Gly Gly Tyr Asp Ile Pro Ala Glu Ser Lys Ile Leu Val Asn Ala
385                 390                 395                 400

Trp Trp Leu Ala Asn Asn Pro Glu Asn Trp Arg Lys Pro Glu Glu Phe
                405                 410                 415

Arg Pro Glu Arg Phe Leu Glu Glu Ser Lys Val Asp Ala Asn Gly
            420                 425                 430

Asn Asp Phe Arg Tyr Leu Pro Phe Gly Val Gly Arg Arg Ser Cys Pro
                435                 440                 445

Gly Ile Ile Leu Ala Leu Pro Ile Leu Gly Ile Thr Leu Gly Arg Leu
450                 455                 460

Val Gln Asn Phe Glu Leu Leu Pro Pro Gly Gln Ser Lys Ile Asp
465                 470                 475                 480

Thr Ala Glu Lys Gly Gly Gln Phe Ser Leu His Ile Leu Lys His Ser
                485                 490                 495

Thr Ile Val Leu Lys Pro Arg Ser Leu
            500                 505

<210> SEQ ID NO 24
<211> LENGTH: 541
<212> TYPE: PRT
<213> ORGANISM: Coffea arabica

<400> SEQUENCE: 24

Met Ala Val Lys Thr Lys Gln Glu Glu Ile Ile Phe Arg Ser Arg Leu
1               5                   10                  15

Pro Asp Ile Tyr Ile Pro Lys His Leu Pro Leu His Thr Tyr Cys Phe
                20                  25                  30

Glu Asp Leu Pro Lys Phe Arg Ser Gln Ala Cys Leu Ile Asn Gly Ala
            35                  40                  45

Thr Asp Glu Ile Tyr Thr Phe Glu Gln Val Glu Leu Thr Ala Arg Arg
        50                  55                  60

Val Ala Ser Gly Leu Asn Lys Val Gly Val Gln Gln Gly Asp Thr Val
65                  70                  75                  80

Met Ile Leu Leu Pro Asn Ser Pro Glu Phe Val Phe Ala Phe Leu Gly
                85                  90                  95

```
Ala Ser Phe Arg Gly Ala Ile Ser Thr Met Ala Asn Pro Tyr Phe Thr
            100                 105                 110

Ser Ala Glu Val Ile Lys Gln Ala Lys Ala Ser Asn Ala Lys Leu Ile
        115                 120                 125

Ile Thr Gln Gly Cys Tyr Val Glu Lys Val Arg Asp Tyr Ala Cys Glu
    130                 135                 140

Asn Gly Val Lys Val Val Cys Ile Asp Ser Ala Pro Glu Gly Cys Leu
145                 150                 155                 160

His Phe Ser Glu Leu Thr Glu Ala Asp Glu Arg Glu Met Pro Asp Val
                165                 170                 175

Glu Ile Ser Pro Asp Val Val Ala Leu Pro Tyr Ser Gly Thr
            180                 185                 190

Thr Gly Leu Pro Lys Gly Val Met Leu Thr His Lys Gly Leu Val Thr
        195                 200                 205

Ser Val Ala Gln Gln Val Asp Gly Glu Asn Pro Asn Phe Tyr Ile His
    210                 215                 220

Asn Gln Val Met Met Cys Val Leu Ser Leu Phe His Ile Tyr Ser Leu
225                 230                 235                 240

Asn Ser Ile Leu Leu Cys Gly Leu Arg Ala Gly Thr Thr Ile Leu Ile
                245                 250                 255

Met Gln Lys Phe Asp Ile Ile Pro Phe Leu Glu Leu Ile Gln Lys Tyr
            260                 265                 270

Lys Val Thr Thr Gly Pro Phe Val Pro Pro Ile Val Leu Ala Ile Ala
        275                 280                 285

Lys Ser Pro Glu Val Asp Lys Tyr Asp Leu Ser Ser Val Lys Thr Val
    290                 295                 300

Met Ser Gly Ala Ala Pro Leu Gly Lys Glu Leu Glu Asp Ala Val Arg
305                 310                 315                 320

Thr Lys Phe Pro Lys Ala Lys Leu Gly Gln Gly Tyr Gly Met Thr Glu
                325                 330                 335

Ala Gly Pro Val Leu Ala Met Cys Ser Ala Phe Ala Lys Asp Pro Phe
            340                 345                 350

Glu Val Lys Ser Gly Gly Cys Gly Ser Val Val Arg Asn Ala Glu Met
        355                 360                 365

Lys Ile Val Asp Pro Glu Thr Gly Ser Ser Leu Pro Arg Asn Gln Pro
    370                 375                 380

Gly Glu Ile Cys Ile Arg Gly Asp Gln Ile Met Lys Gly Tyr Leu Asp
385                 390                 395                 400

Asp Pro Glu Ala Thr Lys Ala Thr Ile Asp Glu Asp Gly Trp Leu His
                405                 410                 415

Thr Gly Asp Val Gly Tyr Ile Asp Glu Asp Asp Glu Leu Phe Ile Val
            420                 425                 430

Asp Arg Leu Lys Glu Leu Ile Lys Tyr Lys Gly Phe Gln Val Ala Pro
        435                 440                 445

Ala Glu Leu Glu Ala Leu Leu Leu Ala His Ser Asp Ile Ser Asp Ala
    450                 455                 460

Ala Val Val Pro Met Lys Asp Asp Ala Ala Gly Glu Val Pro Val Ala
465                 470                 475                 480

Phe Val Val Lys Ser Lys Asp Ser Asn Ile Thr Glu Asp Glu Ile Lys
                485                 490                 495

Glu Tyr Ile Lys Lys Gln Val Ile Phe Tyr Lys Arg Ile Asn Arg Val
            500                 505                 510

Phe Phe Val Asp Ala Ile Pro Lys Ser Pro Ser Gly Lys Ile Leu Arg
        515                 520                 525
```

```
Lys Asp Leu Arg Ala Arg Leu Ala Ala Gly Val Pro Lys
    530                 535                 540

<210> SEQ ID NO 25
<211> LENGTH: 409
<212> TYPE: PRT
<213> ORGANISM: Coffea canephora

<400> SEQUENCE: 25

Val Glu Lys Val Met Asp Phe Ala Lys Glu Asn Asn Val Lys Val Met
1               5                   10                  15

Cys Thr Asp Ala Pro Pro Glu Gly Cys Leu His Phe Ser Glu Leu Ser
            20                  25                  30

Ser Ala Asp Glu Lys Val Ile Pro Ala Val Lys Ile Asn Pro Asn Asp
        35                  40                  45

Ala Val Ala Leu Pro Tyr Ser Ser Gly Thr Thr Gly Leu Pro Lys Gly
    50                  55                  60

Val Met Leu Thr His Lys Gly Leu Val Thr Ser Val Ala Gln Gln Val
65                  70                  75                  80

Asp Gly Glu Asn Pro Asn Leu Tyr Phe His Lys Glu Asp Val Ile Leu
                85                  90                  95

Cys Val Leu Pro Leu Phe His Ile Tyr Ser Leu Asn Ser Val Leu Leu
            100                 105                 110

Cys Gly Leu Arg Val Gly Ala Ala Ile Leu Ile Met Gln Lys Phe Glu
        115                 120                 125

Ile Asn Ala Leu Met Glu Leu Val Gln Lys Tyr Lys Val Thr Ile Ala
    130                 135                 140

Pro Phe Val Pro Pro Ile Val Leu Glu Ile Ala Lys Ser Pro Val Val
145                 150                 155                 160

Asp Lys Tyr Asp Leu Ser Ser Ile Arg Met Val Met Ser Gly Ala Ala
                165                 170                 175

Pro Met Gly Lys Glu Leu Glu Asp Thr Val Arg Ala Lys Leu Pro Lys
            180                 185                 190

Ala Val Leu Gly Gln Gly Tyr Gly Met Thr Glu Ala Gly Pro Leu Leu
        195                 200                 205

Ser Met Cys Leu Ala Phe Ala Lys Glu Pro Phe Asp Val Lys Ser Gly
    210                 215                 220

Ala Cys Gly Thr Val Val Arg Asn Ala Glu Met Lys Ile Val Asp Pro
225                 230                 235                 240

Glu Thr Asn Leu Ser Leu Pro Arg Asn Gln Ala Gly Glu Ile Cys Ile
                245                 250                 255

Arg Gly Asp Gln Ile Met Lys Gly Tyr Leu Asn Asp Pro Glu Ala Thr
            260                 265                 270

Glu Asn Thr Ile Asp Lys Glu Gly Trp Leu His Thr Gly Asp Ile Gly
        275                 280                 285

Tyr Ile Asp Asp Asp Asp Glu Ile Phe Ile Val Asp Arg Leu Lys Glu
    290                 295                 300

Leu Ile Lys Tyr Lys Gly Phe Gln Val Ala Pro Ala Glu Leu Glu Ala
305                 310                 315                 320

Met Leu Leu Ser His Pro Gly Ile Ser Asp Ala Ala Val Val Ser Met
                325                 330                 335

Lys Asp Glu Ala Ala Gly Glu Val Pro Val Ala Phe Val Val Arg Ala
            340                 345                 350

Ser Gly Ser Lys Ile Ser Glu Asp Glu Ile Lys Gln Phe Ile Ser Asn
        355                 360                 365
```

```
Gln Val Ile Phe Tyr Lys Arg Ile His Arg Val Phe Phe Met Asp Lys
        370                 375                 380

Ile Pro Lys Ala Pro Ser Gly Lys Ile Leu Arg Lys Asp Leu Arg Ala
385                 390                 395                 400

Lys Leu Ala Ala Glu Val Ala Cys Asn
                405
```

<210> SEQ ID NO 26
<211> LENGTH: 541
<212> TYPE: PRT
<213> ORGANISM: Coffea canephora

<400> SEQUENCE: 26

```
Met Ala Ala Lys Thr Lys Gln Glu Glu Ile Ile Phe Arg Ser Arg Leu
1               5                   10                  15

Pro Asp Ile Tyr Ile Pro Lys His Leu Pro Leu His Thr Tyr Cys Phe
                20                  25                  30

Glu Asp Leu Pro Lys Phe Arg Ser Gln Ala Cys Leu Ile Asn Gly Ala
            35                  40                  45

Thr Asp Glu Ile Tyr Thr Phe Glu Gln Val Glu Leu Thr Ala Arg Arg
        50                  55                  60

Val Ala Ser Gly Leu Asn Lys Val Gly Ile Gln Gln Gly Asp Thr Ile
65                  70                  75                  80

Met Ile Leu Leu Pro Asn Ser Pro Glu Phe Val Phe Ala Phe Leu Gly
                85                  90                  95

Ala Ser Phe Arg Gly Ala Ile Ser Thr Met Ala Asn Pro Tyr Phe Thr
                100                 105                 110

Ser Ala Glu Val Ile Lys Gln Ala Lys Ala Ser Asn Ala Lys Leu Ile
            115                 120                 125

Ile Thr Gln Gly Trp Tyr Val Glu Lys Val Met Asp Tyr Ala Cys Glu
        130                 135                 140

Asn Gly Val Lys Val Val Cys Ile Asp Ser Ala Pro Glu Gly Cys Leu
145                 150                 155                 160

Arg Phe Ser Glu Leu Thr Glu Ala Asp Glu Arg Glu Met Leu Asp Val
                165                 170                 175

Glu Ile Ser Pro Glu Asp Val Val Ala Leu Pro Tyr Ser Ser Gly Thr
                180                 185                 190

Thr Gly Leu Pro Lys Gly Val Met Leu Thr His Lys Gly Leu Val Thr
            195                 200                 205

Ser Val Ala Gln Gln Val Asp Gly Glu Asn Pro Asn Phe Tyr Ile His
        210                 215                 220

Asn Gln Val Met Met Cys Val Leu Pro Leu Phe His Ile Tyr Ser Leu
225                 230                 235                 240

Asn Ser Ile Leu Leu Cys Gly Leu Arg Ala Gly Thr Thr Ile Leu Ile
                245                 250                 255

Met Gln Lys Phe Asp Ile Ile Pro Phe Leu Glu Leu Ile Gln Lys Tyr
                260                 265                 270

Lys Val Thr Thr Gly Pro Phe Val Pro Ile Val Leu Ala Ile Ala
            275                 280                 285

Lys Ser Pro Glu Val Asp Lys Tyr Asp Leu Ser Ser Val Lys Thr Val
        290                 295                 300

Met Ser Gly Ala Ala Pro Leu Gly Lys Glu Leu Glu Asp Ala Val Arg
305                 310                 315                 320

Thr Lys Phe Pro Lys Ala Lys Leu Gly Gln Gly Tyr Gly Met Thr Glu
                325                 330                 335
```

```
Ala Gly Pro Val Leu Ala Met Cys Ser Ala Phe Ala Lys Asp Pro Phe
            340                 345                 350

Glu Val Lys Ser Gly Gly Cys Gly Ser Val Val Arg Asn Ala Glu Met
            355                 360                 365

Lys Ile Val Asp Pro Glu Thr Gly Ser Ser Leu Pro Arg Asn Gln Pro
370                 375                 380

Gly Glu Ile Cys Ile Arg Gly Asp Gln Ile Met Lys Gly Tyr Leu Asp
385                 390                 395                 400

Asp Pro Glu Ala Thr Lys Ala Thr Ile Asp Glu Asp Gly Trp Leu His
            405                 410                 415

Thr Gly Asp Val Gly Tyr Ile Asp Glu Asp Glu Leu Phe Ile Val
            420                 425                 430

Asp Arg Leu Lys Glu Leu Ile Lys Tyr Lys Gly Phe Gln Val Ala Pro
            435                 440                 445

Ala Glu Leu Glu Ala Leu Leu Leu Ala His Ser Asp Ile Ser Asp Ala
            450                 455                 460

Ala Val Val Pro Met Lys Asp Ala Ala Gly Glu Val Pro Val Ala
465                 470                 475                 480

Phe Val Val Lys Ser Lys Asp Ser Asn Ile Thr Glu Asp Glu Ile Lys
            485                 490                 495

Glu Tyr Ile Lys Lys Gln Val Ile Phe Tyr Lys Arg Ile Asn Arg Val
            500                 505                 510

Phe Phe Val Asp Ala Ile Pro Lys Ser Pro Ser Gly Lys Ile Leu Arg
            515                 520                 525

Lys Asp Leu Arg Ala Arg Leu Ala Ala Gly Val Pro Lys
            530                 535                 540

<210> SEQ ID NO 27
<211> LENGTH: 391
<212> TYPE: PRT
<213> ORGANISM: Coffea canephora

<400> SEQUENCE: 27

Met Val Thr Val Glu Glu Val Arg Arg Ala Gln Arg Ala Glu Gly Pro
1               5                   10                  15

Ala Thr Ile Met Ala Ile Gly Thr Ala Thr Pro Pro Asn Cys Val Glu
            20                  25                  30

Gln Ser Thr Tyr Pro Asp Tyr Tyr Phe Arg Ile Thr Asp Ser Glu His
            35                  40                  45

Lys Thr Glu Leu Lys Glu Lys Phe Lys Arg Met Cys Asp Lys Ser Met
50                  55                  60

Ile Lys Lys Arg Tyr Met Tyr Leu Thr Glu Glu Ile Leu Lys Glu Asn
65                  70                  75                  80

Pro Asn Ile Cys Ala Tyr Met Ala Pro Ser Leu Asp Ala Arg Gln Asp
            85                  90                  95

Met Val Val Glu Val Pro Lys Leu Gly Lys Glu Ala Ala Gln Lys
            100                 105                 110

Ala Ile Lys Glu Trp Gly Gln Pro Lys Ser Lys Ile Thr His Leu Val
            115                 120                 125

Phe Cys Thr Thr Ser Gly Val Asp Met Pro Gly Ala Asp Tyr Gln Leu
            130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
            165                 170                 175
```

```
Leu Ala Glu Asn Asn Lys Gly Ala Arg Val Leu Val Val Cys Ser Glu
            180                 185                 190

Ile Thr Ala Val Thr Phe Arg Gly Pro Ser Asp Ser His Leu Asp Ser
        195                 200                 205

Leu Val Gly Gln Ala Leu Phe Gly Asp Gly Ala Ala Ile Ile Ile
    210                 215                 220

Gly Ala Asp Pro Val Pro Glu Val Arg Pro Leu Phe Glu Leu Val
225                 230                 235                 240

Thr Ala Ala Gln Thr Ile Leu Pro Asp Ser His Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Lys Glu Ala Phe Glu
        275                 280                 285

Pro Leu Gly Ile Ser Asp Trp Asn Ser Leu Phe Trp Ile Ala His Pro
    290                 295                 300

Gly Gly Pro Ala Ile Leu Asp Gln Val Glu Gln Lys Leu Ala Leu Lys
305                 310                 315                 320

Pro Glu Lys Leu Arg Ala Thr Arg His Val Leu Ser Glu Tyr Gly Asn
                325                 330                 335

Met Ser Ser Ala Cys Val Val Phe Ile Leu Asp Glu Met Arg Lys Ala
            340                 345                 350

Ser Ala Lys Asp Gly Phe Asn Thr Thr Gly Glu Gly Leu Asp Trp Gly
        355                 360                 365

Val Leu Phe Gly Phe Gly Pro Gly Leu Thr Val Glu Thr Val Val Leu
    370                 375                 380

His Ser Ala Thr Ile Gln Lys
385                 390

<210> SEQ ID NO 28
<211> LENGTH: 323
<212> TYPE: PRT
<213> ORGANISM: Coffea canephora

<400> SEQUENCE: 28

Met Glu Lys Ala Gly Glu Thr Ile Pro Glu Ile Val Leu Asn Thr Gly
1               5                   10                  15

His Lys Met Pro Leu Val Gly Phe Gly Cys Ala Ala Gln Pro Leu Pro
            20                  25                  30

Pro Ser Glu Gln Leu Val Ser Thr Phe Ile Asp Ala Met Glu Ile Gly
        35                  40                  45

Tyr Arg His Phe Asp Thr Ala Ala Cys Tyr Gly Thr Glu Glu Ala Leu
    50                  55                  60

Gly Lys Ala Val Ala Lys Ala Leu Glu Ile Gly Leu Ile Lys Ser Arg
65                  70                  75                  80

Asp Glu Leu Phe Ile Thr Ser Lys Leu Trp Cys Thr Asp Ala Asp His
                85                  90                  95

Asp Leu Val Leu Pro Ala Leu Lys Gln Thr Leu Gly Lys Leu Gly Leu
            100                 105                 110

Glu Tyr Leu Asp Leu Tyr Leu Ile His Trp Pro Leu Arg Leu Lys Gln
        115                 120                 125

Gly Thr Glu Met Leu Asn Phe Thr Lys Asp Ala Ile Leu Pro Phe Asp
    130                 135                 140

Met His Gly Thr Trp Lys Ala Met Glu Glu Cys Ser Lys Leu Gly Leu
145                 150                 155                 160
```

```
Thr Lys Ser Ile Gly Leu Ser Asn Phe Thr Cys Glu Lys Ile Ser Lys
                165                 170                 175

Leu Gln Glu Ser Ala Thr Ile Leu Pro Ala Val Asn Gln Val Glu Met
            180                 185                 190

Asn Val Gly Trp Gln Gln Arg Lys Leu Val Pro Phe Ala Lys Glu Lys
        195                 200                 205

Gly Ile His Ile Ser Ala Trp Ser Pro Leu Gly Gly Tyr Gly Thr Ser
    210                 215                 220

Trp Gly Ser Asn Ala Val Met Glu Ser Pro Ile Ile Lys Asn Ile Ala
225                 230                 235                 240

Asp Ser Arg Asn Lys Thr Val Ala Glu Val Ala Leu Arg Trp Val Tyr
                245                 250                 255

Leu Gln Gly Ala Ser Val Ile Val Lys Ser Phe Ser Lys Glu Arg Met
            260                 265                 270

Lys Gln Asn Leu Gln Val Phe Asp Trp Glu Leu Thr Lys Glu Glu Met
        275                 280                 285

Asp Gln Ile Leu Gln Ile Pro Gln Arg Arg Ala Pro Gly Thr Glu Ala
    290                 295                 300

Leu Val Asp Pro Thr Gly Pro Tyr Lys Ser Leu Glu Glu Phe Trp Asp
305                 310                 315                 320

Gly Asp Val

<210> SEQ ID NO 29
<211> LENGTH: 323
<212> TYPE: PRT
<213> ORGANISM: Coffea canephora

<400> SEQUENCE: 29

Glu Lys Val Glu Gln Glu Ile Pro Glu Ile Ala Val Leu Asn Ser Gly
1               5                   10                  15

His Lys Met Pro Val Ala Gly Leu Gly Cys Ala Ala His Pro Leu Pro
            20                  25                  30

Pro Leu Glu Gln Leu Val Thr Thr Phe Ile Asp Ala Met Glu Ile Gly
        35                  40                  45

Tyr Arg His Phe Asp Thr Ala Ala Cys Tyr Gly Thr Glu Glu Ala Leu
    50                  55                  60

Gly Arg Ala Val Ala Lys Ala Leu Glu Ile Gly Leu Ile Lys Ser Arg
65                  70                  75                  80

Asp Glu Leu Phe Ile Thr Ser Lys Leu Trp Cys Thr Asp Ala Asp His
                85                  90                  95

Asp Leu Val Gln Pro Ala Leu Lys Gln Thr Leu Gly Lys Leu Gly Leu
            100                 105                 110

Glu Tyr Leu Asp Leu Tyr Leu Val His Trp Pro Val Arg Val Lys His
        115                 120                 125

Gly Ala Glu Lys Phe Asn Phe Ala Lys Asp Glu Ile Leu Pro Phe Asp
    130                 135                 140

Ile His Gly Thr Trp Gln Ala Met Glu Gly Cys Thr Lys Leu Gly Leu
145                 150                 155                 160

Thr Lys Ser Ile Gly Leu Ser Asn Phe Thr Cys Glu Lys Ile Cys Lys
                165                 170                 175

Leu Leu Glu Ile Ala Thr Ile Pro Pro Ala Val Asn Gln Val Glu Met
            180                 185                 190

Asn Val Gly Trp Gln Gln Arg Lys Leu Val Pro Phe Ala Lys Asp Arg
        195                 200                 205
```

```
Gly Ile Arg Ile Cys Ala Trp Ser Pro Leu Ala Ser Tyr Gly Gly Leu
            210                 215                 220

Trp Gly Asn Ser Ala Val Met Glu Asn Pro Val Leu Lys Asp Ile Ala
225                 230                 235                 240

Ala Ser Lys Ser Lys Ser Val Ala Gln Val Ala Leu Arg Trp Ile Tyr
                245                 250                 255

Gln Gln Gly Ala Ser Phe Val Ala Lys Ser Phe Asn Lys Glu Arg Met
                260                 265                 270

Lys Gln Asn Leu Gln Ile Phe Asp Trp Glu Leu Thr Lys Glu Met
            275                 280                 285

Asp Gln Ile Leu Gln Ile Pro Gln Arg Arg Gly Phe Ala Gly Glu Val
            290                 295                 300

Phe Val His Pro Thr Gly Pro Tyr Lys Ser Val Glu Glu Leu Trp Asp
305                 310                 315                 320

Gly Asp Thr

<210> SEQ ID NO 30
<211> LENGTH: 328
<212> TYPE: PRT
<213> ORGANISM: Coffea canephora

<400> SEQUENCE: 30

Met Pro Glu Thr Met Glu Lys Val Glu Gln Lys Ile Pro Glu Ile Ala
1               5                   10                  15

Val Leu Asn Ser Gly His Lys Met Pro Val Ala Gly Leu Gly Cys Ala
            20                  25                  30

Ala His Pro Leu Pro Pro Ser Glu Gln Leu Val Thr Thr Phe Ile Asp
            35                  40                  45

Ala Met Glu Ile Gly Tyr Arg His Phe Asp Thr Ala Ala Cys Tyr Gly
50                  55                  60

Thr Glu Glu Ala Leu Gly Arg Ala Val Ala Lys Ala Leu Glu Ile Gly
65                  70                  75                  80

Leu Ile Lys Ser Arg Asp Glu Leu Phe Ile Thr Ser Lys Leu Trp Cys
                85                  90                  95

Thr Asp Ala Asp His Asp Leu Val Leu Pro Ala Leu Lys Gln Thr Leu
            100                 105                 110

Gly Lys Leu Gly Leu Glu Tyr Leu Asp Leu Tyr Leu Val His Trp Pro
            115                 120                 125

Val Arg Val Lys His Gly Ala Glu Lys Phe Asn Phe Ala Lys Asp Glu
130                 135                 140

Ile Leu Pro Phe Asp Ile His Gly Thr Trp Gln Ala Met Glu Glu Cys
145                 150                 155                 160

Thr Lys Leu Gly Leu Thr Lys Ser Ile Gly Leu Ser Asn Phe Thr Cys
                165                 170                 175

Glu Lys Ile Cys Lys Leu Leu Gly Ile Ala Thr Ile Pro Pro Ala Val
            180                 185                 190

Asn Gln Val Glu Met Asn Val Gly Trp Gln Gln Arg Lys Leu Val Pro
            195                 200                 205

Phe Ala Lys Asp Arg Gly Ile Arg Ile Cys Ala Trp Ser Pro Leu Ala
210                 215                 220

Ser Tyr Gly Gly Leu Trp Gly Asn Ser Ala Val Met Glu Asn Pro Val
225                 230                 235                 240

Leu Lys Asp Ile Ala Ala Ser Lys Ser Lys Ser Val Ala Gln Val Ala
                245                 250                 255

Leu Arg Trp Ile Tyr Gln Gln Gly Ala Ser Phe Val Ala Lys Ser Phe
```

```
                        260                 265                 270
Asn Lys Glu Arg Met Lys Gln Asn Leu Gln Ile Phe Asp Trp Glu Leu
                275                 280                 285

Thr Lys Glu Glu Met Asp Gln Ile Leu Gln Ile Pro Gln Arg Arg Gly
            290                 295                 300

Phe Ala Gly Glu Val Phe Val His Pro Thr Gly Pro Tyr Lys Ser Val
305                 310                 315                 320

Glu Glu Leu Trp Asp Gly Asp Thr
                325

<210> SEQ ID NO 31
<211> LENGTH: 259
<212> TYPE: PRT
<213> ORGANISM: Coffea canephora

<400> SEQUENCE: 31

Met Ser Leu Ser Leu Ser Val Gly Glu Val His Val Asp Gly His Val
1               5                   10                  15

Phe Pro Pro Ala Ala Lys Lys Pro Gly Ser Asp Gln Asn Phe Phe
            20                  25                  30

Leu Gly Gly Ala Gly Ala Arg Gly Leu Glu Ile Glu Gly Lys Phe Ile
        35                  40                  45

Lys Phe Thr Ala Ile Gly Val Tyr Met Glu Gly Thr Ala Ile Pro Ser
    50                  55                  60

Leu Ala Val Lys Trp Lys Gly Lys Thr Ala Glu Glu Leu Thr Glu Ser
65                  70                  75                  80

Val Glu Phe Phe Arg Asp Ile Val Thr Gly Pro Phe Glu Lys Phe Ile
                85                  90                  95

Arg Val Thr Met Ile Leu Pro Leu Thr Gly Arg Gln Tyr Ser Glu Lys
            100                 105                 110

Val Ala Glu Asn Cys Ser Ala Tyr Trp Lys Ala Val Gly Ile Tyr Thr
        115                 120                 125

Asp Ala Glu Gly Lys Ala Ile Glu Met Phe Leu Asp Ile Phe Gln Asn
    130                 135                 140

Glu Ser Phe Pro Pro Gly Ala Ser Ile Leu Phe Thr Gln Ser Pro Leu
145                 150                 155                 160

Gly Ser Leu Thr Ile Ser Phe Ser Lys Asp Ser Ser Ile Pro Glu Val
                165                 170                 175

Ser Asn Ala Val Val Glu Asn Lys Leu Leu Ser Glu Ala Val Leu Glu
            180                 185                 190

Ser Ile Ile Gly Lys Asn Gly Val Ser Pro Asp Thr Lys Lys Ser Leu
        195                 200                 205

Ala Ile Arg Leu Ser Glu Leu Leu Lys Val Phe Asp Asn Asn Asn
    210                 215                 220

Asn Val Thr Ala Asp Asn Lys Lys Leu Glu Ala Asp Gly Ala Ile Ala
225                 230                 235                 240

Ala Glu Ala Pro Gly Glu Lys Gln Val Asn Gly Val Gln Val Pro Val
                245                 250                 255

Gln Val Pro

<210> SEQ ID NO 32
<211> LENGTH: 213
<212> TYPE: PRT
<213> ORGANISM: Coffea canephora
<220> FEATURE:
<221> NAME/KEY: misc_feature
<222> LOCATION: (121)..(121)
```

<223> OTHER INFORMATION: Xaa can be any naturally occurring amino acid

<400> SEQUENCE: 32

Met Gly Thr Glu Val Val Lys Val Asp Glu Ile Pro Phe Pro Leu Gln
1               5                   10                  15

Val Thr Pro Ser Thr Thr Lys Pro Leu Ser Leu Leu Gly His Gly Ile
            20                  25                  30

Thr Asp Ile Glu Ile His Phe Leu Gln Ile Lys Phe Thr Ala Ile Gly
        35                  40                  45

Val Tyr Met Asp Ser Glu Ile Val Thr Tyr Leu Gln Gln Trp Lys Gly
    50                  55                  60

Lys Lys Cys Thr Asp Leu Ala Glu Asp Asp Phe Phe Glu Ala Ile
65                  70                  75                  80

Ile Ser Ala Pro Val Asp Lys Phe Leu Arg Ile Val Ile Lys Glu
                85                  90                  95

Ile Lys Gly Ser Gln Tyr Gly Val Gln Leu Glu Ser Ala Val Arg Asp
            100                 105                 110

Arg Leu Ala Ala Asp Asp Arg Tyr Xaa Asp Glu Glu Ala Ala Leu
        115                 120                 125

Glu Glu Leu Ile Glu Phe Phe Gln Pro Lys Tyr Phe Lys Lys Asp Ser
    130                 135                 140

Ile Leu Thr Tyr Tyr Phe Pro Ala Gly Ser Ser Ala Ser Ala Glu Ile
145                 150                 155                 160

Ala Phe Thr Thr Glu Gly Lys Glu Glu Ser Lys Ile Lys Val Glu Asn
                165                 170                 175

Ala Asn Val Val Glu Thr Ile Lys Lys Trp Tyr Leu Gly Gly Thr Arg
            180                 185                 190

Gly Val Ser Gln Thr Thr Ile Ser Ser Leu Ala Asn Thr Leu Ala Ala
        195                 200                 205

Glu Leu Ser Lys Glu
    210

<210> SEQ ID NO 33
<211> LENGTH: 363
<212> TYPE: PRT
<213> ORGANISM: Coffea canephora

<400> SEQUENCE: 33

Met Ala Pro Ser Thr Leu Thr Ala Leu Ala Glu Glu Lys Thr Leu Gln
1               5                   10                  15

Ser Ser Phe Ile Arg Asp Glu Asp Glu Arg Pro Lys Val Ala Tyr Asn
            20                  25                  30

Gln Phe Ser Asn Glu Ile Pro Ile Ile Ser Leu Lys Gly Leu Asp Asp
        35                  40                  45

Thr Asp Gly Ala Arg Pro Glu Ile Cys Lys Lys Ile Val Glu Ala Cys
    50                  55                  60

Glu Asp Trp Gly Ile Phe Gln Val Ile Asp His Gly Val Asp Asp Lys
65                  70                  75                  80

Leu Ile Ser Asp Met Thr Arg Leu Ala Arg Glu Phe Phe Ala Leu Pro
                85                  90                  95

Pro Glu Glu Lys Leu Arg Phe Asp Met Ser Gly Gly Lys Lys Gly Gly
            100                 105                 110

Phe Ile Val Ser Ser His Leu Gln Gly Glu Thr Val Gln Asp Trp Arg
        115                 120                 125

Glu Ile Val Thr Tyr Phe Ser Tyr Pro Ile Arg Ala Arg Asp Tyr Ser
    130                 135                 140

```
Arg Trp Pro Asp Arg Pro Glu Ala Trp Arg Ala Val Thr Glu Lys Tyr
145                 150                 155                 160

Ser Glu Lys Leu Met Glu Leu Ala Cys Lys Leu Leu Glu Val Leu Ser
                165                 170                 175

Glu Ala Met Gly Leu Glu Lys Glu Ala Leu Thr Asn Ala Cys Val Asp
            180                 185                 190

Met Asp Gln Lys Val Val Val Asn Phe Tyr Pro Lys Cys Pro Gln Pro
        195                 200                 205

Asp Leu Thr Leu Gly Leu Lys Arg His Thr Asp Pro Gly Thr Ile Thr
    210                 215                 220

Leu Leu Leu Gln Asp Gln Val Gly Gly Leu Gln Ala Thr Arg Asp Gly
225                 230                 235                 240

Gly Lys Thr Trp Ile Thr Val Gln Pro Val Glu Gly Ala Phe Val Val
                245                 250                 255

Asn Leu Gly Asp His Gly His Tyr Leu Ser Asn Gly Arg Phe Lys Asn
            260                 265                 270

Ala Asp His Gln Ala Val Val Asn Ser Asn Cys Ser Arg Leu Ser Ile
        275                 280                 285

Ala Thr Phe Gln Asn Pro Ala Pro Glu Ala Thr Val Tyr Pro Leu Lys
    290                 295                 300

Ile Arg Glu Gly Glu Lys Ala Val Leu Asp Ala Pro Met Thr Phe Ser
305                 310                 315                 320

Glu Met Tyr Arg Lys Met Ser Lys Asp Leu Glu Leu Ala Arg Leu
                325                 330                 335

Lys Lys Leu Ala Lys Glu Gln Glu Leu Gln Ala Val Glu Lys Ala Lys
                340                 345                 350

Leu Glu Ala Lys Pro Ile Asp Glu Ile Phe Ala
                355                 360

<210> SEQ ID NO 34
<211> LENGTH: 183
<212> TYPE: PRT
<213> ORGANISM: Coffea canephora
<220> FEATURE:
<221> NAME/KEY: misc_feature
<222> LOCATION: (18)..(18)
<223> OTHER INFORMATION: Xaa can be any naturally occurring amino acid

<400> SEQUENCE: 34

Ala Gln Glu Glu Met Asp Arg Val Thr Gly Arg Asn Arg Arg Ile Val
1               5                   10                  15

Asp Xaa Leu Glu Ser Asp Ile Pro Lys Leu Arg Tyr Leu Gln Ala Ile
            20                  25                  30

Cys Lys Glu Ala Phe Trp Lys His Leu Ser Ala Pro Leu Asn Leu Pro
        35                  40                  45

Arg Ile Ala Ser Gln Ala Cys Glu Val Asn Gly Tyr Cys Ile Pro Lys
    50                  55                  60

Asn Thr Gly Leu Ser Val Asn Ile Trp Ala Ile Gly Arg Asp Pro Asp
65                  70                  75                  80

Val Trp Glu Asn Pro Leu Asp Phe His Pro Asp Arg Phe Leu Ser Gly
                85                  90                  95

Lys His Ala Lys Leu Asp Pro Pro Pro Val Asn Asp Phe Glu Leu
            100                 105                 110

Phe His Ser Ile Trp Gly Leu Glu Glu Asn Leu Cys Trp Ser Gln Lys
        115                 120                 125

Val Gly Ser Ala Ser Val Glu Tyr Val Leu Gly Thr Leu Val His Ser
```

```
                    130                 135                 140
Phe Asp Trp Lys Leu Pro Ala Glu Val Ile Glu Leu Asn Met Glu Glu
145                 150                 155                 160

Ser Phe Gly Leu Ala Val Pro Leu Lys Ala Lys Val Ser Pro Arg Leu
                165                 170                 175

Ala Leu Asn Ser Tyr Ser Ala
            180

<210> SEQ ID NO 35
<211> LENGTH: 369
<212> TYPE: PRT
<213> ORGANISM: Coffea canephora

<400> SEQUENCE: 35

Met Glu Gly Asp Ile Ala Thr Ser Ala Ala Lys Gly Thr Val Cys
1               5                   10                  15

Val Thr Gly Ala Ala Gly Phe Ile Gly Ser Trp Leu Val Met Arg Leu
                20                  25                  30

Leu Glu Arg Gly Tyr Val Val Arg Ala Thr Val Arg Asp Pro Gly Asn
            35                  40                  45

Met Lys Lys Val Lys His Leu Leu Asp Leu Pro Lys Ala Ser Thr His
50                  55                  60

Leu Thr Leu Trp Lys Ala Asp Met Thr Glu Glu Gly Ser Phe Asp Glu
65                  70                  75                  80

Ala Thr Gln Gly Cys Glu Gly Val Phe His Val Ala Thr Pro Met Asp
                85                  90                  95

Phe Asp Ser Lys Asp Pro Glu Asn Glu Ile Ile Lys Pro Thr Ile Asn
            100                 105                 110

Gly Ala Leu Asn Ile Ile Arg Ser Cys Val Lys Ala Lys Thr Val Lys
        115                 120                 125

Arg Leu Val Tyr Thr Ser Ser Ala Gly Thr Val Asn Val Gln Glu His
130                 135                 140

Gln Gln Pro Val Tyr Asp Glu Thr Asn Trp Ser Asp Leu Asp Phe Ile
145                 150                 155                 160

Tyr Ser Thr Lys Met Thr Gly Trp Met Tyr Phe Val Ser Lys Leu Leu
                165                 170                 175

Ala Glu Lys Glu Ala Trp Glu Val Ser Lys Gln Ser Asn Ile Asp Phe
            180                 185                 190

Ile Ser Ile Ile Pro Thr Leu Val Val Gly Pro Phe Ile Met Pro Thr
        195                 200                 205

Phe Pro Pro Ser Leu Ile Thr Ala Leu Ser Leu Ile Thr Gly Asn Glu
210                 215                 220

Ala His Tyr Ser Ile Ile Arg Gln Gly Gln Phe Val His Val Asp Asp
225                 230                 235                 240

Leu Cys Glu Ala His Ile Phe Leu Tyr Glu Asp Pro Thr Ala Glu Gly
                245                 250                 255

Arg Tyr Ile Cys Ser Ser His Asp Ala Thr Ile His Asp Leu Ala Lys
            260                 265                 270

Leu Ile Ala Glu Lys Trp Pro Glu Tyr Ser Ile Pro Glu Leu Lys Gly
        275                 280                 285

Val Asp Lys Asp Ile Pro Val Ser Phe Ser Lys Lys Leu Val
290                 295                 300

Gly Lys Gly Phe Gln Tyr Lys Tyr Thr Leu Glu Asp Met Phe Arg Ala
305                 310                 315                 320

Ala Ile Asp Thr Cys Arg Glu Lys Gly Leu Leu Pro Tyr Ser Thr Gln
```

```
            325                 330                 335
Thr His Glu Asn Gly Lys Glu Lys Glu Pro Leu Pro Val Ala Asn Lys
                340                 345                 350

Asp Gln Ala Ser Gly Gln Val Asn Ala Pro Leu Pro Asp Ser Ala Glu
            355                 360                 365

Lys

<210> SEQ ID NO 36
<211> LENGTH: 375
<212> TYPE: PRT
<213> ORGANISM: Coffea canephora

<400> SEQUENCE: 36

Met Thr Thr Ala Ala Val Thr Ser Arg Val Glu Arg Leu Ala Asn Ser
1               5                   10                  15

Gly Ile Gln Leu Ile Pro Lys Glu Tyr Val Arg Gln Glu Leu Thr Asn
                20                  25                  30

Met Gly Asn Val Phe Glu Glu Lys Asn Asn Glu Gly Pro Gln Val
            35                  40                  45

Pro Thr Ile Asp Leu Gly Asp Ile Glu Ala Glu Asp Glu Ala Val Arg
50                  55                  60

Glu Arg Cys His Asn Glu Leu Lys Lys Ala Ala Met Glu Trp Gly Val
65                  70                  75                  80

Met His Leu Val Asn His Gly Ile Ser Asn Glu Leu Ile Asn Arg Val
                85                  90                  95

Lys Val Ala Gly Glu Ala Phe Phe Asn Ser Pro Phe Glu Glu Lys Glu
            100                 105                 110

Lys Tyr Ala Asn Asp Gln Ala Ser Gly Lys Leu Gln Gly Tyr Gly Ser
            115                 120                 125

Lys Leu Ala Asn Thr Ala Ser Gly Gln Leu Glu Trp Glu Asp Tyr Phe
130                 135                 140

Phe His Cys Val Phe Pro Glu Asp Lys Arg Asp Leu Ser Ile Trp Pro
145                 150                 155                 160

Lys Thr Pro Glu Asp Tyr Ile Pro Ala Ala Ser Glu Tyr Ala Lys Gln
                165                 170                 175

Leu Arg Gly Leu Ala Thr Lys Leu Leu Ala Val Leu Ser Leu Gly Leu
            180                 185                 190

Gly Leu Glu Glu Gly Arg Leu Glu Lys Glu Val Gly Gly Ile Glu Glu
            195                 200                 205

Leu Ile Leu Gln Met Lys Ile Asn Tyr Tyr Pro Lys Cys Pro Gln Pro
210                 215                 220

Glu Leu Ala Leu Gly Val Glu Ala His Thr Asp Val Ser Ser Leu Thr
225                 230                 235                 240

Phe Ile Leu His Asn Met Val Pro Gly Leu Gln Leu Phe Tyr Glu Asp
                245                 250                 255

Lys Trp Ile Thr Ala Lys Cys Val Pro Asn Ser Ile Ile Met His Ile
            260                 265                 270

Gly Asp Thr Ile Glu Ile Leu Ser Asn Gly Lys Tyr Lys Ser Ile Leu
            275                 280                 285

His Arg Ser Leu Val Asn Lys Asp Lys Val Arg Ile Ser Trp Ala Val
            290                 295                 300

Phe Cys Glu Pro Pro Lys Glu Lys Ile Ile Leu Lys Pro Leu Pro Glu
305                 310                 315                 320

Thr Val Ser Glu Thr Glu Pro Pro Arg Tyr Leu Pro Arg Thr Phe Ala
                325                 330                 335
```

```
Gln His Ile Asp His Lys Leu Phe Arg Lys Thr Glu Glu Ala Val Glu
            340                 345                 350

Lys Asn Gln Ser Thr Glu Asp Asn Lys Ser Pro Glu Asp Asn Gln Pro
            355                 360                 365

Arg Glu Asp Gly Lys Arg Ser
        370                 375

<210> SEQ ID NO 37
<211> LENGTH: 187
<212> TYPE: PRT
<213> ORGANISM: Coffea canephora

<400> SEQUENCE: 37

Met Thr Ala Ser Pro Ser Pro Asn Gly Gln Ala Glu Lys Arg Ser Arg
1               5                   10                  15

Ile Leu Ile Ile Gly Ala Thr Gly Phe Ile Gly His Phe Ile Ala Gln
            20                  25                  30

Ala Ser Leu Ala Ser Gly Lys Ser Thr Tyr Ile Leu Ser Arg Ala Ala
        35                  40                  45

Ala Ser Cys Pro Ser Lys Ala Arg Ala Ile Lys Ala Leu Glu Asp Gln
    50                  55                  60

Gly Ala Ile Ser Ile His Trp Glu Glu Gln Glu Met Leu Glu Lys Gly
65                  70                  75                  80

Glu Asp Ser Glu Arg Arg Gln Lys Ile Lys Gly Ser Val Asn Asp Gln
                85                  90                  95

Glu Phe Met Glu Lys Thr Leu Lys Glu His Glu Ile Asp Ile Val Ile
            100                 105                 110

Ser Ala Val Gly Gly Gly Asn Leu Leu Glu Gln Val Ile Leu Ile Arg
        115                 120                 125

Ala Met Lys Ala Val Gly Thr Ile Lys Arg Phe Leu Pro Ser Glu Phe
    130                 135                 140

Gly His Asp Val Asp Arg Ala Glu Pro Val Glu Pro Gly Leu Thr Met
145                 150                 155                 160

Tyr Asn Glu Lys Arg Arg Val Arg Arg Leu Ile Glu Glu Ser Gly Ile
                165                 170                 175

Pro Tyr Thr Tyr Ile Cys Cys Asn Ser Ile Ala
            180                 185

<210> SEQ ID NO 38
<211> LENGTH: 337
<212> TYPE: PRT
<213> ORGANISM: Coffea canephora

<400> SEQUENCE: 38

Met Ala Ala Gln Ala Ile Glu Leu Lys Lys Ala Cys Val Ile Gly Gly
1               5                   10                  15

Ser Gly Phe Leu Ala Ser Phe Leu Val Lys Leu Leu Leu Gln Lys Gly
            20                  25                  30

Tyr Ala Val Asn Thr Thr Val Arg Asp Pro Gly Asn Gln Lys Lys Ile
        35                  40                  45

Thr His Leu Leu Ala Leu Gln Ser Leu Gly Asp Leu Lys Val Phe Lys
    50                  55                  60

Ala Asp Leu Thr Asp Glu Ala Ser Phe Asp Ala Pro Val Ala Gly Cys
65                  70                  75                  80

Asp Leu Val Phe His Val Ala Ala Pro Val Asn Phe Ala Ser Glu Asp
                85                  90                  95
```

```
Pro Glu Asn Asp Met Ile Lys Pro Ala Ile Gln Gly Val Val Asn Val
                100                 105                 110

Leu Lys Ala Cys Val Lys Ala Gly Ser Val Lys Arg Val Ile Phe Thr
            115                 120                 125

Ser Ser Ala Ala Ala Val Thr Ile Asn Glu Ile Lys Gly Thr Gly Leu
130                 135                 140

Ile Met Asp Glu Gly Asn Trp Thr Asp Val Glu Phe Leu Ser Ser Ala
145                 150                 155                 160

Lys Pro Pro Thr Trp Gly Tyr Pro Val Ser Lys Thr Leu Ala Glu Lys
                165                 170                 175

Glu Ala Trp Lys Phe Ala Glu Glu Lys Lys Ile Asp Leu Ile Thr Val
            180                 185                 190

Ile Pro Ser Leu Ile Ala Gly Pro Pro Leu Thr Pro Asp Val Pro Ser
        195                 200                 205

Ser Val Asn Leu Ala Met Ser Leu Ile Thr Gly Asn Glu Phe Leu Ile
    210                 215                 220

Asn Gly Leu Lys Gly Met Gln Met Leu Ala Gly Ser Ile Ser Ile Thr
225                 230                 235                 240

His Val Glu Asp Val Cys Glu Ala His Ile Phe Leu Ala Glu Lys Lys
                245                 250                 255

Ser Ala Ser Gly Arg Tyr Ile Cys Cys Ala Ala Asn Thr Ser Val Pro
            260                 265                 270

Asp Leu Ala Asn Phe Leu Ser Lys Arg Tyr Pro Asp Tyr Lys Ile Pro
        275                 280                 285

Thr Glu Phe Glu Gly Phe Pro Ser Lys Ala Lys Leu Ile Ile Ser Ser
    290                 295                 300

Glu Lys Leu Ile Lys Glu Gly Phe Asn Phe Lys His Gly Ile Glu Asp
305                 310                 315                 320

Ile Tyr Asp Asp Ala Leu Ala Tyr Phe Lys Ala Lys Gly Leu Leu Gln
                325                 330                 335

His

<210> SEQ ID NO 39
<211> LENGTH: 1637
<212> TYPE: DNA
<213> ORGANISM: Coffea canephora

<400> SEQUENCE: 39 cttttcgag ctgcagccta agaaggcct tgctcttgtt aacggaacag cagttggttc      60
tggcttggcc tctattgttc tatttgaggc taacgtgctt gctgtcttat ctgtagtgct     120
gtcagcaatc tttgctgaag tgatgaatgg caaacccgag ttcaccgatc atttgacgca     180
taagttgaag catcatccgg gccaaattga agccgcagct atcatggagc atatcttgga     240
tggaagctct tacgtcaagg ctgctcaaaa gttgcatgag ttggatcccc tgcaaaagcc     300
aaagcaggac cgatacgctc tcaggacgtc tccgcagtgg ctgggtccac aaatcgaagt     360
tattcgtgca gcaacaaaaa tgattgagag ggagatcaat tcagttaatg ataaccctct     420
cattgatgtg tccaggaaca aggccttaca tggtggcaac tttcagggta ccccgattgg     480
agtgagcatg gacaacgctc gactggccat tgcatctatt ggcaaactga tgtttgctca     540
attttccgag ctcgttaatg attactacaa caatggggttg ccgtccaatc tctctggagg     600
aaggaatcca agtttggact atggattcaa gggagctgag attgctatgg ctgcatactg     660
ttctgaactc cagtatttgg gcaatccagt gaccaaccat gtccagagtg ccgagcaaca     720
caaccaagac gtcaactcct tgggattaat ctcttcaaga aaaacggcag aagccattga     780
```

```
tatcttgaag cttatgtcat ccacttattt ggtggcactt tgtcaggcaa tcgatttgag    840 gttttttggaa gaaaacctga aaaatgctgt taagaatatt gtcagccaag tggcaaagcg    900
aactctgaca atgggtgcta atggagaact gcatccttca cggttttgtg agaaggattt    960
gctcagagtg gtggaccgcg aatacgcctt tgcctatgtg gatgacccctt gcagcgctac   1020 ctatccatta atgcaaaagt taaggcaagt gctcgtggat catgcgttga agaatggtga   1080
tcaggagaag aacgtcaaca cctccatctt ccaaaagatt gctgcatttg aagatgaact   1140
gaaggctgtc ctaccaaaag aagtggagag tgccagaagc gctgtggaga atggaaatcc   1200
agcaatccct aatcggataa ggaagtgcag atcttaccca ttgtacaagt tcgttcgaga   1260
agtgttgggg acaggactgc tgactggaga gaaagctcag tcacctggtg aggtgttcga   1320
ccaggtgttc acagcaatga acaaggggca gattgtagat cctttgttgg aatgtctcca   1380
agaatggaat ggtgctcctc tccccatctg ttgatttact ttcatccatt caaacatttg   1440
tttatcaaat ccttcaatgt aatttttatg tatgtcaaat tcaatgatat gtctgtaaca   1500
cccatgtatt gctcaaggtt tcttaaaatg tgaacaaaaa tttcaaaaaa aaaaaaaaa    1560 aaaaaaaaaa aaaaaaaaa  aaaaaaaaa aaaaaaaaa aaaaaaaaa aaaaaaaaa       1620 aaaaaaaaaa aaaaaaa                                                   1637
```

<210> SEQ ID NO 40
<211> LENGTH: 1037
<212> TYPE: DNA
<213> ORGANISM: Coffea canephora
<400> SEQUENCE: 40

```
ctagttagta gtcaccactg ctactgcttc agttcctttt atcacttgct ttacatgaat     60
taagtcgata ctcttccttg aatacctagc gattagtttc gtggtgacct atctagcacg    120
tctagccatt tttcctgttt cggtggcatc aatcctgaac agagaaagct gcaagatgga    180
aaatggtcat gacgaaggcg tgaaagtctc ggagttttgc ttgaaatcag atcctctgaa    240
ctggggagtg gcagctgagt cactgatggg aagtcatttg gacgaagtga agcgcatggt    300
agctgagttt aggaagccgg tggtaaagct cggcggtgag agcttgaccg ttgctcaggt    360
ggccgcgatt gccgccaaag gtgatcaggg tgtgaaggtg gagctggcgg aggacgcaag    420
ggctggggtg aaggcaagca gcgactgggt gatggagagt atgaacaaag gcactgatag    480
ttacggagtt accactgggt ttggtgccac ttcacacagg cggaccaatc aaggcggtgc    540
ccttcagaag gagcttatta gatttctgaa cgcgggaatc ttcggaaacg gcacggaaac    600
ttgccacacg ctgccacact cagcaacaag ggcagcgatg cttgtaagaa tcaacaccct    660
tcttcaaggt tattccggga tcagattcga aatcttggaa gccatcacca ctttccttaa    720
ccacaacatc accccatgct tgcctcttcg cggtacaatc actgcatcag gtgatcttgt    780
ccccttgtcc tacattgccg gttactaac tggccgcccc aactccaagg ccgttgggcc    840
caacggagaa gctttcagcg ccgaagaagc atttcgcctt gctggcctca gcggtggctt    900
tttcgagctg cagcctaaag aaggccttgc tcttgttaac ggaacagcag ttggttctgg    960
cttggcctct attgttctat ttgaggctaa cgtgcttgct gtcttatctg tagtgctgtc   1020
agcaatcttg gctgaag                                                   1037
```

<210> SEQ ID NO 41
<211> LENGTH: 673
<212> TYPE: DNA
<213> ORGANISM: Coffea canephora

<400> SEQUENCE: 41

```
caaaagctaa ggcaagtcct tgttgatcat gccctgatca acaatgagga cctaaatccg      60
aacacttcga ttttcctcaa agttggagct tttgaagaag agctgaagac ccttttgcca     120
atagaagttg aaagtgcaag aaatgcatgt gaaagtggta atcctgcagt cccaaatagg     180
atcaagaaat gcaggtctta ccctttatac aaatttgtga gggaagattt ggcgactgga     240
ttcttgacag agaaaaggc aaagtcacct ggagaggaat tgataaggt tttctccgca       300
atttgtgatg gtaagatggt cgatccattg ctcgagtgtc tcaaagattg gaatggtgct     360
ccgctaccct tgtgttaaat gccactccac ggcacgttga gcagatttta gctgttgtac     420
tcggtgaagg ccgacagaag agcaggcttc cttgaggaat attttgtttt actgtagtag     480
caaactgttt ttctctactt tttttttttt tttttttttg gtgttgttgt tgtcaattat     540
caccatctac tcctacttcc atctattatt tttctctatc tttttgtctc tcgtgattta     600
tgtacagata aattattgta atttgttggg atttctcaaa ttttgtgagg atttgaatca     660
aaaaaaaaaa aaa                                                        673
```

<210> SEQ ID NO 42
<211> LENGTH: 840
<212> TYPE: DNA
<213> ORGANISM: Coffea canephora

<400> SEQUENCE: 42

```
gttcaaaggc gccgaaattg caatggccgc ctattgttct gagcttcaat ttttggccaa      60
ccctgtcaca aatcatgtac agagtgccga gcaacacaat caggatgtta actctttagg     120
attgatttct tctagaaaag cagctgaagc agtagacatc ttgaaactga tgtcttcaac     180
ttacctagtg gcactttgtc aggcaattga tctgaggcat ttggaggaaa atttgaaaaa     240
cgctgtcaag agcacagttc accaagtcgc taaaaaggtt ctgaccacag gcatcaatgg     300
ggagcttcat ccttcaagat tctgtgaaaa agatttactt aaagtggttg agcgtgaata     360
cgtgtttaca tacatagatg atccttgcag tgcaacttat ccactgatgc aaaagctaag     420
gcaagtcctt gttgatcatg ccctgatcaa caatgaggac ctaaatccga acacttcgat     480
tttcctcaaa gttggagctt tgaagaaga gctgaagacc cttttgccaa tagaagttga     540
aagtgcaaga aatgcatgtg aaagtggtaa tcctgcagtc ccaaatagga tcaagaaatg     600
caggtcttac cctttataca aatttgtgag ggaagatttg gcgactggat tcttgacagg     660
agaaaaggca aagtcacctg agaggaatt tgataaggtt ttctccgcaa tttgtgatgg     720
taagatggtc gatccattgc tcgagtgtct caaagattgg aatggtgctc cgctaccctt     780
gtgttaaatg ccactccacg gcacgttgag cagattttag ctgttgtact cggtgaaggc     840
```

<210> SEQ ID NO 43
<211> LENGTH: 406
<212> TYPE: DNA
<213> ORGANISM: Coffea canephora

<400> SEQUENCE: 43

```
cggatcccct ccagaagcct aaacaggata gatatgcact tcgtacttca ccacagtggc      60
taggacccct gattgaagtt attagatcat cgacaaaatc gattgaacgg agatcaatt     120
ctgtcaatga caaccctttg attgacgtgt cgagaaacaa agccttgcat ggagggaatt     180
tcagggac tccaattggt gtgtcaatgg acaacaccag attagctata gcgtccatag       240
ggaaactcat gtttgctcaa ttttctgagc tcgtcaatga tttctacaat aatggcttgc     300
```

```
cttctaatct atctggagga agaaatccta gcttggatta tgggttcaaa ggcgccgaaa    360
ttgcaatggc cgcctattgt tctgagcttc aattttttggc caaccc                  406
```

<210> SEQ ID NO 44
<211> LENGTH: 2118
<212> TYPE: DNA
<213> ORGANISM: Coffea canephora

<400> SEQUENCE: 44

```
aaagaacagt taaattctca aatgcagcaa ataatttgaa acggaggagg aagtaagtat     60
acacgaagcg acagggtagg aaaaaggagg gtgactggtt gggttcaaag agttgataag    120
ttattggttg tgttttattg ccgaggggga attgtttgtt gtcaggcaaa cagttaaagg    180
gaaaaagcaa gagggttgct ttcagagggg tggtaaataa ttaagaggat gggacaaaga    240
gtaaaagaat ccttcctgat ttcctccctc tttatgtcat tacatcgatt tcagcctttt    300
tctaagtgtg tttgctttgc ttgtaaatac tgttttttgt ttttggtttg taaagtaggg    360 tcttttactct ttatggacca aattgttagg tacgttgctt aaccaataat gagaacttgt    420
tgcccaacaa aacagggaca gctttataaa gttctgcttg attatctctt ttgacttgca    480
ttcttgtcca ggatttcttg gaaatttcat cagcatgctg tctaatcttg tagcggttcc    540
gtaccttcca gattccctat atatagaata tagaatttat cgtgtcgaga aaaaaagaa     600 aagagagaac ttttgtcaa aaaagatgaa taagttaggc gcattgccta ttttatttta     660 ttttatttt tgctaggag tcttttctaat acagttcatt gggaaaaaaa acaaaaagat     720
ggaatataga agaaaaaaaa atttattgct agtacagtta gatactccac aaggtgggac    780
gacaatttat tgctagtagg gaaaacaatt ttcgttttct tgtagtcgca caaggtggga    840
gggacacttg aaggggcgcc cggaggggaa gaaaggaagt agtactatct tctacctaac    900
cccactttga ctgtaggcga gatcgccccc agcgagcatt atcaaagctt gtatccttga    960
gcagggctgc tctgcaaagc taggagtagt tggctaaatt gggacactac cttctgttga   1020
aaaaaaaaat aaaaaacaac taaaaactaa agtagtagg cgggatagcc catcataata    1080
tagccgattt tgttgcctaa ataaaattga aacccacac ttttgcttaa aagctgcttt    1140
tttttttttt tttttttttgt ggttaactga ttgaccttta tcccatcct gagggcatgg    1200 gttctgtgtt gattggacca tagttatgaa gagccaacat ggcctatccc tgaaaattaa    1260
atgtcatggc agaattgttg ccctatcatt aatgtcatag aaaaaaaata ccatgctctt   1320
ggacatttgt agcgtgaaat atttatgaaa ttattaatat gttaattagt gtaaatcaat    1380
tttgtaaagc caccgaaaaa gaaactattt gacccaatgc tgttgaaaaa tcaggttctt    1440
gaatgctgga attttggaa atggaacaga gtcaggtcac acgttgccac attctgcgac    1500
gagggctgca atgctagtga ggatcaacac ccttctacag gggtattcgg ggatcagatt   1560
tgagatatta gaagctctta caaagcttct caatcacaac atcactccgt gttttgcctct   1620 ccgtggcacg atcactgcct ctggcgattt ggttcctctg tcatacattg ccggactgtt   1680
gaccggccgt cctaattcta ggtgtgttgg gcccaatggt cggtcccttg atgccacgga   1740
ggcatttcag attgctggga tgaattccgg gttctttgag ttgcagccta aggagggtct   1800
agcactggtt aatggcacgg ctgttgggtc gggtttggcc tccatggttc tatttgaggc   1860
aaatttattg gtaatcttat ctgaagtttt ttcagcaatt tttgctgaag ttatgcacgg   1920
gaaaccggag ttcattgatc atttgatgca taaactgaag caccaccctg gtcagataga   1980
agccgcagcc ataatggaac acattttaga tggcagttcc tatgtcaagg cagcaaaggc   2040
```

```
attgcatgaa acggatcccc tccagaagcc taaacaggat agatatgcac ttcgtacttc   2100
accacagtgg ctaggacc                                                 2118

<210> SEQ ID NO 45
<211> LENGTH: 1060
<212> TYPE: DNA
<213> ORGANISM: Coffea canephora

<400> SEQUENCE: 45
caaaggtgct gaaattgcca tggcagctta ctgctctgaa cttcagttcc tagccaatcc     60
tgtcacaaac catgtgcaaa gtgcagagca acacaaccaa gatgtcaact cattaggatt    120
gatctcatca agaaaaacag cagaagctgt ggacatattg aagctcatgt catcgaccta    180
tttggttgca ttgtgccagg caattgacct gaggcacctg gaggagaact tgaaggcctc    240
agtgaaaaac acggttagcc ttgtagccaa gaaagtgcta acaatgggct acaatggcga    300
attgcaccca tctagattct gcgaaaaaga cttgctcaaa gtggtggaca gagagcatgt    360
ttttgcttac attgatgacc cctgtagtgg aacctacccc ctgatgcaaa agctaaggca    420
agtcctagtg gagcactcct tagcaaatgg ggacaaggag aaggacgcaa ccacttcaat    480
tttccaaaag atcggtgcct ttgaggatga actaaaggcc ttttgcccca agaagcgga     540 gagtgctaga tgtgagttgg agaatggaaa gccaggcatt gccaaccgta tcaaggattg    600
caggtcctac tcattgtaca gtttgtgag gggagagttg gggaccaatt tcctgactgg     660
tgagaaggtg agatcacctg gagaagaatt tgacaaggta ttcactgcca tatgtgaagg    720
gaagttgatt gatccattgc tggattgttt gaaagagtgg aatggtgctc cccgtccaat    780
ttgctaagat gttttcttca tactgtggta catttattaa atttcttgaa atttgttttt    840
tttccttgtt tgccctcttt tggaatgtt gtatccaagt tgtcactagc ttgtttaaga     900
tccttgtatt ttcgtcccat actgatattg ttcgttgcca taaatgttga acttcaacaa    960
gtgtaattat ggataaacgt cttttcgcgaa aaaaaaaaa aaaaaaaaaa aaaaaaaaaa   1020
aaaaaaaaaa aaaaaaaaaa aaaaaaaaaa aaaaaaaaaa                         1060

<210> SEQ ID NO 46
<211> LENGTH: 377
<212> TYPE: DNA
<213> ORGANISM: Coffea canephora

<400> SEQUENCE: 46
tgacgtcttg gttgtgttgc tctgcacttt gtacatggtt tgtgacagga ttggctagga     60
actgaagttc agagcagtaa gctgccatgg caatttcagc acctttgaaa ccatagtcca    120
aacttggatt acgtccccca gataggtttg aaggcaatcc attgttgtaa aagtcattaa    180
ccagctcaga aaattgtgcg aacatgagtt ttccaattga tgcaattgct agacgggtgt    240
tatccatcga gactccaatt ggtgtacctt gaaagttccc accatgtaag gccttattgc    300
gggaaacgtc gattaaagga ttgtcattca cagaattgat ctctctttcg atggattttg    360
tcgaagccct gatgact                                                   377

<210> SEQ ID NO 47
<211> LENGTH: 717
<212> TYPE: PRT
<213> ORGANISM: Coffea canephora

<400> SEQUENCE: 47

Met Glu Cys Ala Asn Gly Asn Gly Asn Asp Leu Ala Glu Thr Phe Cys
```

-continued

```
1               5                   10                  15
Thr Gln Arg Ala Gly Pro Ala Pro Asp Pro Leu Asn Trp Asn Ala Ala
                20                  25                  30

Ala Glu Ser Leu Lys Gly Ser His Leu Asp Glu Val Lys Arg Met Val
            35                  40                  45

Asp Glu Phe Arg Arg Pro Leu Val Arg Leu Gly Gly Glu Thr Leu Thr
        50                  55                  60

Ile Ala Gln Val Ala Ala Val Ala Ser Ser Asp Ala Ala Val Lys
65                  70                  75                  80

Val Glu Leu Ser Glu Gly Ala Arg Ala Gly Val Lys Ala Ser Ser Asp
                85                  90                  95

Trp Val Met Glu Ser Met Arg Lys Gly Thr Asp Ser Tyr Gly Ile Thr
            100                 105                 110

Thr Gly Phe Gly Ala Thr Ser His Arg Arg Thr Lys Gln Gly Gly Ala
        115                 120                 125

Leu Gln Glu Glu Leu Ile Arg Phe Leu Asn Ala Gly Ile Phe Gly Asn
    130                 135                 140

Gly Thr Glu Thr Cys His Thr Leu Pro His Ser Ala Thr Arg Ala Ser
145                 150                 155                 160

Met Leu Val Arg Ile Asn Thr Leu Leu Gln Gly Tyr Ser Gly Ile Arg
                165                 170                 175

Phe Glu Ile Leu Glu Ala Ile Thr Lys Leu Leu Asn Asn Asn Ile Thr
            180                 185                 190

Pro Cys Leu Pro Leu Arg Gly Thr Ile Thr Ala Ser Gly Asp Leu Val
        195                 200                 205

Pro Leu Ser Tyr Ile Val Gly Leu Leu Thr Gly Arg Pro Asn Ser Lys
    210                 215                 220

Ala Val Gly Pro Asp Gly Lys Phe Val Asn Ala Thr Glu Ala Phe Ser
225                 230                 235                 240

Leu Ala Gly Ile Asp Thr Gly Phe Phe Glu Leu Gln Ala Lys Glu Gly
                245                 250                 255

Leu Ala Leu Val Asn Gly Thr Ala Val Gly Ser Ala Leu Ala Ser Met
            260                 265                 270

Val Leu Phe Glu Ala Asn Ile Leu Ala Val Leu Ala Glu Val Leu Ser
        275                 280                 285

Gly Ile Phe Ala Glu Val Met His Gly Lys Pro Glu Phe Thr Asp His
    290                 295                 300

Leu Thr His Lys Leu Lys His His Pro Gly Gln Ile Glu Ala Ala Ala
305                 310                 315                 320

Ile Met Glu His Ile Leu Asp Gly Ser Ser Phe Val Lys Glu Ala Gln
                325                 330                 335

Arg Val His Glu Phe Asp Pro Leu Gln Lys Pro Lys Gln Asp Arg Tyr
            340                 345                 350

Ala Leu Arg Thr Ser Pro Gln Trp Leu Gly Pro Leu Ile Glu Val Ile
        355                 360                 365

Arg Ala Ser Thr Lys Ser Ile Glu Arg Glu Ile Asn Ser Val Asn Asp
    370                 375                 380

Asn Pro Leu Ile Asp Val Ser Arg Asn Lys Ala Leu His Gly Gly Asn
385                 390                 395                 400

Phe Gln Gly Thr Pro Ile Gly Val Ser Met Asp Asn Thr Arg Leu Ala
                405                 410                 415

Ile Ala Ser Ile Gly Lys Leu Met Phe Ala Gln Phe Ser Glu Leu Val
            420                 425                 430
```

```
Asn Asp Phe Tyr Asn Asn Gly Leu Pro Ser Asn Leu Ser Gly Gly Arg
        435                 440                 445

Asn Pro Ser Leu Asp Tyr Gly Phe Lys Gly Ala Glu Ile Ala Met Ala
    450                 455                 460

Ala Tyr Cys Ser Glu Leu Gln Phe Leu Ala Asn Pro Val Thr Asn His
465                 470                 475                 480

Val Gln Ser Ala Glu Gln His Asn Gln Asp Val Asn Ser Leu Gly Leu
                485                 490                 495

Ile Ser Ser Arg Lys Thr Ala Glu Ala Val Asp Ile Leu Lys Leu Met
            500                 505                 510

Ser Ser Thr Tyr Leu Val Ala Leu Cys Gln Ala Ile Asp Leu Arg His
        515                 520                 525

Leu Glu Glu Asn Leu Lys Ala Ser Val Lys Asn Thr Val Ser Leu Val
    530                 535                 540

Ala Lys Lys Val Leu Thr Met Gly Tyr Asn Gly Glu Leu His Pro Ser
545                 550                 555                 560

Arg Phe Cys Glu Lys Asp Leu Leu Lys Val Val Asp Arg Glu His Val
                565                 570                 575

Phe Ala Tyr Ile Asp Asp Pro Cys Ser Gly Thr Tyr Pro Leu Met Gln
            580                 585                 590

Lys Leu Arg Gln Val Leu Val Glu His Ser Leu Ala Asn Gly Asp Lys
        595                 600                 605

Glu Lys Asp Ala Thr Thr Ser Ile Phe Gln Lys Ile Gly Ala Phe Glu
    610                 615                 620

Asp Glu Leu Lys Ala Leu Leu Pro Lys Glu Val Glu Ser Ala Arg Cys
625                 630                 635                 640

Glu Leu Glu Asn Gly Lys Pro Gly Ile Ala Asn Arg Ile Lys Asp Cys
                645                 650                 655

Arg Ser Tyr Ser Leu Tyr Lys Phe Val Arg Gly Glu Leu Gly Thr Asn
            660                 665                 670

Phe Leu Thr Gly Glu Lys Val Arg Ser Pro Gly Glu Glu Phe Asp Lys
        675                 680                 685

Val Phe Thr Ala Ile Cys Glu Gly Lys Leu Ile Asp Pro Leu Leu Asp
    690                 695                 700

Cys Leu Lys Glu Trp Asn Gly Ala Pro Arg Pro Ile Cys
705                 710                 715

<210> SEQ ID NO 48
<211> LENGTH: 717
<212> TYPE: PRT
<213> ORGANISM: Coffea canephora

<400> SEQUENCE: 48

Met Glu Cys Ala Asn Gly Asn Gly Asn Asp Leu Ala Glu Thr Phe Cys
1               5                   10                  15

Thr Gln Arg Ala Gly Pro Ala Pro Asp Pro Leu Asn Trp Asn Ala Ala
            20                  25                  30

Ala Glu Ser Leu Lys Gly Ser His Leu Asp Glu Val Lys Arg Met Val
        35                  40                  45

Asp Glu Phe Arg Arg Pro Leu Val Arg Leu Gly Gly Glu Thr Leu Thr
    50                  55                  60

Ile Ala Gln Val Ala Ala Val Ala Ala Ser Ser Asp Ala Ala Val Lys
65                  70                  75                  80

Val Glu Leu Ser Glu Gly Ala Arg Ala Gly Val Lys Ala Ser Ser Asp
                85                  90                  95
```

-continued

```
Trp Val Met Glu Ser Met Arg Lys Gly Thr Asp Ser Tyr Gly Ile Thr
            100                 105                 110

Thr Gly Phe Gly Ala Thr Ser His Arg Arg Thr Lys Gln Gly Gly Ala
        115                 120                 125

Leu Gln Glu Glu Leu Ile Arg Phe Leu Asn Ala Gly Ile Phe Gly Asn
    130                 135                 140

Gly Thr Glu Thr Cys His Thr Leu Pro His Ser Ala Thr Arg Ala Ser
145                 150                 155                 160

Met Leu Val Arg Ile Asn Thr Leu Leu Gln Gly Tyr Ser Gly Ile Arg
                165                 170                 175

Phe Glu Ile Leu Glu Ala Ile Thr Lys Leu Leu Asn Asn Asn Ile Thr
            180                 185                 190

Pro Cys Leu Pro Leu Arg Gly Thr Ile Thr Ala Ser Gly Asp Leu Val
        195                 200                 205

Pro Leu Ser Tyr Ile Val Gly Leu Leu Thr Gly Arg Pro Asn Ser Lys
    210                 215                 220

Ala Val Gly Pro Asp Gly Lys Phe Val Asn Ala Thr Glu Ala Phe Ser
225                 230                 235                 240

Leu Ala Gly Ile Asp Thr Gly Phe Phe Glu Leu Gln Ala Lys Glu Gly
                245                 250                 255

Leu Ala Leu Val Asn Gly Thr Ala Val Gly Ser Ala Leu Ala Ser Met
            260                 265                 270

Val Leu Phe Glu Ala Asn Ile Leu Ala Val Leu Ala Glu Val Leu Ser
        275                 280                 285

Gly Ile Phe Ala Glu Val Met His Gly Lys Pro Glu Phe Thr Asp His
    290                 295                 300

Leu Thr His Lys Leu Lys His His Pro Gly Gln Ile Glu Ala Ala Ala
305                 310                 315                 320

Ile Met Glu His Ile Leu Asp Gly Ser Ser Phe Val Lys Glu Ala Gln
                325                 330                 335

Arg Val His Glu Phe Asp Pro Leu Gln Lys Pro Lys Gln Asp Arg Tyr
            340                 345                 350

Ala Leu Arg Thr Ser Pro Gln Trp Leu Gly Pro Leu Ile Glu Val Ile
        355                 360                 365

Arg Ala Ser Thr Lys Ser Ile Glu Arg Glu Ile Asn Ser Val Asn Asp
    370                 375                 380

Asn Pro Leu Ile Asp Val Ser Arg Asn Lys Ala Leu His Gly Gly Asn
385                 390                 395                 400

Phe Gln Gly Thr Pro Ile Gly Val Ser Met Asp Asn Thr Arg Leu Ala
                405                 410                 415

Ile Ala Ser Ile Gly Lys Leu Met Phe Ala Gln Phe Ser Glu Leu Val
            420                 425                 430

Asn Asp Phe Tyr Asn Asn Gly Leu Pro Ser Asn Leu Ser Gly Gly Arg
        435                 440                 445

Asn Pro Ser Leu Asp Tyr Gly Phe Lys Gly Ala Glu Ile Ala Met Ala
    450                 455                 460

Ala Tyr Cys Ser Glu Leu Gln Phe Leu Ala Asn Pro Val Thr Asn His
465                 470                 475                 480

Val Gln Ser Ala Glu Gln His Asn Gln Asp Val Asn Ser Leu Gly Leu
                485                 490                 495

Ile Ser Ser Arg Lys Thr Ala Glu Ala Val Asp Ile Leu Lys Leu Met
            500                 505                 510

Ser Ser Thr Tyr Leu Val Ala Leu Cys Gln Ala Ile Asp Leu Arg His
        515                 520                 525
```

```
Leu Glu Glu Asn Leu Lys Ala Ser Val Lys Asn Thr Val Ser Leu Val
    530                 535                 540

Ala Lys Lys Val Leu Thr Met Gly Tyr Asn Gly Glu Leu His Pro Ser
545                 550                 555                 560

Arg Phe Cys Glu Lys Asp Leu Lys Val Val Asp Arg Glu His Val
            565                 570                 575

Phe Ala Tyr Ile Asp Asp Pro Cys Ser Gly Thr Tyr Pro Leu Met Gln
                580                 585                 590

Lys Leu Arg Gln Val Leu Val Glu His Ser Leu Ala Asn Gly Asp Lys
            595                 600                 605

Glu Lys Asp Ala Thr Thr Ser Ile Phe Gln Lys Ile Gly Ala Phe Glu
610                 615                 620

Asp Glu Leu Lys Ala Leu Leu Pro Lys Glu Val Glu Ser Ala Arg Cys
625                 630                 635                 640

Glu Leu Glu Asn Gly Lys Pro Gly Ile Ala Asn Arg Ile Lys Asp Cys
                645                 650                 655

Arg Ser Tyr Ser Leu Tyr Lys Phe Val Arg Gly Glu Leu Gly Thr Asn
            660                 665                 670

Phe Leu Thr Gly Glu Lys Val Arg Ser Pro Gly Glu Phe Asp Lys
        675                 680                 685

Val Phe Thr Ala Ile Cys Glu Gly Lys Leu Ile Asp Pro Leu Leu Asp
        690                 695                 700

Cys Leu Lys Glu Trp Asn Gly Ala Pro Arg Pro Ile Cys
705                 710                 715

<210> SEQ ID NO 49
<211> LENGTH: 619
<212> TYPE: PRT
<213> ORGANISM: Coffea canephora

<400> SEQUENCE: 49

Met Glu Ser Met Arg Lys Gly Thr Asp Ser Tyr Gly Ile Thr Thr Gly
1               5                   10                  15

Phe Gly Ala Thr Ser His Arg Arg Thr Lys Gln Gly Gly Ala Leu Gln
            20                  25                  30

Glu Glu Leu Ile Arg Phe Leu Asn Ala Gly Ile Phe Gly Asn Gly Thr
        35                  40                  45

Glu Thr Ser His Thr Leu Pro His Ser Ala Thr Arg Ala Ser Met Leu
    50                  55                  60

Val Arg Ile Asn Thr Leu Leu Gln Gly Tyr Ser Gly Ile Arg Phe Glu
65                  70                  75                  80

Ile Leu Glu Ala Ile Thr Lys Leu Leu Asn Asn Asn Ile Thr Pro Cys
                85                  90                  95

Leu Pro Leu Arg Gly Thr Ile Thr Ala Ser Gly Asp Leu Val Pro Leu
            100                 105                 110

Ser Tyr Ile Val Gly Leu Leu Thr Gly Arg Pro Asn Ser Lys Ala Val
        115                 120                 125

Gly Pro Asp Gly Lys Phe Val Asn Ala Thr Glu Ala Phe Ser Leu Ala
    130                 135                 140

Gly Ile Asp Thr Gly Phe Phe Glu Leu Gln Ala Lys Glu Gly Leu Ala
145                 150                 155                 160

Leu Val Asn Gly Thr Ala Val Gly Ser Ala Leu Ala Ser Met Val Leu
                165                 170                 175

Phe Glu Ala Asn Ile Leu Ala Val Leu Ala Glu Val Leu Ser Gly Ile
            180                 185                 190
```

-continued

Phe Ala Glu Val Met His Gly Lys Pro Glu Phe Thr Asp His Leu Thr
            195                 200                 205

His Lys Leu Lys His His Pro Gly Gln Ile Glu Ala Ala Ile Met
    210                 215                 220

Glu His Ile Leu Asp Gly Ser Ser Phe Val Lys Glu Ala Gln Arg Val
225                 230                 235                 240

His Glu Phe Asp Pro Leu Gln Lys Pro Lys Gln Asp Arg Tyr Ala Leu
                245                 250                 255

Arg Thr Ser Pro Gln Trp Leu Gly Pro Leu Ile Glu Val Ile Arg Ala
                260                 265                 270

Ser Thr Lys Ser Ile Glu Arg Glu Ile Asn Ser Val Asn Asp Asn Pro
    275                 280                 285

Leu Ile Asp Val Ser Arg Asn Lys Ala Leu His Gly Gly Asn Phe Gln
    290                 295                 300

Gly Thr Pro Ile Gly Val Ser Met Asp Asn Thr Arg Leu Ala Ile Ala
305                 310                 315                 320

Ser Ile Gly Lys Leu Met Phe Ala Gln Phe Ser Glu Leu Val Asn Asp
                325                 330                 335

Phe Tyr Asn Asn Gly Leu Pro Ser Asn Leu Ser Gly Gly Arg Asn Pro
                340                 345                 350

Ser Leu Asp Tyr Gly Phe Lys Gly Ala Glu Ile Ala Met Ala Ala Tyr
                355                 360                 365

Cys Ser Glu Leu Gln Phe Leu Ala Asn Pro Val Thr Asn His Val Gln
    370                 375                 380

Ser Ala Glu Gln His Asn Gln Asp Val Asn Ser Leu Gly Leu Ile Ser
385                 390                 395                 400

Ser Arg Lys Thr Ala Glu Ala Val Asp Ile Leu Lys Leu Met Ser Ser
                405                 410                 415

Thr Tyr Leu Val Ala Leu Cys Gln Ala Ile Asp Leu Arg His Leu Glu
                420                 425                 430

Glu Asn Leu Lys Ala Ser Val Lys Asn Thr Val Ser Leu Val Ala Lys
                435                 440                 445

Lys Val Leu Thr Met Gly Tyr Asn Gly Glu Leu His Pro Ser Arg Phe
    450                 455                 460

Cys Glu Lys Asp Leu Leu Lys Val Val Asp Arg Glu His Val Phe Ala
465                 470                 475                 480

Tyr Ile Asp Asp Pro Cys Ser Gly Thr Tyr Pro Leu Met Gln Lys Leu
                485                 490                 495

Arg Gln Val Leu Val Glu His Ser Leu Ala Asn Gly Asp Lys Glu Lys
                500                 505                 510

Asp Ala Thr Thr Ser Ile Phe Gln Lys Ile Gly Ala Phe Glu Asp Glu
                515                 520                 525

Leu Lys Ala Leu Leu Pro Lys Glu Val Glu Ser Ala Arg Cys Glu Leu
    530                 535                 540

Glu Asn Gly Lys Pro Gly Ile Ala Asn Arg Ile Lys Asp Cys Arg Ser
545                 550                 555                 560

Tyr Ser Leu Tyr Lys Phe Val Arg Gly Glu Leu Gly Thr Asn Phe Leu
                565                 570                 575

Thr Gly Glu Lys Val Arg Ser Pro Gly Glu Glu Phe Lys Val Phe
                580                 585                 590

Thr Ala Ile Cys Glu Gly Lys Leu Ile Asp Pro Leu Leu Asp Cys Leu
    595                 600                 605

Lys Glu Trp Asn Gly Ala Pro Arg Pro Ile Cys

```
                    610                 615

<210> SEQ ID NO 50
<211> LENGTH: 703
<212> TYPE: PRT
<213> ORGANISM: Zea mays

<400> SEQUENCE: 50

Met Ala Gly Asn Gly Ala Ile Val Glu Ser Asp Pro Leu Asn Trp Gly
1               5                   10                  15

Ala Ala Ala Ala Glu Leu Ala Gly Ser His Leu Asp Glu Val Lys Arg
            20                  25                  30

Met Val Ala Gln Ala Arg Gln Pro Val Val Lys Ile Glu Gly Ser Thr
        35                  40                  45

Leu Arg Val Gly Gln Val Ala Ala Val Ser Ala Lys Asp Ala Ser
    50                  55                  60

Gly Val Ala Val Glu Leu Asp Glu Gly Ala Arg Pro Arg Val Lys Ala
65                  70                  75                  80

Ser Ser Glu Trp Ile Leu Asp Cys Ile Ala His Gly Gly Asp Ile Tyr
                85                  90                  95

Gly Val Thr Thr Gly Phe Gly Gly Thr Ser His Arg Arg Thr Lys Asp
            100                 105                 110

Gly Pro Ala Leu Gln Val Glu Leu Leu Arg His Leu Asn Ala Gly Ile
        115                 120                 125

Phe Gly Thr Gly Ser Asp Gly His Thr Leu Pro Ser Glu Val Thr Arg
    130                 135                 140

Ala Ala Met Leu Val Arg Ile Asn Thr Leu Leu Gln Gly Tyr Ser Gly
145                 150                 155                 160

Ile Arg Phe Glu Ile Leu Glu Ala Ile Thr Lys Leu Leu Asn Thr Gly
                165                 170                 175

Val Ser Pro Cys Leu Pro Leu Arg Gly Thr Ile Thr Ala Ser Gly Asp
            180                 185                 190

Leu Val Pro Leu Ser Tyr Ile Ala Gly Leu Ile Thr Gly Arg Pro Asn
        195                 200                 205

Ala Gln Ala Val Thr Val Asp Gly Arg Lys Val Asp Ala Ala Glu Ala
    210                 215                 220

Phe Lys Ile Ala Gly Ile Glu Gly Gly Phe Phe Lys Leu Asn Pro Lys
225                 230                 235                 240

Glu Gly Leu Ala Ile Val Asn Gly Thr Ser Val Gly Ser Ala Leu Ala
                245                 250                 255

Ala Thr Val Met Tyr Asp Ala Asn Val Leu Ala Val Leu Ser Glu Val
            260                 265                 270

Leu Ser Ala Val Phe Cys Glu Val Met Asn Gly Lys Pro Glu Tyr Thr
        275                 280                 285

Asp His Leu Thr His Lys Leu Lys His His Pro Gly Ser Ile Glu Ala
    290                 295                 300

Ala Ile Met Glu His Ile Leu Asp Gly Ser Ser Phe Met Lys Gln
305                 310                 315                 320

Ala Lys Lys Val Asn Glu Leu Asp Pro Leu Lys Pro Lys Gln Asp
                325                 330                 335

Arg Tyr Ala Leu Arg Thr Ser Pro Gln Trp Leu Gly Pro Gln Ile Glu
            340                 345                 350

Val Ile Arg Ala Ala Thr Lys Ser Ile Glu Arg Glu Val Asn Ser Val
        355                 360                 365

Asn Asp Asn Pro Val Ile Asp Val His Arg Gly Lys Ala Leu His Gly
```

```
              370                 375                 380
Gly Asn Phe Gln Gly Thr Pro Ile Gly Val Ser Met Asp Asn Ala Arg
385                 390                 395                 400

Leu Ala Ile Ala Asn Ile Gly Lys Leu Met Phe Ala Gln Phe Ser Glu
                405                 410                 415

Leu Val Asn Glu Phe Tyr Asn Asn Gly Leu Thr Ser Asn Leu Ala Gly
            420                 425                 430

Ser Arg Asn Pro Ser Leu Asp Tyr Gly Phe Lys Gly Thr Glu Ile Ala
        435                 440                 445

Met Ala Ser Tyr Cys Ser Glu Leu Gln Tyr Leu Gly Asn Pro Ile Thr
    450                 455                 460

Asn His Val Gln Ser Ala Asp Glu His Asn Gln Asp Val Asn Ser Leu
465                 470                 475                 480

Gly Leu Val Ser Ala Arg Lys Thr Ala Glu Ala Ile Asp Ile Leu Lys
                485                 490                 495

Leu Met Ser Ser Thr Tyr Ile Val Ala Leu Cys Gln Ala Val Asp Leu
            500                 505                 510

Arg His Leu Glu Glu Asn Ile Lys Ala Ser Val Lys Asn Thr Val Thr
        515                 520                 525

Gln Val Ala Lys Lys Val Leu Thr Met Asn Pro Ser Gly Glu Leu Ser
    530                 535                 540

Ser Ala Arg Phe Ser Glu Lys Glu Leu Ile Ser Ala Ile Asp Arg Glu
545                 550                 555                 560

Ala Val Phe Thr Tyr Ala Glu Asp Ala Ala Ser Ala Ser Leu Pro Leu
                565                 570                 575

Met Gln Lys Leu Arg Ala Val Leu Val Asp His Ala Leu Ser Ser Gly
            580                 585                 590

Glu Arg Gly Ala Gly Ala Leu Arg Val Leu Gln Asp His Gln Val Arg
        595                 600                 605

Gly Gly Ala Pro Arg Gly Ala Pro Gly Gly Gly Arg Pro
    610                 615                 620

Gly Val Ala Glu Gly Thr Ala Pro Val Ala Asn Arg Ile Ala Asp Ser
625                 630                 635                 640

Arg Ser Phe Pro Leu Tyr Arg Phe Val Arg Glu Glu Leu Gly Cys Val
                645                 650                 655

Phe Leu Thr Gly Glu Arg Leu Lys Ser Pro Gly Glu Glu Cys Asn Lys
            660                 665                 670

Val Phe Val Gly Ile Ser Gln Gly Lys Leu Val Asp Pro Met Leu Glu
        675                 680                 685

Cys Leu Lys Glu Trp Asp Gly Lys Pro Leu Pro Ile Asn Ile Lys
    690                 695                 700

<210> SEQ ID NO 51
<211> LENGTH: 725
<212> TYPE: PRT
<213> ORGANISM: Arabidopsis thaliana

<400> SEQUENCE: 51

Met Glu Ile Asn Gly Ala His Lys Ser Asn Gly Gly Val Asp Ala
1               5                   10                  15

Met Leu Cys Gly Gly Asp Ile Lys Thr Lys Asn Met Val Ile Asn Ala
                20                  25                  30

Glu Asp Pro Leu Asn Trp Gly Ala Ala Ala Glu Gln Met Lys Gly Ser
            35                  40                  45

His Leu Asp Glu Val Lys Arg Met Val Ala Glu Phe Arg Lys Pro Val
```

```
                50                  55                  60
Val Asn Leu Gly Gly Glu Thr Leu Thr Ile Gly Gln Val Ala Ala Ile
 65                  70                  75                  80

Ser Thr Ile Gly Asn Ser Val Lys Val Glu Leu Ser Glu Thr Ala Arg
                 85                  90                  95

Ala Gly Val Asn Ala Ser Ser Asp Trp Val Met Glu Ser Met Asn Lys
                100                 105                 110

Gly Thr Asp Ser Tyr Gly Val Thr Thr Gly Phe Gly Ala Thr Ser His
                115                 120                 125

Arg Arg Thr Lys Asn Gly Val Ala Leu Gln Lys Glu Leu Ile Arg Phe
            130                 135                 140

Leu Asn Ala Gly Ile Phe Gly Ser Thr Lys Glu Thr Ser His Thr Leu
145                 150                 155                 160

Pro His Ser Ala Thr Arg Ala Ala Met Leu Val Arg Ile Asn Thr Leu
                165                 170                 175

Leu Gln Gly Phe Ser Gly Ile Arg Phe Glu Ile Leu Glu Ala Ile Thr
                180                 185                 190

Ser Phe Leu Asn Asn Asn Ile Thr Pro Ser Leu Pro Leu Arg Gly Thr
            195                 200                 205

Ile Thr Ala Ser Gly Asp Leu Val Pro Leu Ser Tyr Ile Ala Gly Leu
210                 215                 220

Leu Thr Gly Arg Pro Asn Ser Lys Ala Thr Gly Pro Asn Gly Glu Ala
225                 230                 235                 240

Leu Thr Ala Glu Glu Ala Phe Lys Leu Ala Gly Ile Ser Ser Gly Phe
                245                 250                 255

Phe Asp Leu Gln Pro Lys Glu Gly Leu Ala Leu Val Asn Gly Thr Ala
            260                 265                 270

Val Gly Ser Gly Met Ala Ser Met Val Leu Phe Glu Thr Asn Val Leu
            275                 280                 285

Ser Val Leu Ala Glu Ile Leu Ser Ala Val Phe Ala Glu Val Met Ser
290                 295                 300

Gly Lys Pro Glu Phe Thr Asp His Leu Thr His Arg Leu Lys His His
305                 310                 315                 320

Pro Gly Gln Ile Glu Ala Ala Ala Ile Met Glu His Ile Leu Asp Gly
                325                 330                 335

Ser Ser Tyr Met Lys Leu Ala Gln Lys Leu His Glu Met Asp Pro Leu
                340                 345                 350

Gln Lys Pro Lys Gln Asp Arg Tyr Ala Leu Arg Thr Ser Pro Gln Trp
            355                 360                 365

Leu Gly Pro Gln Ile Glu Val Ile Arg Tyr Ala Thr Lys Ser Ile Glu
370                 375                 380

Arg Glu Ile Asn Ser Val Asn Asp Asn Pro Leu Ile Asp Val Ser Arg
385                 390                 395                 400

Asn Lys Ala Ile His Gly Gly Asn Phe Gln Gly Thr Pro Ile Gly Val
                405                 410                 415

Ser Met Asp Asn Thr Arg Leu Ala Ile Ala Ala Ile Gly Lys Leu Met
                420                 425                 430

Phe Ala Gln Phe Ser Glu Leu Val Asn Asp Phe Tyr Asn Asn Gly Leu
            435                 440                 445

Pro Ser Asn Leu Thr Ala Ser Arg Asn Pro Ser Leu Asp Tyr Gly Phe
            450                 455                 460

Lys Gly Ala Glu Ile Ala Met Ala Ser Tyr Cys Ser Glu Leu Gln Tyr
465                 470                 475                 480
```

```
Leu Ala Asn Pro Val Thr Ser His Val Gln Ser Ala Glu Gln His Asn
            485                 490                 495
Gln Asp Val Asn Ser Leu Gly Leu Ile Ser Ser Arg Lys Thr Ser Glu
        500                 505                 510
Ala Val Asp Ile Leu Lys Leu Met Ser Thr Thr Phe Leu Val Ala Ile
    515                 520                 525
Cys Gln Ala Val Asp Leu Arg His Leu Glu Glu Asn Leu Arg Gln Thr
530                 535                 540
Val Lys Asn Thr Val Ser Gln Val Ala Lys Lys Val Leu Thr Thr Gly
545                 550                 555                 560
Val Asn Gly Glu Leu His Pro Ser Arg Phe Cys Glu Lys Asp Leu Leu
                565                 570                 575
Lys Val Val Asp Arg Glu Gln Val Tyr Thr Tyr Ala Asp Asp Pro Cys
            580                 585                 590
Ser Ala Thr Tyr Pro Leu Ile Gln Lys Leu Arg Gln Val Ile Val Asp
        595                 600                 605
His Ala Leu Ile Asn Gly Glu Ser Glu Lys Asn Ala Val Thr Ser Ile
    610                 615                 620
Phe His Lys Ile Gly Ala Phe Glu Glu Leu Lys Ala Val Leu Pro
625                 630                 635                 640
Lys Glu Val Glu Ala Ala Arg Ala Ala Tyr Asp Asn Gly Thr Ser Ala
                645                 650                 655
Ile Pro Asn Arg Ile Lys Glu Cys Arg Ser Tyr Pro Leu Tyr Arg Phe
            660                 665                 670
Val Arg Glu Glu Leu Gly Thr Glu Leu Leu Thr Gly Glu Lys Val Thr
        675                 680                 685
Ser Pro Gly Glu Glu Phe Asp Lys Val Phe Thr Ala Ile Cys Glu Gly
    690                 695                 700
Lys Ile Ile Asp Pro Met Met Glu Cys Leu Asn Glu Trp Asn Gly Ala
705                 710                 715                 720
Pro Ile Pro Ile Cys
                725

<210> SEQ ID NO 52
<211> LENGTH: 717
<212> TYPE: PRT
<213> ORGANISM: Arabidopsis thaliana

<400> SEQUENCE: 52

Met Asp Gln Ile Glu Ala Met Leu Cys Gly Gly Gly Glu Lys Thr Lys
1               5                   10                  15
Val Ala Val Thr Thr Lys Thr Leu Ala Asp Pro Leu Asn Trp Gly Leu
            20                  25                  30
Ala Ala Asp Gln Met Lys Gly Ser His Leu Asp Glu Val Lys Lys Met
        35                  40                  45
Val Glu Glu Tyr Arg Arg Pro Val Val Asn Leu Gly Gly Glu Thr Leu
    50                  55                  60
Thr Ile Gly Gln Val Ala Ala Ile Ser Thr Val Gly Gly Ser Val Lys
65                  70                  75                  80
Val Glu Leu Ala Glu Thr Ser Arg Ala Gly Val Lys Ala Ser Ser Asp
                85                  90                  95
Trp Val Met Glu Ser Met Asn Lys Gly Thr Asp Ser Tyr Gly Val Thr
            100                 105                 110
Thr Gly Phe Gly Ala Thr Ser His Arg Arg Thr Lys Asn Gly Thr Ala
        115                 120                 125
```

```
Leu Gln Thr Glu Leu Ile Arg Phe Leu Asn Ala Gly Ile Phe Gly Asn
    130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
                165                 170                 175

Phe Glu Ile Leu Glu Ala Ile Thr Ser Leu Leu Asn His Asn Ile Ser
            180                 185                 190

Pro Ser Leu Pro Leu Arg Gly Thr Ile Thr Ala Ser Gly Asp Leu Val
        195                 200                 205

Pro Leu Ser Tyr Ile Ala Gly Leu Leu Thr Gly Arg Pro Asn Ser Lys
210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
        275                 280                 285

Ala Ile Phe Ala Glu Val Met Ser Gly Lys Pro Glu Phe Thr Asp His
290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Gln Asp Arg Tyr
            340                 345                 350

Ala Leu Arg Thr Ser Pro Gln Trp Leu Gly Pro Gln Ile Glu Val Ile
        355                 360                 365

Arg Gln Ala Thr Lys Ser Ile Glu Arg Glu Ile Asn Ser Val Asn Asp
370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
        435                 440                 445

Asn Pro Ser Leu Asp Tyr Gly Phe Lys Gly Ala Glu Ile Ala Met Ala
450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
                485                 490                 495

Ile Ser Ser Arg Lys Thr Ser Glu Ala Val Asp Ile Leu Lys Leu Met
            500                 505                 510

Ser Thr Thr Phe Leu Val Gly Ile Cys Gln Ala Val Asp Leu Arg His
        515                 520                 525

Leu Glu Glu Asn Leu Arg Gln Thr Val Lys Asn Thr Val Ser Gln Val
530                 535                 540

Ala Lys Lys Val Leu Thr Thr Gly Ile Asn Gly Glu Leu His Pro Ser
545                 550                 555                 560
```

```
Arg Phe Cys Glu Lys Asp Leu Leu Lys Val Val Asp Arg Glu Gln Val
                565                 570                 575

Phe Thr Tyr Val Asp Asp Pro Cys Ser Ala Thr Tyr Pro Leu Met Gln
            580                 585                 590

Arg Leu Arg Gln Val Ile Val Asp His Ala Leu Ser Asn Gly Glu Thr
        595                 600                 605

Glu Lys Asn Ala Val Thr Ser Ile Phe Gln Lys Ile Gly Ala Phe Glu
    610                 615                 620

Glu Glu Leu Lys Ala Val Leu Pro Lys Glu Val Glu Ala Ala Arg Ala
625                 630                 635                 640

Ala Tyr Gly Asn Gly Thr Ala Pro Ile Pro Asn Arg Ile Lys Glu Cys
                645                 650                 655

Arg Ser Tyr Pro Leu Tyr Arg Phe Val Arg Glu Glu Leu Gly Thr Lys
            660                 665                 670

Leu Leu Thr Gly Glu Lys Val Val Ser Pro Gly Glu Glu Phe Asp Lys
        675                 680                 685

Val Phe Thr Ala Met Cys Glu Gly Lys Leu Ile Asp Pro Leu Met Asp
    690                 695                 700

Cys Leu Lys Glu Trp Asn Gly Ala Pro Ile Pro Ile Cys
705                 710                 715

<210> SEQ ID NO 53
<211> LENGTH: 707
<212> TYPE: PRT
<213> ORGANISM: Arabidopsis thaliana

<400> SEQUENCE: 53

Met Glu Leu Cys Asn Gln Asn Asn His Ile Thr Ala Val Ser Gly Asp
1               5                   10                  15

Pro Leu Asn Trp Asn Ala Thr Ala Glu Ala Leu Lys Gly Ser His Leu
            20                  25                  30

Asp Glu Val Lys Arg Met Val Lys Glu Tyr Arg Lys Glu Ala Val Lys
        35                  40                  45

Leu Gly Gly Glu Thr Leu Thr Ile Gly Gln Val Ala Ala Val Ala Arg
    50                  55                  60

Gly Gly Gly Gly Ser Thr Val Glu Leu Ala Glu Glu Ala Arg Ala Gly
65                  70                  75                  80

Val Lys Ala Ser Ser Glu Trp Val Met Glu Ser Met Asn Arg Gly Thr
                85                  90                  95

Asp Ser Tyr Gly Val Thr Thr Gly Phe Gly Ala Thr Ser His Arg Arg
            100                 105                 110

Thr Lys Gln Gly Gly Ala Leu Gln Asn Glu Leu Ile Arg Phe Leu Asn
        115                 120                 125

Ala Gly Ile Phe Gly Pro Gly Ala Gly Asp Thr Ser His Thr Leu Pro
    130                 135                 140

Lys Pro Thr Thr Arg Ala Ala Met Leu Val Arg Val Asn Thr Leu Leu
145                 150                 155                 160

Gln Gly Tyr Ser Gly Ile Arg Phe Glu Ile Leu Glu Ala Ile Thr Lys
                165                 170                 175

Leu Leu Asn His Glu Ile Thr Pro Cys Leu Pro Leu Arg Gly Thr Ile
            180                 185                 190

Thr Ala Ser Gly Asp Leu Val Pro Leu Ser Tyr Ile Ala Gly Leu Leu
        195                 200                 205

Thr Gly Arg Pro Asn Ser Lys Ala Val Gly Pro Ser Gly Glu Thr Leu
    210                 215                 220
```

```
Thr Ala Ser Glu Ala Phe Lys Leu Ala Gly Val Ser Ser Phe Phe Glu
225                 230                 235                 240

Leu Gln Pro Lys Glu Gly Leu Ala Leu Val Asn Gly Thr Ala Val Gly
            245                 250                 255

Ser Gly Leu Ala Ser Thr Val Leu Phe Asp Ala Asn Ile Leu Ala Val
                260                 265                 270

Leu Ser Glu Val Met Ser Ala Met Phe Ala Glu Val Met Gln Gly Lys
            275                 280                 285

Pro Glu Phe Thr Asp His Leu Thr His Lys Leu Lys His His Pro Gly
        290                 295                 300

Gln Ile Glu Ala Ala Ala Ile Met Glu His Ile Leu Asp Gly Ser Ser
305                 310                 315                 320

Tyr Val Lys Glu Ala Gln Leu Leu His Glu Met Asp Pro Leu Gln Lys
                325                 330                 335

Pro Lys Gln Asp Arg Tyr Ala Leu Arg Thr Ser Pro Gln Trp Leu Gly
            340                 345                 350

Pro Gln Ile Glu Val Ile Arg Ala Ala Thr Lys Met Ile Glu Arg Glu
        355                 360                 365

Ile Asn Ser Val Asn Asp Asn Pro Leu Ile Asp Val Ser Arg Asn Lys
370                 375                 380

Ala Leu His Gly Gly Asn Phe Gln Gly Thr Pro Ile Gly Val Ala Met
385                 390                 395                 400

Asp Asn Ser Arg Leu Ala Ile Ala Ser Ile Gly Lys Leu Met Phe Ala
                405                 410                 415

Gln Phe Ser Glu Leu Val Asn Asp Phe Tyr Asn Asn Gly Leu Pro Ser
            420                 425                 430

Asn Leu Ser Gly Gly Arg Asn Pro Ser Leu Asp Tyr Gly Phe Lys Gly
            435                 440                 445

Ala Glu Ile Ala Met Ala Ser Tyr Cys Ser Glu Leu Gln Phe Leu Ala
450                 455                 460

Asn Pro Val Thr Asn His Val Gln Ser Ala Glu Gln His Asn Gln Asp
465                 470                 475                 480

Val Asn Ser Leu Gly Leu Ile Ser Ser Arg Lys Thr Ala Glu Ala Val
                485                 490                 495

Asp Ile Leu Lys Leu Met Ser Thr Thr Tyr Leu Val Ala Leu Cys Gln
            500                 505                 510

Ala Val Asp Leu Arg His Leu Glu Glu Asn Leu Lys Lys Ala Val Lys
            515                 520                 525

Ser Ala Val Ser Gln Val Ala Lys Arg Val Leu Thr Val Gly Ala Asn
530                 535                 540

Gly Glu Leu His Pro Ser Arg Phe Thr Glu Arg Asp Val Leu Gln Val
545                 550                 555                 560

Val Asp Arg Glu Tyr Val Phe Ser Tyr Ala Asp Asp Pro Cys Ser Leu
                565                 570                 575

Thr Tyr Pro Leu Met Gln Lys Leu Arg His Ile Leu Val Asp His Ala
            580                 585                 590

Leu Ala Asp Pro Glu Arg Glu Ala Asn Ser Ala Thr Ser Val Phe His
        595                 600                 605

Lys Ile Gly Ala Phe Glu Ala Glu Leu Lys Leu Leu Pro Lys Glu
        610                 615                 620

Val Glu Arg Val Arg Val Glu Tyr Glu Glu Gly Thr Ser Ala Ile Ala
625                 630                 635                 640

Asn Arg Ile Lys Glu Cys Arg Ser Tyr Pro Leu Tyr Arg Phe Val Arg
```

```
                        645                 650                 655
Asp Glu Leu Asn Thr Glu Leu Leu Thr Gly Glu Asn Val Arg Ser Pro
            660                 665                 670

Gly Glu Glu Phe Asp Lys Val Phe Leu Ala Ile Ser Asp Gly Lys Leu
        675                 680                 685

Ile Asp Pro Leu Leu Glu Cys Leu Lys Glu Trp Asn Gly Ala Pro Val
    690                 695                 700

Ser Ile Cys
705

<210> SEQ ID NO 54
<211> LENGTH: 716
<212> TYPE: PRT
<213> ORGANISM: Petroselinum crispum

<400> SEQUENCE: 54

Met Glu Asn Gly Asn Gly Ala Thr Thr Asn Gly His Val Asn Gly Asn
1               5                   10                  15

Gly Met Asp Phe Cys Met Lys Thr Glu Asp Pro Leu Tyr Trp Gly Ile
            20                  25                  30

Ala Ala Glu Ala Met Thr Gly Ser His Leu Asp Glu Val Lys Lys Met
        35                  40                  45

Val Ala Glu Tyr Arg Lys Pro Val Val Lys Leu Gly Gly Glu Thr Leu
    50                  55                  60

Thr Ile Ser Gln Val Ala Ala Ile Ser Ala Arg Asp Gly Ser Gly Val
65                  70                  75                  80

Thr Val Glu Leu Ser Glu Ala Ala Arg Ala Gly Val Lys Ala Ser Ser
                85                  90                  95

Asp Trp Val Met Asp Ser Met Asn Lys Gly Thr Asp Ser Tyr Gly Val
            100                 105                 110

Thr Thr Gly Phe Gly Ala Thr Ser His Arg Arg Thr Lys Gln Gly Gly
        115                 120                 125

Ala Leu Gln Lys Glu Leu Ile Arg Phe Leu Asn Ala Gly Ile Phe Gly
    130                 135                 140

Asn Gly Ser Asp Asn Thr Leu Pro His Ser Ala Thr Arg Ala Ala Met
145                 150                 155                 160

Leu Val Arg Ile Asn Thr Leu Leu Gln Gly Tyr Ser Gly Ile Arg Phe
                165                 170                 175

Glu Ile Leu Glu Ala Ile Thr Lys Phe Leu Asn Gln Asn Ile Thr Pro
            180                 185                 190

Cys Leu Pro Leu Arg Gly Thr Ile Thr Ala Ser Gly Asp Leu Val Pro
        195                 200                 205

Leu Ser Tyr Ile Ala Gly Leu Leu Thr Gly Arg Pro Asn Ser Lys Ala
    210                 215                 220

Val Gly Pro Thr Gly Val Ile Leu Ser Pro Glu Glu Ala Phe Lys Leu
225                 230                 235                 240

Ala Gly Val Glu Gly Gly Phe Phe Glu Leu Gln Pro Lys Glu Gly Leu
                245                 250                 255

Ala Leu Val Asn Gly Thr Ala Val Gly Ser Gly Met Ala Ser Met Val
            260                 265                 270

Leu Phe Glu Ala Asn Ile Leu Ala Val Leu Ala Glu Val Met Ser Ala
        275                 280                 285

Ile Phe Ala Glu Val Met Gln Gly Lys Pro Glu Phe Thr Asp His Leu
    290                 295                 300

Thr His Lys Leu Lys His His Pro Gly Gln Ile Glu Ala Ala Ala Ile
```

```
                305                 310                 315                 320
Met Glu His Ile Leu Asp Gly Ser Ala Tyr Val Lys Ala Ala Gln Lys
                    325                 330                 335
Leu His Glu Met Asp Pro Leu Gln Lys Pro Lys Gln Asp Arg Tyr Ala
                    340                 345                 350
Leu Arg Thr Ser Pro Gln Trp Leu Gly Pro Gln Ile Glu Val Ile Arg
                    355                 360                 365
Ser Ser Thr Lys Met Ile Glu Arg Glu Ile Asn Ser Val Asn Asp Asn
                    370                 375                 380
Pro Leu Ile Asp Val Ser Arg Asn Lys Ala Ile His Gly Gly Asn Phe
385                 390                 395                 400
Gln Gly Thr Pro Ile Gly Val Ser Met Asp Asn Thr Arg Leu Ala Ile
                    405                 410                 415
Ala Ala Ile Gly Lys Leu Met Phe Ala Gln Phe Ser Glu Leu Val Asn
                    420                 425                 430
Asp Phe Tyr Asn Asn Gly Leu Pro Ser Asn Leu Ser Gly Gly Arg Asn
                    435                 440                 445
Pro Ser Leu Asp Tyr Gly Phe Lys Gly Ala Glu Ile Ala Met Ala Ser
450                 455                 460
Tyr Cys Ser Glu Leu Gln Phe Leu Ala Asn Pro Val Thr Asn His Val
465                 470                 475                 480
Gln Ser Ala Glu Gln His Asn Gln Asp Val Asn Ser Leu Gly Leu Ile
                    485                 490                 495
Ser Ser Arg Lys Thr Ser Glu Ala Val Glu Ile Leu Lys Leu Met Ser
                    500                 505                 510
Thr Thr Phe Leu Val Gly Leu Cys Gln Ala Ile Asp Leu Arg His Leu
                    515                 520                 525
Glu Glu Asn Leu Lys Ser Thr Val Lys Asn Thr Val Ser Ser Val Ala
                    530                 535                 540
Lys Arg Val Leu Thr Met Gly Val Asn Gly Glu Leu His Pro Ser Arg
545                 550                 555                 560
Phe Cys Glu Lys Asp Leu Leu Arg Val Val Asp Arg Glu Tyr Ile Phe
                    565                 570                 575
Ala Tyr Ile Asp Asp Pro Cys Ser Ala Thr Tyr Pro Leu Met Gln Lys
                    580                 585                 590
Leu Arg Gln Thr Leu Val Glu His Ala Leu Lys Asn Gly Asp Asn Glu
                    595                 600                 605
Arg Asn Leu Ser Thr Ser Ile Phe Gln Lys Ile Ala Thr Phe Glu Asp
                    610                 615                 620
Glu Leu Lys Ala Leu Leu Pro Lys Glu Val Glu Ser Ala Arg Ala Ala
625                 630                 635                 640
Leu Glu Ser Gly Asn Pro Ala Ile Pro Asn Arg Ile Glu Glu Cys Arg
                    645                 650                 655
Ser Tyr Pro Leu Tyr Lys Phe Val Arg Lys Glu Leu Gly Thr Glu Tyr
                    660                 665                 670
Leu Thr Gly Glu Lys Val Thr Ser Pro Gly Glu Glu Phe Glu Lys Val
                    675                 680                 685
Phe Ile Ala Met Ser Lys Gly Glu Ile Ile Asp Pro Leu Leu Glu Cys
                    690                 695                 700
Leu Glu Ser Trp Asn Gly Ala Pro Leu Pro Ile Cys
705                 710                 715

<210> SEQ ID NO 55
<211> LENGTH: 716
```

```
<212> TYPE: PRT
<213> ORGANISM: Petroselinum crispum

<400> SEQUENCE: 55
```

| | | | | | | | | | | | | | | |
|---|---|---|---|---|---|---|---|---|---|---|---|---|---|---|
| Met | Glu | Asn | Gly | Asn | Gly | Ala | Ile | Thr | Asn | Gly | His | Val | Asn | Gly | Asn |
| 1 | | | | 5 | | | | | 10 | | | | | 15 | |

| Gly | Met | Asp | Phe | Cys | Met | Lys | Thr | Glu | Asp | Pro | Leu | Tyr | Trp | Gly | Ile |
|---|---|---|---|---|---|---|---|---|---|---|---|---|---|---|---|
| | | | 20 | | | | | 25 | | | | | 30 | | |

| Ala | Ala | Glu | Ala | Met | Thr | Gly | Ser | His | Leu | Asp | Glu | Val | Lys | Lys | Met |
|---|---|---|---|---|---|---|---|---|---|---|---|---|---|---|---|
| | | 35 | | | | | 40 | | | | | 45 | | | |

| Val | Ala | Glu | Tyr | Arg | Lys | Pro | Val | Val | Lys | Leu | Gly | Gly | Glu | Thr | Leu |
|---|---|---|---|---|---|---|---|---|---|---|---|---|---|---|---|
| | 50 | | | | | 55 | | | | | 60 | | | | |

| Thr | Ile | Ser | Gln | Val | Ala | Ala | Ile | Ser | Ala | Arg | Asp | Gly | Ser | Gly | Val |
|---|---|---|---|---|---|---|---|---|---|---|---|---|---|---|---|
| 65 | | | | | 70 | | | | | 75 | | | | | 80 |

| Thr | Val | Glu | Leu | Ser | Glu | Ala | Ala | Arg | Ala | Gly | Val | Lys | Ala | Ser | Ser |
|---|---|---|---|---|---|---|---|---|---|---|---|---|---|---|---|
| | | | | 85 | | | | | 90 | | | | | 95 | |

| Asp | Trp | Val | Met | Asp | Ser | Met | Asn | Lys | Gly | Thr | Asp | Ser | Tyr | Gly | Val |
|---|---|---|---|---|---|---|---|---|---|---|---|---|---|---|---|
| | | | 100 | | | | | 105 | | | | | 110 | | |

| Thr | Thr | Gly | Phe | Gly | Ala | Thr | Ser | His | Arg | Arg | Thr | Lys | Gln | Gly | Gly |
|---|---|---|---|---|---|---|---|---|---|---|---|---|---|---|---|
| | | 115 | | | | | 120 | | | | | 125 | | | |

| Ala | Leu | Gln | Lys | Glu | Leu | Ile | Arg | Phe | Leu | Asn | Ala | Gly | Ile | Phe | Gly |
|---|---|---|---|---|---|---|---|---|---|---|---|---|---|---|---|
| | 130 | | | | | 135 | | | | | 140 | | | | |

| Asn | Gly | Ser | Asp | Asn | Thr | Leu | Pro | His | Ser | Ala | Thr | Arg | Ala | Ala | Met |
|---|---|---|---|---|---|---|---|---|---|---|---|---|---|---|---|
| 145 | | | | | 150 | | | | | 155 | | | | | 160 |

| Leu | Val | Arg | Ile | Asn | Thr | Leu | Leu | Gln | Gly | Tyr | Ser | Gly | Ile | Arg | Phe |
|---|---|---|---|---|---|---|---|---|---|---|---|---|---|---|---|
| | | | | 165 | | | | | 170 | | | | | 175 | |

| Glu | Ile | Leu | Glu | Ala | Ile | Thr | Lys | Phe | Leu | Asn | Gln | Asn | Ile | Thr | Pro |
|---|---|---|---|---|---|---|---|---|---|---|---|---|---|---|---|
| | | | 180 | | | | | 185 | | | | | 190 | | |

| Cys | Leu | Pro | Leu | Arg | Gly | Thr | Ile | Thr | Ala | Ser | Gly | Asp | Leu | Val | Pro |
|---|---|---|---|---|---|---|---|---|---|---|---|---|---|---|---|
| | | 195 | | | | | 200 | | | | | 205 | | | |

| Leu | Ser | Tyr | Ile | Ala | Gly | Leu | Leu | Thr | Gly | Arg | Pro | Asn | Ser | Lys | Ala |
|---|---|---|---|---|---|---|---|---|---|---|---|---|---|---|---|
| | 210 | | | | | 215 | | | | | 220 | | | | |

| Val | Gly | Pro | Thr | Gly | Val | Ile | Leu | Ser | Pro | Glu | Glu | Ala | Phe | Lys | Leu |
|---|---|---|---|---|---|---|---|---|---|---|---|---|---|---|---|
| 225 | | | | | 230 | | | | | 235 | | | | | 240 |

| Ala | Gly | Val | Glu | Gly | Gly | Phe | Phe | Glu | Leu | Gln | Pro | Lys | Glu | Gly | Leu |
|---|---|---|---|---|---|---|---|---|---|---|---|---|---|---|---|
| | | | | 245 | | | | | 250 | | | | | 255 | |

| Ala | Leu | Val | Asn | Gly | Thr | Ala | Val | Gly | Ser | Gly | Met | Ala | Ser | Met | Val |
|---|---|---|---|---|---|---|---|---|---|---|---|---|---|---|---|
| | | | 260 | | | | | 265 | | | | | 270 | | |

| Leu | Phe | Glu | Ala | Asn | Ile | Leu | Ala | Val | Leu | Ala | Glu | Val | Met | Ser | Ala |
|---|---|---|---|---|---|---|---|---|---|---|---|---|---|---|---|
| | 275 | | | | | 280 | | | | | 285 | | | | |

| Ile | Phe | Ala | Glu | Val | Met | Gln | Gly | Lys | Pro | Glu | Phe | Thr | Asp | His | Leu |
|---|---|---|---|---|---|---|---|---|---|---|---|---|---|---|---|
| 290 | | | | | 295 | | | | | 300 | | | | | |

| Thr | His | Lys | Leu | Lys | His | His | Pro | Gly | Gln | Ile | Glu | Ala | Ala | Ala | Ile |
|---|---|---|---|---|---|---|---|---|---|---|---|---|---|---|---|
| 305 | | | | | 310 | | | | | 315 | | | | | 320 |

| Met | Glu | His | Ile | Leu | Asp | Gly | Ser | Ala | Tyr | Val | Lys | Ala | Ala | Gln | Lys |
|---|---|---|---|---|---|---|---|---|---|---|---|---|---|---|---|
| | | | | 325 | | | | | 330 | | | | | 335 | |

| Leu | His | Glu | Met | Asp | Pro | Leu | Gln | Lys | Pro | Lys | Gln | Asp | Arg | Tyr | Ala |
|---|---|---|---|---|---|---|---|---|---|---|---|---|---|---|---|
| | | | 340 | | | | | 345 | | | | | 350 | | |

| Leu | Arg | Thr | Ser | Pro | Gln | Trp | Leu | Gly | Pro | Gln | Ile | Glu | Val | Ile | Arg |
|---|---|---|---|---|---|---|---|---|---|---|---|---|---|---|---|
| | | 355 | | | | | 360 | | | | | 365 | | | |

| Ser | Ser | Thr | Lys | Met | Ile | Glu | Arg | Glu | Ile | Asn | Ser | Val | Asn | Asp | Asn |
|---|---|---|---|---|---|---|---|---|---|---|---|---|---|---|---|
| | 370 | | | | | 375 | | | | | 380 | | | | |

| Pro | Leu | Ile | Asp | Val | Ser | Arg | Asn | Lys | Ala | Ile | His | Gly | Gly | Asn | Phe |
|---|---|---|---|---|---|---|---|---|---|---|---|---|---|---|---|
| 385 | | | | | 390 | | | | | 395 | | | | | 400 |

```
Gln Gly Thr Pro Ile Gly Met Ser Met Asp Asn Thr Arg Leu Ala Ile
            405                 410                 415

Ala Ala Ile Gly Lys Leu Met Phe Ala Gln Phe Ser Glu Leu Val Asn
        420                 425                 430

Asp Phe Tyr Asn Asn Gly Leu Pro Ser Asn Leu Ser Gly Gly Arg Asn
            435                 440                 445

Pro Ser Leu Asp Tyr Gly Phe Lys Gly Ala Glu Ile Ala Met Ala Ser
    450                 455                 460

Tyr Cys Ser Glu Leu Gln Phe Leu Ala Asn Pro Val Thr Asn His Val
465                 470                 475                 480

Gln Ser Ala Glu Gln His Asn Gln Asp Val Asn Ser Leu Gly Leu Ile
                485                 490                 495

Ser Ser Arg Lys Thr Ser Glu Ala Val Glu Ile Leu Lys Leu Met Ser
            500                 505                 510

Thr Thr Phe Leu Val Gly Leu Cys Gln Ala Ile Asp Leu Arg His Leu
        515                 520                 525

Glu Glu Asn Leu Lys Ser Thr Val Lys Asn Thr Val Ser Ser Val Ala
            530                 535                 540

Lys Arg Val Leu Thr Met Gly Val Asn Gly Glu Leu His Pro Ser Arg
545                 550                 555                 560

Phe Cys Glu Lys Asp Leu Leu Arg Phe Val Asp Arg Glu Tyr Ile Phe
                565                 570                 575

Ala Tyr Ile Asp Asp Pro Cys Ser Ala Thr Tyr Pro Leu Met Gln Lys
            580                 585                 590

Leu Arg Gln Thr Leu Val Glu His Ala Leu Lys Asn Gly Asp Asn Glu
        595                 600                 605

Arg Asn Met Asn Thr Ser Ile Phe Gln Lys Ile Ala Thr Phe Glu Asp
610                 615                 620

Glu Leu Lys Ala Leu Leu Pro Lys Glu Val Glu Ser Ala Arg Ala Ala
625                 630                 635                 640

Leu Glu Ser Gly Asn Pro Ala Ile Pro Asn Arg Ile Glu Glu Cys Arg
                645                 650                 655

Ser Tyr Pro Leu Tyr Lys Phe Val Arg Lys Glu Leu Gly Ile Glu Tyr
            660                 665                 670

Leu Thr Gly Glu Lys Val Thr Ser Pro Gly Glu Glu Phe Asp Lys Val
        675                 680                 685

Phe Ile Ala Met Ser Lys Gly Glu Ile Ile Asp Pro Leu Leu Glu Cys
690                 695                 700

Leu Glu Ser Trp Asn Gly Ala Pro Leu Pro Ile Cys
705                 710                 715

<210> SEQ ID NO 56
<211> LENGTH: 718
<212> TYPE: PRT
<213> ORGANISM: Petroselinum crispum

<400> SEQUENCE: 56

Met Ala Tyr Val Asn Gly Thr Thr Asn Gly His Ala Asn Gly Asn Gly
1               5                   10                  15

Leu Asp Leu Cys Met Lys Lys Glu Asp Pro Leu Asn Trp Gly Val Ala
            20                  25                  30

Ala Glu Ala Leu Thr Gly Ser His Leu Asp Glu Val Lys Arg Met Val
        35                  40                  45

Ala Glu Tyr Arg Lys Pro Val Val Lys Leu Glu Gly Glu Thr Leu Thr
    50                  55                  60
```

```
Ile Ser Gln Val Ala Ala Ile Ser Ala Arg Asp Asp Ser Gly Val Lys
 65                  70                  75                  80

Val Glu Leu Ser Glu Ala Arg Ala Gly Val Lys Ala Ser Ser Asp
             85                  90                  95

Trp Val Met Asp Ser Met Asn Lys Gly Thr Asp Ser Tyr Gly Val Thr
            100                 105                 110

Thr Gly Phe Gly Ala Thr Ser His Arg Arg Thr Lys Gln Gly Gly Ala
        115                 120                 125

Leu Gln Lys Glu Leu Ile Arg Phe Leu Asn Ala Gly Ile Phe Gly Ser
    130                 135                 140

Gly Ala Glu Ala Gly Asn Asn Thr Leu Pro His Ser Ala Thr Arg Ala
145                 150                 155                 160

Ala Met Leu Val Arg Ile Asn Thr Leu Leu Gln Gly Tyr Ser Gly Ile
                165                 170                 175

Arg Phe Glu Ile Leu Glu Ala Ile Thr Lys Phe Leu Asn His Asn Ile
            180                 185                 190

Thr Pro Cys Leu Pro Leu Arg Gly Thr Ile Thr Ala Ser Gly Asp Leu
        195                 200                 205

Val Pro Leu Ser Tyr Ile Ala Gly Leu Leu Thr Gly Arg Pro Asn Ser
210                 215                 220

Lys Ala Val Gly Pro Thr Gly Val Thr Leu Ser Pro Glu Glu Ala Phe
225                 230                 235                 240

Lys Leu Ala Gly Val Glu Gly Gly Phe Phe Glu Leu Gln Pro Lys Glu
                245                 250                 255

Gly Leu Ala Leu Val Asn Gly Thr Ala Val Gly Ser Gly Met Ala Ser
            260                 265                 270

Met Val Leu Phe Glu Ala Asn Ile Leu Ala Val Leu Ala Glu Val Met
        275                 280                 285

Ser Ala Ile Phe Ala Glu Val Met Gln Gly Lys Pro Glu Phe Thr Asp
    290                 295                 300

His Leu Thr His Lys Leu Lys His His Pro Gly Gln Ile Glu Ala Ala
305                 310                 315                 320

Ala Ile Met Glu His Ile Leu Asp Gly Ser Ala Tyr Val Lys Ala Ala
                325                 330                 335

Gln Lys Leu His Glu Met Asp Pro Leu Gln Lys Pro Lys Gln Asp Arg
            340                 345                 350

Tyr Ala Leu Arg Thr Ser Pro Gln Trp Leu Gly Pro Gln Ile Glu Val
        355                 360                 365

Ile Arg Ser Ser Thr Lys Met Ile Glu Arg Glu Ile Asn Ser Val Asn
    370                 375                 380

Asp Asn Pro Leu Ile Asp Val Ser Arg Asn Lys Ala Ile His Gly Gly
385                 390                 395                 400

Asn Phe Gln Gly Ser Pro Ile Gly Val Ser Met Asp Asn Thr Arg Leu
                405                 410                 415

Ala Ile Ala Ala Ile Gly Lys Leu Met Phe Ala Gln Phe Ser Glu Leu
            420                 425                 430

Val Asn Asp Phe Tyr Asn Asn Gly Leu Pro Ser Asn Leu Ser Gly Gly
        435                 440                 445

Arg Asn Pro Ser Leu Asp Tyr Gly Phe Lys Gly Ala Glu Ile Ala Met
450                 455                 460

Ala Ser Tyr Cys Ser Glu Leu Gln Phe Leu Ala Asn Pro Val Thr Asn
465                 470                 475                 480

His Val Gln Ser Ala Glu Gln His Asn Gln Asp Val Asn Ser Leu Gly
                485                 490                 495
```

```
Leu Ile Ser Ser Arg Lys Thr Ser Glu Ala Val Glu Ile Leu Lys Leu
                500                 505                 510

Met Ser Thr Thr Phe Leu Val Gly Leu Cys Gln Ala Ile Asp Leu Arg
            515                 520                 525

His Leu Glu Glu Asn Leu Lys Ser Thr Val Lys Asn Thr Val Ser Gln
530                 535                 540

Val Ala Lys Arg Val Leu Thr Met Gly Val Asn Gly Glu Leu His Pro
545                 550                 555                 560

Ser Arg Phe Cys Glu Lys Asp Leu Leu Arg Val Val Asp Arg Glu Tyr
                565                 570                 575

Ile Phe Ala Tyr Ile Asp Asp Pro Cys Ser Ala Thr Tyr Pro Leu Met
            580                 585                 590

Gln Lys Leu Arg Glu Thr Leu Val Glu His Ala Leu Asn Asn Gly Asp
        595                 600                 605

Lys Glu Arg Asn Leu Ser Thr Ser Ile Phe Gln Lys Ile Ala Ala Phe
610                 615                 620

Glu Asp Glu Leu Lys Ala Leu Leu Pro Lys Glu Val Glu Thr Ala Arg
625                 630                 635                 640

Ala Ala Leu Glu Ser Gly Asn Pro Ala Ile Pro Asn Arg Ile Lys Glu
                645                 650                 655

Cys Arg Ser Tyr Pro Leu Tyr Lys Phe Val Arg Glu Glu Leu Gly Thr
            660                 665                 670

Glu Tyr Leu Thr Gly Glu Lys Val Arg Ser Pro Gly Glu Glu Phe Glu
        675                 680                 685

Lys Val Phe Thr Ala Met Ser Lys Gly Glu Ile Ile Asp Pro Leu Leu
690                 695                 700

Glu Cys Leu Glu Ser Trp Asn Gly Ala Pro Leu Pro Ile Cys
705                 710                 715

<210> SEQ ID NO 57
<211> LENGTH: 505
<212> TYPE: PRT
<213> ORGANISM: Arabidopsis thaliana

<400> SEQUENCE: 57

Met Asp Leu Leu Leu Glu Lys Ser Leu Ile Ala Val Phe Val Ala
1               5                   10                  15

Val Ile Leu Ala Thr Val Ile Ser Lys Leu Arg Gly Lys Lys Leu Lys
            20                  25                  30

Leu Pro Pro Gly Pro Ile Pro Ile Pro Ile Phe Gly Asn Trp Leu Gln
        35                  40                  45

Val Gly Asp Asp Leu Asn His Arg Asn Leu Val Asp Tyr Ala Lys Lys
    50                  55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu Leu Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Asn Arg Glu Gly Trp Glu Phe Glu Ala Ala Ser Val Val Glu Asp
145                 150                 155                 160
```

Val Lys Lys Asn Pro Asp Ser Ala Thr Lys Gly Ile Val Leu Arg Lys
            165                 170                 175

Arg Leu Gln Leu Met Met Tyr Thr Asn Met Phe Arg Ile Met Phe Asp
            180                 185                 190

Arg Arg Phe Glu Ser Glu Asp Asp Pro Leu Phe Leu Arg Leu Lys Ala
            195                 200                 205

Leu Asn Gly Glu Arg Ser Arg Leu Ala Gln Ser Phe Glu Tyr Asn Tyr
            210                 215                 220

Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
            245                 250                 255

Phe Val Asp Glu Arg Lys Gln Ile Ala Ser Ser Lys Pro Thr Gly Ser
            260                 265                 270

Glu Gly Leu Lys Cys Ala Ile Asp His Ile Leu Glu Ala Glu Gln Lys
            275                 280                 285

Gly Glu Ile Asn Glu Asp Asn Val Leu Tyr Ile Val Glu Asn Ile Asn
            290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Gly Asn Glu Leu
            325                 330                 335

Asp Thr Val Leu Gly Pro Gly Val Gln Val Thr Glu Pro Asp Leu His
            340                 345                 350

Lys Leu Pro Tyr Leu Gln Ala Val Val Lys Glu Thr Leu Arg Leu Arg
            355                 360                 365

Met Ala Ile Pro Leu Leu Val Pro His Met Asn Leu His Asp Ala Lys
            370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
            405                 410                 415

Arg Pro Glu Arg Phe Phe Glu Glu Ser His Val Glu Ala Asn Gly
            420                 425                 430

Asn Asp Phe Arg Tyr Val Pro Phe Gly Val Gly Arg Arg Ser Cys Pro
            435                 440                 445

Gly Ile Ile Leu Ala Leu Pro Ile Leu Gly Ile Thr Ile Gly Arg Met
450                 455                 460

Val Gln Asn Phe Glu Leu Leu Pro Pro Gly Gln Ser Lys Val Asp
465                 470                 475                 480

Thr Ser Glu Lys Gly Gly Gln Phe Ser Leu His Ile Leu Asn His Ser
            485                 490                 495

Ile Ile Val Met Lys Pro Arg Asn Cys
            500                 505

<210> SEQ ID NO 58
<211> LENGTH: 505
<212> TYPE: PRT
<213> ORGANISM: Populus balsamifera subsp. trichocarpa X Populus
      deltoides

<400> SEQUENCE: 58

Met Asp Leu Leu Leu Leu Glu Lys Thr Leu Leu Gly Ser Phe Val Ala
1               5                   10                  15

Ile Leu Val Ala Ile Leu Val Ser Lys Leu Arg Gly Lys Arg Phe Lys

```
                    20                  25                  30
Leu Pro Pro Gly Pro Ile Pro Val Pro Val Phe Gly Asn Trp Leu Gln
                35                  40                  45

Val Gly Asp Asp Leu Asn His Arg Asn Leu Thr Asp Leu Ala Lys Lys
        50                  55                  60

Phe Gly Asp Ile Phe Leu Leu Arg Met Gly Gln Arg Asn Leu Val Val
 65                  70                  75                  80

Val Ser Ser Pro Asp Leu Ser Lys Glu Val Leu His Thr Gln Gly Val
                85                  90                  95

Glu Phe Gly Ser Arg Thr Arg Asn Val Val Phe Asp Ile Phe Thr Gly
               100                 105                 110

Lys Gly Gln Asp Met Val Phe Thr Val Tyr Gly Glu His Trp Arg Lys
               115                 120                 125

Met Arg Arg Ile Met Thr Val Pro Phe Phe Thr Asn Lys Val Val Gln
           130                 135                 140

Gln Tyr Arg Tyr Gly Trp Glu Glu Ala Ala Gln Val Val Glu Asp
145                 150                 155                 160

Val Lys Lys Asn Pro Glu Ala Ala Thr Asn Gly Ile Val Leu Arg Arg
               165                 170                 175

Arg Leu Gln Leu Met Met Tyr Asn Asn Met Tyr Arg Ile Met Phe Asp
               180                 185                 190

Arg Arg Phe Glu Ser Glu Asp Asp Pro Leu Phe Asn Lys Leu Lys Ala
           195                 200                 205

Leu Asn Gly Glu Arg Ser Arg Leu Ala Gln Ser Phe Asp Tyr Asn Tyr
           210                 215                 220

Gly Asp Phe Ile Pro Ile Leu Arg Pro Phe Leu Arg Gly Tyr Leu Lys
225                 230                 235                 240

Ile Cys Gln Glu Val Lys Glu Arg Arg Leu Gln Leu Phe Lys Asp Tyr
                   245                 250                 255

Phe Val Asp Glu Arg Lys Lys Leu Ala Ser Thr Lys Asn Met Ser Asn
               260                 265                 270

Glu Gly Leu Lys Cys Ala Ile Asp His Ile Leu Asp Ala Gln Lys Lys
           275                 280                 285

Gly Glu Ile Asn Glu Asp Asn Val Leu Tyr Ile Val Glu Asn Ile Asn
       290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Lys Lys Leu Arg His Glu Leu
               325                 330                 335

Asp Thr Leu Leu Gly Pro Gly His Gln Ile Thr Glu Pro Asp Thr Tyr
           340                 345                 350

Lys Leu Pro Tyr Leu Asn Ala Val Ile Lys Glu Thr Leu Arg Leu Arg
           355                 360                 365

Met Ala Ile Pro Leu Leu Val Pro His Met Asn Leu His Asp Ala Lys
           370                 375                 380

Leu Gly Gly Phe Asp Ile Pro Ala Glu Ser Lys Ile Leu Val Asn Ala
385                 390                 395                 400

Trp Trp Leu Ala Asn Asn Pro Ala His Trp Lys Asn Pro Glu Glu Phe
               405                 410                 415

Arg Pro Glu Arg Phe Leu Glu Glu Ala Lys Val Glu Ala Asn Gly
           420                 425                 430

Asn Asp Phe Arg Tyr Leu Pro Phe Gly Val Gly Arg Arg Ser Cys Pro
               435                 440                 445
```

```
Gly Ile Ile Leu Ala Leu Pro Ile Leu Gly Ile Thr Leu Gly Arg Leu
        450                 455                 460

Val Gln Asn Phe Glu Leu Leu Pro Pro Gly Gln Ser Lys Ile Asp
465                 470                 475                 480

Thr Ala Glu Lys Gly Gly Gln Phe Ser Leu His Ile Leu Lys His Ser
                485                 490                 495

Thr Ile Val Ala Lys Pro Arg Ser Phe
            500                 505

<210> SEQ ID NO 59
<211> LENGTH: 1124
<212> TYPE: DNA
<213> ORGANISM: Coffea canephora

<400> SEQUENCE: 59
gtgatattgt gcgttttgcc tttgttccac atatattcac tgaattctgt gttgctttgt      60
gggctaagag ttggtgcggc aattttgatc atgcaaaagt ttgagattaa tgcactaatg     120
gagcttgtgc aaaaatataa ggtgacaatt gctccatttg tgccaccaat tgttttggaa     180
attgccaaaa gtcctgtggt ggataagtat gatctttcat ccataagaat ggtgatgtcc     240
ggcgcggcac ccatggggaa ggagctcgag acaccgttc gagctaagct cccaaaggca     300
gtgctcggac agggatacgg catgacggag caggacctc tgctgtcgat gtgcttagcg     360
tttgcaaagg agccatttga tgtcaaatca ggtgcttgcg ggacagttgt gaggaatgct     420
gaaatgaaaa ttgtagatcc cgaaactaat ctctctctac cccgcaatca agctggagaa     480
atttgcatca gaggcgacca gatcatgaaa ggctaccta atgatccgga ggcaactgag     540
aatacaatcg acaaagaagg atggttcac acaggagaca tagggtacat tgatgatgat     600
gatgaaattt tcatagtgga ccgattgaag gaattaatca agtataaagg gtttcaagtg     660
gcacctgcag agctggaagc catgctcctt tctcaccctg gtattctga tgcagctgtt     720 gtctccatga aagatgaggc agctggagaa gttcctgttg cttttgtggt gagagcaagt     780
ggttccaaaa tttccgagga tgagatcaaa caatttatct caaaccaggt gattttttat     840
aagcgaatcc atcgggtgtt tttcatggat aaaattccta agctccatc tggcaaaata     900 ttgagaaagg acctaagagc taagcttgca gctgaagttg cttgcaatta gagtactgta     960
ttatatacat aacagtctct acaacaacgc tgttaatttg tatgcgtttt gggagaaaag    1020
gagagaaagt agtgtatgtt tcttctgatc tggtgtcaga tctcctctca tcctcaactc    1080
aagttgatcc tgtttctctt tttctcaaaa aaaaaaaaa aaaa                      1124

<210> SEQ ID NO 60
<211> LENGTH: 335
<212> TYPE: DNA
<213> ORGANISM: Coffea canephora

<400> SEQUENCE: 60
tgttgagaag gtgatggact tgctaagga aaataatgtc aaagtcatgt gcactgatgc      60
ccctccggag ggttgtttgc attttttcgga gctgtcgtcg gctgacgaaa agtcattcc    120 agcggtgaaa atcaatccaa acgatgccgt tgcactgcct tattcatcag gcaccactgg    180
tctaccgaaa ggggtcatgc tgacgcacaa agggttggtc acaagtgttg ctcagcaggt    240
tgatggagaa atcccaatc tttatttca caaggaagat gtgatattgt gcgttttgcc    300
tttgttccac atatattcac tgaattctgt gttgc                               335

<210> SEQ ID NO 61
```

```
<211> LENGTH: 1569
<212> TYPE: DNA
<213> ORGANISM: Coffea canephora

<400> SEQUENCE: 61
ccatcttcac gcttcgtcat caaccgccca caccccctccg gcgaagctac ttgtggtagg      60
taaaagccaa cgtggaaaag tctcatctac gtaggtcaac agatcatcat gtccaccacc     120
accaaacctt aatcctttag gtggtcccat ttccccctggc cccaccccct cgggccaggg     180
aacggacggc ttagattggt agttcccaac acaatttctt tcttttttttg aatggaaaat     240 aattttgaca tatggaatat gtattttaat gttgtacatc aagggacatt attgatgtgt     300
acagatttac ataaacatta ctcgaatatt atatccttgt tttaattcgt aaaaaaaaaa     360
aaaaaatcgt ccgagacatt ctgcaatgtg atatatcata cgtgtaaaat caagagtgtg     420
acaaaaaaaa aaaggtata agatatcaca aatgtttggt ataatcctca cgtcttcttc     480
ttcaatatat tcattcaatt ataatttatt cgggtttgac aagggaaatt agctagctct     540
caattcccac ctaccacaag tccacaagcc aaagcccccc aaatcaatca tgaacatcaa     600
acatcttttc tcggttttac ccctgaacaa ccccatata cccgatcatc ctccatttca     660
ccaaccaaac cccctccat ctacctacaa caacaacagg agccccgcat attaatattg     720
ccccatctgc agtatggact cccaggagag cagaataatt acatcgcgcc tccttttgac     780
tggttccatt tcttgagtct cttaatttct tccctagctc gtagtaaccc ttcaacaagc     840
cctttgtcaa tggctgtcaa acaaagcaa gaagaaatca tattccgatc aaggctccct     900
gatatttaca tcccaaaaca tctgcccctg cacacttact gtttcgaaga ccttcctaag     960
ttcagatcac aggcttgttt gataaatggc gccaccgatg aaatttacac tttcgaacaa    1020
gttgagctca cagccagaag agttgcatcc gggcttaaca aagttggtgt acagcaagga    1080
gatacgatca tgatcctgct gccaaactcg ccggaattcg tgttcgcctt cctcgatgca    1140
tctttccggg gagccatatc cacgatggcc aatccatatt tcacctctgc cgaagtcata    1200
aagcaagcca aggcatccaa cgcaaagctc atcatcacgc aaggctgtta cgtcgaaaag    1260
gtcagggact atgcatgtga aatgggggtg aaaggcgtgt gcatcgactc tgcgccggaa    1320
ggttgtttac acttctcgga gctaaccgag gccgatgaaa gggaaatgcc ggacgtcgag    1380
atcagccctg atgatgtggt ggcgctgccg tactcctccg ggaccactgg actgcctaag    1440
ggggtgatgt tgacccacaa gggacttgtc actagcgtgg cacaacaggt tgacggagag    1500
aacccaaatt tctatataca caatcaagtg atgatgtgcg ttttgccatg tgcgttttgc    1560
ctctgttcc                                                            1569

<210> SEQ ID NO 62
<211> LENGTH: 1102
<212> TYPE: DNA
<213> ORGANISM: Coffea canephora

<400> SEQUENCE: 62
atcacaaatg tttggtataa tcctcacgtc ttcttcttca atacattcat tcaattataa      60
tttattcggg tttgacgagg gaaaatagct agctctcaat tcccacctac cacacacgtc     120
cacaaaccaa atcaatcatg aacatcaaac atcttttctc ggttttaccc ctgaacaacc     180
cccatatacc cgatcatcct ccatttcacc aaccaaaccc cctccatcta cctacaacaa     240
caacaggagc cccgcatatt aatattgccc catctgcagt atggactccc aggagagcag     300
aataattaca tcgcgcctcc ttttgactgg ttccatttct tgagtctctt aatttcttcc     360
```

-continued

```
ctagctcgta gtaacccttc aacaagccct tgtcaatgg ctgtcaaaac aaagcaagaa      420
gaaatcatat tccgatcaag gctccctgat atttacatcc caaaacatct gcccctgcac      480
acttactgtt tcgaagacct tcctaagttc agatcacagg cttgttcgat aaatggcgcc      540
accgatgaaa tttacacttt cgaacaagtt gagctcacag ccagaagagt tgcatccggg      600
cttaacaaag ttggtataca gcaaggagat acgatcatga tcctgctgcc aaactcgccg      660
gaattcgtgt tcgtcttcct cggtgcatct ttccggggag ccatatccac gatggccaat      720
ccatatttca cctctgccga agtcataaag caagccaagg catccaacgc aaagctcatc      780
atcacgcaag gctgttacgt cgaaaaggtc agggactatg catgtgaaaa tggggtggaa      840
gtcgtgtgca tcgactctgc accggaaggt tgtttacact tctcggagct aaccgaggcc      900
gatgaaaggg aaatgccgga cgtcgagatc agccctgaag atgtggtggc gctgccgtac      960
tcctccggga ctactggact gcctaagggg gtgatgttga cccacaaggg acttgtcact     1020
agcgtggcac aacaggttga cggagagaac ccaaatttct atatacacaa tcaaatgatg     1080
atgtgcgttt tgcctctgtt cc                                              1102
```

<210> SEQ ID NO 63
<211> LENGTH: 561
<212> TYPE: PRT
<213> ORGANISM: Arabidopsis thaliana

<400> SEQUENCE: 63

| Met | Ala | Pro | Gln | Glu | Gln | Ala | Val | Ser | Gln | Val | Met | Glu | Lys | Gln | Ser |
|---|---|---|---|---|---|---|---|---|---|---|---|---|---|---|---|
| 1 | | | | 5 | | | | | 10 | | | | | 15 | |

| Asn | Asn | Asn | Asn | Ser | Asp | Val | Ile | Phe | Arg | Ser | Lys | Leu | Pro | Asp | Ile |
|---|---|---|---|---|---|---|---|---|---|---|---|---|---|---|---|
| | | | 20 | | | | | 25 | | | | | 30 | | |

| Tyr | Ile | Pro | Asn | His | Leu | Ser | Leu | His | Asp | Tyr | Ile | Phe | Gln | Asn | Ile |
| | | | 35 | | | | | 40 | | | | | 45 | | |

| Ser | Glu | Phe | Ala | Thr | Lys | Pro | Cys | Leu | Ile | Asn | Gly | Pro | Thr | Gly | His |
| | 50 | | | | | 55 | | | | | 60 | | | | |

| Val | Tyr | Thr | Tyr | Ser | Asp | Val | His | Val | Ile | Ser | Arg | Gln | Ile | Ala | Ala |
| 65 | | | | | 70 | | | | | 75 | | | | | 80 |

| Asn | Phe | His | Lys | Leu | Gly | Val | Asn | Gln | Asn | Asp | Val | Val | Met | Leu | Leu |
| | | | | 85 | | | | | 90 | | | | | 95 | |

| Leu | Pro | Asn | Cys | Pro | Glu | Phe | Val | Leu | Ser | Phe | Leu | Ala | Ala | Ser | Phe |
| | | | 100 | | | | | 105 | | | | | 110 | | |

| Arg | Gly | Ala | Thr | Ala | Thr | Ala | Ala | Asn | Pro | Phe | Phe | Thr | Pro | Ala | Glu |
| | | 115 | | | | | 120 | | | | | 125 | | | |

| Ile | Ala | Lys | Gln | Ala | Lys | Ala | Ser | Asn | Thr | Lys | Leu | Ile | Ile | Thr | Glu |
| 130 | | | | | 135 | | | | | 140 | | | | | |

| Ala | Arg | Tyr | Val | Asp | Lys | Ile | Lys | Pro | Leu | Gln | Asn | Asp | Asp | Gly | Val |
| 145 | | | | | 150 | | | | | 155 | | | | | 160 |

| Val | Ile | Val | Cys | Ile | Asp | Asp | Asn | Glu | Ser | Val | Pro | Ile | Pro | Glu | Gly |
| | | | | 165 | | | | | 170 | | | | | 175 | |

| Cys | Leu | Arg | Phe | Thr | Glu | Leu | Thr | Gln | Ser | Thr | Thr | Glu | Ala | Ser | Glu |
| | | | 180 | | | | | 185 | | | | | 190 | | |

| Val | Ile | Asp | Ser | Val | Glu | Ile | Ser | Pro | Asp | Asp | Val | Ala | Leu | Pro |
| | | 195 | | | | | 200 | | | | | 205 | | | |

| Tyr | Ser | Ser | Gly | Thr | Thr | Gly | Leu | Pro | Lys | Gly | Val | Met | Leu | Thr | His |
| 210 | | | | | 215 | | | | | 220 | | | | | |

| Lys | Gly | Leu | Val | Thr | Ser | Val | Ala | Gln | Gln | Val | Asp | Gly | Glu | Asn | Pro |
| 225 | | | | | 230 | | | | | 235 | | | | | 240 |

| Asn | Leu | Tyr | Phe | His | Ser | Asp | Asp | Val | Ile | Leu | Cys | Val | Leu | Pro | Met |

-continued

```
                245                 250                 255
Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
    290                 295                 300

Ile Val Leu Ala Ile Ala Lys Ser Ser Glu Thr Glu Lys Tyr Asp Leu
305                 310                 315                 320

Ser Ser Ile Arg Val Val Lys Ser Gly Ala Ala Pro Leu Gly Lys Glu
                325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly
        355                 360                 365

Phe Ala Lys Glu Pro Phe Pro Val Lys Ser Gly Ala Cys Gly Thr Val
    370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
                405                 410                 415

Met Lys Gly Tyr Leu Asn Asn Pro Ala Ala Thr Ala Glu Thr Ile Asp
            420                 425                 430

Lys Asp Gly Trp Leu His Thr Gly Asp Ile Gly Leu Ile Asp Asp Asp
        435                 440                 445

Asp Glu Leu Phe Ile Val Asp Arg Leu Lys Glu Leu Ile Lys Tyr Lys
    450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
                485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
        515                 520                 525

Lys Arg Ile Asn Lys Val Phe Phe Thr Glu Ser Ile Pro Lys Ala Pro
    530                 535                 540

Ser Gly Lys Ile Leu Arg Lys Asp Leu Arg Ala Lys Leu Ala Asn Gly
545                 550                 555                 560

Leu
```

<210> SEQ ID NO 64
<211> LENGTH: 556
<212> TYPE: PRT
<213> ORGANISM: Arabidopsis thaliana

<400> SEQUENCE: 64

```
Met Thr Thr Gln Asp Val Ile Val Asn Asp Gln Asn Asp Gln Lys Gln
1               5                   10                  15

Cys Ser Asn Asp Val Ile Phe Arg Ser Arg Leu Pro Asp Ile Tyr Ile
            20                  25                  30

Pro Asn His Leu Pro Leu His Asp Tyr Ile Phe Glu Asn Ile Ser Glu
        35                  40                  45

Phe Ala Ala Lys Pro Cys Leu Ile Asn Gly Pro Thr Gly Glu Val Tyr
    50                  55                  60
```

Thr Tyr Ala Asp Val His Val Thr Ser Arg Lys Leu Ala Ala Gly Leu
65                  70                  75                  80

His Asn Leu Gly Val Lys Gln His Asp Val Val Met Ile Leu Leu Pro
                85                  90                  95

Asn Ser Pro Glu Val Val Leu Thr Phe Leu Ala Ala Ser Phe Ile Gly
            100                 105                 110

Ala Ile Thr Thr Ser Ala Asn Pro Phe Phe Thr Pro Ala Glu Ile Ser
        115                 120                 125

Lys Gln Ala Lys Ala Ser Ala Ala Lys Leu Ile Val Thr Gln Ser Arg
    130                 135                 140

Tyr Val Asp Lys Ile Lys Asn Leu Gln Asn Asp Gly Val Leu Ile Val
145                 150                 155                 160

Thr Thr Asp Ser Asp Ala Ile Pro Glu Asn Cys Leu Arg Phe Ser Glu
                165                 170                 175

Leu Thr Gln Ser Glu Glu Pro Arg Val Asp Ser Ile Pro Glu Lys Ile
            180                 185                 190

Ser Pro Glu Asp Val Val Ala Leu Pro Phe Ser Ser Gly Thr Thr Gly
        195                 200                 205

Leu Pro Lys Gly Val Met Leu Thr His Lys Gly Leu Val Thr Ser Val
    210                 215                 220

Ala Gln Gln Val Asp Gly Glu Asn Pro Asn Leu Tyr Phe Asn Arg Asp
225                 230                 235                 240

Asp Val Ile Leu Cys Val Leu Pro Met Phe His Ile Tyr Ala Leu Asn
                245                 250                 255

Ser Ile Met Leu Cys Ser Leu Arg Val Gly Ala Thr Ile Leu Ile Met
            260                 265                 270

Pro Lys Phe Glu Ile Thr Leu Leu Leu Glu Gln Ile Gln Arg Cys Lys
        275                 280                 285

Val Thr Val Ala Met Val Val Pro Pro Ile Val Leu Ala Ile Ala Lys
    290                 295                 300

Ser Pro Glu Thr Glu Lys Tyr Asp Leu Ser Ser Val Arg Met Val Lys
305                 310                 315                 320

Ser Gly Ala Ala Pro Leu Gly Lys Glu Leu Glu Asp Ala Ile Ser Ala
                325                 330                 335

Lys Phe Pro Asn Ala Lys Leu Gly Gln Gly Tyr Gly Met Thr Glu Ala
            340                 345                 350

Gly Pro Val Leu Ala Met Ser Leu Gly Phe Ala Lys Glu Pro Phe Pro
        355                 360                 365

Val Lys Ser Gly Ala Cys Gly Thr Val Val Arg Asn Ala Glu Met Lys
    370                 375                 380

Ile Leu Asp Pro Asp Thr Gly Asp Ser Leu Pro Arg Asn Lys Pro Gly
385                 390                 395                 400

Glu Ile Cys Ile Arg Gly Asn Gln Ile Met Lys Gly Tyr Leu Asn Asp
                405                 410                 415

Pro Leu Ala Thr Ala Ser Thr Ile Asp Lys Asp Gly Trp Leu His Thr
            420                 425                 430

Gly Asp Val Gly Phe Ile Asp Asp Asp Glu Leu Phe Ile Val Asp
        435                 440                 445

Arg Leu Lys Glu Leu Ile Lys Tyr Lys Gly Phe Gln Val Ala Pro Ala
    450                 455                 460

Glu Leu Glu Ser Leu Leu Ile Gly His Pro Glu Ile Asn Asp Val Ala
465                 470                 475                 480

Val Val Ala Met Lys Glu Glu Asp Ala Gly Glu Val Pro Val Ala Phe

-continued

```
                485                 490                 495
Val Val Arg Ser Lys Asp Ser Asn Ile Ser Glu Asp Glu Ile Lys Gln
            500                 505                 510

Phe Val Ser Lys Gln Val Val Phe Tyr Lys Arg Ile Asn Lys Val Phe
            515                 520                 525

Phe Thr Asp Ser Ile Pro Lys Ala Pro Ser Gly Lys Ile Leu Arg Lys
            530                 535                 540

Asp Leu Arg Ala Arg Leu Ala Asn Gly Leu Met Asn
545                 550                 555

<210> SEQ ID NO 65
<211> LENGTH: 561
<212> TYPE: PRT
<213> ORGANISM: Arabidopsis thaliana

<400> SEQUENCE: 65

Met Ile Thr Ala Ala Leu His Glu Pro Gln Ile His Lys Pro Thr Asp
1               5                   10                  15

Thr Ser Val Val Ser Asp Asp Val Leu Pro His Ser Pro Pro Thr Pro
            20                  25                  30

Arg Ile Phe Arg Ser Lys Leu Pro Asp Ile Asp Ile Pro Asn His Leu
        35                  40                  45

Pro Leu His Thr Tyr Cys Phe Glu Lys Leu Ser Ser Val Ser Asp Lys
    50                  55                  60

Pro Cys Leu Ile Val Gly Ser Thr Gly Lys Ser Tyr Thr Tyr Gly Glu
65                  70                  75                  80

Thr His Leu Ile Cys Arg Arg Val Ala Ser Gly Leu Tyr Lys Leu Gly
                85                  90                  95

Ile Arg Lys Gly Asp Val Ile Met Ile Leu Leu Gln Asn Ser Ala Glu
            100                 105                 110

Phe Val Phe Ser Phe Met Gly Ala Ser Met Ile Gly Ala Val Ser Thr
        115                 120                 125

Thr Ala Asn Pro Phe Tyr Thr Ser Gln Glu Leu Tyr Lys Gln Leu Lys
    130                 135                 140

Ser Ser Gly Ala Lys Leu Ile Ile Thr His Ser Gln Tyr Val Asp Lys
145                 150                 155                 160

Leu Lys Asn Leu Gly Glu Asn Leu Thr Leu Ile Thr Thr Asp Glu Pro
                165                 170                 175

Thr Pro Glu Asn Cys Leu Pro Phe Ser Thr Leu Ile Thr Asp Asp Glu
            180                 185                 190

Thr Asn Pro Phe Gln Glu Thr Val Asp Ile Gly Gly Asp Asp Ala Ala
        195                 200                 205

Ala Leu Pro Phe Ser Ser Gly Thr Thr Gly Leu Pro Lys Gly Val Val
    210                 215                 220

Leu Thr His Lys Ser Leu Ile Thr Ser Val Ala Gln Gln Val Asp Gly
225                 230                 235                 240

Asp Asn Pro Asn Leu Tyr Leu Lys Ser Asn Asp Val Ile Leu Cys Val
                245                 250                 255

Leu Pro Leu Phe His Ile Tyr Ser Leu Asn Ser Val Leu Leu Asn Ser
            260                 265                 270

Leu Arg Ser Gly Ala Thr Val Leu Leu Met His Lys Phe Glu Ile Gly
        275                 280                 285

Ala Leu Leu Asp Leu Ile Gln Arg His Arg Val Thr Ile Ala Ala Leu
    290                 295                 300

Val Pro Pro Leu Val Ile Ala Leu Ala Lys Asn Pro Thr Val Asn Ser
```

```
                        305                 310                 315                 320
Tyr Asp Leu Ser Ser Val Arg Phe Val Leu Ser Gly Ala Ala Pro Leu
                    325                 330                 335

Gly Lys Glu Leu Gln Asp Ser Leu Arg Arg Leu Pro Gln Ala Ile
                340                 345                 350

Leu Gly Gln Gly Tyr Gly Met Thr Glu Ala Gly Pro Val Leu Ser Met
                355                 360                 365

Ser Leu Gly Phe Ala Lys Glu Pro Ile Pro Thr Lys Ser Gly Ser Cys
            370                 375                 380

Gly Thr Val Val Arg Asn Ala Glu Leu Lys Val Val His Leu Glu Thr
385                 390                 395                 400

Arg Leu Ser Leu Gly Tyr Asn Gln Pro Gly Glu Ile Cys Ile Arg Gly
                405                 410                 415

Gln Gln Ile Met Lys Glu Tyr Leu Asn Asp Pro Glu Ala Thr Ser Ala
                420                 425                 430

Thr Ile Asp Glu Glu Gly Trp Leu His Thr Gly Asp Ile Gly Tyr Val
                435                 440                 445

Asp Glu Asp Asp Glu Ile Phe Ile Val Asp Arg Leu Lys Glu Val Ile
            450                 455                 460

Lys Phe Lys Gly Phe Gln Val Pro Pro Ala Glu Leu Glu Ser Leu Leu
465                 470                 475                 480

Ile Asn His His Ser Ile Ala Asp Ala Ala Val Val Pro Gln Asn Asp
                485                 490                 495

Glu Val Ala Gly Glu Val Pro Val Ala Phe Val Arg Ser Asn Gly
                500                 505                 510

Asn Asp Ile Thr Glu Glu Asp Val Lys Glu Tyr Val Ala Lys Gln Val
                515                 520                 525

Val Phe Tyr Lys Arg Leu His Lys Val Phe Phe Val Ala Ser Ile Pro
            530                 535                 540

Lys Ser Pro Ser Gly Lys Ile Leu Arg Lys Asp Leu Lys Ala Lys Leu
545                 550                 555                 560

Cys

<210> SEQ ID NO 66
<211> LENGTH: 488
<212> TYPE: PRT
<213> ORGANISM: Arabidopsis thaliana

<400> SEQUENCE: 66

Met Arg Arg Ile Ala Ala Gly Ile His Arg Leu Gly Ile Arg His Gly
1               5                   10                  15

Asp Val Val Met Leu Leu Leu Pro Asn Ser Pro Glu Phe Ala Leu Ser
                20                  25                  30

Phe Leu Ala Val Ala Tyr Leu Gly Ala Val Ser Thr Thr Ala Asn Pro
            35                  40                  45

Phe Tyr Thr Gln Pro Glu Ile Ala Lys Gln Lys Ala Ser Ala Ala
        50                  55                  60

Lys Met Ile Ile Thr Lys Lys Cys Leu Val Asp Lys Leu Thr Asn Leu
65                  70                  75                  80

Lys Asn Asp Gly Val Leu Ile Val Cys Leu Asp Asp Gly Asp Asn
                85                  90                  95

Gly Val Val Ser Ser Ser Asp Asp Gly Cys Val Ser Phe Thr Glu Leu
                100                 105                 110

Thr Gln Ala Asp Glu Thr Glu Leu Leu Lys Pro Lys Ile Ser Pro Glu
            115                 120                 125
```

Asp Thr Val Ala Met Pro Tyr Ser Ser Gly Thr Thr Gly Leu Pro Lys
    130                 135                 140

Gly Val Met Ile Thr His Lys Gly Leu Val Thr Ser Ile Ala Gln Lys
145                 150                 155                 160

Val Asp Gly Glu Asn Pro Asn Leu Asn Phe Thr Ala Asn Asp Val Ile
                165                 170                 175

Leu Cys Phe Leu Pro Met Phe His Ile Tyr Ala Leu Asp Ala Leu Met
            180                 185                 190

Leu Ser Ala Met Arg Thr Gly Ala Ala Leu Leu Ile Val Pro Arg Phe
        195                 200                 205

Glu Leu Asn Leu Val Met Glu Leu Ile Gln Arg Tyr Lys Val Thr Val
    210                 215                 220

Val Pro Val Ala Pro Pro Val Val Leu Ala Phe Ile Lys Ser Pro Glu
225                 230                 235                 240

Thr Glu Arg Tyr Asp Leu Ser Ser Val Arg Ile Met Leu Ser Gly Ala
                245                 250                 255

Ala Thr Leu Lys Lys Glu Leu Glu Asp Ala Val Arg Leu Lys Phe Pro
            260                 265                 270

Asn Ala Ile Phe Gly Gln Gly Tyr Gly Met Thr Glu Ser Gly Thr Val
        275                 280                 285

Ala Lys Ser Leu Ala Phe Ala Lys Asn Pro Phe Lys Thr Lys Ser Gly
    290                 295                 300

Ala Cys Gly Thr Val Ile Arg Asn Ala Glu Met Lys Val Val Asp Thr
305                 310                 315                 320

Glu Thr Gly Ile Ser Leu Pro Arg Asn Lys Ser Gly Glu Ile Cys Val
                325                 330                 335

Arg Gly His Gln Leu Met Lys Gly Tyr Leu Asn Asp Pro Glu Ala Thr
            340                 345                 350

Ala Arg Thr Ile Asp Lys Asp Gly Trp Leu His Thr Gly Asp Ile Gly
        355                 360                 365

Phe Val Asp Asp Asp Glu Ile Phe Ile Val Asp Arg Leu Lys Glu
    370                 375                 380

Leu Ile Lys Phe Lys Gly Tyr Gln Val Ala Pro Ala Glu Leu Glu Ala
385                 390                 395                 400

Leu Leu Ile Ser His Pro Ser Ile Asp Asp Ala Ala Val Val Ala Met
                405                 410                 415

Lys Asp Glu Val Ala Asp Glu Val Pro Val Ala Phe Val Ala Arg Ser
            420                 425                 430

Gln Gly Ser Gln Leu Thr Glu Asp Asp Val Lys Ser Tyr Val Asn Lys
        435                 440                 445

Gln Val Val His Tyr Lys Arg Ile Lys Met Val Phe Phe Ile Glu Val
    450                 455                 460

Ile Pro Lys Ala Val Ser Gly Lys Ile Leu Arg Lys Asp Leu Arg Ala
465                 470                 475                 480

Lys Leu Glu Thr Met Cys Ser Lys
                485

<210> SEQ ID NO 67
<211> LENGTH: 547
<212> TYPE: PRT
<213> ORGANISM: Nicotiana tabacum

<400> SEQUENCE: 67

Met Pro Met Glu Thr Thr Thr Glu Thr Lys Gln Ser Gly Asp Leu Ile
1               5                   10                  15

Phe Arg Ser Lys Leu Pro Asp Ile Tyr Ile Pro Lys His Leu Pro Leu
            20                  25                  30

His Ser Tyr Cys Phe Glu Asn Ile Ser Glu Phe Ser Ser Arg Pro Cys
            35                  40                  45

Leu Ile Asn Gly Ala Asn Asp Gln Ile Tyr Thr Tyr Ala Glu Val Glu
            50                  55                  60

Leu Thr Cys Arg Lys Val Ala Val Gly Leu Asn Lys Leu Gly Ile Gln
65                  70                  75                  80

Gln Lys Asp Thr Ile Met Ile Leu Leu Pro Asn Ser Pro Glu Phe Val
                85                  90                  95

Phe Ala Phe Met Gly Ala Ser Tyr Leu Gly Ala Ile Ser Thr Met Ala
                100                 105                 110

Asn Pro Leu Phe Thr Pro Ala Glu Val Val Lys Gln Ala Lys Ala Ser
            115                 120                 125

Ser Ala Lys Ile Ile Ile Thr Gln Ser Cys Phe Val Gly Lys Val Lys
    130                 135                 140

Asp Tyr Ala Ser Glu Asn Asp Val Lys Val Ile Cys Ile Asp Ser Ala
145                 150                 155                 160

Pro Glu Gly Cys Leu His Phe Ser Glu Leu Thr Gln Ser Asp Glu His
                165                 170                 175

Glu Ile Pro Glu Val Lys Ile Gln Pro Asp Asp Val Val Ala Leu Pro
            180                 185                 190

Tyr Ser Ser Gly Thr Thr Gly Leu Pro Lys Gly Val Met Leu Thr His
            195                 200                 205

Lys Gly Leu Val Thr Ser Val Ala Gln Gln Val Asp Gly Glu Asn Ala
    210                 215                 220

Asn Leu Tyr Met His Ser Glu Asp Val Leu Met Cys Val Leu Pro Leu
225                 230                 235                 240

Phe His Ile Tyr Ser Leu Asn Ser Ile Leu Leu Cys Gly Leu Arg Val
                245                 250                 255

Gly Ala Ala Ile Leu Ile Met Gln Lys Phe Asp Ile Ala Pro Phe Leu
            260                 265                 270

Glu Leu Ile Gln Lys Tyr Lys Val Ser Ile Gly Pro Phe Val Pro Pro
            275                 280                 285

Ile Val Leu Ala Ile Ala Lys Ser Pro Ile Val Asp Ser Tyr Asp Leu
            290                 295                 300

Ser Ser Val Arg Thr Val Met Ser Gly Ala Ala Pro Leu Gly Lys Glu
305                 310                 315                 320

Leu Glu Asp Ala Val Arg Thr Lys Phe Pro Asn Ala Lys Leu Gly Gln
                325                 330                 335

Gly Tyr Gly Met Thr Glu Ala Gly Pro Val Leu Ala Met Cys Leu Ala
            340                 345                 350

Phe Ala Lys Glu Pro Phe Asp Ile Lys Ser Gly Ala Cys Gly Thr Val
            355                 360                 365

Val Arg Asn Ala Glu Met Lys Ile Val Asp Pro Asp Thr Gly Cys Ser
    370                 375                 380

Leu Pro Arg Asn Gln Pro Gly Glu Ile Cys Ile Arg Gly Asp Gln Ile
385                 390                 395                 400

Met Lys Gly Tyr Leu Asn Asp Pro Glu Ala Thr Thr Arg Thr Ile Asp
                405                 410                 415

Lys Glu Gly Trp Leu His Thr Gly Asp Ile Gly Phe Ile Asp Glu Asp
            420                 425                 430

Asp Glu Leu Phe Ile Val Asp Arg Leu Lys Glu Leu Ile Lys Tyr Lys

```
                    435                 440                 445
Gly Phe Gln Val Ala Pro Ala Glu Ile Glu Ala Leu Leu Leu Asn His
    450                 455                 460

Pro Asn Ile Ser Asp Ala Ala Val Val Pro Met Lys Asp Glu Gln Ala
465                 470                 475                 480

Gly Glu Val Pro Val Ala Phe Val Val Arg Ser Asn Gly Ser Ala Ile
                485                 490                 495

Thr Glu Asp Glu Val Lys Asp Phe Ile Ser Lys Gln Val Ile Phe Tyr
            500                 505                 510

Lys Arg Val Lys Arg Val Phe Phe Val Glu Thr Val Pro Lys Ser Pro
        515                 520                 525

Ser Gly Lys Ile Leu Arg Lys Asp Leu Arg Ala Arg Leu Ala Ala Gly
    530                 535                 540

Val Pro Asn
545

<210> SEQ ID NO 68
<211> LENGTH: 542
<212> TYPE: PRT
<213> ORGANISM: Nicotiana tabacum

<400> SEQUENCE: 68

Met Glu Lys Asp Thr Lys Gln Val Asp Ile Ile Phe Arg Ser Lys Leu
1               5                   10                  15

Pro Asp Ile Tyr Ile Pro Asn His Leu Pro Leu His Ser Tyr Cys Phe
            20                  25                  30

Glu Asn Ile Ser Glu Phe Ser Ser Arg Pro Cys Leu Ile Asn Gly Ala
        35                  40                  45

Asn Lys Gln Ile Tyr Thr Tyr Ala Asp Val Glu Leu Asn Ser Arg Lys
    50                  55                  60

Val Ala Ala Gly Leu His Lys Gln Gly Ile Gln Pro Lys Asp Thr Ile
65                  70                  75                  80

Met Ile Leu Leu Pro Asn Ser Pro Glu Phe Val Phe Ala Phe Ile Gly
                85                  90                  95

Ala Ser Tyr Leu Gly Ala Ile Ser Thr Met Ala Asn Pro Leu Phe Thr
            100                 105                 110

Pro Ala Glu Val Val Lys Gln Ala Lys Ala Ser Ser Ala Lys Ile Ile
        115                 120                 125

Val Thr Gln Ala Cys His Val Asn Lys Val Lys Asp Tyr Ala Phe Glu
    130                 135                 140

Asn Asp Val Lys Ile Ile Cys Ile Asp Ser Ala Pro Glu Gly Cys Leu
145                 150                 155                 160

His Phe Ser Val Leu Thr Gln Ala Asn Glu His Asp Ile Pro Glu Val
                165                 170                 175

Glu Ile Gln Pro Asp Asp Val Val Ala Leu Pro Tyr Ser Ser Gly Thr
            180                 185                 190

Thr Gly Leu Pro Lys Gly Val Met Leu Thr His Lys Gly Leu Val Thr
        195                 200                 205

Ser Val Ala Gln Gln Val Asp Gly Glu Asn Pro Asn Leu Tyr Ile His
    210                 215                 220

Ser Glu Asp Val Met Leu Cys Val Leu Pro Leu Phe His Ile Tyr Ser
225                 230                 235                 240

Leu Asn Ser Val Leu Leu Cys Gly Leu Arg Val Gly Ala Ala Ile Leu
                245                 250                 255

Ile Met Gln Lys Phe Asp Ile Val Ser Phe Leu Glu Leu Ile Gln Arg
```

```
                260                 265                 270
Tyr Lys Val Thr Ile Gly Pro Phe Val Pro Ile Val Leu Ala Ile
            275                 280                 285
Ala Lys Ser Pro Met Val Asp Asp Tyr Asp Leu Ser Ser Val Arg Thr
            290                 295                 300
Val Met Ser Gly Ala Ala Pro Leu Gly Lys Glu Leu Glu Asp Thr Val
305                 310                 315                 320
Arg Ala Lys Phe Pro Asn Ala Lys Leu Gly Gln Gly Tyr Gly Met Thr
            325                 330                 335
Glu Ala Gly Pro Val Leu Ala Met Cys Leu Ala Phe Ala Lys Glu Pro
            340                 345                 350
Phe Glu Ile Lys Ser Gly Ala Cys Gly Thr Val Val Arg Asn Ala Glu
            355                 360                 365
Met Lys Ile Val Asp Pro Lys Thr Gly Asn Ser Leu Pro Arg Asn Gln
            370                 375                 380
Ser Gly Glu Ile Cys Ile Arg Gly Asp Gln Ile Met Lys Gly Tyr Leu
385                 390                 395                 400
Asn Asp Pro Glu Ala Thr Ala Arg Thr Ile Asp Lys Glu Gly Trp Leu
                405                 410                 415
Tyr Thr Gly Asp Ile Gly Tyr Ile Asp Asp Asp Glu Leu Phe Ile
            420                 425                 430
Val Asp Arg Leu Lys Glu Leu Ile Lys Tyr Lys Gly Phe Gln Val Ala
            435                 440                 445
Pro Ala Glu Leu Glu Ala Leu Leu Leu Asn His Pro Asn Ile Ser Asp
            450                 455                 460
Ala Ala Val Val Pro Met Lys Asp Glu Gln Ala Gly Glu Val Pro Val
465                 470                 475                 480
Ala Phe Val Val Arg Ser Asn Gly Ser Thr Ile Thr Glu Asp Glu Val
                485                 490                 495
Lys Asp Phe Ile Ser Lys Gln Val Ile Phe Tyr Lys Arg Ile Lys Arg
            500                 505                 510
Val Phe Phe Val Asp Ala Ile Pro Lys Ser Pro Ser Gly Lys Ile Leu
            515                 520                 525
Arg Lys Asp Leu Arg Ala Lys Leu Ala Ala Gly Leu Pro Asn
            530                 535                 540

<210> SEQ ID NO 69
<211> LENGTH: 390
<212> TYPE: PRT
<213> ORGANISM: Hypericum androsaemum

<400> SEQUENCE: 69

Met Val Thr Val Glu Glu Val Arg Lys Ala Gln Arg Ala Glu Gly Pro
1               5                   10                  15
Ala Thr Val Met Ala Ile Gly Thr Ala Val Pro Pro Asn Cys Val Asp
            20                  25                  30
Gln Ala Thr Tyr Pro Asp Tyr Tyr Phe Arg Ile Thr Asn Ser Glu His
            35                  40                  45
Lys Ala Glu Leu Lys Glu Lys Phe Gln Arg Met Cys Asp Lys Ser Gln
        50                  55                  60
Ile Lys Lys Arg Tyr Met Tyr Leu Asn Glu Glu Val Leu Lys Glu Asn
65                  70                  75                  80
Pro Asn Met Cys Ala Tyr Met Ala Pro Ser Leu Asp Ala Arg Gln Asp
                85                  90                  95
Ile Val Val Val Glu Val Pro Lys Leu Gly Lys Glu Ala Ala Val Lys
```

```
                100             105             110
Ala Ile Lys Glu Trp Gly Gln Pro Lys Ser Lys Ile Thr His Leu Val
            115                 120             125
Phe Cys Thr Thr Ser Gly Val Asp Met Pro Gly Ala Asp Tyr Gln Leu
    130                 135                 140
Thr Lys Leu Leu Gly Leu Arg Pro Ser Val Lys Arg Leu Met Met Tyr
145                 150                 155                 160
Gln Gln Gly Cys Phe Ala Gly Gly Thr Val Leu Arg Leu Ala Lys Asp
                165                 170                 175
Leu Ala Glu Asn Asn Lys Gly Ala Arg Val Leu Val Val Cys Ser Glu
            180                 185                 190
Ile Thr Ala Val Thr Phe Arg Gly Pro Thr Asp Thr His Leu Asp Ser
        195                 200                 205
Leu Val Gly Gln Ala Leu Phe Gly Asp Gly Ala Ala Ile Ile Ile
        210                 215                 220
Gly Ser Asp Pro Ile Pro Glu Val Glu Lys Pro Leu Phe Glu Leu Val
225                 230                 235                 240
Ser Ala Ala Gln Thr Ile Leu Pro Asp Ser Glu Gly Ala Ile Asp Gly
                245                 250                 255
His Leu Arg Glu Val Gly Leu Thr Phe His Leu Leu Lys Asp Val Pro
            260                 265                 270
Gly Leu Ile Ser Lys Asn Val Glu Lys Ser Leu Thr Glu Ala Phe Lys
        275                 280                 285
Pro Leu Gly Ile Ser Asp Trp Asn Ser Leu Phe Trp Ile Ala His Pro
    290                 295                 300
Gly Gly Pro Ala Ile Leu Asp Gln Val Glu Ala Lys Leu Ser Leu Lys
305                 310                 315                 320
Pro Glu Lys Leu Arg Ala Thr Arg His Val Leu Ser Glu Tyr Gly Asn
                325                 330                 335
Met Ser Ser Ala Cys Val Leu Phe Ile Leu Asp Glu Met Arg Arg Lys
            340                 345                 350
Ser Lys Glu Asp Gly Leu Lys Thr Thr Gly Glu Gly Ile Glu Trp Gly
        355                 360                 365
Val Leu Phe Gly Phe Gly Pro Gly Leu Thr Val Glu Thr Val Val Leu
    370                 375                 380
His Ser Val Ala Ile Asn
385                 390

<210> SEQ ID NO 70
<211> LENGTH: 389
<212> TYPE: PRT
<213> ORGANISM: Solanum lycopersicum

<400> SEQUENCE: 70

Met Val Thr Val Glu Glu Val Arg Arg Ala Gln Arg Ala Lys Gly Pro
1               5                   10                  15
Ala Thr Ile Met Ala Ile Gly Thr Ala Thr Pro Ser Asn Cys Val Asp
            20                  25                  30
Gln Ser Thr Tyr Pro Asp Tyr Tyr Phe Arg Ile Thr Asn Ser Glu His
        35                  40                  45
Met Thr Glu Leu Lys Glu Lys Phe Lys Arg Met Cys Asp Lys Ser Met
    50                  55                  60
Ile Asn Lys Arg Tyr Met His Leu Thr Glu Glu Ile Leu Lys Glu Asn
65                  70                  75                  80
Pro Asn Ile Cys Glu Tyr Met Ala Pro Ser Leu Asp Ala Arg Gln Asp
```

```
                    85                  90                  95
Ile Val Val Glu Val Pro Lys Leu Gly Lys Glu Ala Ala Gln Lys
            100                 105                 110

Ala Ile Lys Glu Trp Gly Gln Pro Lys Ser Lys Ile Thr His Val Val
            115                 120                 125

Phe Cys Thr Thr Ser Gly Val Asp Met Pro Gly Ala Asp Tyr Gln Leu
            130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Ile Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Asp Thr His Leu Asp Ser
            195                 200                 205

Met Val Gly Gln Ala Leu Phe Gly Asp Arg Ala Ala Met Ile Ile
            210                 215                 220

Gly Ser Asp Pro Leu Pro Glu Val Glu Arg Pro Leu Phe Glu Leu Val
225                 230                 235                 240

Ser Ala Ala Gln Thr Leu Leu Pro Asp Ser Glu Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Ile Glu Ala Phe Gln
            275                 280                 285

Pro Leu Gly Ile Ser Asp Trp Asn Ser Ile Phe Trp Ile Ala His Pro
            290                 295                 300

Gly Gly Pro Ala Ile Leu Asp Gln Val Glu Leu Lys Leu Ser Leu Lys
305                 310                 315                 320

Pro Glu Lys Leu Arg Ala Thr Arg Gln Val Leu Ser Asp Tyr Gly Asn
                325                 330                 335

Met Ser Ser Ala Cys Val Leu Phe Ile Leu Asp Glu Met Arg Lys Ala
            340                 345                 350

Ser Ser Lys Glu Gly Leu Ser Thr Thr Gly Glu Gly Leu Asp Trp Gly
            355                 360                 365

Val Leu Phe Gly Phe Gly Pro Gly Leu Thr Val Glu Thr Val Val Leu
            370                 375                 380

His Ser Val Ser Thr
385

<210> SEQ ID NO 71
<211> LENGTH: 392
<212> TYPE: PRT
<213> ORGANISM: Vitis sp.

<400> SEQUENCE: 71

Met Ala Ser Val Glu Glu Ile Arg Asn Ala Gln Arg Ala Lys Gly Pro
1               5                   10                  15

Ala Thr Ile Leu Ala Ile Gly Thr Ala Thr Pro Asp His Cys Val Tyr
                20                  25                  30

Gln Ser Asp Tyr Ala Asp Tyr Tyr Phe Arg Val Thr Lys Ser Glu His
            35                  40                  45

Met Thr Ala Leu Lys Lys Lys Phe Asn Arg Ile Cys Asp Lys Ser Met
        50                  55                  60

Ile Lys Lys Arg Tyr Ile His Leu Thr Glu Glu Met Leu Glu Glu His
```

```
            65                  70                  75                  80
Pro Asn Ile Gly Ala Tyr Met Ala Pro Ser Leu Asn Ile Arg Gln Glu
                    85                  90                  95

Ile Ile Thr Ala Glu Val Pro Lys Leu Gly Lys Glu Ala Ala Leu Lys
            100                 105                 110

Ala Leu Lys Glu Trp Gly Gln Pro Lys Ser Lys Ile Thr His Leu Val
            115                 120                 125

Phe Cys Thr Thr Ser Gly Val Glu Met Pro Gly Ala Asp Tyr Lys Leu
        130                 135                 140

Ala Asn Leu Leu Gly Leu Glu Pro Ser Val Arg Arg Val Met Leu Asp
145                 150                 155                 160

Gln Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ser Thr Val Val Thr Phe Arg Gly Pro Ser Glu Asp Ala Leu Asp Ser
        195                 200                 205

Leu Val Gly Gln Ala Leu Phe Gly Asp Gly Ser Ala Ala Val Ile Val
        210                 215                 220

Gly Ser Asp Pro Asp Ile Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Lys Cys Leu Thr Gln Ala Phe Asp
        275                 280                 285

Pro Leu Gly Ile Ser Asp Trp Asn Ser Leu Phe Trp Ile Ala His Pro
        290                 295                 300

Gly Gly Pro Ala Ile Leu Asp Ala Val Glu Ala Lys Leu Asn Leu Asp
305                 310                 315                 320

Lys Lys Lys Leu Glu Ala Thr Arg His Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Leu Lys Gly Glu Arg Ala Thr Thr Gly Gly Leu Asp Trp Gly
        355                 360                 365

Val Leu Phe Gly Phe Gly Pro Gly Leu Thr Ile Glu Thr Val Val Leu
        370                 375                 380

His Ser Ile Pro Met Val Thr Asn
385                 390

<210> SEQ ID NO 72
<211> LENGTH: 396
<212> TYPE: PRT
<213> ORGANISM: Pinus strobus

<400> SEQUENCE: 72

Met Ser Val Gly Met Gly Val Asp Leu Glu Ala Phe Arg Lys Ser Gln
1               5                   10                  15

Arg Ala Asp Gly Phe Ala Ser Ile Leu Ala Ile Gly Thr Ala Asn Pro
            20                  25                  30

Pro Asn Val Val Asp Gln Ser Thr Tyr Pro Asp Tyr Tyr Phe Arg Asn
        35                  40                  45

Thr Asn Asn Glu Asp Asn Thr Asp Leu Lys Asp Lys Phe Lys Arg Ile
```

```
            50                  55                  60
Cys Glu Arg Ser Ala Ile Lys Lys Arg His Met Tyr Leu Thr Glu Glu
 65                  70                  75                  80

Ile Leu Lys Lys Asn Pro Glu Leu Cys Ala Phe Leu Glu Val Pro Ser
                 85                  90                  95

Leu Asp Thr Arg Gln Ala Met Leu Ala Val Glu Val Pro Arg Leu Gly
             100                 105                 110

Lys Glu Ala Ala Glu Lys Ala Ile Glu Glu Trp Gly Gln Pro Lys Ser
         115                 120                 125

Arg Ile Thr His Leu Ile Phe Cys Thr Thr Thr Thr Pro Asp Leu Pro
    130                 135                 140

Gly Ala Asp Phe Glu Val Ala Lys Leu Leu Gly Leu His Pro Ser Val
145                 150                 155                 160

Lys Arg Val Gly Val Phe Gln His Gly Cys Phe Ala Gly Gly Thr Val
                165                 170                 175

Leu Arg Leu Ala Lys Asp Leu Ala Glu Asn Asn Arg Gly Ala Arg Val
            180                 185                 190

Leu Val Val Cys Ser Glu Asn Thr Ala Val Thr Phe Arg Gly Pro Ser
        195                 200                 205

Glu Thr His Leu Asp Gly Leu Val Gly Leu Ala Leu Phe Gly Asp Gly
    210                 215                 220

Ala Ala Ala Leu Ile Val Gly Ala Asp Pro Ile Pro Gln Val Glu Lys
225                 230                 235                 240

Pro Cys Phe Glu Ile Val Trp Thr Ala Gln Thr Val Val Pro Asn Ser
                245                 250                 255

Asp Gly Ala Ile Ser Gly Lys Leu Arg Glu Val Gly Leu Thr Phe Gln
            260                 265                 270

Leu Lys Gly Ala Val Pro Asp Leu Ile Ser Thr Asn Ile Glu Lys Cys
        275                 280                 285

Leu Val Glu Ala Phe Ser Gln Phe Asn Ile Ser Asp Trp Asn Gln Leu
    290                 295                 300

Phe Trp Ile Ala His Pro Gly Gly Arg Ala Ile Leu Asp Gln Val Glu
305                 310                 315                 320

Ala Ser Leu Asn Leu Asp Pro Thr Lys Leu Arg Ala Thr Arg His Val
                325                 330                 335

Met Ser Glu Tyr Gly Asn Met Ser Ser Ala Cys Val His Phe Ile Leu
            340                 345                 350

Asp Glu Thr Arg Lys Ala Ser Arg Gln Asn Gly Cys Ser Thr Ser Gly
        355                 360                 365

Gly Gly Phe Gln Met Gly Val Leu Phe Gly Phe Gly Pro Gly Leu Thr
    370                 375                 380

Val Glu Thr Val Val Leu Lys Ser Ile Pro Phe Pro
385                 390                 395

<210> SEQ ID NO 73
<211> LENGTH: 322
<212> TYPE: PRT
<213> ORGANISM: Sesbania rostrata

<400> SEQUENCE: 73

Met Ala Glu Lys Lys Ile Pro Glu Val Leu Leu Asn Ser Gly His Lys
  1               5                  10                  15

Met Pro Val Ile Gly Met Gly Thr Ser Val Glu Ser Arg Pro Ser Asn
                 20                  25                  30

Asp Val Leu Ala Ser Ile Phe Val Asp Ala Ile Gln Val Gly Tyr Arg
```

His Phe Asp Ser Ala Ser Val Tyr Gly Thr Glu Glu Ala Ile Gly Met
                50                  55                  60

Ala Val Ser Lys Ala Ile Glu Gln Gly Leu Ile Lys Ser Arg Asp Glu
 65                  70                  75                  80

Val Phe Ile Thr Ser Lys Pro Trp Asn Thr Asp Ala His His Asp Leu
                 85                  90                  95

Ile Val Pro Ala Leu Lys Thr Thr Leu Lys Lys Leu Gly Met Glu Tyr
            100                 105                 110

Val Asp Leu Tyr Leu Ile His Trp Pro Val Arg Leu Arg His Asp Leu
            115                 120                 125

Glu Asn Pro Val Ile Phe Ser Lys Glu Asp Leu Leu Pro Phe Asp Ile
        130                 135                 140

Glu Gly Thr Trp Lys Ala Met Glu Glu Cys Tyr Arg Leu Gly Leu Ala
145                 150                 155                 160

Lys Ser Ile Gly Ile Cys Asn Tyr Gly Thr Lys Leu Thr Lys Leu
                165                 170                 175

Leu Glu Ile Ala Thr Ile Pro Pro Ala Val Asn Gln Val Glu Met Asn
            180                 185                 190

Pro Ser Trp Gln Gln Gly Asn Leu Arg Glu Phe Cys Lys Gln Lys Gly
        195                 200                 205

Ile His Val Ser Ala Trp Ser Pro Leu Gly Ala Tyr Lys Ile Phe Trp
    210                 215                 220

Gly Ser Gly Ala Val Met Glu Asn Gln Ile Leu Gln Asp Ile Ala Thr
225                 230                 235                 240

Ala Lys Gly Lys Thr Ile Ala Gln Val Ala Leu Arg Trp Val Tyr Gln
                245                 250                 255

Gln Gly Ser Ser Ala Met Ala Lys Ser Phe Asn Lys Glu Arg Met Lys
            260                 265                 270

Gln Asn Leu Glu Ile Phe Asp Phe Glu Leu Ser Glu Glu Glu Leu Glu
        275                 280                 285

Lys Ile Lys Gln Ile Pro Gln Arg Arg Gln Tyr Thr Gly Asp Met Trp
290                 295                 300

Leu Ser Glu Asn Gly Ser Cys Lys Thr Leu Glu Glu Leu Trp Asp Gly
305                 310                 315                 320

Asp Val

<210> SEQ ID NO 74
<211> LENGTH: 314
<212> TYPE: PRT
<213> ORGANISM: Pueraria lobata

<400> SEQUENCE: 74

Met Ala Ala Ile Glu Ile Pro Thr Ile Val Phe Pro Asn Ser Phe Ala
  1               5                  10                  15

Gln His Arg Val Pro Val Val Glu Met Gly Ser Ala Pro Asp Phe Thr
                 20                  25                  30

Cys Lys Lys Asp Thr Lys Glu Ala Ile Ile Glu Ala Val Lys Gln Gly
             35                  40                  45

Tyr Arg His Phe Asp Thr Ala Ala Ala Tyr Gly Ser Glu Gln Ala Leu
         50                  55                  60

Gly Glu Ala Leu Lys Glu Ala Val Asp Leu Gly Leu Val Ser Arg Gln
 65                  70                  75                  80

Asp Leu Phe Val Thr Ser Lys Leu Trp Val Thr Asp Asn His Pro His
                 85                  90                  95

-continued

Leu Val Val Ser Ala Leu Arg Lys Ser Leu Lys Thr Leu Gln Leu Glu
            100                 105                 110

Tyr Leu Asp Leu Tyr Leu Ile His Trp Pro Leu Ser Ser Gln Pro Gly
            115                 120                 125

Lys Phe Ser Phe Pro Ile Glu Val Glu Asp Leu Leu Pro Phe Asp Val
            130                 135                 140

Lys Gly Val Trp Glu Ala Met Gln Glu Cys Gln Lys Leu Gly Leu Thr
145                 150                 155                 160

Lys Ala Ile Gly Val Ser Asn Phe Ser Val Lys Lys Leu Gln Asn Leu
                165                 170                 175

Leu Ser Val Ala Thr Ile Arg Pro Val Val Asn Gln Val Glu Met Asn
            180                 185                 190

Leu Ala Trp Gln Gln Lys Lys Leu Arg Glu Phe Cys Lys Glu Asn Gly
            195                 200                 205

Ile Val Ile Thr Ala Phe Ser Pro Leu Arg Lys Gly Ala Ser Arg Gly
            210                 215                 220

Pro Asn Glu Val Met Glu Asn Asp Val Leu Lys Glu Ile Ala Asp Ala
225                 230                 235                 240

His Gly Lys Ser Ile Ala Gln Val Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Gln Ile Phe Asp Trp Ala Leu Thr Gln Glu Asp His His Lys
            275                 280                 285

Ile Ser Gln Ile Ser Gln Ser Arg Leu Ile Ser Gly Pro Thr Lys Pro
            290                 295                 300

Gln Leu Ser Asp Leu Trp Asp Asp Glu Ile
305                 310

<210> SEQ ID NO 75
<211> LENGTH: 312
<212> TYPE: PRT
<213> ORGANISM: Medicago sativa

<400> SEQUENCE: 75

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
            35                  40                  45

Tyr Arg His Phe Asp Thr Ala Ala Ala Tyr Gly Ser Glu Gln Ala Leu
            50                  55                  60

Gly Glu Ala Leu Lys Glu Ala Ile Glu Leu Gly Leu Val Thr Arg Asp
65                  70                  75                  80

Asp Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
            115                 120                 125

Lys Phe Ser Phe Pro Ile Asp Val Ala Asp Leu Leu Pro Phe Asp Val
            130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Leu Glu Asn Leu
                165                 170                 175

Leu Ser Val Ala Thr Val Leu Pro Ala Val Asn Gln Val Glu Met Asn
                180                 185                 190

Leu Ala Trp Gln Gln Lys Lys Leu Arg Glu Phe Cys Asn Ala His Gly
                195                 200                 205

Ile Val Leu Thr Ala Phe Ser Pro Val Arg Lys Gly Ala Ser Arg Gly
                210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
                260                 265                 270

Asn Leu Arg Ile Phe Asp Trp Ser Leu Thr Lys Glu Asp His Glu Lys
                275                 280                 285

Ile Ala Gln Ile Lys Gln Asn Arg Leu Ile Pro Gly Pro Thr Lys Pro
                290                 295                 300

Gly Leu Asn Asp Leu Tyr Asp Asp
305                 310

<210> SEQ ID NO 76
<211> LENGTH: 241
<212> TYPE: PRT
<213> ORGANISM: Petunia x hybrida

<400> SEQUENCE: 76

Met Ser Pro Ser Val Ser Val Thr Glu Met His Val Glu Asn Tyr Val
1               5                   10                  15

Phe Ala Pro Thr Val Asn Pro Ala Gly Ser Ser Asn Thr Leu Phe Leu
                20                  25                  30

Ala Gly Ala Gly His Arg Gly Leu Glu Ile Gln Gly Lys Phe Val Lys
                35                  40                  45

Phe Thr Ala Ile Gly Val Tyr Leu Glu Glu Ser Ala Ile Pro Phe Leu
                50                  55                  60

Ala Glu Lys Trp Lys Gly Lys Thr Pro Glu Glu Leu Thr Asp Ser Val
65              70                  75                  80

Glu Phe Phe Arg Asp Val Val Thr Gly Pro Phe Glu Lys Phe Thr Arg
                85                  90                  95

Val Thr Met Ile Leu Pro Leu Thr Gly Lys Gln Tyr Ser Glu Lys Val
                100                 105                 110

Ala Glu Asn Cys Val Ala His Trp Lys Gly Ile Gly Thr Tyr Thr Asp
                115                 120                 125

Asp Glu Gly Arg Ala Ile Glu Lys Phe Leu Asp Val Phe Arg Ser Glu
                130                 135                 140

Thr Phe Pro Pro Gly Ala Ser Ile Met Phe Thr Gln Ser Pro Leu Gly
145                 150                 155                 160

Ser Leu Thr Ile Ser Phe Ala Lys Asp Asp Ser Leu Thr Gly Thr Ala
                165                 170                 175

Asn Ala Val Ile Glu Asn Lys Gln Leu Ser Glu Ala Val Leu Glu Ser
                180                 185                 190

Ile Ile Gly Lys His Gly Val Ser Pro Ala Ala Lys Cys Ser Val Ala
                195                 200                 205

Glu Arg Val Ala Glu Leu Leu Lys Lys Ser Tyr Ala Glu Glu Ala Ser
                210                 215                 220

```
Val Phe Gly Lys Pro Glu Thr Glu Lys Ser Thr Ile Pro Val Ile Gly
225                 230                 235                 240

Val
```

```
<210> SEQ ID NO 77
<211> LENGTH: 221
<212> TYPE: PRT
<213> ORGANISM: Lotus japonicus

<400> SEQUENCE: 77

Met Ala Leu Pro Ser Val Thr Ala Leu Gln Val Glu Asn Val Ala Phe
1               5                   10                  15

Pro Pro Thr Leu Ile Lys Pro Pro Ala Ser Ala Asn Thr Leu Phe Leu
            20                  25                  30

Gly Gly Ala Gly Glu Arg Gly Leu His Ile Gln Asp Lys Phe Val Lys
        35                  40                  45

Phe Thr Ala Ile Gly Ile Tyr Leu Gln Asp Thr Ala Val Pro Ser Leu
    50                  55                  60

Ala Val Lys Trp Lys Gly Lys Pro Val Asp Glu Leu Thr Glu Ser Val
65                  70                  75                  80

Gln Phe Phe Arg Asp Ile Val Thr Gly Pro Phe Glu Lys Phe Met Gln
                85                  90                  95

Val Thr Met Ile Leu Pro Leu Thr Gly Gln Gln Tyr Ser Glu Lys Val
            100                 105                 110

Ser Glu Asn Cys Val Ala Ile Trp Lys His Leu Gly Ile Tyr Thr Asp
        115                 120                 125

Glu Glu Gly Lys Ala Ile Asp Lys Phe Val Ser Val Phe Lys Asp Gln
    130                 135                 140

Thr Phe Pro Pro Gly Ser Ser Ile Leu Phe Thr Val Leu Pro Lys Gly
145                 150                 155                 160

Ser Leu Ala Ile Ser Phe Ser Lys Asp Gly Ser Ile Pro Glu Val Glu
                165                 170                 175

Ser Ala Val Ile Asp Asn Lys Leu Leu Ser Glu Ala Val Leu Glu Ser
            180                 185                 190

Met Ile Gly Ala His Gly Val Ser Pro Ala Ala Lys Gln Ser Leu Ala
        195                 200                 205

Ser Arg Leu Ser Glu Leu Phe Lys His His Ala Glu Val
    210                 215                 220
```

```
<210> SEQ ID NO 78
<211> LENGTH: 226
<212> TYPE: PRT
<213> ORGANISM: Glycine max

<400> SEQUENCE: 78

Met Ala Phe Pro Ser Val Thr Ser Val Thr Val Glu Asn Val Thr Phe
1               5                   10                  15

Pro Pro Thr Val Lys Pro Pro Cys Ser Pro Asn Thr Phe Phe Leu Ala
            20                  25                  30

Gly Ala Gly Val Arg Gly Leu Gln Ile His His Ala Phe Val Lys Phe
        35                  40                  45

Thr Ala Ile Cys Ile Tyr Leu Gln Tyr Asp Ala Leu Ser Phe Leu Ser
    50                  55                  60

Val Lys Trp Lys Thr Lys Ser Thr His Gln Leu Thr Glu Ser Asp Gln
65                  70                  75                  80

Phe Phe Ser Asp Ile Val Thr Gly Pro Phe Glu Lys Phe Met Gln Val
```

```
                        85                  90                  95
Thr Met Ile Lys Pro Leu Thr Gly Gln Gln Tyr Ser Glu Lys Val Ala
                100                 105                 110
Glu Asn Cys Val Ala Ile Trp Arg Ser Leu Gly Ile Tyr Thr Asp Ser
                115                 120                 125
Glu Ala Glu Ala Ile Asp Lys Phe Leu Ser Val Phe Lys Asp Leu Thr
                130                 135                 140
Phe Pro Pro Gly Ser Ser Ile Leu Phe Thr Val Ser Pro Asn Gly Ser
145                 150                 155                 160
Leu Thr Ile Ser Phe Ser Gly Asp Glu Thr Ile Pro Glu Val Thr Ser
                    165                 170                 175
Ala Val Ile Glu Asn Lys Leu Leu Ser Glu Ala Val Leu Glu Ser Met
                180                 185                 190
Ile Gly Lys Asn Gly Val Ser Pro Ala Ala Lys Gln Ser Leu Ala Ser
                195                 200                 205
Arg Leu Ser His Leu Phe Lys Glu Pro Gly Val Cys Asp Pro Gln Ser
                210                 215                 220
His Lys
225

<210> SEQ ID NO 79
<211> LENGTH: 209
<212> TYPE: PRT
<213> ORGANISM: Glycine max

<400> SEQUENCE: 79

Met Ala Thr Glu Glu Val Leu Val Asp Glu Ile Thr Tyr Pro Thr Lys
1               5                   10                  15
Ile Thr Thr Thr Lys Pro Leu Ser Leu Leu Gly His Gly Ile Thr Asp
                20                  25                  30
Met Glu Ile His Phe Ile His Val Lys Phe Tyr Ser Ile Gly Val Tyr
                35                  40                  45
Leu Glu Pro Glu Val Val Gly His Leu Asp Gln Phe Lys Gly Lys Ser
            50                  55                  60
Ala Lys Glu Leu Glu Asp Asn Glu Glu Phe Phe Asn Ala Leu Ile Ser
65                  70                  75                  80
Ala Pro Val Glu Lys Phe Ile Arg Leu Val Ile Lys Glu Ile Lys
                85                  90                  95
Gly Ala Gln Tyr Gly Val Gln Ile Glu Thr Ala Val Arg Asp Arg Leu
                100                 105                 110
Ala Ala Glu Asp Lys Tyr Glu Glu Glu Glu Glu Ala Leu Glu Lys
                115                 120                 125
Val Ile Glu Phe Phe Gln Ser Lys Tyr Phe Lys Lys Leu Ser Val Ile
                130                 135                 140
Thr Tyr His Phe Pro Ala Asn Ser Ala Thr Ala Glu Ile Val Val Ser
145                 150                 155                 160
Leu Glu Gly Lys Glu Asp Ser Lys Tyr Val Ile Glu Asn Ala Asn Val
                    165                 170                 175
Val Glu Ala Ile Lys Lys Trp Tyr Leu Gly Gly Ser Ser Ala Val Ser
                180                 185                 190
Ser Ser Thr Ile Gln Ser Leu Ala Ser Thr Phe Ser Gln Glu Leu Ser
                195                 200                 205
Lys

<210> SEQ ID NO 80
```

```
<211> LENGTH: 218
<212> TYPE: PRT
<213> ORGANISM: Glycine max

<400> SEQUENCE: 80

Met Ala Thr Ile Ser Ala Val Gln Val Glu Phe Leu Glu Phe Pro Ala
1               5                   10                  15

Val Val Thr Ser Pro Ala Ser Gly Lys Thr Tyr Phe Leu Gly Gly Ala
                20                  25                  30

Gly Glu Arg Gly Leu Thr Ile Glu Gly Lys Phe Ile Lys Phe Thr Gly
            35                  40                  45

Ile Gly Val Tyr Leu Glu Asp Lys Ala Val Pro Ser Leu Ala Ala Lys
50                  55                  60

Trp Lys Gly Lys Thr Ser Glu Glu Leu Val His Thr Leu His Phe Tyr
65                  70                  75                  80

Arg Asp Ile Ile Ser Gly Pro Phe Glu Lys Leu Ile Arg Gly Ser Lys
                85                  90                  95

Ile Leu Pro Leu Ala Gly Ala Glu Tyr Ser Lys Lys Val Met Glu Asn
                100                 105                 110

Cys Val Ala His Met Lys Ser Val Gly Thr Tyr Gly Asp Ala Glu Ala
                115                 120                 125

Ala Ala Ile Glu Lys Phe Ala Glu Ala Phe Lys Asn Val Asn Phe Ala
130                 135                 140

Pro Gly Ala Ser Val Phe Tyr Arg Gln Ser Pro Asp Gly Ile Leu Gly
145                 150                 155                 160

Leu Ser Phe Ser Glu Asp Ala Thr Ile Pro Gly Lys Glu Ala Ala Val
                165                 170                 175

Ile Glu Asn Lys Ala Val Ser Ala Ala Val Leu Glu Thr Met Ile Gly
                180                 185                 190

Glu His Ala Val Ser Pro Asp Leu Lys Arg Ser Leu Ala Ser Arg Leu
                195                 200                 205

Pro Ala Val Leu Ser His Gly Ile Ile Val
                210                 215

<210> SEQ ID NO 81
<211> LENGTH: 358
<212> TYPE: PRT
<213> ORGANISM: Arabidopsis thaliana

<400> SEQUENCE: 81

Met Ala Pro Gly Thr Leu Thr Glu Leu Ala Gly Glu Ser Lys Leu Asn
1               5                   10                  15

Ser Lys Phe Val Arg Asp Glu Asp Arg Pro Lys Val Ala Tyr Asn
                20                  25                  30

Val Phe Ser Asp Glu Ile Pro Val Ile Ser Leu Ala Gly Ile Asp Asp
            35                  40                  45

Val Asp Gly Lys Arg Gly Glu Ile Cys Arg Gln Ile Val Glu Ala Cys
50                  55                  60

Glu Asn Trp Gly Ile Phe Gln Val Val Asp His Gly Val Asp Thr Asn
65                  70                  75                  80

Leu Val Ala Asp Met Thr Arg Leu Ala Arg Asp Phe Ala Leu Pro
                85                  90                  95

Pro Glu Asp Lys Leu Arg Phe Asp Met Ser Gly Gly Lys Lys Gly Gly
                100                 105                 110

Phe Ile Val Ser Ser His Leu Gln Gly Glu Ala Val Gln Asp Trp Arg
                115                 120                 125
```

Glu Ile Val Thr Tyr Phe Ser Tyr Pro Val Arg Asn Arg Asp Tyr Ser
            130                 135                 140

Arg Trp Pro Asp Lys Pro Glu Gly Trp Val Lys Val Thr Glu Glu Tyr
145                 150                 155                 160

Ser Glu Arg Leu Met Ser Leu Ala Cys Lys Leu Leu Glu Val Leu Ser
                165                 170                 175

Glu Ala Met Gly Leu Glu Lys Glu Ser Leu Thr Asn Ala Cys Val Asp
            180                 185                 190

Met Asp Gln Lys Ile Val Val Asn Tyr Tyr Pro Lys Cys Pro Gln Pro
        195                 200                 205

Asp Leu Thr Leu Gly Leu Lys Arg His Thr Asp Pro Gly Thr Ile Thr
210                 215                 220

Leu Leu Leu Gln Asp Gln Val Gly Gly Leu Gln Ala Thr Arg Asp Asn
225                 230                 235                 240

Gly Lys Thr Trp Ile Thr Val Gln Pro Val Glu Gly Ala Phe Val Val
                245                 250                 255

Asn Leu Gly Asp His Gly His Phe Leu Ser Asn Gly Arg Phe Lys Asn
            260                 265                 270

Ala Asp His Gln Ala Val Val Asn Ser Asn Ser Ser Arg Leu Ser Ile
        275                 280                 285

Ala Thr Phe Gln Asn Pro Ala Pro Asp Ala Thr Val Tyr Pro Leu Lys
    290                 295                 300

Val Arg Glu Gly Glu Lys Ala Ile Leu Glu Glu Pro Ile Thr Phe Ala
305                 310                 315                 320

Glu Met Tyr Lys Arg Lys Met Gly Arg Asp Leu Glu Leu Ala Arg Leu
                325                 330                 335

Lys Lys Leu Ala Lys Glu Glu Arg Asp His Lys Glu Val Asp Lys Pro
            340                 345                 350

Val Asp Gln Ile Phe Ala
        355

<210> SEQ ID NO 82
<211> LENGTH: 375
<212> TYPE: PRT
<213> ORGANISM: Glycine max

<400> SEQUENCE: 82

Met Ala Pro Thr Ala Lys Thr Leu Thr Tyr Leu Ala Gln Glu Lys Thr
1               5                   10                  15

Leu Glu Ser Ser Phe Val Arg Asp Glu Glu Arg Pro Lys Val Ala
                20                  25                  30

Tyr Asn Glu Phe Ser Asp Glu Ile Pro Val Ile Ser Leu Ala Gly Ile
            35                  40                  45

Asp Glu Val Asp Gly Arg Arg Glu Ile Cys Glu Lys Ile Val Glu
    50                  55                  60

Ala Cys Glu Asn Trp Gly Ile Phe Gln Val Val Asp His Gly Val Asp
65                  70                  75                  80

Gln Gln Leu Val Ala Glu Met Thr Arg Leu Ala Lys Glu Phe Phe Ala
                85                  90                  95

Leu Pro Pro Asp Glu Lys Leu Arg Phe Asp Met Ser Gly Ala Lys Lys
            100                 105                 110

Gly Gly Phe Ile Val Ser Ser His Leu Gln Gly Glu Ser Val Gln Asp
        115                 120                 125

Trp Arg Glu Ile Val Thr Tyr Phe Ser Tyr Pro Lys Arg Glu Arg Asp
    130                 135                 140

```
Tyr Ser Arg Trp Pro Asp Thr Pro Glu Gly Trp Arg Ser Val Thr Glu
145                 150                 155                 160

Glu Tyr Ser Asp Lys Val Met Gly Leu Ala Cys Lys Leu Met Glu Val
            165                 170                 175

Leu Ser Glu Ala Met Gly Leu Glu Lys Glu Gly Leu Ser Lys Ala Cys
        180                 185                 190

Val Asp Met Asp Gln Lys Val Val Asn Tyr Tyr Pro Lys Cys Pro
        195                 200                 205

Gln Pro Asp Leu Thr Leu Gly Leu Lys Arg His Thr Asp Pro Gly Thr
    210                 215                 220

Ile Thr Leu Leu Leu Gln Asp Gln Val Gly Gly Leu Gln Ala Thr Arg
225                 230                 235                 240

Asp Asn Gly Lys Thr Trp Ile Thr Val Gln Pro Val Glu Ala Ala Phe
                245                 250                 255

Val Val Asn Leu Gly Asp His Ala His Tyr Leu Ser Asn Gly Arg Phe
            260                 265                 270

Lys Asn Ala Asp His Gln Ala Val Val Asn Ser Asn His Ser Arg Leu
        275                 280                 285

Ser Ile Ala Thr Phe Gln Asn Pro Ala Pro Asn Ala Thr Val Tyr Pro
    290                 295                 300

Leu Lys Ile Arg Glu Gly Glu Lys Pro Val Met Glu Glu Pro Ile Thr
305                 310                 315                 320

Phe Ala Glu Met Tyr Arg Arg Lys Met Ser Lys Asp Ile Glu Ile Ala
                325                 330                 335

Arg Met Lys Lys Leu Ala Lys Glu Lys His Leu Gln Asp Leu Glu Asn
            340                 345                 350

Glu Lys His Leu Gln Glu Leu Asp Gln Lys Ala Lys Leu Glu Ala Lys
        355                 360                 365

Pro Leu Lys Glu Ile Leu Ala
    370                 375

<210> SEQ ID NO 83
<211> LENGTH: 512
<212> TYPE: PRT
<213> ORGANISM: Catharanthus roseus

<400> SEQUENCE: 83

Met Ala Leu Glu Lys Leu Val Leu Phe Asp Phe Leu Ala Ala Ile Ser
1               5                   10                  15

Ile Leu Ile Leu Val Gln Lys Phe Ile Gln Ile Val Phe Leu Arg Ser
            20                  25                  30

Ser Ser Arg Ile Arg Leu Pro Pro Gly Pro Lys Gly Trp Pro Ile Ile
        35                  40                  45

Gly Ala Leu Pro Tyr Leu Gly Thr Met Pro His Ser Ile Leu Ala Asn
    50                  55                  60

Met Ala Lys Lys Tyr Gly Pro Ile Met Tyr Leu Lys Leu Gly Thr Asn
65                  70                  75                  80

Gly Met Val Val Ala Ser Thr Pro Asp Ala Val Lys Ala Phe Leu Arg
                85                  90                  95

Thr Leu Asp Met Asn Phe Ser Asn Arg Pro Ile Asp Ala Gly Ala Thr
            100                 105                 110

His Leu Ala Tyr Asn Ala Gln Asp Met Val Phe Ala His Tyr Gly Pro
        115                 120                 125

Lys Trp Lys Leu Leu Arg Lys Leu Ser Asn Leu His Met Leu Gly Gly
    130                 135                 140
```

```
Lys Ala Leu Glu Asn Trp Ser Asn Val Arg Ala Thr Glu Leu Gly Tyr
145                 150                 155                 160

Met Leu Gln Ala Met Tyr Glu Ser Ser Arg Lys Gly Glu Thr Val Val
                165                 170                 175

Val Pro Glu Met Leu Thr Tyr Ala Met Ala Asn Met Ile Gly Gln Val
            180                 185                 190

Ile Leu Ser Arg Arg Val Phe Val Thr Lys Ser Leu Glu Ser Asn Glu
        195                 200                 205

Phe Lys Asp Met Val Val Glu Leu Met Thr Thr Ala Gly Tyr Phe Asn
    210                 215                 220

Ile Gly Asp Phe Ile Pro Ser Ile Ala Trp Met Asp Leu Gln Gly Ile
225                 230                 235                 240

Glu Arg Gly Met Lys Arg Leu His Lys Lys Phe Asp Ala Leu Leu Thr
                245                 250                 255

Lys Met Leu Glu Glu His Lys Ser Ser His Lys Arg Lys Glu Lys
                260                 265                 270

Pro Asp Phe Leu Asp Tyr Val Leu Ala Asn Arg Asp Asn Ser Glu Gly
            275                 280                 285

Glu Arg Leu Thr Thr Thr Asn Ile Lys Ala Leu Leu Leu Asn Leu Phe
        290                 295                 300

Thr Ala Gly Thr Asp Thr Ser Ser Ser Val Ile Glu Trp Ala Ile Ser
305                 310                 315                 320

Glu Met Leu Lys Asn Pro Thr Ile Leu Lys Arg Ala Gln Glu Met
                325                 330                 335

Asp Gln Val Ile Gly Arg Asn Arg Arg Leu Met Glu Ser Asp Ile Pro
            340                 345                 350

Lys Leu Pro Tyr Leu Gln Ala Ile Cys Lys Glu Thr Phe Arg Lys His
        355                 360                 365

Pro Ser Thr Pro Leu Asn Leu Pro Arg Ile Ala Gln Lys Asp Cys Gln
    370                 375                 380

Val Asn Gly Tyr Tyr Ile Pro Lys Gly Thr Arg Leu Ser Val Asn Ile
385                 390                 395                 400

Trp Ala Ile Gly Arg Asp Pro Asn Val Trp Glu Asn Pro Leu Glu Phe
                405                 410                 415

Asn Pro Asp Arg Phe Leu Ser Gly Lys Met Ala Lys Ile Glu Pro Arg
            420                 425                 430

Gly Asn Asp Phe Glu Leu Ile Pro Phe Gly Ala Gly Arg Arg Ile Cys
        435                 440                 445

Ala Gly Thr Arg Met Gly Ile Val Leu Val Glu Tyr Ile Leu Gly Thr
    450                 455                 460

Leu Val His Ser Phe Asp Trp Lys Leu Pro Phe Asp Asp Ile Asn Glu
465                 470                 475                 480

Leu Asn Met Asp Glu Ser Phe Gly Leu Ala Leu Gln Lys Ala Val Pro
                485                 490                 495

Leu Val Ala Met Val Ser Pro Arg Leu Pro Ile Asn Ala Tyr Ser Pro
            500                 505                 510

<210> SEQ ID NO 84
<211> LENGTH: 516
<212> TYPE: PRT
<213> ORGANISM: Gentiana triflora

<400> SEQUENCE: 84

Met Ser Pro Ile Tyr Thr Thr Leu Thr Leu His Leu Ala Thr Ala Leu
1               5                   10                  15
```

-continued

```
Phe Leu Phe Phe His Val Gln Lys Leu Val His Tyr Leu His Gly Lys
         20                  25                  30

Ala Thr Gly His Arg Cys Arg Leu Pro Pro Gly Pro Thr Gly Trp
         35                  40                  45

Pro Ile Leu Gly Ala Leu Pro Leu Leu Gly Asn Met Pro His Val Thr
 50                  55                  60

Phe Ala Asn Met Ala Lys Lys Tyr Gly Ser Val Met Tyr Leu Lys Val
 65                  70                  75                  80

Gly Ser His Gly Leu Ala Ile Ala Ser Thr Pro Asp Ala Ala Lys Ala
                 85                  90                  95

Phe Leu Lys Thr Leu Asp Leu Asn Phe Ser Asn Arg Pro Pro Asn Ala
                100                 105                 110

Gly Ala Thr His Leu Ala Tyr Asn Ala Gln Asp Met Val Phe Ala His
                115                 120                 125

Tyr Gly Pro Lys Trp Lys Leu Leu Arg Lys Leu Ser Asn Leu His Met
                130                 135                 140

Leu Gly Gly Lys Ala Leu Glu Asn Trp Ala Asp Val Arg Lys Thr Glu
145                 150                 155                 160

Leu Gly Tyr Met Leu Lys Ala Met Phe Glu Ser Ser Gln Asn Asn Glu
                165                 170                 175

Pro Val Met Ile Ser Glu Met Leu Thr Tyr Ala Met Ala Asn Met Leu
                180                 185                 190

Ser Gln Val Ile Leu Ser Arg Arg Val Phe Asn Lys Lys Gly Ala Lys
                195                 200                 205

Ser Asn Glu Phe Lys Asp Met Val Val Glu Leu Met Thr Ser Ala Gly
                210                 215                 220

Tyr Phe Asn Ile Gly Asp Phe Ile Pro Ser Ile Gly Trp Met Asp Leu
225                 230                 235                 240

Gln Gly Ile Glu Gly Met Lys Arg Leu His Lys Lys Phe Asp Val
                245                 250                 255

Leu Leu Thr Arg Leu Leu Asp Asp His Lys Arg Thr Ser Gln Glu Arg
                260                 265                 270

Lys Gln Lys Pro Asp Phe Leu Asp Phe Val Ile Ala Asn Gly Asp Asn
                275                 280                 285

Ser Asp Gly Glu Arg Leu Asn Thr Asp Asn Ile Lys Ala Leu Leu Leu
290                 295                 300

Asn Leu Phe Thr Ala Gly Thr Asp Thr Ser Ser Ile Ile Glu Trp
305                 310                 315                 320

Ala Leu Ala Glu Leu Leu Lys Asn Arg Thr Leu Leu Thr Arg Ala Gln
                325                 330                 335

Asp Glu Met Asp Arg Val Ile Gly Arg Asp Arg Leu Leu Glu Ser
                340                 345                 350

Asp Ile Pro Asn Leu Pro Tyr Leu Gln Ala Ile Cys Lys Glu Thr Phe
                355                 360                 365

Arg Lys His Pro Ser Thr Pro Leu Asn Leu Pro Arg Asn Cys Ile Arg
                370                 375                 380

Gly His Val Asp Val Asn Gly Tyr Tyr Ile Pro Lys Gly Thr Arg Leu
385                 390                 395                 400

Asn Val Asn Ile Trp Ala Ile Gly Arg Asp Pro Ser Val Trp Gly Asp
                405                 410                 415

Asn Pro Asn Glu Phe Asp Pro Glu Arg Phe Leu Tyr Gly Arg Asn Ala
                420                 425                 430

Lys Ile Asp Pro Arg Gly Asn His Phe Glu Leu Ile Pro Phe Gly Ala
                435                 440                 445
```

```
Gly Arg Arg Ile Cys Ala Gly Thr Arg Met Gly Ile Leu Leu Val Glu
            450                 455                 460

Tyr Ile Leu Gly Thr Leu Val His Ser Phe Asp Trp Lys Leu Gly Phe
465                 470                 475                 480

Ser Glu Asp Glu Leu Asn Met Asp Glu Thr Phe Gly Leu Ala Leu Gln
                485                 490                 495

Lys Ala Val Pro Leu Ala Ala Met Val Ile Pro Arg Leu Pro Leu His
            500                 505                 510

Val Tyr Ala Pro
        515

<210> SEQ ID NO 85
<211> LENGTH: 334
<212> TYPE: PRT
<213> ORGANISM: Medicago truncatula

<400> SEQUENCE: 85

Met Gly Ser Met Ala Glu Thr Val Cys Val Thr Gly Ala Ser Gly Phe
1               5                   10                  15

Ile Gly Ser Trp Leu Val Met Arg Leu Met Glu Arg Gly Tyr Met Val
            20                  25                  30

Arg Ala Thr Val Arg Asp Pro Glu Asn Leu Lys Lys Val Ser His Leu
        35                  40                  45

Leu Glu Leu Pro Gly Ala Lys Gly Lys Leu Ser Leu Trp Lys Ala Asp
    50                  55                  60

Leu Gly Glu Glu Gly Ser Phe Asp Glu Ala Ile Lys Gly Cys Thr Gly
65                  70                  75                  80

Val Phe His Val Ala Thr Pro Met Asp Phe Glu Ser Lys Asp Pro Glu
                85                  90                  95

Asn Glu Met Ile Lys Pro Thr Ile Lys Gly Val Leu Asp Ile Met Lys
            100                 105                 110

Ala Cys Leu Lys Ala Lys Thr Val Arg Arg Phe Ile Phe Thr Ser Ser
        115                 120                 125

Ala Gly Thr Leu Asn Val Thr Glu Asp Gln Lys Pro Leu Trp Asp Glu
    130                 135                 140

Ser Cys Trp Ser Asp Val Glu Phe Cys Arg Arg Val Lys Met Thr Gly
145                 150                 155                 160

Trp Met Tyr Phe Val Ser Lys Thr Leu Ala Glu Gln Glu Ala Trp Lys
                165                 170                 175

Phe Ala Lys Glu His Asn Met Asp Phe Ile Thr Ile Ile Pro Pro Leu
            180                 185                 190

Val Val Gly Pro Phe Leu Ile Pro Thr Met Pro Pro Ser Leu Ile Thr
        195                 200                 205

Ala Leu Ser Pro Ile Thr Gly Asn Glu Ala His Tyr Ser Ile Ile Lys
    210                 215                 220

Gln Gly Gln Phe Val His Leu Asp Asp Leu Cys Glu Ala His Ile Phe
225                 230                 235                 240

Leu Phe Glu His Met Glu Val Glu Gly Arg Tyr Leu Cys Ser Ala Cys
                245                 250                 255

Glu Ala Asn Ile His Asp Ile Ala Lys Leu Ile Asn Thr Lys Tyr Pro
            260                 265                 270

Glu Tyr Asn Ile Pro Thr Lys Phe Asn Asn Ile Pro Asp Glu Leu Glu
        275                 280                 285

Leu Val Arg Phe Ser Ser Lys Lys Ile Lys Asp Leu Gly Phe Glu Phe
    290                 295                 300
```

```
Lys Tyr Ser Leu Glu Asp Met Tyr Thr Glu Ala Ile Asp Thr Cys Ile
305                 310                 315                 320

Glu Lys Gly Leu Leu Pro Lys Phe Val Lys Ser Thr Asn Lys
                325                 330
```

<210> SEQ ID NO 86
<211> LENGTH: 339
<212> TYPE: PRT
<213> ORGANISM: Medicago truncatula

<400> SEQUENCE: 86

```
Met Gly Ser Val Ser Glu Thr Val Cys Val Thr Gly Ala Ser Gly Phe
1               5                   10                  15

Ile Gly Ser Trp Leu Val Met Arg Leu Met Glu Arg Gly Tyr Thr Val
            20                  25                  30

Arg Ala Thr Val Arg Asp Pro Asp Asn Met Lys Lys Val Lys His Leu
        35                  40                  45

Leu Glu Leu Pro Gly Ala Asn Ser Lys Leu Ser Leu Trp Lys Ala Asp
    50                  55                  60

Leu Gly Glu Gly Ser Phe Asp Glu Ala Ile Lys Gly Cys Thr Gly
65                  70                  75                  80

Val Phe His Val Ala Thr Pro Met Asp Phe Glu Ser Lys Asp Pro Glu
                85                  90                  95

Lys Glu Val Ile Asn Pro Thr Ile Asn Gly Leu Leu Asp Ile Met Lys
            100                 105                 110

Ala Cys Lys Lys Ala Lys Thr Val Arg Arg Leu Val Phe Thr Ser Ser
        115                 120                 125

Ala Gly Thr Leu Asp Val Thr Glu Gln Gln Asn Ser Val Ile Asp Glu
    130                 135                 140

Thr Cys Trp Ser Asp Val Glu Phe Cys Arg Arg Val Lys Met Thr Gly
145                 150                 155                 160

Trp Met Tyr Phe Val Ser Lys Thr Leu Ala Glu Gln Glu Ala Trp Lys
                165                 170                 175

Phe Ser Lys Glu His Asn Ile Asp Phe Val Ser Ile Ile Pro Pro Leu
            180                 185                 190

Val Val Gly Pro Phe Ile Met Pro Ser Met Pro Pro Ser Leu Ile Thr
        195                 200                 205

Ala Leu Ser Leu Ile Thr Gly Tyr Glu Ala His Tyr Ser Ile Ile Lys
    210                 215                 220

Gln Gly Gln Tyr Ile His Leu Asp Leu Cys Leu Ala His Ile Phe
225                 230                 235                 240

Leu Phe Glu Asn Pro Lys Ala His Gly Arg Tyr Ile Cys Cys Ser His
                245                 250                 255

Glu Ala Thr Ile His Glu Val Ala Lys Leu Ile Asn Lys Lys Tyr Pro
            260                 265                 270

Glu Phe Asn Val Pro Thr Lys Phe Lys Asp Ile Pro Asp Asp Leu Glu
        275                 280                 285

Ile Ile Lys Phe Ser Ser Lys Lys Ile Thr Asp Leu Gly Phe Ile Phe
    290                 295                 300

Lys Tyr Ser Leu Glu Asp Met Phe Thr Gly Ala Ile Glu Thr Cys Arg
305                 310                 315                 320

Glu Lys Gly Leu Leu Pro Lys Val Thr Glu Thr Pro Val Asn Asp Thr
                325                 330                 335

Met Lys Lys
```

```
<210> SEQ ID NO 87
<211> LENGTH: 356
<212> TYPE: PRT
<213> ORGANISM: Arabidopsis thaliana

<400> SEQUENCE: 87

Met Val Ala Val Glu Arg Val Glu Ser Leu Ala Lys Ser Gly Ile Ile
 1               5                  10                  15

Ser Ile Pro Lys Glu Tyr Ile Arg Pro Lys Glu Glu Leu Glu Ser Ile
                20                  25                  30

Asn Asp Val Phe Leu Glu Glu Lys Glu Asp Gly Pro Gln Val Pro
            35                  40                  45

Thr Ile Asp Leu Lys Asn Ile Glu Ser Asp Glu Lys Ile Arg Glu
 50                  55                  60

Asn Cys Ile Glu Glu Leu Lys Lys Ala Ser Leu Asp Trp Gly Val Met
65                  70                  75                  80

His Leu Ile Asn His Gly Ile Pro Ala Asp Leu Met Glu Arg Val Lys
                85                  90                  95

Lys Ala Gly Glu Glu Phe Phe Ser Leu Ser Val Glu Glu Lys Glu Lys
                100                 105                 110

Tyr Ala Asn Asp Gln Ala Thr Gly Lys Ile Gln Gly Tyr Gly Ser Lys
            115                 120                 125

Leu Ala Asn Asn Ala Ser Gly Gln Leu Glu Trp Glu Asp Tyr Phe Phe
130                 135                 140

His Leu Ala Tyr Pro Glu Glu Lys Arg Asp Leu Ser Ile Trp Pro Lys
145                 150                 155                 160

Thr Pro Ser Asp Tyr Ile Glu Ala Thr Ser Glu Tyr Ala Lys Cys Leu
                165                 170                 175

Arg Leu Leu Ala Thr Lys Val Phe Lys Ala Leu Ser Val Gly Leu Gly
            180                 185                 190

Leu Glu Pro Asp Arg Leu Glu Lys Glu Val Gly Gly Leu Glu Glu Leu
        195                 200                 205

Leu Leu Gln Met Lys Ile Asn Tyr Tyr Pro Lys Cys Pro Gln Pro Glu
210                 215                 220

Leu Ala Leu Asp Val Glu Ala His Thr Asp Val Ser Ala Leu Thr Phe
225                 230                 235                 240

Ile Leu His Asn Met Val Pro Gly Leu Gln Leu Phe Tyr Glu Gly Lys
                245                 250                 255

Trp Val Thr Ala Lys Cys Val Pro Asp Ser Ile Val Met His Ile Gly
            260                 265                 270

Asp Thr Leu Glu Ile Leu Ser Asn Gly Lys Tyr Lys Ser Ile Leu His
        275                 280                 285

Arg Gly Leu Val Asn Lys Glu Lys Val Arg Ile Ser Trp Ala Val Phe
    290                 295                 300

Cys Glu Pro Pro Lys Asp Lys Ile Val Leu Lys Pro Leu Pro Glu Met
305                 310                 315                 320

Val Ser Val Glu Ser Pro Ala Lys Phe Pro Pro Arg Thr Phe Ala Gln
                325                 330                 335

His Ile Glu His Lys Leu Phe Gly Lys Glu Gln Glu Glu Leu Val Ser
            340                 345                 350

Glu Lys Asn Asp
        355

<210> SEQ ID NO 88
<211> LENGTH: 362
```

```
<212> TYPE: PRT
<213> ORGANISM: Perilla frutescens

<400> SEQUENCE: 88

Met Val Thr Ser Ala Met Gly Pro Ser Pro Arg Val Glu Glu Leu Ala
1               5                   10                  15

Arg Ser Gly Leu Asp Thr Ile Pro Lys Asp Tyr Val Arg Pro Glu Glu
            20                  25                  30

Glu Leu Lys Ser Ile Ile Gly Asn Ile Leu Ala Glu Lys Ser Ser
        35                  40                  45

Glu Gly Pro Gln Leu Pro Thr Ile Asp Leu Glu Glu Met Asp Ser Arg
    50                  55                  60

Asp Glu Glu Gly Arg Lys Lys Cys His Glu Leu Lys Lys Ala Ala
65              70                  75                  80

Thr Asp Trp Gly Val Met His Leu Ile Asn His Gly Ile Pro Glu Glu
                85                  90                  95

Leu Ile Asp Arg Val Lys Ala Ala Gly Lys Glu Phe Phe Glu Leu Pro
            100                 105                 110

Val Glu Glu Lys Glu Ala Tyr Ala Asn Asp Gln Ala Ala Gly Asn Val
        115                 120                 125

Gln Gly Tyr Gly Ser Lys Leu Ala Asn Asn Ala Ser Gly Gln Leu Glu
    130                 135                 140

Trp Glu Asp Tyr Phe Phe His Cys Val Tyr Pro Glu His Lys Thr Asp
145                 150                 155                 160

Leu Ser Ile Trp Pro Thr Lys Pro Pro Asp Tyr Ile Pro Ala Thr Ser
                165                 170                 175

Glu Tyr Ala Lys Gln Leu Arg Ala Leu Ala Thr Lys Ile Leu Ser Val
            180                 185                 190

Leu Ser Ile Gly Leu Gly Leu Glu Lys Gly Arg Leu Glu Lys Glu Val
        195                 200                 205

Gly Gly Ala Glu Asp Leu Ile Val Gln Met Lys Ile Asn Phe Tyr Pro
    210                 215                 220

Lys Cys Pro Gln Pro Glu Leu Ala Leu Gly Trp Glu Ala His Thr Asp
225                 230                 235                 240

Val Ser Ala Leu Thr Phe Ile Leu His Asn Met Val Pro Gly Leu Gln
                245                 250                 255

Leu Phe Tyr Glu Asp Lys Trp Val Thr Ala Lys Cys Val Pro Asn Ser
            260                 265                 270

Ile Ile Met His Ile Gly Asp Thr Leu Glu Ile Leu Ser Asn Gly Lys
        275                 280                 285

Tyr Lys Ser Ile Leu His Arg Gly Leu Val Asn Lys Glu Lys Val Arg
    290                 295                 300

Ile Ser Trp Ala Val Phe Cys Glu Pro Pro Lys Glu Lys Ile Val Leu
305                 310                 315                 320

Gln Pro Leu Pro Glu Thr Val Ser Glu Val Pro Pro Arg Phe Pro
                325                 330                 335

Pro Arg Thr Phe Ala Gln His Leu Lys His Lys Leu Phe Arg Lys Thr
            340                 345                 350

Asp Gly Asp Leu Asp Glu Lys Pro Thr Tyr
        355                 360

<210> SEQ ID NO 89
<211> LENGTH: 354
<212> TYPE: PRT
<213> ORGANISM: Forsythia x intermedia
```

<400> SEQUENCE: 89

| | | | | | | | | | | | | | | | |
|---|---|---|---|---|---|---|---|---|---|---|---|---|---|---|---|
|Met|Ala|Lys|Val|Val|Asn|Pro|Arg|Val|Glu|Ile|Leu|Ala|Ser|Asn|Gly|
|1| | | |5| | | | |10| | | | |15| |

Ile Gln Ser Ile Pro Lys Glu Tyr Val Arg Pro Gln Glu Glu Leu Glu
                20                  25                  30

Ser Ile Arg Asp Val Phe Glu Glu Met Ser Asp Glu Gly Pro Gln
            35                  40                  45

Leu Pro Thr Ile Asp Leu Glu Gly Leu Asp Ser Asp Lys Gln Val
    50                  55                  60

Arg Glu Lys Cys His Gln Glu Leu Ile Lys Ala Ser Lys Glu Trp Gly
65                  70                  75                  80

Val Met His Leu Val Lys His Gly Ile Ser Asp Glu Leu Ile Asp Arg
                85                  90                  95

Val Lys Met Ala Gly Lys Ala Phe Phe Asn Gln Ser Val Glu Lys Glu
            100                 105                 110

Lys Tyr Ala Asn Asp Gln Ala Ser Gly Asn Val Gln Gly Tyr Gly Ser
    115                 120                 125

Lys Leu Ala Asn Asn Ala Ser Gly Gln Leu Glu Trp Gln Asp Tyr Phe
130                 135                 140

Phe His Cys Ile Phe Pro Glu Glu Lys Arg Asp Leu Ser Ile Cys Pro
145                 150                 155                 160

Lys Thr Pro Thr Asp Tyr Ile Pro Ala Ile Ser Glu Tyr Ala Lys Gln
                165                 170                 175

Leu Arg Asp Leu Thr Ser Lys Met Leu Ser Val Leu Ser Leu Gly Leu
            180                 185                 190

Gly Leu Glu Gln Gly Arg Leu Glu Lys Glu Val Gly Gly Met Glu Glu
    195                 200                 205

Leu Leu Leu Gln Leu Lys Ile Asn Tyr Tyr Pro Lys Cys Pro Gln Pro
210                 215                 220

Glu Leu Ala Leu Gly Val Glu Ala His Thr Asp Ile Ser Ala Leu Thr
225                 230                 235                 240

Phe Ile Leu His Asn Met Val Pro Gly Leu Gln Leu Phe Tyr Lys Gly
                245                 250                 255

Lys Trp Val Thr Ala Lys Cys Val Pro Asn Ser Ile Ile Met His Ile
            260                 265                 270

Gly Asp Thr Ile Glu Ile Leu Ser Asn Gly Lys Tyr Lys Ser Ile Leu
    275                 280                 285

His Arg Gly Leu Val Asn Lys Glu Lys Val Arg Ile Ser Trp Ala Val
290                 295                 300

Phe Cys Glu Pro Pro Arg Glu Lys Ile Leu Lys Pro Leu Pro Glu
305                 310                 315                 320

Thr Val Ser Glu Ala Glu Pro Ser Arg Phe Pro Pro Arg Thr Phe Ala
                325                 330                 335

Gln His Val Met Asn Lys Leu Phe Arg Lys Ser Glu Asp Ser Gly Glu
            340                 345                 350

Thr Lys

<210> SEQ ID NO 90
<211> LENGTH: 371
<212> TYPE: PRT
<213> ORGANISM: Ipomoea nil

<400> SEQUENCE: 90

Met Val Ser Thr Ile Thr Ala Thr Val Pro Ser Arg Val Glu Arg Leu
1               5                   10                  15

Ala Ser Ser Gly Ile Glu Arg Ile Pro Lys Glu Tyr Ile Arg Pro Glu
                20                  25                  30

Glu Glu Arg Arg Ser Ile Gly Asp Ile Phe Glu Glu Lys Ile Ala
        35                  40                  45

Gly Gly Pro Gln Val Pro Thr Val Asp Leu Lys Gly Ile Asn Ser Glu
    50                  55                  60

Asp Leu Glu Val Arg Glu Lys Cys Arg Glu Glu Leu Arg Lys Ala Ala
65                  70                  75                  80

Val Asp Trp Gly Val Met His Leu Val Asn His Gly Ile Ser Glu Glu
                85                  90                  95

Leu Thr Gly Arg Val Lys Ala Ala Gly Glu Gly Phe Phe Gly Gln Pro
            100                 105                 110

Ile Glu Glu Lys Glu Lys Tyr Ala Asn Asp Gln Ala Ala Gly Asn Val
            115                 120                 125

Gln Gly Tyr Gly Ser Lys Leu Ala Asn Asn Ala Ser Gly Gln Leu Glu
        130                 135                 140

Trp Glu Asp Tyr Phe Phe His Cys Ile Phe Pro Glu Asp Lys Thr Asp
145                 150                 155                 160

Leu Ser Ile Trp Pro Lys Thr Pro Ser Asp Tyr Ile Asp Ala Thr Lys
                165                 170                 175

Glu Tyr Ala Lys Gln Leu Arg Ala Leu Ala Thr Lys Val Leu Ala Val
            180                 185                 190

Leu Ser Leu Gly Leu Gly Leu Glu Gly Arg Leu Glu Lys Glu Val
            195                 200                 205

Gly Gly Met Glu Glu Leu Leu Leu Gln Met Lys Ile Asn Tyr Tyr Pro
    210                 215                 220

Lys Cys Pro Gln Pro Glu Leu Ala Leu Gly Val Glu Ala His Thr Asp
225                 230                 235                 240

Val Ser Ala Leu Thr Phe Ile Leu His Asn Met Val Ala Gly Leu Gln
                245                 250                 255

Leu Phe Tyr Gly Gly Lys Trp Val Thr Ala Lys Cys Val Pro Asn Ser
            260                 265                 270

Ile Ile Met His Val Gly Asp Thr Val Glu Ile Leu Ser Asn Gly Lys
            275                 280                 285

Tyr Lys Ser Ile Leu His Arg Gly Val Val Asn Arg Glu Lys Val Arg
    290                 295                 300

Val Ser Trp Ala Val Phe Cys Glu Pro Pro Lys Asp Lys Ile Leu Leu
305                 310                 315                 320

Gln Pro Leu Pro Glu Thr Val Ser Glu Ala Glu Pro Arg Phe Pro
                325                 330                 335

Pro Arg Thr Phe Ala Gln His Ile Lys His Lys Leu Phe Arg Gln Ser
            340                 345                 350

Asp Gln Glu Ala Ala Asp Thr Pro Lys Pro Asp Asn Asp Asp His His
        355                 360                 365

Gln Ser Asn
    370

<210> SEQ ID NO 91
<211> LENGTH: 346
<212> TYPE: PRT
<213> ORGANISM: Vitis vinifera

<400> SEQUENCE: 91

Met Thr Val Ser Pro Val Pro Ser Pro Lys Gly Arg Val Leu Ile Ala
1               5                   10                  15

Gly Ala Thr Gly Phe Ile Gly Gln Phe Val Ala Ala Ser Leu Asp
              20                  25                  30

Ala His Arg Pro Thr Tyr Ile Leu Ala Arg Pro Gly Pro Arg Ser Pro
             35                  40                  45

Ser Lys Ala Asn Ile Phe Lys Ala Leu Glu Asp Lys Gly Ala Ile Ile
 50                  55                  60

Val Tyr Gly Leu Ile Asn Glu Gln Glu Ala Met Glu Lys Ile Leu Lys
 65                  70                  75                  80

Glu His Glu Ile Asp Ile Val Val Ser Thr Val Gly Gly Ser Ile
                 85                  90                  95

Leu Asp Gln Ile Ala Leu Val Lys Ala Met Lys Ala Val Gly Thr Ile
             100                 105                 110

Lys Arg Phe Leu Pro Ser Glu Phe Gly His Asp Val Asn Arg Ala Asp
             115                 120                 125

Pro Val Glu Pro Gly Leu Asn Met Tyr Arg Glu Lys Arg Val Arg
         130                 135                 140

Gln Leu Val Glu Glu Ser Gly Ile Pro Phe Thr Tyr Ile Cys Cys Asn
145                 150                 155                 160

Ser Ile Ala Ser Trp Pro Tyr Tyr Asn Asn Ile His Pro Ser Glu Val
                165                 170                 175

Leu Pro Pro Thr Asp Phe Phe Gln Ile Tyr Gly Asp Gly Asn Val Lys
             180                 185                 190

Ala Tyr Phe Val Ala Gly Thr Asp Ile Gly Lys Phe Thr Met Lys Thr
         195                 200                 205

Val Asp Asp Val Arg Thr Leu Asn Lys Ser Val His Phe Arg Pro Ser
210                 215                 220

Cys Asn Cys Leu Asn Ile Asn Glu Leu Ala Ser Val Trp Glu Lys Lys
225                 230                 235                 240

Ile Gly Arg Thr Leu Pro Arg Val Thr Val Thr Glu Asp Asp Leu Leu
                245                 250                 255

Ala Ala Ala Gly Glu Asn Ile Ile Pro Gln Ser Val Val Ala Ala Phe
             260                 265                 270

Thr His Asp Ile Phe Ile Lys Gly Cys Gln Val Asn Phe Ser Ile Asp
         275                 280                 285

Gly Pro Glu Asp Val Glu Val Thr Thr Leu Tyr Pro Glu Asp Ser Phe
290                 295                 300

Arg Thr Val Glu Glu Cys Phe Gly Glu Tyr Ile Val Lys Ile Glu Glu
305                 310                 315                 320

Lys Gln Pro Thr Ala Asp Ser Ala Ile Ala Asn Thr Gly Pro Val Val
                325                 330                 335

Gly Met Arg Gln Val Thr Ala Thr Cys Ala
            340                 345

<210> SEQ ID NO 92
<211> LENGTH: 348
<212> TYPE: PRT
<213> ORGANISM: Lotus uliginosus

<400> SEQUENCE: 92

Met Val Ser Thr Ala Ala Ile Pro Pro Ala Thr Ala Gly Arg Ile Leu
1               5                   10                  15

Ile Ile Gly Ala Thr Gly Phe Met Gly Gln Phe Val Thr Lys Ala Ser
              20                  25                  30

Leu Gly Phe Gly Arg Ser Thr Tyr Leu Leu Arg Pro Gly Pro Leu
             35                  40                  45

-continued

```
Thr Pro Ser Lys Ala Ala Ile Val Lys Ser Phe Gln Asp Arg Gly Ala
     50                  55                  60

Lys Val Ile His Gly Val Ile Asn Asp Lys Glu Leu Met Val Lys Ile
 65                  70                  75                  80

Leu Lys Asp Tyr Glu Ile Asp Val Val Ile Ser Leu Val Gly Gly Gly
                 85                  90                  95

Asn Leu Met Asp Gln Arg Thr Leu Val Asp Ala Ile Lys Ser Val Lys
                100                 105                 110

Thr Val Lys Arg Phe Leu Pro Ser Glu Phe Gly His Asp Thr Asp Arg
            115                 120                 125

Ala Asn Pro Val Glu Pro Gly Leu Ala Met Tyr Lys Glu Lys Arg Leu
        130                 135                 140

Ile Arg Arg Leu Ile Glu Glu Ser Gly Ile Pro Tyr Thr Tyr Ile Cys
145                 150                 155                 160

Cys Asn Ser Ile Ala Ser Trp Pro Tyr His Asp Asn Cys His Pro Ser
                165                 170                 175

Lys Val Pro Pro Val Asp Gln Phe Leu Ile Tyr Gly Asp Gly Thr
            180                 185                 190

Val Lys Ala Tyr Phe Val Asp Gly Asn Asp Ile Gly Lys Phe Thr Met
        195                 200                 205

Lys Ala Ile Asp Asp Ile Arg Thr Arg Asn Lys Asn Val His Phe Arg
    210                 215                 220

Pro Pro Ser Asn Cys Tyr Ser Ile Asn Glu Leu Ala Ser Leu Trp Glu
225                 230                 235                 240

Lys Ile Ile Gly Arg Lys Ile Pro Arg Ala Ile Ile Ser Ala Asp Asp
                245                 250                 255

Leu Leu Ala Ala Ala Glu Asn Cys Ile Pro Gly Ser Ile Val Ala
            260                 265                 270

Ala Phe Thr His Asp Ile Phe Ile Asn Gly Cys Gln Ile Asn Phe Thr
        275                 280                 285

Ile Asp Gly Pro Asn Asp Ile Glu Ile Gly Thr Leu Tyr Pro Asp Glu
    290                 295                 300

Lys Phe Arg Cys Leu Glu Glu Cys Phe Lys Asp Phe Val Pro Met Thr
305                 310                 315                 320

His Asp Met Asn Val His Val Gly Thr Thr Glu Asn Asn Asn Arg Lys
                325                 330                 335

Ser Leu Val Glu Val Ala Pro Ile Ser Ala Met Gly
            340                 345
```

<210> SEQ ID NO 93
<211> LENGTH: 382
<212> TYPE: PRT
<213> ORGANISM: Desmodium uncinatum

<400> SEQUENCE: 93

```
Met Thr Val Ser Gly Ala Ile Pro Ser Met Thr Lys Asn Arg Thr Leu
  1               5                  10                  15

Val Val Gly Gly Thr Gly Phe Ile Gly Gln Phe Ile Thr Lys Ala Ser
                 20                  25                  30

Leu Gly Phe Gly Tyr Pro Thr Phe Leu Leu Val Arg Pro Gly Pro Val
             35                  40                  45

Ser Pro Ser Lys Ala Val Ile Ile Lys Thr Phe Gln Asp Lys Gly Ala
     50                  55                  60

Lys Val Ile Tyr Gly Val Ile Asn Asp Lys Glu Cys Met Glu Lys Ile
 65                  70                  75                  80
```

```
Leu Lys Glu Tyr Glu Ile Asp Val Val Ile Ser Leu Val Gly Gly Ala
                 85                  90                  95

Arg Leu Leu Asp Gln Leu Thr Leu Leu Glu Ala Ile Lys Ser Val Lys
            100                 105                 110

Thr Ile Lys Arg Phe Leu Pro Ser Glu Phe Gly His Asp Val Asp Arg
            115                 120                 125

Thr Asp Pro Val Glu Pro Gly Leu Thr Met Tyr Lys Glu Lys Arg Leu
        130                 135                 140

Val Arg Arg Ala Val Glu Glu Tyr Gly Ile Pro Phe Thr Asn Ile Cys
145                 150                 155                 160

Cys Asn Ser Ile Ala Ser Trp Pro Tyr Tyr Asp Asn Cys His Pro Ser
                165                 170                 175

Gln Val Pro Pro Met Asp Gln Phe Gln Ile Tyr Gly Asp Gly Asn
            180                 185                 190

Thr Lys Ala Tyr Phe Ile Asp Gly Asn Asp Ile Gly Lys Phe Thr Met
            195                 200                 205

Lys Thr Ile Asp Asp Ile Arg Thr Leu Asn Lys Asn Val His Phe Arg
        210                 215                 220

Pro Ser Ser Asn Cys Tyr Ser Ile Asn Glu Leu Ala Ser Leu Trp Glu
225                 230                 235                 240

Lys Lys Ile Gly Arg Thr Leu Pro Arg Phe Thr Val Thr Ala Asp Lys
                245                 250                 255

Leu Leu Ala His Ala Ala Glu Asn Ile Ile Pro Glu Ser Ile Val Ser
            260                 265                 270

Ser Phe Thr His Asp Ile Phe Ile Asn Gly Cys Gln Val Asn Phe Ser
        275                 280                 285

Ile Asp Glu His Ser Asp Val Glu Ile Asp Thr Leu Tyr Pro Asp Glu
        290                 295                 300

Lys Phe Arg Ser Leu Asp Asp Cys Tyr Glu Asp Phe Val Pro Met Val
305                 310                 315                 320

His Asp Lys Ile His Ala Gly Lys Ser Gly Glu Ile Lys Ile Lys Asp
                325                 330                 335

Gly Lys Pro Leu Val Gln Thr Gly Thr Ile Glu Glu Ile Asn Lys Asp
            340                 345                 350

Ile Lys Thr Leu Val Glu Thr Gln Pro Asn Glu Glu Ile Lys Lys Asp
        355                 360                 365

Met Lys Ala Leu Val Glu Ala Val Pro Ile Ser Ala Met Gly
        370                 375                 380

<210> SEQ ID NO 94
<211> LENGTH: 338
<212> TYPE: PRT
<213> ORGANISM: Medicago truncatula

<400> SEQUENCE: 94

Met Ala Ser Ile Lys Gln Ile Glu Ile Glu Lys Lys Lys Ala Cys Val
1               5                   10                  15

Ile Gly Gly Thr Gly Phe Val Ala Ser Leu Leu Ile Lys Gln Leu Leu
            20                  25                  30

Glu Lys Gly Tyr Ala Val Asn Thr Thr Val Arg Asp Leu Asp Ser Ala
        35                  40                  45

Asn Lys Thr Ser His Leu Ile Ala Leu Gln Ser Leu Gly Glu Leu Asn
    50                  55                  60

Leu Phe Lys Ala Glu Leu Thr Ile Glu Glu Asp Phe Asp Ala Pro Ile
65                  70                  75                  80
```

Ser Gly Cys Glu Leu Val Phe Gln Leu Ala Thr Pro Val Asn Phe Ala
                85                  90                  95

Ser Gln Asp Pro Glu Asn Asp Met Ile Lys Pro Ala Ile Lys Gly Val
            100                 105                 110

Leu Asn Val Leu Lys Ala Cys Val Arg Ala Lys Glu Val Lys Arg Val
            115                 120                 125

Ile Leu Thr Ser Ser Ala Ala Ala Val Thr Ile Asn Glu Leu Glu Gly
    130                 135                 140

Thr Gly His Val Met Asp Glu Thr Asn Trp Ser Asp Val Glu Phe Leu
145                 150                 155                 160

Asn Thr Ala Lys Pro Pro Thr Trp Gly Tyr Pro Val Ser Lys Val Leu
                165                 170                 175

Ala Glu Lys Ala Ala Trp Lys Phe Ala Glu Glu Asn Asn Ile Asp Leu
            180                 185                 190

Ile Thr Val Ile Pro Thr Leu Thr Ile Gly Pro Ser Leu Thr Gln Asp
            195                 200                 205

Ile Pro Ser Ser Val Ala Met Gly Met Ser Leu Leu Thr Gly Asn Asp
    210                 215                 220

Phe Leu Ile Asn Ala Leu Lys Gly Met Gln Phe Leu Ser Gly Ser Ile
225                 230                 235                 240

Ser Ile Thr His Val Glu Asp Ile Cys Arg Ala His Ile Phe Val Ala
                245                 250                 255

Glu Lys Glu Ser Thr Ser Gly Arg Tyr Ile Cys Cys Ala His Asn Thr
            260                 265                 270

Ser Val Pro Glu Leu Ala Lys Phe Leu Ser Lys Arg Tyr Pro Gln Tyr
            275                 280                 285

Lys Val Pro Thr Glu Phe Asp Asp Phe Pro Ser Lys Ala Lys Leu Ile
    290                 295                 300

Ile Ser Ser Gly Lys Leu Ile Lys Glu Gly Phe Ser Phe Lys His Ser
305                 310                 315                 320

Ile Ala Glu Thr Phe Asp Gln Thr Val Glu Tyr Leu Lys Thr Gln Gly
                325                 330                 335

Ile Lys

<210> SEQ ID NO 95
<211> LENGTH: 342
<212> TYPE: PRT
<213> ORGANISM: Arabidopsis thaliana

<400> SEQUENCE: 95

Met Asp Gln Thr Leu Thr His Thr Gly Ser Lys Lys Ala Cys Val Ile
1               5                   10                  15

Gly Gly Thr Gly Asn Leu Ala Ser Ile Leu Ile Lys His Leu Leu Gln
            20                  25                  30

Ser Gly Tyr Lys Val Asn Thr Thr Val Arg Asp Pro Glu Asn Glu Lys
        35                  40                  45

Lys Ile Ala His Leu Arg Gln Leu Gln Glu Leu Gly Asp Leu Lys Ile
    50                  55                  60

Phe Lys Ala Asp Leu Thr Asp Glu Asp Ser Phe Glu Ser Ser Phe Ser
65                  70                  75                  80

Gly Cys Glu Tyr Ile Phe His Val Ala Thr Pro Ile Asn Phe Lys Ser
                85                  90                  95

Glu Asp Pro Glu Lys Asp Met Ile Lys Pro Ala Ile Gln Gly Val Ile
            100                 105                 110

Asn Val Leu Lys Ser Cys Leu Lys Ser Lys Ser Val Lys Arg Val Ile
            115                 120                 125

Tyr Thr Ser Ser Ala Ala Val Ser Ile Asn Asn Leu Ser Gly Thr
        130                 135                 140

Gly Leu Val Met Asn Glu Glu Asn Trp Thr Asp Ile Asp Phe Leu Thr
145                 150                 155                 160

Glu Glu Lys Pro Phe Asn Trp Gly Tyr Pro Ile Ser Lys Val Leu Ala
                165                 170                 175

Glu Lys Lys Ala Trp Glu Phe Ala Glu Glu Asn Lys Ile Asn Leu Val
            180                 185                 190

Thr Val Ile Pro Ala Leu Ile Ala Gly Asn Ser Leu Leu Ser Asp Pro
        195                 200                 205

Pro Ser Ser Leu Ser Leu Ser Met Ser Phe Ile Thr Gly Lys Glu Met
210                 215                 220

His Val Thr Gly Leu Lys Glu Met Gln Lys Leu Ser Gly Ser Ile Ser
225                 230                 235                 240

Phe Val His Val Asp Asp Leu Ala Arg Ala His Leu Phe Leu Ala Glu
                245                 250                 255

Lys Glu Thr Ala Ser Gly Arg Tyr Ile Cys Cys Ala Tyr Asn Thr Ser
            260                 265                 270

Val Pro Glu Ile Ala Asp Phe Leu Ile Gln Arg Tyr Pro Lys Tyr Asn
        275                 280                 285

Val Leu Ser Glu Phe Glu Gly Leu Ser Ile Pro Lys Leu Thr Leu
        290                 295                 300

Ser Ser Gln Lys Leu Ile Asn Glu Gly Phe Arg Phe Glu Tyr Gly Ile
305                 310                 315                 320

Asn Glu Met Tyr Asp Gln Met Ile Glu Tyr Phe Glu Ser Lys Gly Leu
                325                 330                 335

Ile Lys Ala Lys Glu Ser
            340

<210> SEQ ID NO 96
<211> LENGTH: 337
<212> TYPE: PRT
<213> ORGANISM: Camellia sinensis

<400> SEQUENCE: 96

Met Glu Ala Gln Pro Thr Ala Pro Lys Ala Cys Val Val Gly Gly
1               5                   10                  15

Thr Gly Phe Val Ala Ala Thr Leu Ile Lys Leu Leu Leu Glu Lys Gly
            20                  25                  30

Tyr Ala Val Asn Thr Thr Val Arg Asp Pro Gly Asn Gln Lys Lys Thr
        35                  40                  45

Ser His Leu Leu Ala Leu Lys Gly Ser Gly Asn Leu Lys Ile Phe Arg
    50                  55                  60

Ala Asp Leu Thr Asp Glu Gln Ser Phe Asp Thr Pro Val Ala Gly Cys
65                  70                  75                  80

Asp Leu Val Phe His Val Ala Thr Pro Val Asn Phe Ala Ser Glu Asp
                85                  90                  95

Pro Glu Asn Asp Met Ile Lys Pro Ala Ile Gln Gly Val Val Asn Val
            100                 105                 110

Leu Lys Ala Cys Ala Lys Ala Gly Thr Val Lys Arg Val Ile Leu Thr
        115                 120                 125

Ser Ser Ala Ala Ala Val Ser Ile Asn Lys Leu Asn Gly Thr Gly Leu
    130                 135                 140

```
Val Met Asp Glu Ser His Trp Thr Asp Thr Glu Phe Leu Asn Ser Ala
145                 150                 155                 160

Lys Pro Pro Thr Trp Gly Tyr Pro Leu Ser Lys Thr Leu Ala Glu Lys
                165                 170                 175

Ala Ala Trp Lys Phe Ala Glu Glu Asn Asn Ile Asn Leu Ile Thr Val
            180                 185                 190

Ile Pro Thr Leu Met Ala Gly Pro Ser Leu Thr Ala Asp Val Pro Ser
        195                 200                 205

Ser Ile Gly Leu Ala Met Ser Leu Ile Thr Gly Asn Glu Phe Leu Ile
    210                 215                 220

Asn Gly Leu Lys Gly Met Gln Met Leu Ser Gly Ser Ile Ser Ile Ser
225                 230                 235                 240

His Val Glu Asp Val Cys Arg Ala His Val Phe Val Ala Glu Lys Glu
                245                 250                 255

Ser Ala Ser Gly Arg Tyr Ile Cys Cys Ala Val Ser Thr Ser Val Pro
                260                 265                 270

Glu Leu Ala Lys Phe Leu Asn Lys Arg Tyr Pro Glu Tyr Asn Val Pro
            275                 280                 285

Thr Asp Phe Gly Asp Phe Pro Ser Lys Ala Lys Leu Ile Leu Ser Ser
        290                 295                 300

Glu Lys Leu Thr Lys Glu Gly Phe Ser Phe Lys Tyr Gly Ile Glu Glu
305                 310                 315                 320

Ile Tyr Asp Gln Ser Val Glu Tyr Phe Lys Ala Lys Gly Ile Leu Lys
                325                 330                 335

Asn

<210> SEQ ID NO 97
<211> LENGTH: 1397
<212> TYPE: DNA
<213> ORGANISM: Coffea canephora

<400> SEQUENCE: 97
cggagctaca aagctagcag ctacctgcaa aactctacgt accttaattt ttctcttttt       60
ccgagcaaaa atggttaccg tcgaggaagt taggagggct caaagggccg aaggaccggc      120
gacgatcatg gccatcggaa cagctacgcc accaaattgt gtcgagcaaa gcacttatcc      180
ggattattat tttcgcatta ctgatagtga cataagact gagctcaaag aaaagtttaa       240
gcgcatgtgt gacaaatcca tgattaagaa gcgctacatg tacttgacag aggaaatctt      300
gaaggaaaat cccaatattt gtgcttacat ggcaccctca ctagatgcta ggcaagacat      360
ggtggttgtt gaagtaccaa aactgggcaa agaagcagcc caaaaggcca ttaaggaatg      420
gggtcagccc aagtccaaga tcacccatct agtcttctgt accaccagtg gtgtggacat      480
gcctggagca gactatcagc tcaccaaact cttgggcctt cgcccgtccg tcaagcgcct      540
catgatgtac caacagggtt gttttgccgg tgggacggtc ctccggctag ccaaggacct      600
ggctgagaac aacaaaggtg cccgtgtcct cgtcgtctgc tcagaaatca ctgcagttac      660
attccgtggc ccaagtgatt cgcatttgga tagccttgta ggccaagccc tgtttggaga      720
tggggcagct gccatcatta tcggcgccga tcccgttccc gaagttgaga ggcccttgtt      780
tgagctcgtt acagcagccc aaaccattct tccagacagt cacggggcta tcgacgccca      840
tcttcgtgag gttgggctta cgttccatct tctcaaggat gttcccgggt taatctccaa      900
gaacattgaa aagagcctga agaagcattg tgagcctctc ggtatttctg attggaactc      960
actcttctgg attgcacatc ctggtgggcc tgcaatttta gaccaggtgg agcaaaaact     1020
```

-continued

```
ggctcttaaa cccgaaaaat tacgggctac taggcatgtg ctgagtgagt atggaaatat    1080
gtcaagtgcc tgtgtcgtgt tcattcttga cgagatgaga aaggcctcag ccaaggatgg    1140
attcaacacc acaggggaag cttagactg gggtgtgctc tttggttttg ggcctggact     1200
cacagttgag acagtggttc ttcacagcgc cacgattcaa aagtaatcat gtttgaatct    1260
ttcaatgaat attccaaatc tgtattacta tggagtacta agtaattttt tttttatgtg    1320
tgccttaagt ttatgtaaca atcatgatga caataaggtg ttacaccttg ttctggcaaa    1380
aaaaaaaaaa aaaaaaa                                                   1397
```

<210> SEQ ID NO 98
<211> LENGTH: 19
<212> TYPE: DNA
<213> ORGANISM: Artificial Sequence
<220> FEATURE:
<223> OTHER INFORMATION: Primer or probe.

<400> SEQUENCE: 98
gacgtaagag cttccatcc                                                 19

<210> SEQ ID NO 99
<211> LENGTH: 18
<212> TYPE: DNA
<213> ORGANISM: Artificial Sequence
<220> FEATURE:
<223> OTHER INFORMATION: Primer or probe.

<400> SEQUENCE: 99
ggccttcaag ttctcctc                                                  18

<210> SEQ ID NO 100
<211> LENGTH: 19
<212> TYPE: DNA
<213> ORGANISM: Artificial Sequence
<220> FEATURE:
<223> OTHER INFORMATION: Primer or probe.

<400> SEQUENCE: 100
catacttatc caccacagg                                                 19

<210> SEQ ID NO 101
<211> LENGTH: 36
<212> TYPE: DNA
<213> ORGANISM: Artificial Sequence
<220> FEATURE:
<223> OTHER INFORMATION: Primer or probe.
<220> FEATURE:
<221> NAME/KEY: modified_base
<222> LOCATION: (24)..(25)
<223> OTHER INFORMATION: I
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: modified_base
<222> LOCATION: (29)..(30)
<223> OTHER INFORMATION: I
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (34)..(35)
<223> OTHER INFORMATION: I
<220> FEATURE:
<221> NAME/KEY: misc_feature
<222> LOCATION: (34)..(35)

<223> OTHER INFORMATION: n is a, c, g, or t

<400> SEQUENCE: 101
ggccacgcgt cgactagtac gggnngggnn gggnng                36

<210> SEQ ID NO 102
<211> LENGTH: 20
<212> TYPE: DNA
<213> ORGANISM: Artificial Sequence
<220> FEATURE:
<223> OTHER INFORMATION: Primer or probe.

<400> SEQUENCE: 102
ggccacgcgt cgactagtac                20

<210> SEQ ID NO 103
<211> LENGTH: 19
<212> TYPE: DNA
<213> ORGANISM: Artificial Sequence
<220> FEATURE:
<223> OTHER INFORMATION: Primer or probe.

<400> SEQUENCE: 103
ctcgggtttg ccattcatc                19

<210> SEQ ID NO 104
<211> LENGTH: 19
<212> TYPE: DNA
<213> ORGANISM: Artificial Sequence
<220> FEATURE:
<223> OTHER INFORMATION: Primer or probe.

<400> SEQUENCE: 104
cctccaaatg cctcagatc                19

<210> SEQ ID NO 105
<211> LENGTH: 19
<212> TYPE: DNA
<213> ORGANISM: Artificial Sequence
<220> FEATURE:
<223> OTHER INFORMATION: Primer or probe.

<400> SEQUENCE: 105
cctgattgtg ttgctcggc                19

<210> SEQ ID NO 106
<211> LENGTH: 22
<212> TYPE: DNA
<213> ORGANISM: Artificial Sequence
<220> FEATURE:
<223> OTHER INFORMATION: Primer or probe.

<400> SEQUENCE: 106
ttcaatatgt ccacagcttc tg                22

<210> SEQ ID NO 107
<211> LENGTH: 22
<212> TYPE: DNA
<213> ORGANISM: Artificial Sequence
<220> FEATURE:
<223> OTHER INFORMATION: Primer or probe.

<400> SEQUENCE: 107
tgacgtcttg gttgtgttgc tc                22

<210> SEQ ID NO 108

```
<211> LENGTH: 26
<212> TYPE: DNA
<213> ORGANISM: Artificial Sequence
<220> FEATURE:
<223> OTHER INFORMATION: Primer or probe.

<400> SEQUENCE: 108
gcaattgtca ccttatatttt ttgcac                                            26

<210> SEQ ID NO 109
<211> LENGTH: 23
<212> TYPE: DNA
<213> ORGANISM: Artificial Sequence
<220> FEATURE:
<223> OTHER INFORMATION: Primer or probe.

<400> SEQUENCE: 109
ccacaaagca acacagaatt cag                                                23

<210> SEQ ID NO 110
<211> LENGTH: 20
<212> TYPE: DNA
<213> ORGANISM: Artificial Sequence
<220> FEATURE:
<223> OTHER INFORMATION: Primer or probe.

<400> SEQUENCE: 110
taatacgact cactataggg                                                    20

<210> SEQ ID NO 111
<211> LENGTH: 20
<212> TYPE: DNA
<213> ORGANISM: Artificial Sequence
<220> FEATURE:
<223> OTHER INFORMATION: Primer or probe.

<400> SEQUENCE: 111
attaaccctc actaaaggga                                                    20

<210> SEQ ID NO 112
<211> LENGTH: 21
<212> TYPE: DNA
<213> ORGANISM: Artificial Sequence
<220> FEATURE:
<223> OTHER INFORMATION: Primer or probe.

<400> SEQUENCE: 112
tacccgaccc gaaccccaat t                                                  21

<210> SEQ ID NO 113
<211> LENGTH: 21
<212> TYPE: DNA
<213> ORGANISM: Artificial Sequence
<220> FEATURE:
<223> OTHER INFORMATION: Primer or probe.

<400> SEQUENCE: 113
acaccagatg aatgcacact g                                                  21

<210> SEQ ID NO 114
<211> LENGTH: 24
<212> TYPE: DNA
<213> ORGANISM: Artificial Sequence
<220> FEATURE:
<223> OTHER INFORMATION: Primer or probe.

<400> SEQUENCE: 114
```

-continued

```
gatcccgttc cgaagttga gagg                                            24

<210> SEQ ID NO 115
<211> LENGTH: 25
<212> TYPE: DNA
<213> ORGANISM: Artificial Sequence
<220> FEATURE:
<223> OTHER INFORMATION: Primer or probe.

<400> SEQUENCE: 115
catgattact tttgaatcgt ggcgc                                          25

<210> SEQ ID NO 116
<211> LENGTH: 24
<212> TYPE: DNA
<213> ORGANISM: Artificial Sequence
<220> FEATURE:
<223> OTHER INFORMATION: Primer or probe.

<400> SEQUENCE: 116
cccacctgga gcctctattc tgtt                                           24

<210> SEQ ID NO 117
<211> LENGTH: 20
<212> TYPE: DNA
<213> ORGANISM: Artificial Sequence
<220> FEATURE:
<223> OTHER INFORMATION: Primer or probe.

<400> SEQUENCE: 117
ccccgtcggc ctcaagtttc                                                20

<210> SEQ ID NO 118
<211> LENGTH: 24
<212> TYPE: DNA
<213> ORGANISM: Artificial Sequence
<220> FEATURE:
<223> OTHER INFORMATION: Primer or probe.

<400> SEQUENCE: 118
gctataattt ctgcccccgt ggac                                           24

<210> SEQ ID NO 119
<211> LENGTH: 24
<212> TYPE: DNA
<213> ORGANISM: Artificial Sequence
<220> FEATURE:
<223> OTHER INFORMATION: Primer or probe.

<400> SEQUENCE: 119
gaagaccatg aatcccaaca ccag                                           24

<210> SEQ ID NO 120
<211> LENGTH: 21
<212> TYPE: DNA
<213> ORGANISM: Artificial Sequence
<220> FEATURE:
<223> OTHER INFORMATION: Primer or probe.

<400> SEQUENCE: 120
gaacaggccc atcccttatt g                                              21

<210> SEQ ID NO 121
<211> LENGTH: 17
<212> TYPE: DNA
<213> ORGANISM: Artificial Sequence
<220> FEATURE:
```

-continued

<223> OTHER INFORMATION: Primer or probe.

<400> SEQUENCE: 121
cggcgcttgg cattgta					17

<210> SEQ ID NO 122
<211> LENGTH: 16
<212> TYPE: DNA
<213> ORGANISM: Artificial Sequence
<220> FEATURE:
<223> OTHER INFORMATION: Primer or probe.

<400> SEQUENCE: 122
atgcgcactg acaaca					16

<210> SEQ ID NO 123
<211> LENGTH: 23
<212> TYPE: DNA
<213> ORGANISM: Artificial Sequence
<220> FEATURE:
<223> OTHER INFORMATION: Primer or probe.

<400> SEQUENCE: 123
gtcaacacct ccatcttcca aaa				23

<210> SEQ ID NO 124
<211> LENGTH: 22
<212> TYPE: DNA
<213> ORGANISM: Artificial Sequence
<220> FEATURE:
<223> OTHER INFORMATION: Primer or probe.

<400> SEQUENCE: 124
tggtaggaca gccttcagtt ca				22

<210> SEQ ID NO 125
<211> LENGTH: 16
<212> TYPE: DNA
<213> ORGANISM: Artificial Sequence
<220> FEATURE:
<223> OTHER INFORMATION: Primer or probe.

<400> SEQUENCE: 125
attgctgcat ttgaag					16

<210> SEQ ID NO 126
<211> LENGTH: 21
<212> TYPE: DNA
<213> ORGANISM: Artificial Sequence
<220> FEATURE:
<223> OTHER INFORMATION: Primer or probe.

<400> SEQUENCE: 126
gctccgctac ccttgtgtta a					21

<210> SEQ ID NO 127
<211> LENGTH: 25
<212> TYPE: DNA
<213> ORGANISM: Artificial Sequence
<220> FEATURE:
<223> OTHER INFORMATION: Primer or probe.

<400> SEQUENCE: 127
caccgagtac aacagctaaa atctg				25

<210> SEQ ID NO 128

```
<211> LENGTH: 15
<212> TYPE: DNA
<213> ORGANISM: Artificial Sequence
<220> FEATURE:
<223> OTHER INFORMATION: Primer or probe.

<400> SEQUENCE: 128
tccacggcac gttga                                                        15

<210> SEQ ID NO 129
<211> LENGTH: 23
<212> TYPE: DNA
<213> ORGANISM: Artificial Sequence
<220> FEATURE:
<223> OTHER INFORMATION: Primer or probe.

<400> SEQUENCE: 129
gtttgccctc tttttggaat gtt                                               23

<210> SEQ ID NO 130
<211> LENGTH: 27
<212> TYPE: DNA
<213> ORGANISM: Artificial Sequence
<220> FEATURE:
<223> OTHER INFORMATION: Primer or probe.

<400> SEQUENCE: 130
tatgggacga aaatacaagg atcttaa                                           27

<210> SEQ ID NO 131
<211> LENGTH: 18
<212> TYPE: DNA
<213> ORGANISM: Artificial Sequence
<220> FEATURE:
<223> OTHER INFORMATION: Primer or probe.

<400> SEQUENCE: 131
tccaagttgt cactagct                                                     18

<210> SEQ ID NO 132
<211> LENGTH: 25
<212> TYPE: DNA
<213> ORGANISM: Artificial Sequence
<220> FEATURE:
<223> OTHER INFORMATION: Primer or probe.

<400> SEQUENCE: 132
ttttggaaga ggagtctaag gttga                                             25

<210> SEQ ID NO 133
<211> LENGTH: 22
<212> TYPE: DNA
<213> ORGANISM: Artificial Sequence
<220> FEATURE:
<223> OTHER INFORMATION: Primer or probe.

<400> SEQUENCE: 133
gcttctccta ccaacaccga at                                                22

<210> SEQ ID NO 134
<211> LENGTH: 18
<212> TYPE: DNA
<213> ORGANISM: Artificial Sequence
<220> FEATURE:
<223> OTHER INFORMATION: Primer or probe.

<400> SEQUENCE: 134
```

```
tggcaacgac ttccggta                                                    18

<210> SEQ ID NO 135
<211> LENGTH: 22
<212> TYPE: DNA
<213> ORGANISM: Artificial Sequence
<220> FEATURE:
<223> OTHER INFORMATION: Primer or probe.

<400> SEQUENCE: 135
gctaagcttg cagctgaagt tg                                               22

<210> SEQ ID NO 136
<211> LENGTH: 22
<212> TYPE: DNA
<213> ORGANISM: Artificial Sequence
<220> FEATURE:
<223> OTHER INFORMATION: Primer or probe.

<400> SEQUENCE: 136
tctctccttt tctcccaaaa cg                                               22

<210> SEQ ID NO 137
<211> LENGTH: 18
<212> TYPE: DNA
<213> ORGANISM: Artificial Sequence
<220> FEATURE:
<223> OTHER INFORMATION: Primer or probe.

<400> SEQUENCE: 137
agtctctaca acaacgct                                                    18

<210> SEQ ID NO 138
<211> LENGTH: 20
<212> TYPE: DNA
<213> ORGANISM: Artificial Sequence
<220> FEATURE:
<223> OTHER INFORMATION: Primer or probe.

<400> SEQUENCE: 138
gctgctgttg tcccaatgaa                                                  20

<210> SEQ ID NO 139
<211> LENGTH: 22
<212> TYPE: DNA
<213> ORGANISM: Artificial Sequence
<220> FEATURE:
<223> OTHER INFORMATION: Primer or probe.

<400> SEQUENCE: 139
cggtgatgtt ggaatctttt ga                                               22

<210> SEQ ID NO 140
<211> LENGTH: 14
<212> TYPE: DNA
<213> ORGANISM: Artificial Sequence
<220> FEATURE:
<223> OTHER INFORMATION: Primer or probe.

<400> SEQUENCE: 140
caggcgaagt tcca                                                        14

<210> SEQ ID NO 141
<211> LENGTH: 22
<212> TYPE: DNA
<213> ORGANISM: Artificial Sequence
<220> FEATURE:
```

```
<223> OTHER INFORMATION: Primer or probe.

<400> SEQUENCE: 141
gtaatacgac tcactatagg gc                                          22

<210> SEQ ID NO 142
<211> LENGTH: 19
<212> TYPE: DNA
<213> ORGANISM: Artificial Sequence
<220> FEATURE:
<223> OTHER INFORMATION: Primer or probe.

<400> SEQUENCE: 142
actatagggc acgcgtggt                                              19

<210> SEQ ID NO 143
<211> LENGTH: 28
<212> TYPE: DNA
<213> ORGANISM: Artificial Sequence
<220> FEATURE:
<223> OTHER INFORMATION: Primer or probe.

<400> SEQUENCE: 143
ttccctccat gcaaggcttt gtttctcg                                    28

<210> SEQ ID NO 144
<211> LENGTH: 28
<212> TYPE: DNA
<213> ORGANISM: Artificial Sequence
<220> FEATURE:
<223> OTHER INFORMATION: Primer or probe.

<400> SEQUENCE: 144
ggtcctagcc actgtggtga agtacgaa                                    28

<210> SEQ ID NO 145
<211> LENGTH: 30
<212> TYPE: DNA
<213> ORGANISM: Artificial Sequence
<220> FEATURE:
<223> OTHER INFORMATION: Primer or probe.

<400> SEQUENCE: 145
gcccacatag caaaattgag ttcagcgaat                                  30

<210> SEQ ID NO 146
<211> LENGTH: 30
<212> TYPE: DNA
<213> ORGANISM: Artificial Sequence
<220> FEATURE:
<223> OTHER INFORMATION: Primer or probe.

<400> SEQUENCE: 146
ggaacagagg caaaacgcac atcatcactt                                  30

<210> SEQ ID NO 147
<211> LENGTH: 19
<212> TYPE: DNA
<213> ORGANISM: Artificial Sequence
<220> FEATURE:
<223> OTHER INFORMATION: Primer or probe.

<400> SEQUENCE: 147
caccactgct actgcttca                                              19

<210> SEQ ID NO 148
```

```
<211> LENGTH: 19
<212> TYPE: DNA
<213> ORGANISM: Artificial Sequence
<220> FEATURE:
<223> OTHER INFORMATION: Primer or probe.

<400> SEQUENCE: 148
acattgaagg atttgataa                                              19

<210> SEQ ID NO 149
<211> LENGTH: 22
<212> TYPE: DNA
<213> ORGANISM: Artificial Sequence
<220> FEATURE:
<223> OTHER INFORMATION: Primer or probe.

<400> SEQUENCE: 149
atggagtgcg ctaatggaaa tg                                          22

<210> SEQ ID NO 150
<211> LENGTH: 22
<212> TYPE: DNA
<213> ORGANISM: Artificial Sequence
<220> FEATURE:
<223> OTHER INFORMATION: Primer or probe.

<400> SEQUENCE: 150
ttcaacattt atggcaacga ac                                          22

<210> SEQ ID NO 151
<211> LENGTH: 23
<212> TYPE: DNA
<213> ORGANISM: Artificial Sequence
<220> FEATURE:
<223> OTHER INFORMATION: Primer or probe.

<400> SEQUENCE: 151
tagctcgtag taacccttca aca                                         23

<210> SEQ ID NO 152
<211> LENGTH: 23
<212> TYPE: DNA
<213> ORGANISM: Artificial Sequence
<220> FEATURE:
<223> OTHER INFORMATION: Primer or probe.

<400> SEQUENCE: 152
tcgacaatca cacaccataa tcg                                         23

<210> SEQ ID NO 153
<211> LENGTH: 24
<212> TYPE: DNA
<213> ORGANISM: Artificial Sequence
<220> FEATURE:
<223> OTHER INFORMATION: Primer or probe.

<400> SEQUENCE: 153
gtgcctttgt tcatactctc catc                                        24

<210> SEQ ID NO 154
<211> LENGTH: 30
<212> TYPE: DNA
<213> ORGANISM: Artificial Sequence
<220> FEATURE:
<223> OTHER INFORMATION: Primer or probe.

<400> SEQUENCE: 154
```

```
gaagatctgc tgtcaaaaca aagcaagaag                                            30
```

<210> SEQ ID NO 155
<211> LENGTH: 30
<212> TYPE: DNA
<213> ORGANISM: Artificial Sequence
<220> FEATURE:
<223> OTHER INFORMATION: Primer or probe.

<400> SEQUENCE: 155

```
cccaagcttt tattttggca cgccagcagc                                            30
```

<210> SEQ ID NO 156
<211> LENGTH: 28
<212> TYPE: DNA
<213> ORGANISM: Artificial Sequence
<220> FEATURE:
<223> OTHER INFORMATION: Primer or probe.

<400> SEQUENCE: 156

```
gaagatctgc tgccaaaaca aagcaaga                                              28
```

<210> SEQ ID NO 157
<211> LENGTH: 1778
<212> TYPE: DNA
<213> ORGANISM: Coffea canephora

<400> SEQUENCE: 157

```
gtttgataaa tggcgccacc gatgaaattt acactttcga acaagttgag ctcacagcca           60
gaagagttgc atccgggctt aacaaagttg gtatacagca aggagatacg atcatgatcc          120
tgctgccaaa ctcgccggaa ttcgtgttcg ccttcctcgg tgcatctttc cggggagcca          180
tatccacgat ggccaatcca tatttcacct ctgccgaagt cataaagcaa gccaaggcat          240
ccaacgcaaa gctcatcatc acgcaaggct gttacgtcga aaaggtcagg gactatgcat          300
gtgaaaatgg ggtgaaagtc gtgtgcatcg actctgcacc ggaaggttgt ttacacttct          360
cggagctaac cgaggccgat gaaagggaaa tgccggacgt cgagatcagc cctgaagatg          420
tggtggcgct gccgtactcc tccgggacta ctggactgcc taaggggtg atgttgaccc           480
acaagggact tgtcactagc gtggcacaac aggttgacgg agagaaccca aatttctata          540
tacacaatca agtgatgatg tgcgttttgc ctctgttcca catatattcg ctgaactcaa          600
ttttgctatg tgggctgagg gccggcacaa caattttgat catgcagaaa tttgacataa          660
ttccgttctt ggaattgatt caaaaatata aggtcacaac tggccatttt gtgccaccaa          720
ttgttctggc catagccaaa agtccagagg ttgataaata tgacctttcg tcggtgaaga          780
ctgtcatgtc cggagcggcg ccattgggga aggagcttga agatgctgtt agaaccaaat          840
ttcctaaggc caaacttggt cagggttatg ggatgacaga agcgggccct gtgctagcaa          900
tgtgctcagc atttgctaag gatccctttg aggttaaatc aggcggatgt ggttccgttg          960
ttagaaatgc tgaaatgaag attgtagatc ccgaaactgg tttctcttta ccccggaacc         1020
aacctggaga atctgcatc agaggtgacc aaatcatgaa aggctatctt gatgaccctg          1080
aagccacaaa agcaaccata gacgaagatg gttggttaca tacaggtgat gtagggtaca         1140
ttgatgagga tgatgaactt ttcatcgttg atcgccttaa ggagctaatc aagtacaaag         1200
ggttccaagt cgcacctgca gaacttgaag ccctgctcct cgctcactct gacatctcag         1260
atgctgctgt tgtcccaatg aaggatgacg cagcaggcga agttccagtt gcttttgttg         1320
tgaaatcaaa agattccaac atcaccgagg atgaaattaa ggaatatatc aagaaacagg         1380
```

```
ttatattcta caagagaata aaccgtgtgt tttttgttga tgccattccg aagtcaccat    1440
caggcaaaat cttgagaaag gacttgagag caagactagc tgctggcgtg ccaaaataag    1500
caaaggcaac agcaaattgg cagctaatcc agagggcatt atagcgcaaa aacatctgga    1560 ttttgatac aaggctctgc agctgccgat tatggtgtgt gattgtcgat ttagctgccc     1620
tttcggaaga gagacaaaat atctgtaaat cttactaaga ctttgtccaa ttttcatatg    1680
cttggtggaa tttctctgaa aaaaagaaa aaacaatcac tatttcatga ggcaaaaaaa     1740
aaaaaaaaaa aaaaaaaaaa aaaaaaaaaa aaaaaaa                             1778
```